United States Patent
Abbott et al.

(10) Patent No.: US 12,268,683 B2
(45) Date of Patent: Apr. 8, 2025

(54) COMPOUNDS AND METHODS FOR SYNERGISTIC ACTIVATION OF M CHANNELS

(71) Applicant: THE REGENTS OF THE UNIVERSITY OF CALIFORNIA, Oakland, CA (US)

(72) Inventors: Geoffrey W. Abbott, Irvine, CA (US); Rian W. Manville, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 17/260,796

(22) PCT Filed: Jul. 18, 2019

(86) PCT No.: PCT/US2019/042476
§ 371 (c)(1),
(2) Date: Jan. 15, 2021

(87) PCT Pub. No.: WO2020/018839
PCT Pub. Date: Jan. 23, 2020

(65) Prior Publication Data
US 2021/0267965 A1  Sep. 2, 2021

Related U.S. Application Data

(60) Provisional application No. 62/700,046, filed on Jul. 18, 2018.

(51) Int. Cl.
| | |
|---|---|
| *A61K 31/4748* | (2006.01) |
| *A61K 31/19* | (2006.01) |
| *A61K 31/195* | (2006.01) |
| *A61K 31/197* | (2006.01) |
| *A61K 31/198* | (2006.01) |
| *A61K 31/27* | (2006.01) |
| *A61K 31/353* | (2006.01) |
| *A61K 31/555* | (2006.01) |

(52) U.S. Cl.
CPC .......... *A61K 31/4748* (2013.01); *A61K 31/19* (2013.01); *A61K 31/195* (2013.01); *A61K 31/197* (2013.01); *A61K 31/198* (2013.01); *A61K 31/27* (2013.01); *A61K 31/353* (2013.01); *A61K 31/555* (2013.01)

(58) Field of Classification Search
CPC .. A61K 31/4748; A61K 31/19; A61K 31/196; A61K 31/197; A61K 31/198; A61K 31/27; A61K 31/353; A61K 31/555
See application file for complete search history.

(56) References Cited

U.S. PATENT DOCUMENTS

| | | | |
|---|---|---|---|
| 7,235,258 B1 * | 6/2007 | Wells | A61K 9/5047 424/464 |
| 10,874,643 B2 | 12/2020 | Baraban | |
| 2008/0199896 A1 | 8/2008 | Guan | |
| 2009/0111868 A1 * | 4/2009 | Marx | C07D 311/58 514/456 |
| 2012/0288544 A1 * | 11/2012 | Burke | A61P 3/04 514/535 |
| 2014/0155368 A1 * | 6/2014 | Byron | A61K 31/415 514/188 |

FOREIGN PATENT DOCUMENTS

WO   WO200101970 A2   1/2001

OTHER PUBLICATIONS

Translation of CN105919990 A, Qingdao Yuntian Biotechnology Co Ltd. Retrieved from Dialog on Feb. 28, 2022. Published on Nov. 7, 2016. (Year: 2016).*
Goldklang MP, Perez-Zoghbi JF, Trischler J, Nkyimbeng T, Zakharov SI, Shiomi T, Zelonina T, Marks AR, D'Armiento JM, Marx SO. Treatment of experimental asthma using a single small molecule with anti-inflammatory and BK channel-activating properties. FASEB J. Dec. 2013. (Year: 2013).*
Zhaobing Gao et al. Isoform-specific Prolongation of Kv7 (KCNQ) Potassium Channel Opening Mediated by New Molecular Determinants for Drug-Channel Interactions*, Journal of Biological Chemistry, Vo. 285, Is. 36, 2010. (Year: 2010).*
Doeing DC, Solway J. Airway smooth muscle in the pathophysiology and treatment of asthma. J Appl Physiol (1985). 2013;114(7):834-843. doi:10.1152/japplphysiol.00950.2012 (Year: 2013).*
Matschke V, Piccini I, Schubert J, Wrobel E, Lang F, Matschke J, Amedonu E, Meuth S, G, Strünker T, Strutz-Seebohm N, Greber B, Scherkenbeck J, Seebohm G: The Natural Plant Product Rottlerin Activates Kv7.1/KCNE1 Channels. Cell Physiol Biochem 2016;40:1549-1558. doi: 10.1159/000453205 (Year: 2016).*
Rivera-Arconada I, Vicente-Baz J, Lopez-Garcia JA. Targeting Kv7 channels in pain pathways. Oncotarget. Feb. 21, 2017;8(8):12554-12555. (Year: 2017).*

(Continued)

*Primary Examiner* — James H Alstrum-Acevedo
*Assistant Examiner* — Lauren Wells
(74) *Attorney, Agent, or Firm* — Karen S. Canady; canady + lortz LLP

(57) ABSTRACT

A method of activating heteromeric KCNQ2/3, KCNQ3/5, or KCNQ4/5 voltage-gated potassium channels in a cell membrane is described, as are compositions for use with same, as well as methods of reducing neuronal excitability and of ameliorating symptoms of epilepsy, anxiety, neuropathic pain, hypertension, cardiovascular disease, a neurodegenerative disorder, alcohol withdrawal, cancer, inflammation, or ophthalmic disease in a subject. These KCNQ2/3 (or KCNQ3/5 or KCNQ4/5) channels are heteromers that comprise KCNQ2 (or KCNQ5) subunits and KCNQ3 (or KCNQ4) subunits. In one embodiment, the method comprises: (a) contacting the cell membrane with a first agent that binds a KCNQ2 (or KCNQ5) subunit; and (b) contacting the cell membrane with a second agent that binds a KCNQ3 (or KCNQ4) subunit.

9 Claims, 65 Drawing Sheets

(56) References Cited

OTHER PUBLICATIONS

Better Health Channel. Medicines and Side Effects. Retrieved from the internet on Nov. 15, 2022, https://www.betterhealth.vic.gov.au/health/conditionsandtreatments/medicines-and-side-effects (Year: 2022).*

FDA, Information on ezogabine (marketed as Potiga). Retrieved from the internet on Nov. 15, 2022, https://www.fda.gov/drugs/postmarket-drug-safety-information-patients-and-providers/information-ezogabine-marketed-potiga (Year: 2022).*

Fda.gov. FDA Drug Safety Communication. Retrieved from the Internet on Mar. 5, 2024, https://www.fda.gov/drugs/drug-safety-and-availability/fda-drug-safety-communication-fda-determines-2013-labeling-adequate-manage-risk-retinal (Year: 2024).*

Manville, Rian, et al., Gabapentin Is a Potent Activator of KCNQ3 and KCNQ5 Potassium Channels, Mol Pharmacol 94:1155-1163, Oct. 2018. http://molpharm.aspetjournals.org/content/suppl/2018/07/18/mol.118.112953.DC1.

Manville, Rian, et al., Direct neurotransmitter activation of voltage-gated potassium channels, Nature Communications, (2018) 9:1847. DOI: 10.1038/s41467-018-04266-w.

Manville, Rian, et al., Ancient and modern anticonvulsants act synergistically in a KCNQ potassium channel binding pocket, Nature Communications, 2018; 9: 3845. doi: 10.1038/s41467-018-06339-2.

Xiong, Qiaojie, et al., Combinatorial augmentation of voltage-gated KCNQ potassium channels by chemical openers, PNAS, Feb. 26, 2008;105(8):3128-33. doi: 10.1073/pnas.0712256105. Epub Feb. 12, 2008.

International Search Report for PCT/US19/42476 (WO2020018839 Published Jan. 23, 2020).

* cited by examiner 3-ethyl-2-hydroxy-2-cyclopenten-1-one

MALLOTOXIN

GLUTACONIC ACID

2-MERCAPTOPHENOL

1-HEPTENE

OLEAMIDE

ISOVALERIC ACID

PALMITIC ACID

SORBIC ACID d
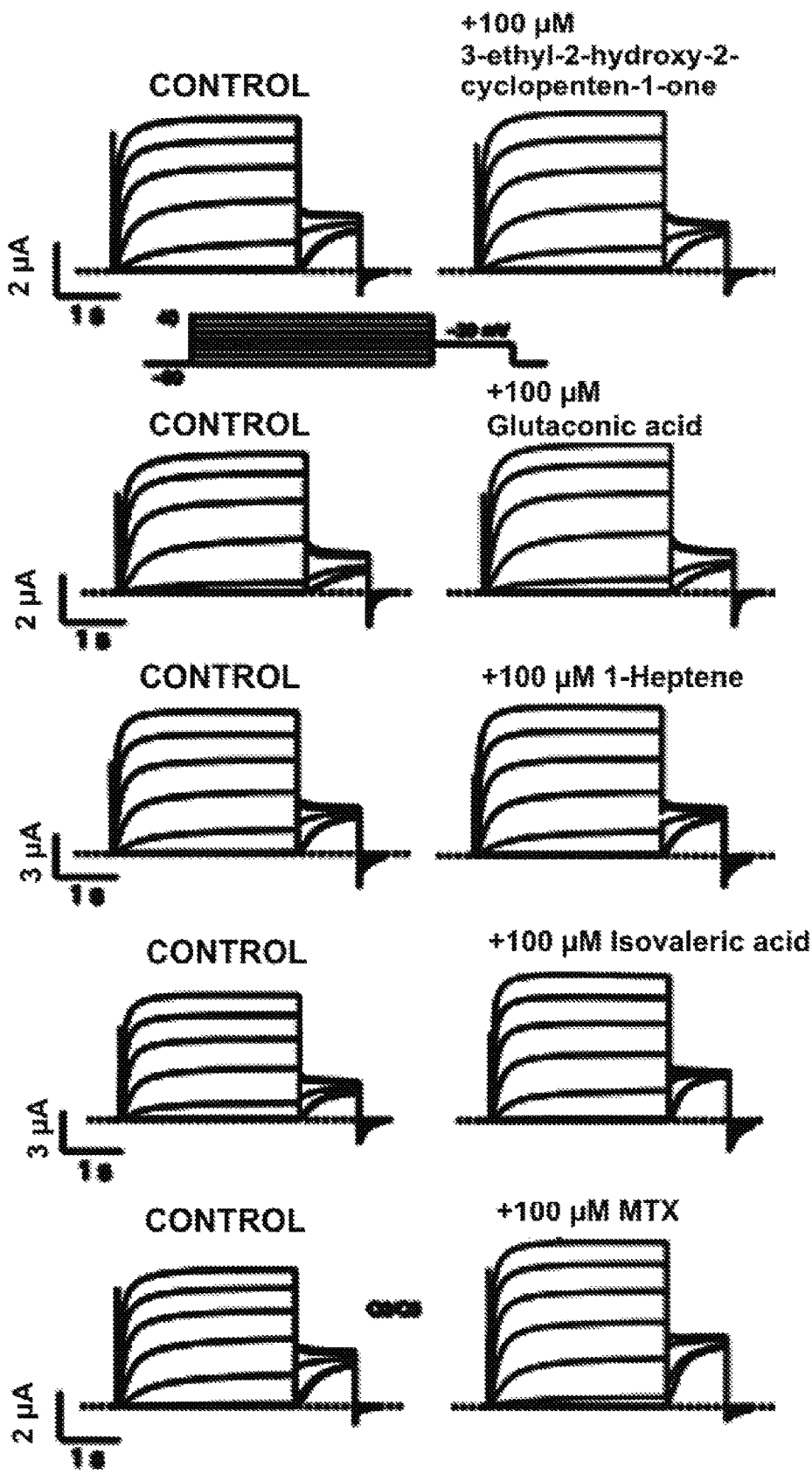

e and f (continued)

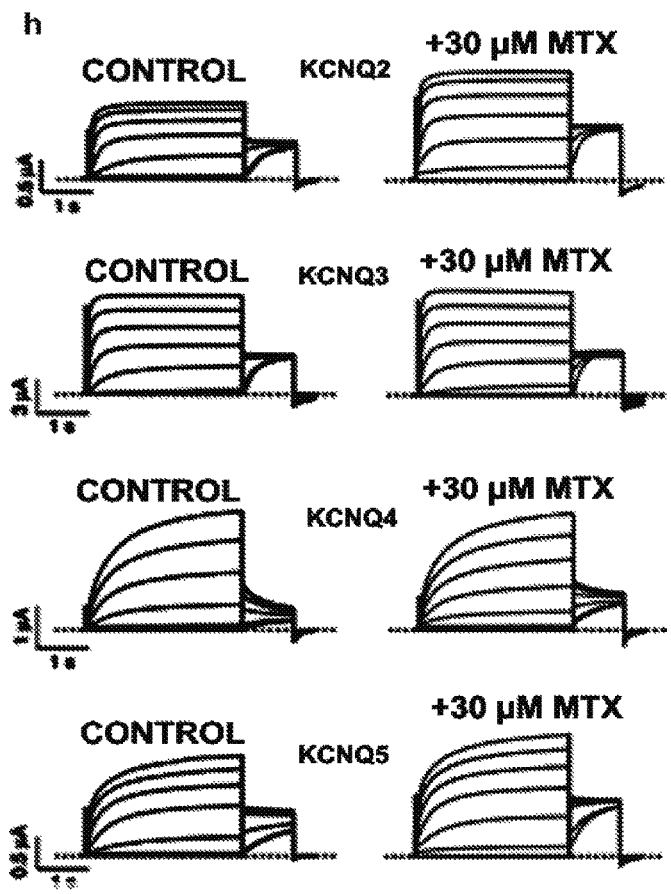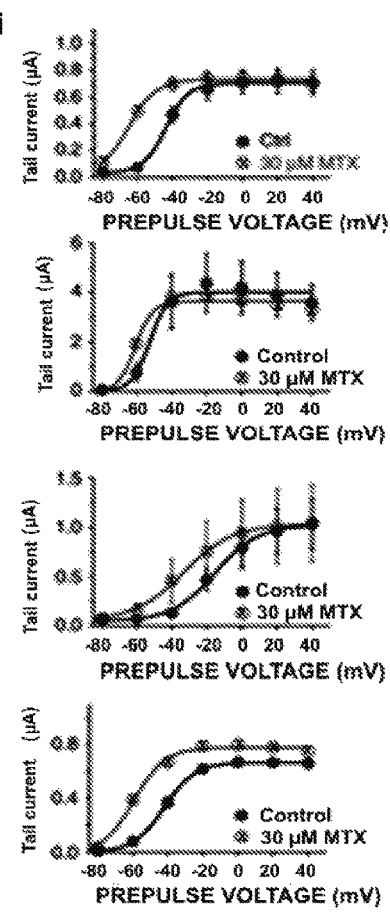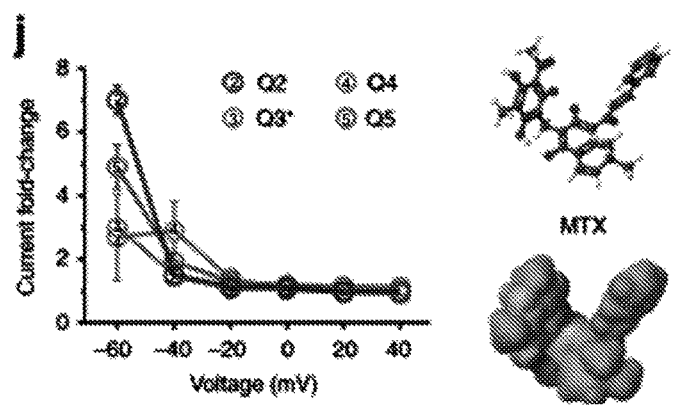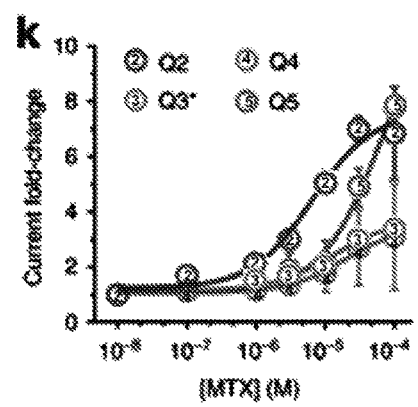

g h i

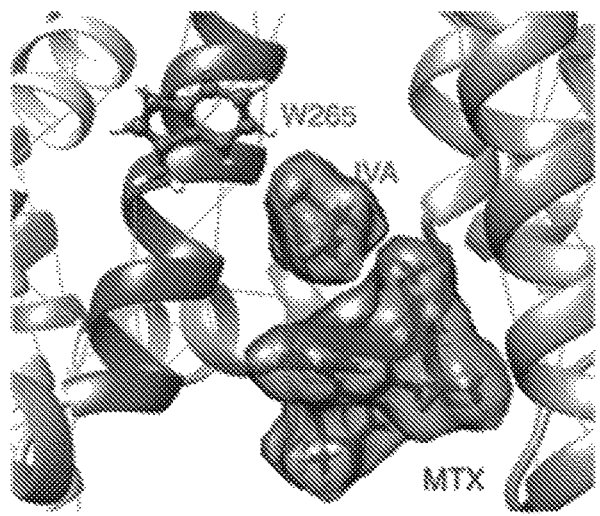
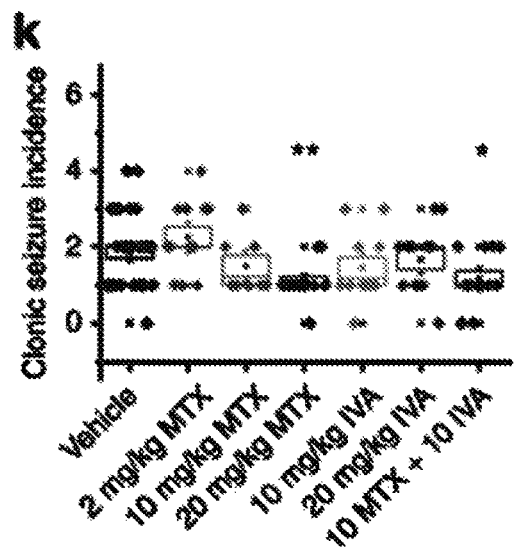
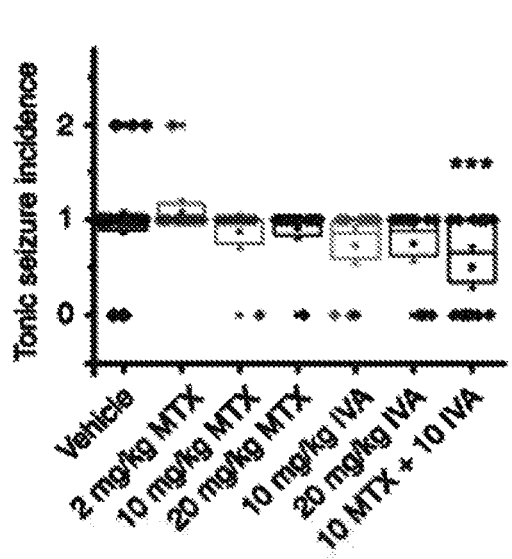
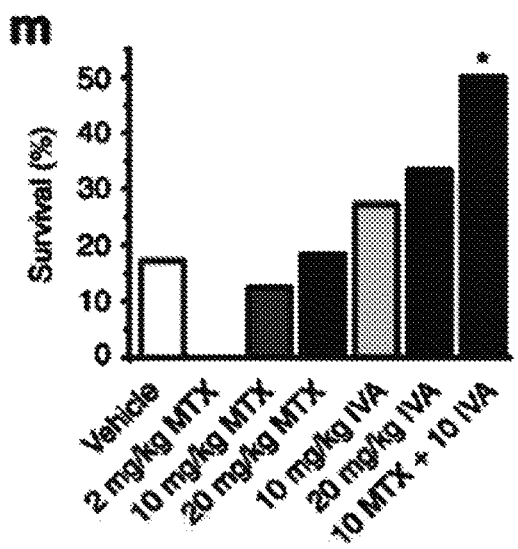

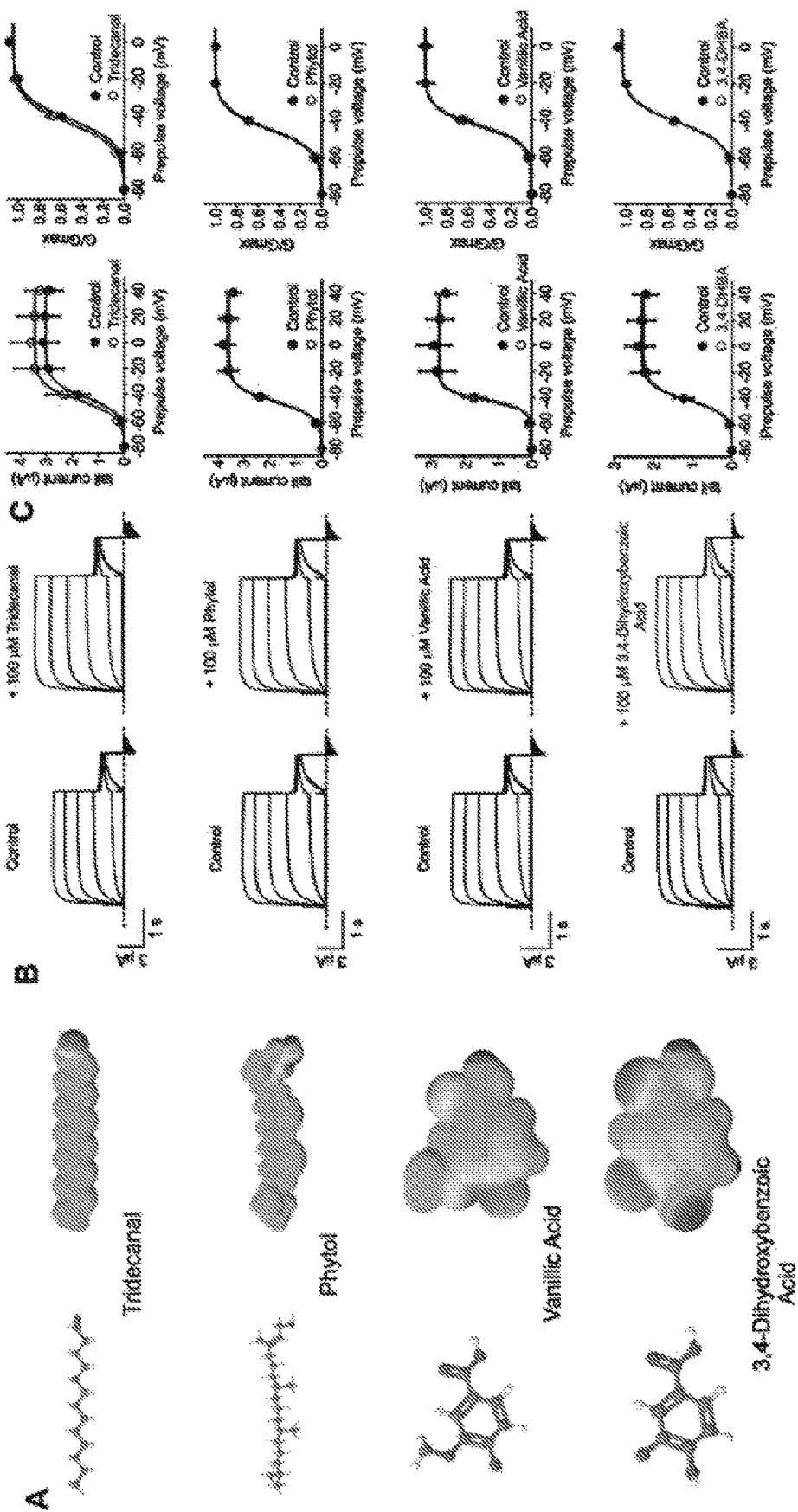
Figure 18 (continued) A, B, C (continued)

COMPOUNDS AND METHODS FOR SYNERGISTIC ACTIVATION OF M CHANNELS

ACKNOWLEDGEMENT OF GOVERNMENT SUPPORT

This invention was made with Government support under grant numbers GM115189 and GM130377_awarded by the National Institutes of Health and National Institute of General Medical Sciences. The Government has certain rights in the invention.

BACKGROUND

KCNQ channels are expressed in many different tissues and serve crucial roles. Opening KCNQ channels with small molecules has therapeutic potential, and KCNQ openers, e.g., retigabine, have been previously approved clinically for epilepsy. However, retigabine was recently taken off the market because of unexpected side effects thought to be unrelated to its targeting of KCNQ channels.

There remains a need for safe, effective, and reliable KCNQ openers, and methods for managing neuronal excitability as well as electrical activity of other cells types outside the brain, including but not limited to cardiac myocytes, epithelial and endothelial cells.

SUMMARY

Described herein is a method of activating heteromeric KCNQ2/3, KCNQ3/5, or KCNQ4/5 voltage-gated potassium channels in a cell membrane. These KCNQ2/3 (or KCNQ3/5 or KCNQ4/5) channels are heteromers that comprise KCNQ2 (or KCNQ5) subunits and KCNQ3 (or KCNQ4) subunits. In one embodiment, the method comprises: (a) contacting the cell membrane with a first agent that binds a KCNQ2 (or KCNQ5) subunit; and (b) contacting the cell membrane with a second agent that binds a KCNQ3 (or KCNQ4) subunit. Representative embodiments of the first agent that binds a KCNQ2 (or KCNQ5) subunit include, but are not limited to, one or more agents selected from mallotoxin (MTX), isovaleric acid (IVA), and zinc pyrithione. Representative embodiments of the second agent that binds a KCNQ3 subunit include, but are not limited to, one or more agents selected from retigabine (RTG) and derivatives thereof, gabapentin, β-hydroxybutyric acid (BHB), and γ-Amino-β-hydroxybutyric acid (GABOB).

Also provided is a composition that activates KCNQ2/3, KCNQ3/5, or KCNQ4/5 voltage-gated potassium channels in a cell membrane, said channels comprising KCNQ2 subunits, KCNQ3 subunits, KCNQ4 subunits, and/or KCNQ5 subunits. In one embodiment, the composition comprises a first agent that binds a KCNQ2 subunit or a KCNQ5 subunit, and a second agent that binds a KCNQ3 subunit or a KCNQ4 subunit, wherein the first and second agents comprise non-identical agents. In some embodiments, the first agent that binds a KCNQ2 or KCNQ5 subunit is one or more agents selected from mallotoxin (MTX), isovaleric acid (IVA), zinc pyrithione (ZnPy), 2-fluorophenylglycine (2FPG), aloperine, 4-(fluorophenyl) glycine (4FPG), ICA-069673, ICA-27243, ztz-240, and (E)-2-dodecenal (E2D); retigabine (RTG) and derivatives thereof, gabapentin (GBP), β-hydroxybutyric acid (BHB), γ-Amino-β-hydroxybutyric acid (GABOB). In some embodiments, the second agent that binds a KCNQ3 or KCNQ4 subunit is one or more agents selected from retigabine (RTG) and derivatives thereof, gabapentin (GBP), β-hydroxybutyric acid (BHB), γ-Amino-β-hydroxybutyric acid (GABOB), and N-(fluorophenyl)-N-(methylsulfonyl) glycine (3FMSG). In some embodiments, the first agent is MTX and/or IVA, and the second agent is RTG. In other embodiments, the first agent is 2FPG, and the second agent is GBP or 3FMSG.

In some embodiments, the first and second agents are present in an amount ranging from 1 to 100 μM. In other embodiments, the agents are present in an amount of 10 μM or less. The composition can be formulated for administration in accordance with the methods described herein. For example, the amount of agents present in the composition can be determined for optimal delivery of the intended daily dosage. In one example, the daily dosage is 10 to 1000 mg. In another example, the daily dosage is 20 to 240 mg.

Also provided is a method of activating KCNQ2/3, KCNQ3/5, or KCNQ4/5 voltage-gated potassium channels in a cell membrane, said channels comprising KCNQ2 or KCNQ5 subunits, and further comprising KCNQ3 or KCNQ4 subunits, the method comprising contacting the cell membrane with a composition as described herein. In some embodiments, the cell is a neuron, myocyte, epithelial cell, or endothelial cell. In one particular embodiment, the cell is a neuron. In some embodiments, the cell membrane potential is −80 mV to +40 mV during the contacting of the cell membrane with the composition. In other embodiments, the cell membrane potential is −80 mV to −40 mV.

Additionally provided is a method of reducing neuronal excitability in a subject, the method comprising administering to the subject a composition as described herein. Another method provided is a method of ameliorating symptoms of epilepsy, anxiety, neuropathic pain, hypertension, cardiovascular disease, a neurodegenerative disorder, alcohol withdrawal, cancer, inflammation, or ophthalmic disease in a subject, the method comprising administering to the subject a composition as described herein. In some embodiments of these methods, the first and second agents of the composition are each administered at a dose of 10-1000 mg/day. In other embodiments, the first and second agents are each administered at a dose of 10-500 mg/day. In some embodiments, the dose is 20-240 mg/day.

In a representative example, the channel is a KCNQ2/3 channel, and the combination of agents comprises one or more agents that bind KCNQ2 and one or more agents that bind KCNQ3. In one such example, the agent that binds a KCNQ3 subunit is RTG, and the RTG is administered at a dose of 20-240 mg/day. In one embodiment, the second agent that binds a KCNQ3 subunit is RTG, and the RTG is administered at a dose of 20-120 mg/day. In one example, the agent that binds a KCNQ3 subunit is gabapentin.

In another representative example, the channel is a KCNQ3/5 channel, and the combination of agents comprises one or more agents that bind KCNQ3 and one or more agents that bind KCNQ5. In one such example, the agent that binds KCNQ3 is RTG, and the agent that binds KCNQ5 is aloperine. In yet another representative example, the channel is a KCNQ4/5 channel, and the combination of agents comprises one or more agents that bind KCNQ4 and one or more agents that bind KCNQ5.

In some embodiments, the contacting steps occur simultaneously. In other embodiments, the contacting occurs near-simultaneously, or sequentially. In a typical embodiment, the cell membrane potential is below +40 mV during the contacting steps. The cell membrane potential can be negative, such as −40 mV or −80 mV, for example.

In some embodiments of the methods for reducing neuronal excitability and for ameliorating symptoms of one of the aforementioned diseases or disorders, the heteromeric channel is KCNQ3/KCNQ5, and the combination of activators comprises one or more compounds that preferentially activate KCNQ3 (e.g., RTG) and one or more compounds that preferentially activate KCNQ5 (e.g., MTX) within KCNQ3/5 heteromers.

The invention thus provides kits and compositions for use in carrying out the methods described herein. In some embodiments, such kits and compositions comprise a first agent that binds a KCNQ2 subunit of a KCNQ2/3 voltage-gated potassium channel and a second agent that binds a KCNQ3 subunit of a KCNQ2/3 voltage-gated potassium channel. In some embodiments, the kits and compositions comprise a first agent that binds a KCNQ3 subunit of a KCNQ3/5 voltage-gated potassium channel and a second agent that binds a KCNQ5 subunit of a KCNQ3/5 voltage-gated potassium channel. In some embodiments, the kits and compositions comprise a first agent that binds a KCNQ4 subunit of a KCNQ4/5 voltage-gated potassium channel and a second agent that binds a KCNQ5 subunit of a KCNQ4/5 voltage-gated potassium channel. The first and second agents can be provided in a single composition, or, in some embodiments, provided separately. For example, a kit may comprise a plurality of containers, each comprising one or more agents that bind a heteromeric KCNQ voltage-gated potassium channel.

DETAILED DESCRIPTION

Figure 1:
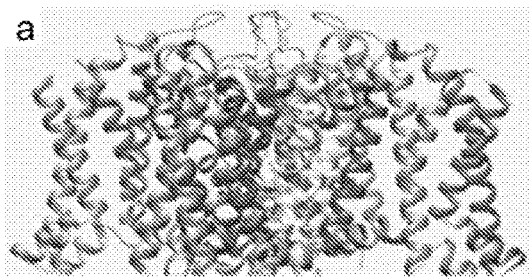
FIG. 1: Multiple *M. oppositifolius* leaf extract compounds activate KCNQ2/3. (a) KCNQ1-KCNQ3 chimeric structure model. (b) KCNQ topology (two of four subunits shown). VSD voltage-sensing domain. (c) Structure and electrostatic surface potential (shading distinguishes positive, neutral, and negative) of *M. oppositifolius* leaf extract components. Open circles highlight strongly negative electrostatic surface potential. (d) Averaged KCNQ2/3 current traces in response to voltage protocol (upper inset) when bathed in the absence (Control) or presence of *M. oppositifolius* leaf extract components (n=4-16). Dashed line indicates zero current level in this and all following current traces. (e),(f) Mean effects of leaf extract components (as in d; n=4-16) on: (e) KCNQ2/3 raw tail currents at −30 mV after prepulses as indicated; (f) G/Gmax. Error bars indicate SEM. First, second, third, and fifth boxes indicate KCNQ2/3 activation; Fourth box indicates KCNQ2/3 inhibition.
Figure 1:
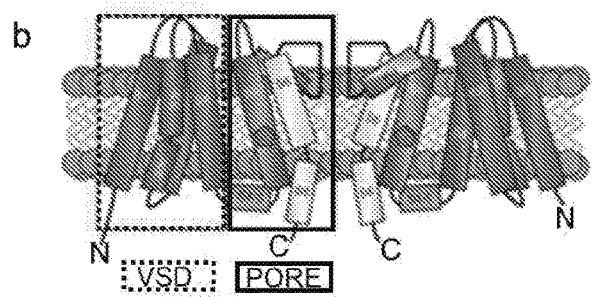
Figure 1:
Figure 1:
Figure 1:
Figure 1:
Figure 1:
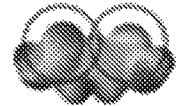
Figure 1:
Figure 1:
Figure 1:
Figure 1:
Figure 1:
Figure 1:
Figure 1:
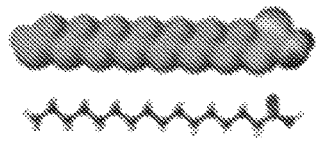
Figure 1:
Figure 1:
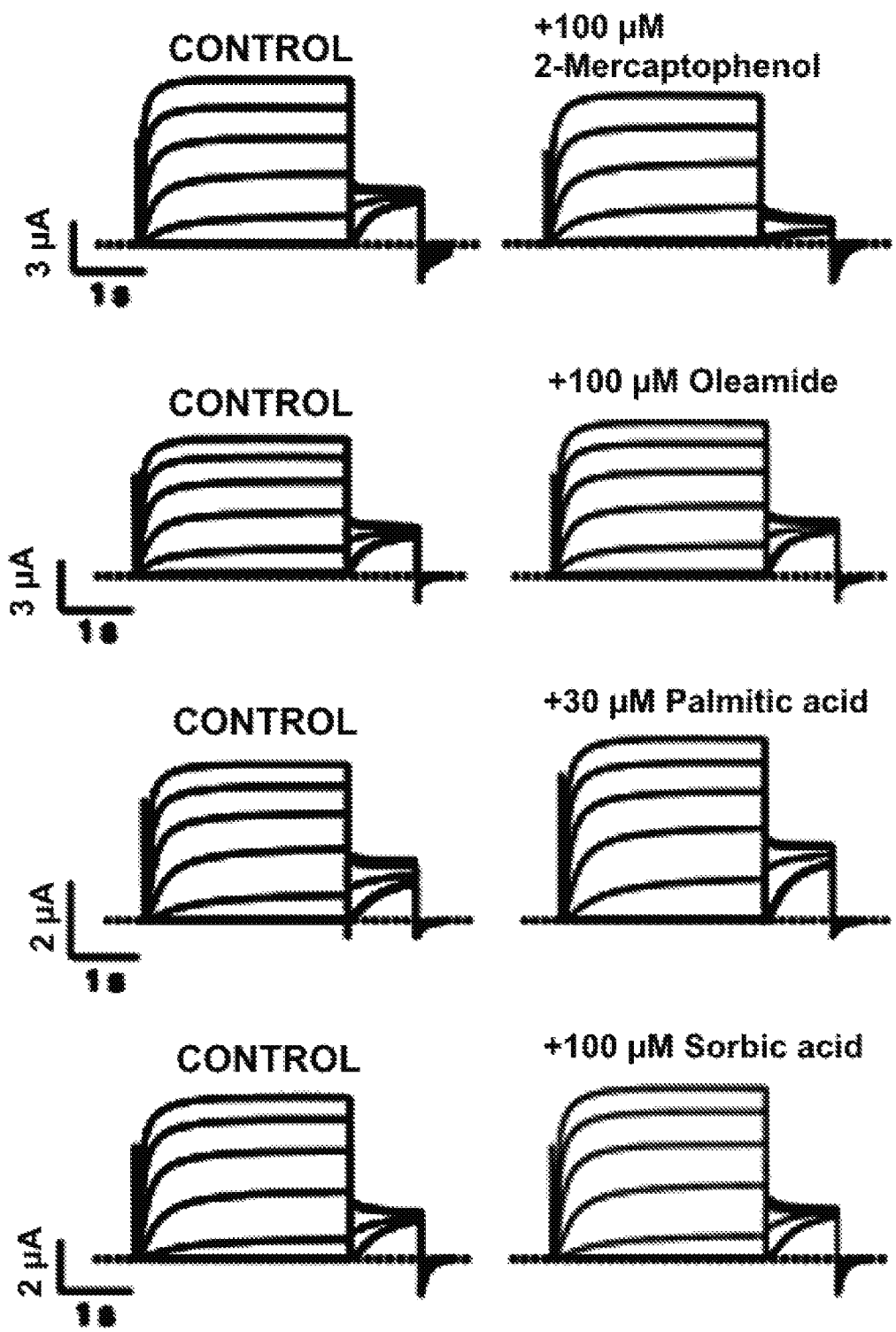
Figure 1:
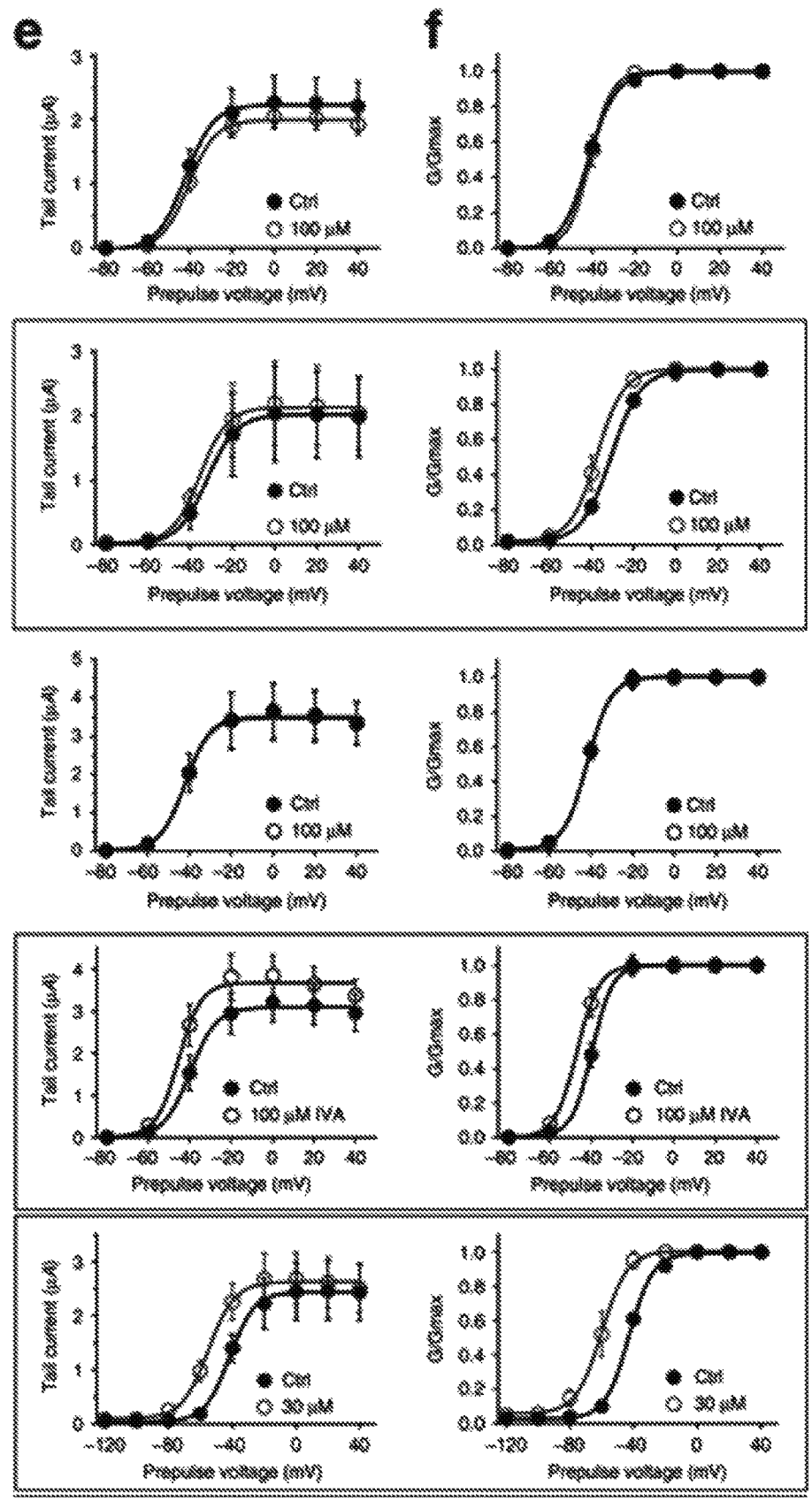
Figure 1:
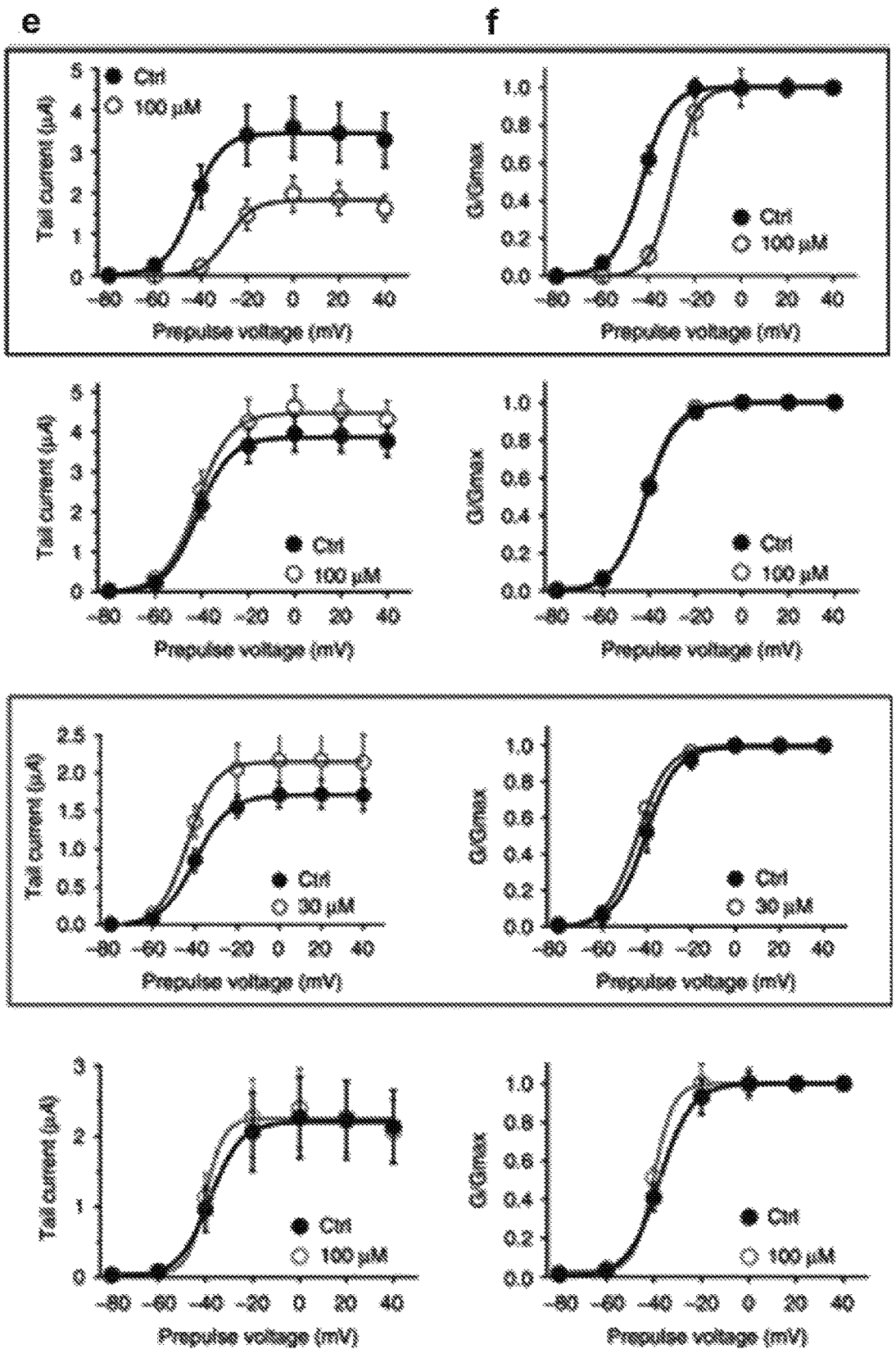

The invention is based on the discovery that surprising advantages can be achieved by activating heteromeric KCNQ2/3, KCNQ3/5, or KCNQ4/5 voltage-gated potassium channels in a cell membrane. The use of combinations of first and second agents that bind both the KCNQ2 and KCNQ3 subunits of the channels provides an unexpectedly synergistic effect. In some cases, triple combinations provide even greater synergy, e.g., two KCNQ2 openers (IVA+MTX) in combination with a KCNQ3 opener (such as RTG), results in a stable open state that locks the KCNQ2/3 channel open in a voltage-independent manner. The synergistic activation of the different isoforms in the KCNQ heteromer produced by double or triple compound combinations increases the potency and efficacy of treatments designed to target M channels, and allows for treatment using lower doses of KCNQ openers that have unwanted side effects and/or toxicity.

DEFINITIONS

All scientific and technical terms used in this application have meanings commonly used in the art unless otherwise specified. As used in this application, the following words or phrases have the meanings specified.

As used herein, "activating" an M channel, such as a KCNQ2/3 voltage-gated potassium channel, means opening the channel sufficiently that current passes through the channel.

As used herein, "a" or "an" means at least one, unless clearly indicated otherwise.

As used herein, to "prevent" or "protect against" a condition or disease means to hinder, reduce or delay the onset or progression of the condition or disease.

As used herein, "treating" a disease or condition means to ameliorate symptoms and/or delay progression of the disease or condition.

Kits and Compositions

The invention provides kits and compositions, which comprise a set or mixture of agents as described herein, and optionally, one or more suitable containers housing agents of the invention. Kits and compositions of the invention optionally further comprise a pharmaceutically acceptable carrier or excipient. The kit or composition can optionally include a buffer.

Also provided is a pharmaceutical composition comprising a therapeutically effective amount of one or more agents as described herein, and, optionally, a pharmaceutically acceptable carrier. In one embodiment, the invention provides an injectable, stable, sterile composition comprising an active compound(s), or a salt thereof, in a unit dosage form in a sealed container. The compound or salt thereof can be provided in the form of a lyophilizate which is capable of being reconstituted with a suitable pharmaceutically acceptable carrier to form a liquid composition suitable for administration to a subject. The unit dosage form may in one variation comprise from about 10 mg to about 10 grams of the compound or salt thereof. In some embodiments the dosage comprises from about 1 to about 100 mg of the compound or salt thereof. When the compound or salt thereof is substantially water-insoluble, a sufficient amount of emulsifying agent which is physiologically acceptable may be employed in sufficient quantity to emulsify the compound or salt in an aqueous carrier.

In some embodiments, the agents of the kit or composition comprise specific combinations as described herein. The kits or compositions can, in some representative embodiments, include one or more agents selected from mallotoxin (MTX), isovaleric acid (IVA), zinc pyrithione (ZnPy), 2-fluorophenylglycine (2FPG), aloperine, 4-(fluorophenyl)glycine (4FPG), ICA-069673, ICA-27243, ztz-240, and (E)-2-dodecenal (E2D); retigabine (RTG) and derivatives thereof, gabapentin (GBP), β-hydroxybutyric acid (BHB), γ-Amino-β-hydroxybutyric acid (GABOB), and/or N-(fluorophenyl)-N-(methylsulfonyl)glycine (3FMSG).

Methods

In some embodiments, the invention provides a method of activating KCNQ2/3, KCNQ3/5, or KCNQ4/5 voltage-gated potassium channels in a cell membrane, said channels comprising KCNQ2 or KCNQ5 subunits, and further comprising KCNQ3 or KCNQ4 subunits. In some embodiments, the method comprises contacting the cell membrane with a composition as described herein. In some embodiments, the cell is a neuron, myocyte, epithelial cell, or endothelial cell. In one particular embodiment, the cell is a neuron. In some embodiments, the cell membrane potential is −120 mV to +40 mV during the contacting of the cell membrane with the composition. In other embodiments, the cell membrane potential is −80 mV to +40 mV, or, in some embodiments, −80 mV to −40 mV.

Additionally provided is a method of reducing neuronal excitability in a subject, the method comprising administering to the subject a composition as described herein. Another method provided is a method of ameliorating symptoms of epilepsy, anxiety, neuropathic pain, hypertension, cardiovascular disease, a neurodegenerative disorder, alcohol withdrawal, cancer, inflammation, or ophthalmic disease in a subject. In a typical embodiment, the method comprises administering to the subject a composition as described herein. In some embodiments of these methods, the first and second agents of the composition are each administered at a dose of 10-1000 mg/day. In other embodiments, the first and second agents are each administered at a dose of 10-500 mg/day. In some embodiments, the dose is 20-240 mg/day. Other exemplary doses are 10-400 mg/day, 10-300 mg/day, 10-200 mg/day, and 10-100 mg/day.

In a representative example, the channel is a KCNQ2/3 channel, and the combination of agents comprises one or more agents that bind KCNQ2 and one or more agents that bind KCNQ3. In one such example, the agent that binds a KCNQ3 subunit is RTG, and the RTG is administered at a dose of 20-240 mg/day. In one embodiment, the second agent that binds a KCNQ3 subunit is RTG, and the RTG is administered at a dose of 20-120 mg/day. In one example, the agent that binds a KCNQ3 subunit is gabapentin.

In another representative example, the channel is a KCNQ3/5 channel, and the combination of agents comprises one or more agents that bind KCNQ3 and one or more agents that bind KCNQ5. In one such example, the agent that binds KCNQ3 is RTG, and the agent that binds KCNQ5 is aloperine. In yet another representative example, the channel is a KCNQ4/5 channel, and the combination of agents comprises one or more agents that bind KCNQ4 and one or more agents that bind KCNQ5.

In some embodiments, the contacting steps occur simultaneously. In other embodiments, the contacting occurs near-simultaneously, or sequentially. In a typical embodiment, the cell membrane potential is below +40 mV during the contacting steps. The cell membrane potential can be negative, such as −40 mV or −80 mV, for example.

In some embodiments of the methods for reducing neuronal excitability and for ameliorating symptoms of one of the aforementioned diseases or disorders, the heteromeric channel is KCNQ3/KCNQ5, and the combination of activators comprises one or more compounds that preferentially activate KCNQ3 (e.g., RTG) and one or more compounds that preferentially activate KCNQ5 (e.g., MTX) within KCNQ3/5 heteromers.

Treatment

The invention provides methods for administering the agents described herein to a subject, and methods of treating subjects in need thereof. Treatment can be administered in a single dose or as a series of doses administered over time, such as, in one example, daily. Dosage and treatment regimens can be determined by the treating physician, taking into account disease severity, patient condition, and other factors. In one representative embodiment, the agent is RTG, and is administered at a dose selected to avoid unwanted side effects. In a representative example, the dose of RTG is 20 mg/day to 120 mg/day.

For use in the methods described herein, the subject includes any human or non-human animal. The term "non-human animal" includes all vertebrates, e.g., mammals and non-mammals, such as non-human primates, horses, sheep, dogs, cows, pigs, chickens, and other veterinary subjects. In a typical embodiment, the subject is human.

EXEMPLARY EMBODIMENTS

Embodiment 1: A method of activating KCNQ2/3 voltage-gated potassium channels in a cell membrane, said channels comprising KCNQ2 subunits and KCNQ3 subunits, the method comprising: (a) contacting the cell membrane with a first agent that binds a KCNQ2 subunit; and (b) contacting the cell membrane with a second agent that binds a KCNQ3 subunit; wherein the first agent that binds a KCNQ2 subunit is one or more agents selected from mallotoxin (MTX), isovaleric acid (IVA), and zinc pyrithione; and wherein the second agent that binds a KCNQ3 subunit is one or more agents selected from retigabine (RTG) and derivatives thereof, gabapentin, β-hydroxybutyric acid (BHB), and γ-Amino-β-hydroxybutyric acid (GABOB).

Embodiment 2: The method of embodiment 1, wherein the cell is a neuron.

Embodiment 3: The method of embodiment 1, wherein the contacting of steps (a) and (b) occurs simultaneously.

Embodiment 4: The method of embodiment 1, wherein the cell membrane potential is below +40 mV during the contacting of steps (a) and (b).

Embodiment 5: A method of reducing neuronal excitability in a subject, the method comprising administering to the subject a combination of a first agent that binds a KCNQ2 subunit of a KCNQ2/3 voltage-gated potassium channel and a second agent that binds a KCNQ3 subunit of a KCNQ2/3 voltage-gated potassium channel.

Embodiment 6: A method of ameliorating symptoms of epilepsy, anxiety, neuropathic pain, a neurodegenerative disorder, alcohol withdrawal, cancer, inflammation, or ophthalmic disease in a subject, the method comprising administering to the subject a combination of a first agent that binds a KCNQ2 subunit of a KCNQ2/3 voltage-gated potassium channel and a second agent that binds a KCNQ3 subunit of a KCNQ2/3 voltage-gated potassium channel.

Embodiment 7: The method of embodiment 5 or 6, wherein the first agent that binds a KCNQ2 subunit is mallotoxin (MTX), isovaleric acid (IVA), zinc pyrithione, or a combination thereof.

Embodiment 8: The method of embodiment 5 or 6, wherein the second agent that binds a KCNQ3 subunit is one or more agents selected from retigabine (RTG) and derivatives thereof, gabapentin, β-hydroxybutyric acid (BHB), and γ-Amino-β-hydroxybutyric acid (GABOB).

Embodiment 9: The method of embodiment 8, wherein the second agent that binds a KCNQ3 subunit is RTG, and wherein the RTG is administered at a dose of 20-120 mg/day.

Embodiment 10: The method of embodiment 8, wherein the agent that binds a KCNQ3 subunit is gabapentin.

Embodiment 11: The method of any of the preceding embodiments, wherein the heteromeric channel is KCNQ3/KCNQ5, and the combination of agents comprises one or more agents that bind KCNQ3 and one or more agents that bind KCNQ5.

Embodiment 12: The method of embodiment 11, wherein the agent that binds KCNQ3 is RTG, and the agent that binds KCNQ5 is MTX.

EXAMPLES

The following examples are presented to illustrate the present invention and to assist one of ordinary skill in making and using the same. The examples are not intended in any way to otherwise limit the scope of the invention. Supplementary figures and tables noted in and confirming the data described the following Examples can be accessed via the online versions of the corresponding publications.

Example 1: Anticonvulsants Act Synergistically in a KCNQ Potassium Channel Binding Pocket Epilepsy has been treated for centuries with herbal remedies, including leaves of the African shrub *Mallotus oppositifolius*, yet the underlying molecular mechanisms have remained unclear. Voltage-gated potassium channel isoforms KCNQ2-5, predominantly KCNQ2/3 heteromers, underlie the neuronal M-current, which suppresses neuronal excitability, protecting against seizures. In this Example, in silico docking, mutagenesis and cellular electrophysiology reveal that two components of *M. oppositifolius* leaf extract, mallotoxin (MTX) and isovaleric acid (IVA), act synergistically to open neuronal KCNQs, including KCNQ2/3 channels. Correspondingly, MTX and IVA combine to suppress pentylene tetrazole-induced tonic seizures in mice, whereas individually they are ineffective. Co-administering MTX and IVA with the modern, synthetic anticonvulsant retigabine creates a further synergy that voltage independently locks KCNQ2/3 open. Leveraging this synergy, which harnesses ancient and modern medicines to exploit differential KCNQ isoform preferences, presents an approach to developing safe yet effective anticonvulsants.

Epilepsy affects over 50 million people worldwide, with approximately 50% being inadequately treated with currently available anti-epileptic drugs[1]. In the developing world, an estimated 80% of epilepsy patients use herbal remedies for primary healthcare[2,3]. Extract taken from leaves of the shrub *Mallotus oppositifolius* has been used traditionally in folk medicine to treat disorders such as seizures in African countries[4,5] including Ghana, where it is known as nyanyaforowa (pimpim), and Nigeria, where it is referred to as okpo-biriba. Accordingly, *M. oppositifolius* extract has been shown to delay the onset, frequency, and duration of seizures in the acute chemoconvulsant (pentylene tetrazole) mouse model[5]. Despite the clear therapeutic effects of *M. oppositifolius*, the active anticonvulsant components of this extract have remained unclear, and their molecular targets unknown. Mallotoxin (MTX; a.k.a. rottlerin) is one suggested anti-seizure component of *M. oppositifolius*. However, a plausible molecular target for MTX that would quell seizures has not previously been identified. In addition, some other plants heavily used in folk medicine also contain MTX but are not traditionally used to treat epilepsy. For example, *Mallotus philippensis*, a perennial shrub distributed in outer Himalayan lowlands, is reported to possess antifilarial, antifertility, antibiotic, anti-inflammatory, and a range of other properties but is not reportedly used to treat seizures[6]. We therefore hypothesized that MTX either is not the active anticonvulsant in *M. oppositifolius* or does not act alone.

Members of the KCNQ (Kv7) subfamily of voltage-gated potassium (Kv) channels are essential for control of cellular excitability and repolarization in a wide range of cell types. Kv channels, including the KCNQs, are composed of tetramers of α subunits each containing six transmembrane segments (S1-S6), split into a voltage-sensing domain (S1-S4) and a pore module (S5 and S6) (FIG. 1a, b)[7]. KCNQ2-5 channels—predominantly KCNQ2/3 heteromers—generate the M-current, a muscarinic-inhibited Kv current that regulates neuronal excitability[8,9]. Mutations in KCNQ2 and KCNQ3 subunits underlie various forms of epilepsy, including early infantile epileptic encephalopathy, benign familial neonatal seizures, and other miscellaneous early onset encephalopathies[10,11,12]. Accordingly, retigabine (RTG) (also known as ezogabine) is a first-in-class anticonvulsant that works by activating KCNQ2/3 channels, negative-shifting their voltage dependence to increase their open probability at subthreshold potentials and prevent aberrant neuronal excitability[13,14,15,16,17,18].

RTG was approved by the FDA in 2011 and was in clinical use as an add-on therapy for the treatment of partial seizures in adults with epilepsy until 2017, when it was withdrawn from the market because of side effects including blue skin discoloration and retinal pigment changes. More recently, the skin discoloration has been found to be reversible after drug discontinuation[19,20]. RTG activates all neuronally expressed KCNQ isoforms (KCNQ2-5), with a preference for KCNQ3 (ref. 21), and in addition to epilepsy showed promise in treating disorders including anxiety, neuropathic pain, neurodegenerative disorders, cancer, inflammation, and ophthalmic diseases[22,23,24,25]. New drugs are therefore needed that share mechanistic commonalties with RTG but lack the side effects, and ideally possessing improved efficacy and/or potency, to reduce the required dosage.

This Example shows that two components of *M. oppositifolius* leaf extract, MTX and IVA, act synergistically in similar binding pockets to activate KCNQ2/3 channels and reduce tonic seizure incidence and related mortality in mice. We also demonstrate that when co-administered, MTX, IVA, and RTG voltage-independently lock KCNQ2/3 open at all voltages. We explain the molecular mechanisms underlying these synergies, which suggest a pathway for developing safer, more effective anticonvulsants.

Results

Multiple *M. oppositifolius* Leaf Compounds Activate KCNQ2/3

Igwe et al.[26] recently identified by mass spectrometry nine primary components of an ethanolic extract of the *M. oppositifolius* leaf, in addition to MTX, which was previously identified in *M. oppositifolius* bark and leaves[27] (FIG. 1c). Using two-electrode voltage-clamp electrophysiology, we screened all ten compounds for their ability to activate heterologously expressed KCNQ2/3 channels in *Xenopus laevis* oocytes, with the exception of valeric acid, which we had previously found to be inactive in this respect[28] (FIG. 1d). Compounds were screened at 100 µM, except MTX and palmitic acid (30 µM). Four components—glutaconic acid, isovaleric acid (IVA), MTX, and palmitic acid, negative-shifted the voltage dependence of KCNQ2/3 activation, as quantified using KCNQ2/3 tail currents at −30 mV immediately following channel activation at voltages between −80 mV and +40 mV (FIG. 1e,f). Three of these compounds (MTX excepted) possessed strong negative electrostatic surface potential close to a carbonyl oxygen, a property previously shown important for KCNQ2/3 activation by RTG and related synthetic anticonvulsants[29]. One component (2-mercaptophenol) positive-shifted KCNQ2/3 voltage dependence, an effect more likely to be pro- rather than anticonvulsant; the other components had little-to-no effect on KCNQ2/3 activation (FIG. 1c-f; Supplementary FIGS. 1-6; Supplementary Tables 1-9).

MTX Potently Activates KCNQ2/3 Channels

MTX, a polyphenol, was the most potent KCNQ2/3 activator in our initial screen (FIG. 1d-f). This was in contrast to a prior report in which MTX was previously found to activate KCNQ1 (a cardiac and epithelial Kv channel) and KCNQ4, while KCNQ2, KCNQ5, and heteromeric KCNQ2/3 channels were concluded to be insensitive[30]. However, the screening in that study was performed using a cell membrane potential of +40 mV, a voltage that often fails to uncover effects of openers that operate by negative-shifting the voltage dependence of activation. Indeed, we likewise found little effect of MTX on KCNQ2/3 at +40 mV, but we observed a prominent activating effect at −60 mV and consequent −17 mV negative shift in the midpoint voltage dependence ($V_{0.5}$) of KCNQ2/3 activation (FIG. 1e,f; FIG. 2a; Supplementary FIG. 3; Supplementary Table 5). At −60 mV, 100 µM MTX increased KCNQ2/3 current seven-fold; the activation $EC_{50}$ was 11.5±0.2 µM (standard error of the mean, SEM) (FIG. 2b). MTX activation of KCNQ2/3 began immediately upon wash-in, plateaued at 5 min, washed out slowly, but was rapidly inhibited by KCNQ-specific blocker XE991 (FIG. 2c). MTX speeded KCNQ2/3 activation and slowed deactivation, consistent with open state stabilization and closed state destabilization (FIG. 2d; Supplementary Tables 10 and 11). MTX exerted potent effects on KCNQ2/3-dependent membrane hyperpolarization (FIG. 2e), illustrative of how MTX can KCNQ2/3-dependently dampen cellular excitability. The observed effects were KCNQ2/3-dependent: MTX had no effect on water-injected control oocytes (FIG. 2f) nor on a different-subfamily Kv channel, KCNA1 (FIG. 2g).

MTX Preferentially Activates KCNQ2 Channels

With respect to homomeric M-channels, KCNQ2 exhibited the highest MTX sensitivity, with an $EC_{50}$ of 6.4 µM at −60 mV. KCNQ3* (an expression-optimized KCNQ3-A315T mutant that ensures robust currents)[31] was twofold less sensitive than KCNQ2 ($EC_{50}$, 13.0 µM), while KCNQ4 and KCNQ5 had MTX $EC_{50}$ values of 20.2 and 67.1 µM, respectively (FIG. 2h,i; Supplementary FIGS. 7-10; Supplementary Tables 12-15). MTX activation of homomeric KCNQs was again most effective at −60 mV (FIG. 2j). Despite relatively lower sensitivity, MTX was an effective KCNQ5 opener at higher concentrations, increasing −60 mV current eight-fold at 100 µM, similar to the effect on KCNQ2 at 100 µM and more than double the effect on KCNQ3* and KCNQ4 (FIG. 2k). Among the neuronal KCNQs, MTX (30 µM) had the greatest effect on the midpoint voltage of KCNQ2 activation (−24 mV), comparable to reported effects of RTG on KCNQ2 (−24 mV for 10 µM RTG[17]), followed by KCNQ2/3 and KCNQ4 (each −17 mV), KCNQ5 (−14 mV), and KCNQ3* (−9 mV) (Supplementary Tables 5 and 12-15). This order of potency is in contrast to that of RTG, which is KCNQ3>KCNQ2/3>KCNQ2>KCNQ4>KCNQ5 (refs. 17, 23).

MTX Binds Close to the Channel Pore to Activate KCNQ2/3

RTG, an established KCNQ2/3 channel activator, requires KCNQ2-W236, which is located on transmembrane segment 5 (S5; FIG. 3a) or its equivalent on KCNQ3 (W265) for activation; these residues are thought to be required for RTG binding[32]. KCNQ2-L275 (or L314, its equivalent in KCNQ3), close to the selectivity filter, also influences RTG activation of KCNQ2 and may impinge on or form part of the binding site[33], as illustrated here using in silico docking to a model chimeric structure derived from the *Xenopus* KCNQ1 cryo-EM structure with KCNQ3 RTG binding residues and close neighbors added (FIG. 3b, upper).

In silico docking simulations predicted binding of MTX in the region of KCNQ3-W265, but not L314 (FIG. 3b, lower), in a location we recently discovered to harbor an evolutionarily conserved neurotransmitter binding pocket in KCNQ2-5 (ref. 28). However, previous studies clearly show that KCNQ1, which lacks the W265 equivalent, is activated by MTX[30]. This, together with our KCNQ3 docking prediction, suggested that MTX might fit in a binding pocket close enough to be influenced by W265, but not absolutely require it for binding. Electrophysiological analysis of KCNQ2 and KCNQ3 channel mutants support this hypothesis. Thus, leucine substitution of either KCNQ2-W236 or KCNQ3-W265, or both, in KCNQ2/3 channel complexes reduced as much as tenfold the potency of MTX, quantified as the negative shift in voltage dependence of activation induced, but a similar maximal efficacy was achieved in the mutant channels (FIG. 3c, d; Supplementary FIGS. 11-13; Supplementary Tables 16-18).

Due to the bulky nature of MTX, we predicted that its binding within a pocket close to S5 would influence pore conformation, potentially altering relative ion permeabilities. To assess this, we first conducted pseudo-bi-ionic substitution experiments, which showed that MTX increased relative permeability of KCNQ2/3 to $Na^+$ and $Cs^+$, and decreased permeability to $Rb^+$, compared to $K^+$ (FIG. 3e,f). Secondly, we assessed the ratio of $Rb^+$ conductance to $K^+$ conductance, $G_{Rb}/G_K$, an alternative method to probe the pore conformation of $K^+$ channels (see Methods). By this method, KCNQ2/3 exhibited a baseline $G_{Rb}/G_K$ value of 0.75±0.10; application of MTX reduced the $G_{Rb}/G_K$ value to 0.52 t 0.06 (FIG. 3g). Thus, MTX binding alters KCNQ2/3 pore conformation sufficiently to alter relative ion permeabilities, and also to sense W236/W265.

Figure 3:
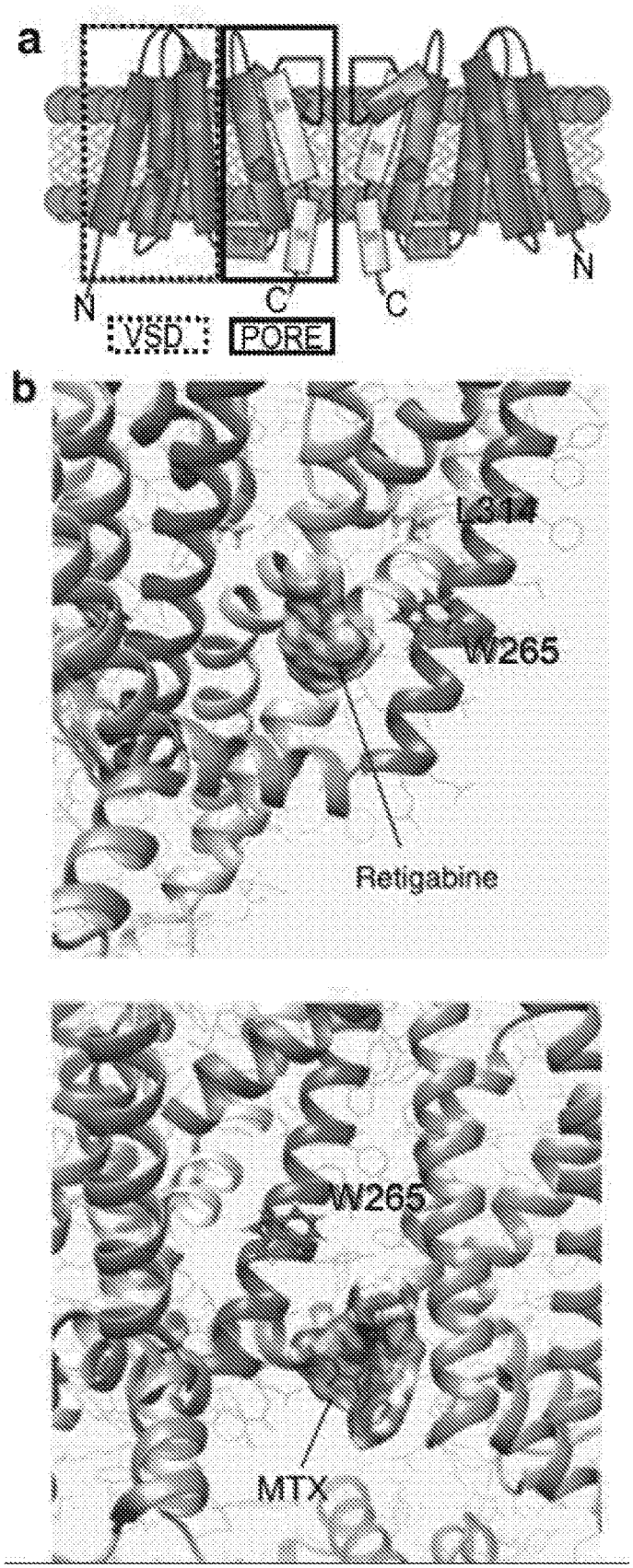
FIG. 3: MTX activates KCNQ2/3 by binding close to the pore. (a) KCNQ topology (two of four subunits shown) indicating approximate position of KCNQ3-W265. VSD voltage-sensing domain. (b) Binding position of (upper) retigabine and (lower) MTX in KCNQ3 predicted by SwissDock using a chimeric KCNQ1-KCNQ3 structure model. (c) Effects of MTX (30 µM) on tail current and $G/G_{max}$ relationships for single- and double-W/L mutant KCNQ2/3 channels as indicated (n=3-5). Voltage protocol as in FIG. 1d. (d) Dose response for mean $\Delta V_{0.5}$ of activation induced by MTX for wild-type KCNQ2/3 and mutant channels as in (c) (n=3-9). (e) Left, exemplar traces; right, mean I/V relationships for KCNQ2/3 channels bathed in 100 mM $K^+$, $Rb^+$, $Cs^+$, or $Na^+$ in the presence or absence (Control) of MTX (30 µM); n=4-7. (f) Relative ion permeabilities of KCNQ2/3 channels in the presence or absence (Ctrl) of MTX (30 µM); n=4-7. Quantified from traces and plots as in panel (e). (g) Relative $Rb^+$ to $K^+$ permeabilities of KCNQ2/3 channels in the presence or absence (Ctrl) of MTX (30 µM); n=4-8. All error bars indicate SEM.
Figure 3:
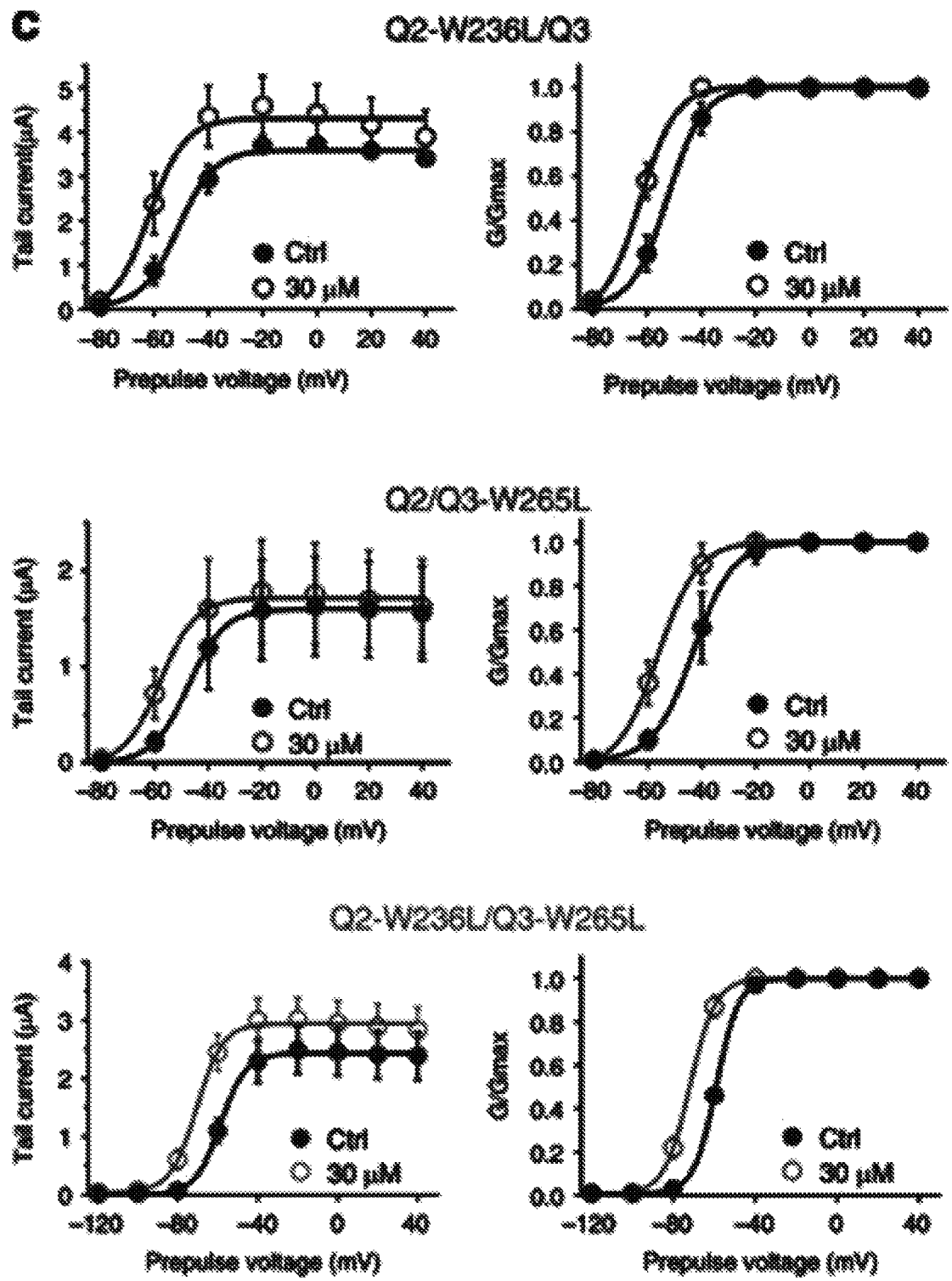
Figure 3:
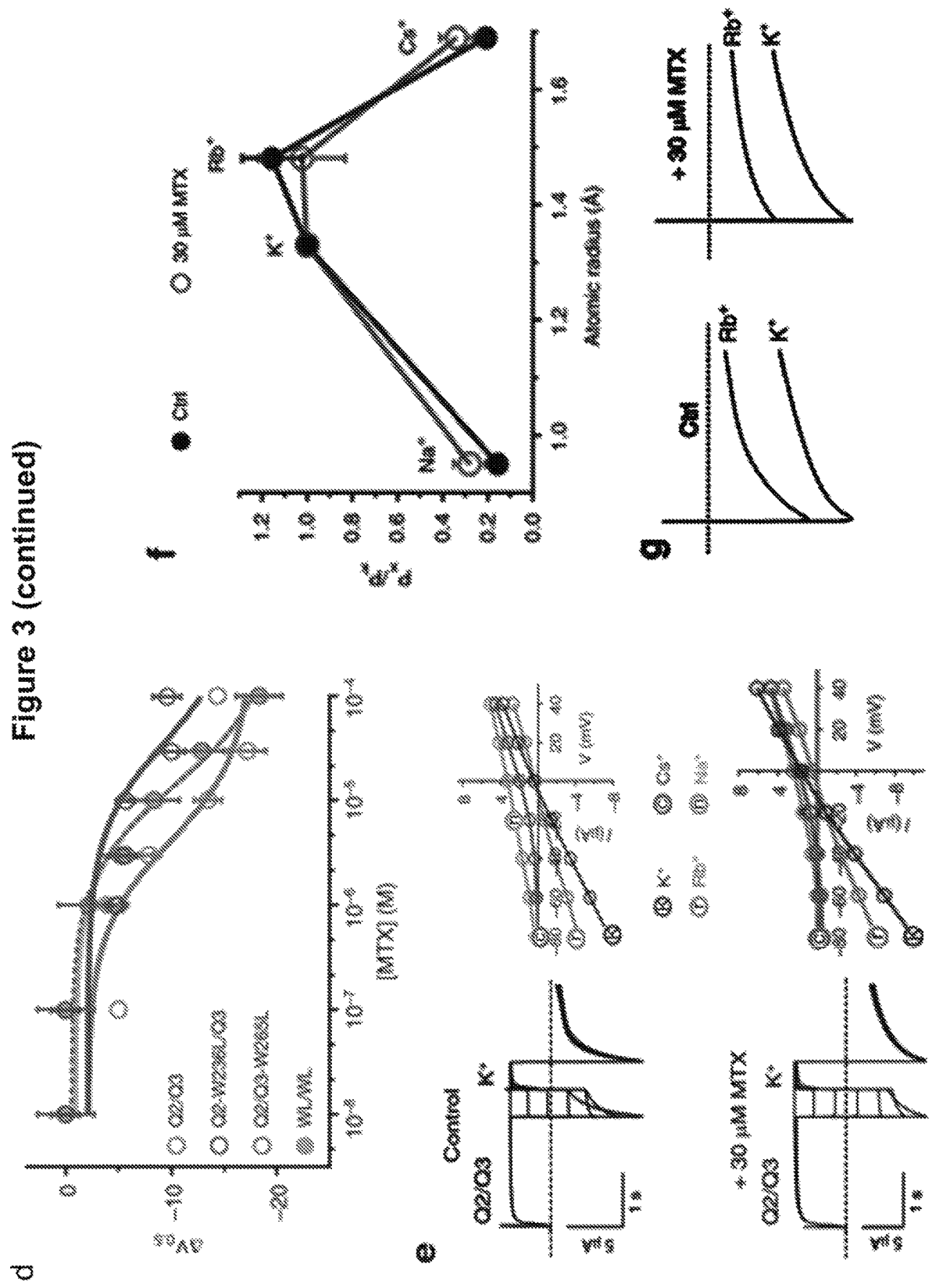
Figure 4:
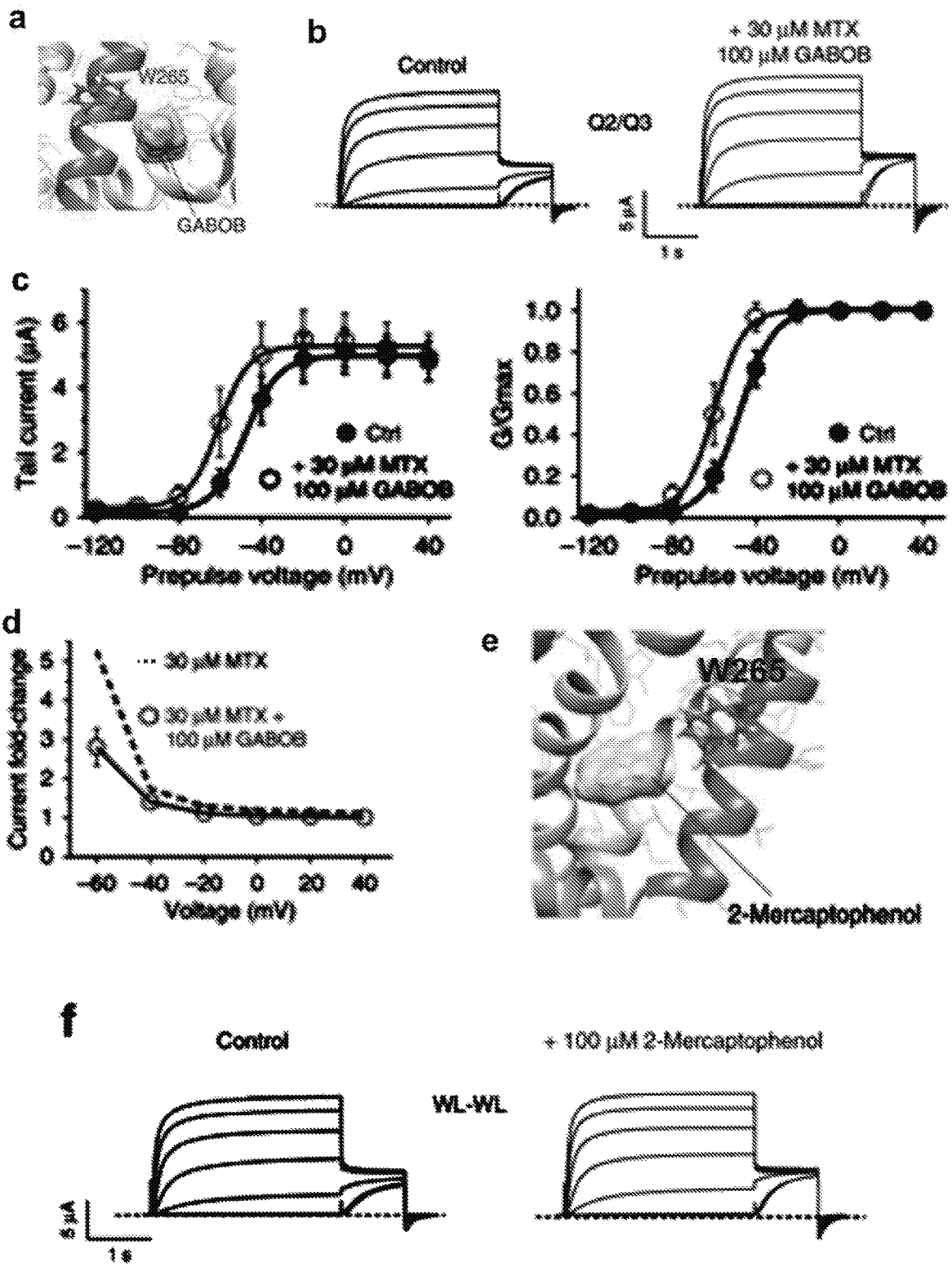
FIG. 4: MTX outcompetes 2-mercaptophenol to activate KCNQ2/3. (a) Binding position of GABOB predicted by SwissDock using a chimeric KCNQ1-KCNQ3 structure model. (b) Exemplar traces showing effects of MTX (30 µM) with GABOB (100 µM) on KCNQ2/3 channels. Voltage protocol as in FIG. 1d. (c) Effects of MTX (30 µM) with GABOB (100 µM) on mean tail current (left) and $G/G_{max}$ (right) relationships for KCNQ2/3 (n=6) calculated from traces as in panel (b). (d) Current fold-change at −60 mV exerted by MTX (30 µM) alone (from FIG. 2a) or with 100 µM GABOB, from data as in panel (c) (n=6). (e) Binding position of 2-mercaptophenol predicted by SwissDock using a chimeric KCNQ1-KCNQ3 structure model. (f) Exemplar traces showing effects of 2-mercaptophenol (100 µM) on KCNQ2-W236L/KCNQ3-W265 (WL-WL) channels. Voltage protocol as in FIG. 1d. (g) Effects of 2-mercaptophenol (100 µM) on mean tail current (left) and $G/G_{max}$ (right) relationships for KCNQ2-W236L/KCNQ3-W265 (WL-WL) channels (n=9) calculated from traces as in panel (f). (h) Exemplar traces showing effects of MTX (30 µM) with 2-mercaptophenol (100 µM) on KCNQ2/3 channels. Voltage protocol as in FIG. 1d. (i) Effects of MTX (30 µM) with 2-mercaptophenol (100 µM) on mean tail current (left) and $G/G_{max}$ (right) relationships for KCNQ2/3 (n=9) calculated from traces as in panel (h). (j) Current fold-change at −60 mV exerted by MTX (30 µM) alone (from FIG. 2a) or with 100 µM 2-mercaptophenol, from data as in panel (i) (n=9). All error bars indicate SEM.
Figure 4:
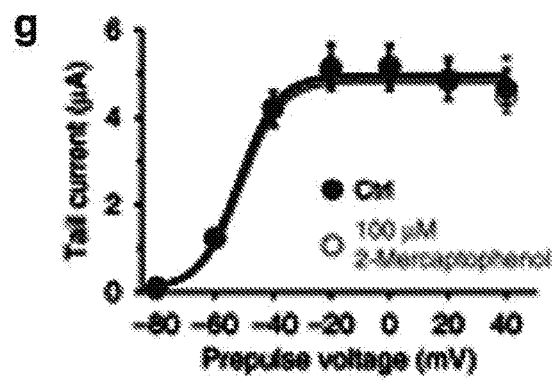
Figure 4:
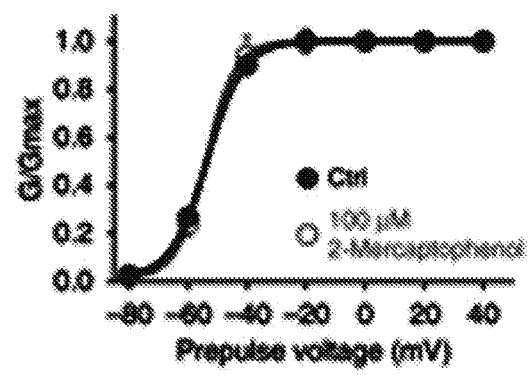
Figure 4:
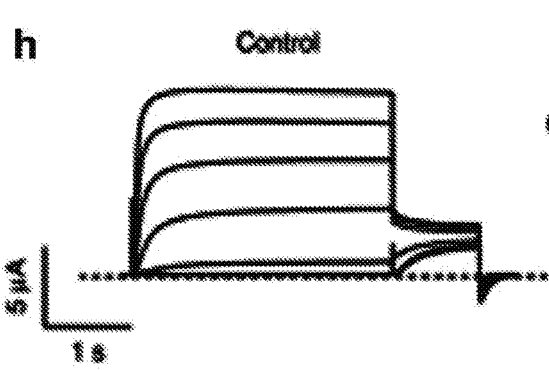
Figure 4:
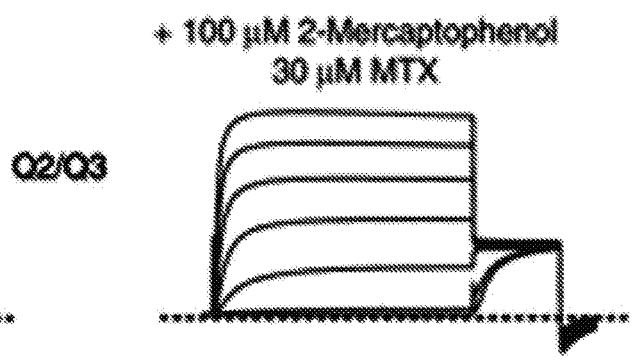
Figure 4:
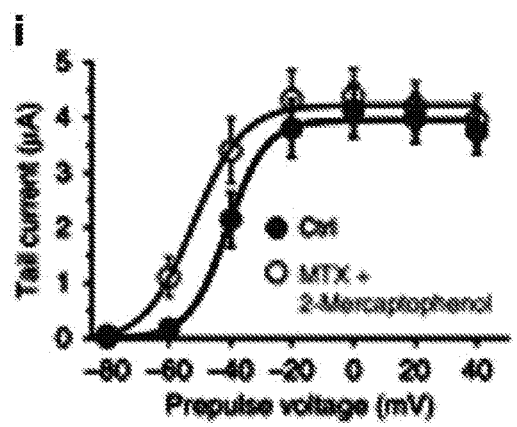
Figure 4:
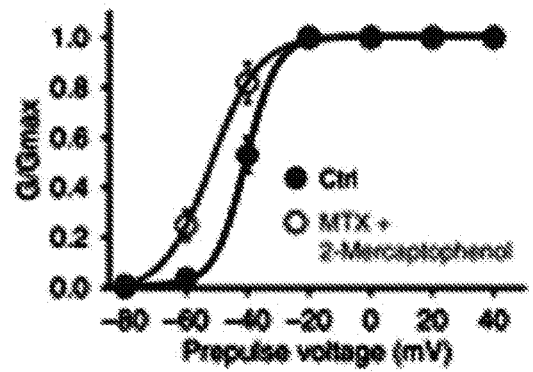
Figure 4:
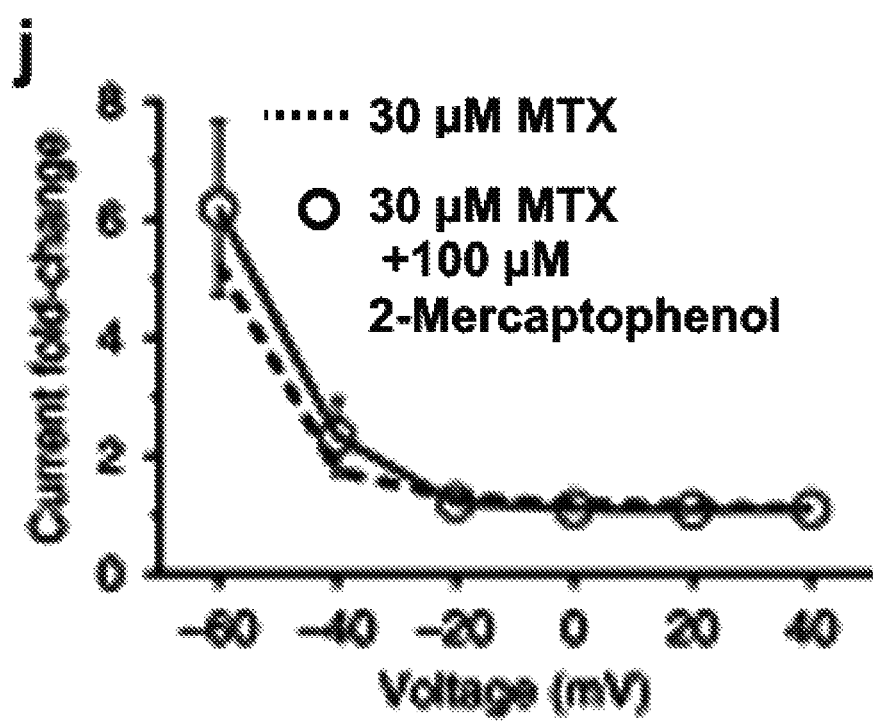

In further support of this hypothesis, we found that GABOB (γ-amino-β-hydroxybutyric acid), a high-affinity KCNQ2/3 partial agonist that binds close to KCNQ3-W265 (ref. 28), only partially diminishes the effects of MTX on KCNQ2/3 channels (FIG. 4a-d; Supplementary Table 19). This is consistent with MTX binding in a similar binding pocket to GABOB, but not directly competing for exactly the same binding site, which would result in proportionately greater inhibition of MTX effects, as we previously observed for GABOB with GABA or retigabine[28]. Interestingly, in our initial screen we found that 2-mercaptophenol inhibits KCNQ2/3 at 100 µM (FIG. 1c-e), while at lower doses it is a mild KCNQ2/3 activator (Supplementary FIG. 4, Supplementary Table 6). In silico docking predicted that 2-mercaptophenol binds close to KCNQ3-W265 (FIG. 4e). Strikingly, mutation to leucine of KCNQ2-W236 and KCNQ3-W265 rendered KCNQ2/3 insensitive to 100 µM 2-mercaptophenol (FIG. 4f, g; Supplementary Table 20). At this dose, 2-mercaptophenol did not alter the ability of MTX (30 µM) to activate KCNQ2/3 channels (FIG. 4h-j; Supplementary Table 21). We conclude that despite the capacity of 2-mercaptophenol to inhibit KCNQ2/3 if administered alone, when co-administered with MTX (as in leaf extract) it cannot compete out MTX. This likely arises for two reasons: first, the 2-mercaptophenol-binding site appears to be closer to W265 (FIG. 4e-g) than that of MTX, which does not absolutely require W265 (FIG. 3). Second, in contrast to GABOB, 2-mercaptophenol is a low-affinity inhibitor, only beginning to inhibit at ~100 µM and activating at lower concentrations (Supplementary FIG. 4, Supplementary Table 6).

*M. oppositifolius* Component IVA Potently Activates KCNQ2

In addition to MTX, previous gas chromatography-mass spectrometry (GCMS) analysis of *M. oppositifolius* extract identified nine additional compounds[26], three of which we found to activate KCNQ2/3 channels in our initial screen (FIG. 1). One, IVA, is a phytocompound found both in *M. oppositifolius* leaf extract and in the extract of valerian root (from *Valeriana officinalis*) (FIG. 5a). Valerian root has been used in herbal medicine for more than two millennia, in ancient Greece and Rome for disorders including insomnia, and since the sixteenth century in northern England and Scotland for convulsions[34,35]. As recently as 2002, an estimated 1.1% of the United States adult population (~2 million people) had used valerian root extract in the past week[36]. IVA shares a chemical feature of RTG important for KCNQ2/3 activation, i.e., strongly negative electrostatic surface potential close to a carbonyl oxygen (FIG. 5a) and is predicted by SwissDock to bind close to KCNQ3-W265 (FIG. 5b). In addition to KCNQ2/3 (FIG. 1), IVA potently and effectively activated homomeric KCNQ2 at −60 mV ($EC_{50}$, 0.34 µM) and, to a lesser extent, KCNQ3* ($EC_{50}$, 0.5 µM) and KCNQ4 ($EC_{50}$, 16.2 µM), with no effect on KCNQ5 (FIG. 5c, d; Supplementary FIGS. 14-17; Supplementary Tables 22-25). Like MTX, IVA did not alter currents generated by KCNA1 (Supplementary FIG. 18; Supplementary Table 26).

As we also observed for MTX, IVA activation was voltage-dependent and had the greatest fold-effect on current at −60 mV (FIG. 5c, e), shifting the KCNQ2 and KCNQ2/3 activation $V_{0.5}$ by −9 and −11 mV, respectively (Supplementary Tables 4 and 22). Unlike what we observed for MTX (FIG. 3c, d), KCNQ2-W236/KCNQ3-W265 were essential for IVA activation of KCNQ2/3 (FIG. 5e). Thus, IVA did not increase KCNQ2/3-W236L/W265L current at −60 mV at any concentration (FIG. 5f; Supplementary FIG. 19; Supplementary Tables 27 and 28). Further, the W236L/V265L mutation prevented IVA from shifting the $V_{0.5}$ of KCNQ2/3 activation at all concentrations, in sharp contrast to the much more subtle effect of the same double mutation on KCNQ2/3 activation by MTX (FIG. 5g; Supplementary Table 29). Supporting the premise that IVA effects require the S5 tryptophan, KCNQ1 (which lacks the W) was IVA-insensitive (FIG. 5h, i), whereas KCNQ1 is activated by MTX[30]. Also in support of a binding site for IVA close to W236/W265, the partial agonist GABOB28 was highly effective at competing out effects of IVA on KCNQ2/3 (FIG. 5j-l; Supplementary Table 30).

We also performed dose responses for the remaining KCNQ2/3-active compounds in *M. oppositifolius* leaf extract, i.e., glutaconic acid, 2-mercaptophenol, and palmitic acid, and in addition tested oleamide because at 100 µM it slightly increased KCNQ2/3 currents at higher voltages (FIG. 1e). However, none of these compounds achieved the maximal efficacy we observed for IVA or MTX; as mentioned earlier, 2-mercaptophenol was inhibitory at higher doses (FIG. 5m; Supplementary FIGS. 1-8; Supplementary Tables 2 and 4-8).

MTX and IVA Synergistically Activate KCNQ2/3 Channels

Because our data identified MTX and IVA as the most active *M. oppositifolius* components with respect to KCNQ2/3 activation, and also suggested different binding positions for MTX and IVA (FIGS. 3b and 5b), we next tested their effects in combination. MTX (30 µM) and IVA (500 µM) in combination strongly activated KCNQ2/3 current, especially at −60 mV, and shifted the $V_{0.5}$ of activation by −23 mV (FIG. 6a-c; Supplementary Table 31). MTX and IVA in combination speeded KCNQ2/3 activation and slowed its deactivation >twofold (FIG. 6d; Supplementary Tables 32 and 33). Strikingly, the IVA+MTX combination synergistically increased KCNQ2/3 current at −60 mV by 24-fold, compared to ~fivefold for either component alone (FIG. 6e). A cocktail of the five KCNQ2/3-active components of *M. oppositifolius* leaf extract produced a similar KCNQ2/3 $V_{0.5}$ activation shift to that of IVA+MTX, again suggesting these two as the most active and synergistic components (FIG. 6f-i). Further, in silico docking studies suggested that IVA and MTX could fit together in the W265-proximal binding pocket, providing a possible mechanistic basis for their synergy (FIG. 6j).

MTX and IVA Synergistically Protect Against Seizures

The cellular electrophysiology data therefore predicted that MTX and IVA would in combination be necessary and sufficient to confer anticonvulsant activity, if KCNQ2/3 activation was the molecular basis for this therapeutic action of the leaf extract. In mouse pentylene tetrazole (PTZ) chemoconvulsant assays, MTX (20 mg/kg) halved the clonic seizure incidence whereas IVA (20 mg/kg) had no effect. At 10 mg/kg neither compound reduced clonic seizures alone, but halved seizure incidence in combination (FIG. 6k). MTX and IVA were only effective at reducing tonic seizure incidence when applied in combination (halving incidence at 10+10 mg/kg; FIG. 6l). Most strikingly, MTX and IVA only increased survival in the seizure assay when administered in combination (tripling survival, compared to vehicle, at 10+10 mg/kg; FIG. 6m). Thus, MTX and IVA act synergistically to reduce seizures and seizure-related mortality in mice, mirroring their effects on KCNQ2/3 activation.

MTX and IVA Combine with RTG to Lock KCNQ2/3 Open

Our results indicate that MTX binds close to the channel pore and senses the KCNQ2/3 S5 tryptophans, while IVA absolutely requires them for binding, and that KCNQ2 is the most MTX- and IVA-sensitive isoform (FIGS. 2-6). Previous studies showed that in contrast, KCNQ3 is the most RTG-sensitive isoform[17,23]. These findings suggested that RTG might synergize with MTX and/or IVA. Accordingly, while RTG (10 µM) negative-shifted the KCNQ2/3 activation $V_{0.5}$ by −13 mV, RTG (10 µM)+IVA (500 µM) increased the $\Delta V_{0.5}$ to −32 mV, and RTG (10 µM)+MTX (30 µM) produced a $\Delta V_{0.5}$ of −57 mV. Most strikingly, the combination of all three compounds at these concentrations locked KCNQ2/3 open, such that its activation was voltage-independent from −120 mV to +40 mV, an effect to our knowledge not previously reported for KCNQ2/3 with any other drugs (FIG. 7a-d; Supplementary Table 34).

Kv channel openers are generally more effective at negative membrane potentials because the lower open probability provides more capacity for augmentation before the maximum open probability is reached (in contrast to positive voltages). However, at extremely hyperpolarized membrane potentials, the capacity of channel openers such as RTG to activate diminishes again (creating a bell-shaped voltage dependence to activation). In the case of KCNQ2/3 this may be because of an inability to open the channel from more stable closed conformations. However, addition of MTX or IVA, and in particular both, to RTG overcame this, resulting in potent current augmentation even at −120 mV. Thus, MTX+IVA+RTG increased KCNQ2/3 current by 60-80-fold at −80 to −120 mV (FIG. 7e).

MTX and IVA have been tolerated as part of herbal medicine for centuries[27,34,35]. RTG was in clinical use for 6 years before being withdrawn because of adverse off-target effects, although these are now known to subside following RTG discontinuation[19,20]. Given the synergy between MTX, IVA, and RTG, we tested whether combining the three at low concentrations could achieve efficacy at potentially tolerable RTG doses. At 1 µM, RTG had negligible effects on KCNQ2/3 (FIG. 7f), as we also observed for 1 µM MTX (FIG. 2b) and 1 µM IVA (FIG. 5f). In contrast, the combination of 1 µM concentrations of RTG, MTX, and IVA was a highly effective KCNQ2/3 opener, shifting the $V_{0.5}$ of activation by −18 mV: a further negative shift in voltage dependence was observed with 1 µM RTG, 10 µM MTX, and 10 µM IVA (FIG. 7f; Supplementary Table 35). The synergy was especially apparent when comparing the fold-change in current at −60 mV induced by low doses of RTG, MTX, and IVA applied alone versus in combination (FIG. 7g, h).

We further tested whether the heteromeric composition of KCNQ2/3 channels afforded greater sensitivity to the synergistic effects of IVA+MTX+RTG than for the homomers. Studies of relative ion permeabilities for heteromeric versus homomeric channels revealed greater increases in relative Na$^+$ and Cs$^+$ permeability (FIG. 8a-c, upper) compared to effects of MTX alone (FIG. 3f), suggesting that the triple-drug combination exerted greater effects than MTX alone on KCNQ2/3 pore conformation. However, the triple-drug combination also induced similar Na$^+$ and Cs$^+$ permeability relative to K$^+$ in homomeric KCNQ2 and KCNQ3 channels (FIG. 8a-c, middle and lower). Thus, heteromerization likely did not confer the ability to adopt a unique pore conformation not accessible to homomeric KCNQ2 or KCNQ3.

We therefore next tested whether homomeric KCNQ channels were as comprehensively activated by MTX+IVA+RTG as was KCNQ2/3. KCNQ3* was the most sensitive of the homomers, and the slowest deactivating at −120 mV of all the homomers in response to MTX+IVA+RTG. Interestingly, even homomeric KCNQ4 and KCNQ5 were activated by the highest triple-drug dose (FIG. 9a-d; Supplementary Tables 36-39). Finally, we compared the capacity of MTX+IVA+RTG to hold open the most sensitive homomer (KCNQ3*) versus heteromeric KCNQ2/3, at −120 mV (FIG. 9e). While KCNQ2/3 deactivation was minimal across 25 s, KCNQ3* current decayed >80% within 10 s (FIG. 9f).

Thus, the MTX+IVA+RTG combination leverages the heteromeric composition of KCNQ2/3 channels to exert optimal synergistic effects on channel opening. Data from FIGS. 7-9 suggest that a similar pore conformation is achieved for both homomers and heteromers in the presence of MTX+IVA+RTG, but that in KCNQ2/3, this conformation is stable at more negative voltages than it is for homomeric channels.

Discussion

We have discovered that IVA and MTX, two components of the traditional African anticonvulsant *M. oppositifolius* leaf extract, synergistically activate KCNQ2/3 and protect against tonic seizures and associated mortality. MTX, the principal component of phenolic extracts of *Mallotus*, has other reported biological activities;[30,37,38,39] none of them readily explain anticonvulsant efficacy, but may contribute to efficacy in other therapeutic uses of *M. oppositifolius*, which include treatment of pain, infection, and inflammation[40]. Historical medicinal usage of *Mallotus* plants spans West Africa (*M. oppositifolius*) and also parts of Asia, including Bangladesh, China, and India (*M. repandus, M. philippinensis*, and others)[6,41]. Oral bioavailability of MTX in rats fed *Mallotus philippensis* extract was previously quantified at >20%, and plasma concentrations exceeded 2 µg/ml, reflecting also the high concentration of MTX in *Mallotus*; e.g., the MTX content of powder prepared from *Mallotus philippensis* fruit was quantified as 21.25% w/w[42]. A plasma concentration of 2 µg/ml is equivalent to 4 µM MTX, a concentration at which we observe KCNQ2/3 activation even by MTX alone.

IVA has been quantified to be ~12% of the methanol extract of the *Mallotus* leaf extract[26]. IVA is also a component of valerian root, an herbal medicine used since ancient Greek and Roman times to treat insomnia, and since medieval times in Europe specifically to treat seizures[34,35].

Valerian root extract is still used extensively today for anxiety and insomnia, although randomized controlled trials evaluating its efficacy have achieved mixed results[43,44,45]. It has been estimated that 10 g of valerian root might yield as much as 100 mg of IVA, and that valerian root doses of 30-50 g per day would have the potential for anticonvulsant activity[46]. Pharmacokinetic studies in humans have been performed for NPS 1776, or isovaleramide, the amide derivative of IVA. Isovaleramide readily passes though biological membranes, and is well tolerated in humans up to at least 2400 mg per day. Absorption is rapid (mean $T_{max}$ of 30-45 min) and mean elimination half-life is 2.5 h[47]. Furthermore, volatile fatty acids similar to IVA, e.g., acetate, readily cross the blood brain barrier[48]. Taken together, these studies together with our current findings suggest that herbal extracts contain sufficient bioavailable IVA to exert effects on KCNQ2/3 channels, particularly if synergizing with MTX.

Figure 2:
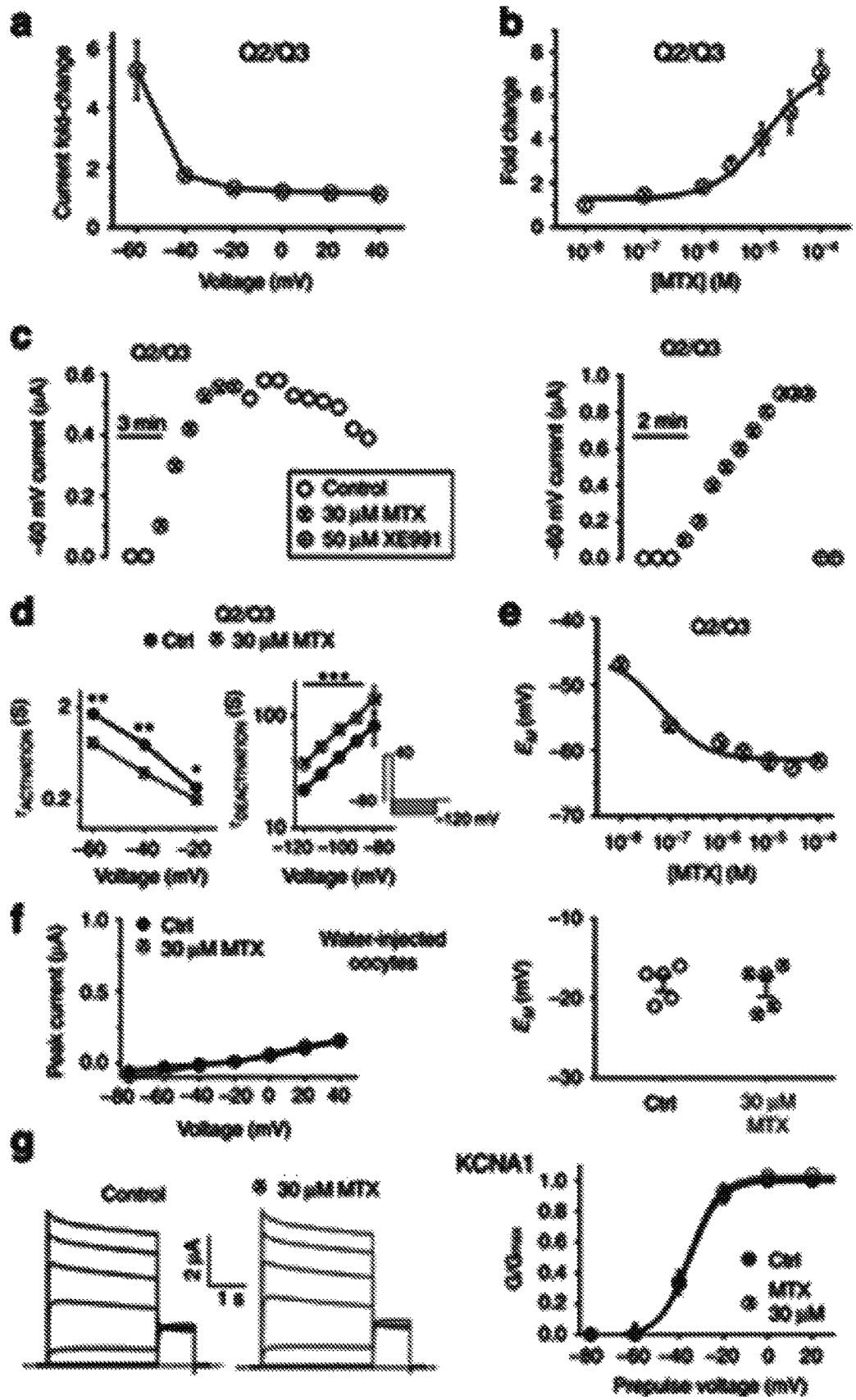
FIG. 2: MTX preferentially activates KCNQ2. (a) Voltage dependence of KCNQ2/3 current fold-increase by MTX (30 µM), plotted from traces as in FIG. 1 (n=9). (b) Dose response of KCNQ2/3 channels at −60 mV for MTX (calculated $EC_{50}$=11.5 µM; n=4-9). (c) Exemplar −60 mV KCNQ2/3 current (left) during wash-in/washout of MTX; right, during wash-in of MTX followed by XE991. (d) Mean activation (left) and deactivation (right) rates for KCNQ2/3 before (Ctrl) and after wash-in of MTX (n=9); ***$p<0.001$. Activation rate was quantified using voltage protocol as in FIG. 1d. Deactivation rate was quantified using voltage protocol shown (lower right inset). (e) MTX dose-dependently hyperpolarizes resting membrane potential ($E_M$) of unclamped oocytes expressing KCNQ2/3; n=9. (f) MTX has no effect on (left) endogenous mean current or (right) $E_M$ of water-injected control oocytes (n=5). Voltage protocol as in FIG. 1d. (g) MTX has no effect on (left) averaged current traces or (right) $G/G_{max}$ of oocytes expressing KCNA1 (n=5). Voltage protocol as in FIG. 1d. (h) Averaged current traces for homomeric KCNQ2-5 channels in the absence (Control) or presence of MTX (30 µM) (n=5-10). Voltage protocol as in FIG. 1d. (i) Mean effects of MTX (30 µM) on −30 mV tail currents for channels and voltage protocol as in (h) (n=5-10). (j) Mean voltage dependence of 30 µM MTX (structure and surface potential, right) activation of homomeric KCNQ2-5 at −60 mV, recorded from tail currents as in (i) (n=5-10). (k) MTX dose response at −60 mV for homomeric KCNQ2-5, quantified from data as in (i) (n=5-10). All error bars indicate SEM.
Figure 5:
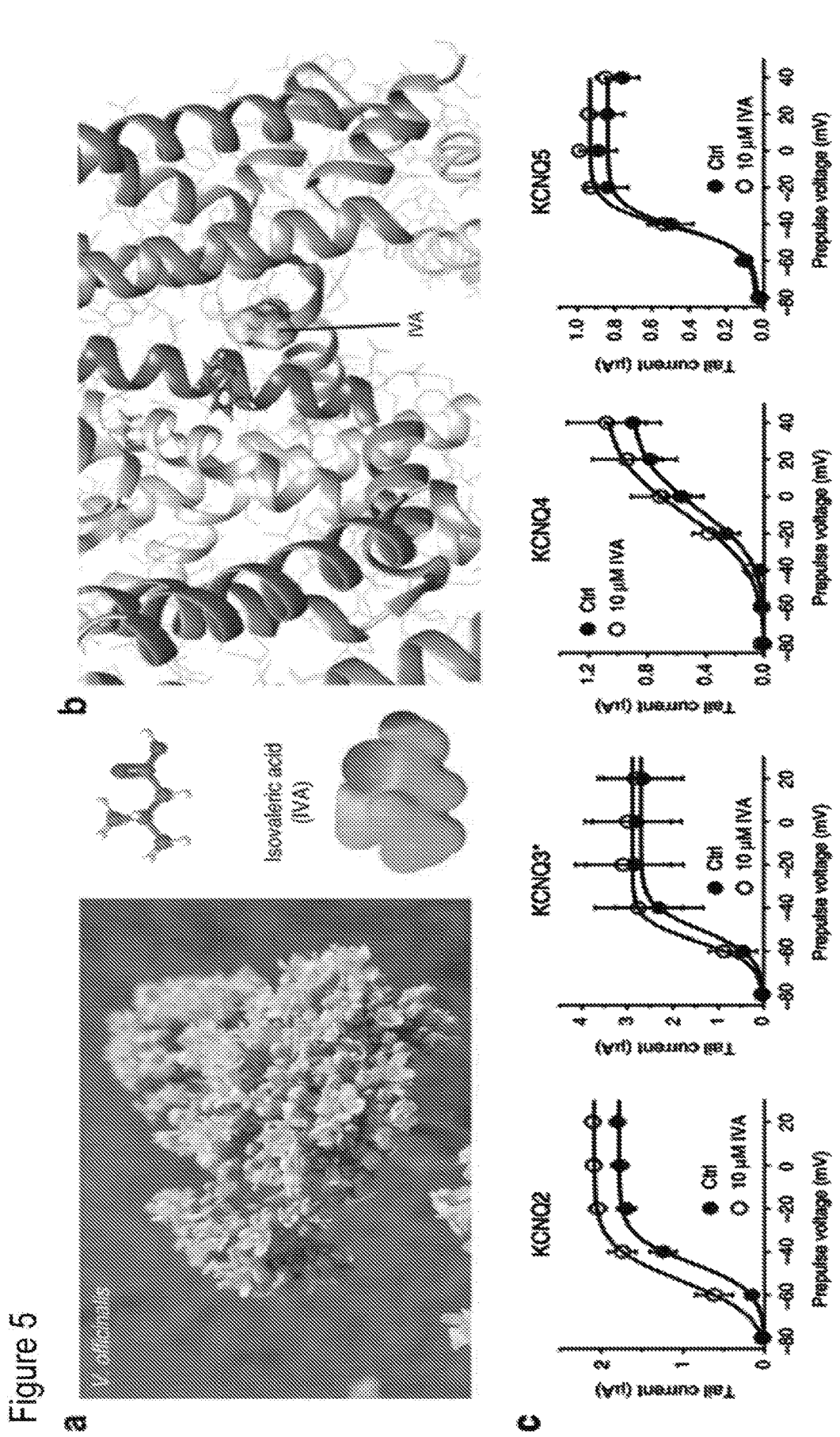
FIG. 5: IVA activates neuronal KCNQs with preference for KCNQ2. (a) Left, *Valeriana officinalis*. Right, structure (upper) and electrostatic surface potential (differential shading indicates negative, positive) (lower) of isovaleric acid (IVA). (b) Binding position of IVA in KCNQ3 predicted by SwissDock using a chimeric KCNQ1-KCNQ3 structure model. (c) Mean tail current versus prepulse voltage relationships recorded by TEVC in *Xenopus laevis* oocytes expressing homomeric KCNQ1-5 channels in the absence (solid circles) and presence (open circles) of IVA (n=4-7). Voltage protocol as in FIG. 1d. (d) IVA dose response at −60 mV for KCNQ2-5, quantified from data as in (c) (n=4-7). (e) Mean tail current versus prepulse voltage relationships for wild-type KCNQ2/3 (left) or KCNQ2-W236L/KCNQ3-W265L (right) channels in the absence or presence of IVA as indicated (n=4-6). Voltage protocol as in FIG. 1d. (f) Dose response for current increase at −60 mV in response to IVA for channels as in (e). (g) Dose response for the $V_{0.5}$ of activation shift induced by IVA versus MTX in wild-type KCNQ2/3 versus KCNQ2-W236L/KCNQ3-W265L (WL/WL) channels. IVA data (n=4-6) quantified from (e); MTX data from FIG. 3d. (h) Averaged traces for KCNQ1 in the absence or presence of IVA (500 μM); n=6. (i) Mean data from traces as in (h). (j) Exemplar traces showing effects of IVA (500 μM) with GABOB (100 μM) on KCNQ2/3 channels. Voltage protocol as in FIG. 1d. (k) Effects of IVA (500 μM) with GABOB (100 μM) on mean tail current (left) and $G/G_{max}$ (right) relationships for KCNQ2/3 (n=5) calculated from traces as in panel j. (l) Current fold-change at −60 mV exerted by IVA (500 μM) alone (from panel f) or with 100 μM GABOB, from data as in panel k (n=5). (m) Right, dose responses for the shift in $V_{0.5}$ of KCNQ2/3 activation induced by the leaf extract compounds shown on left, calculated from traces as shown in FIGS. 1, 2 and 5 (n=4-16). All error bars indicate SEM.
Figure 5:
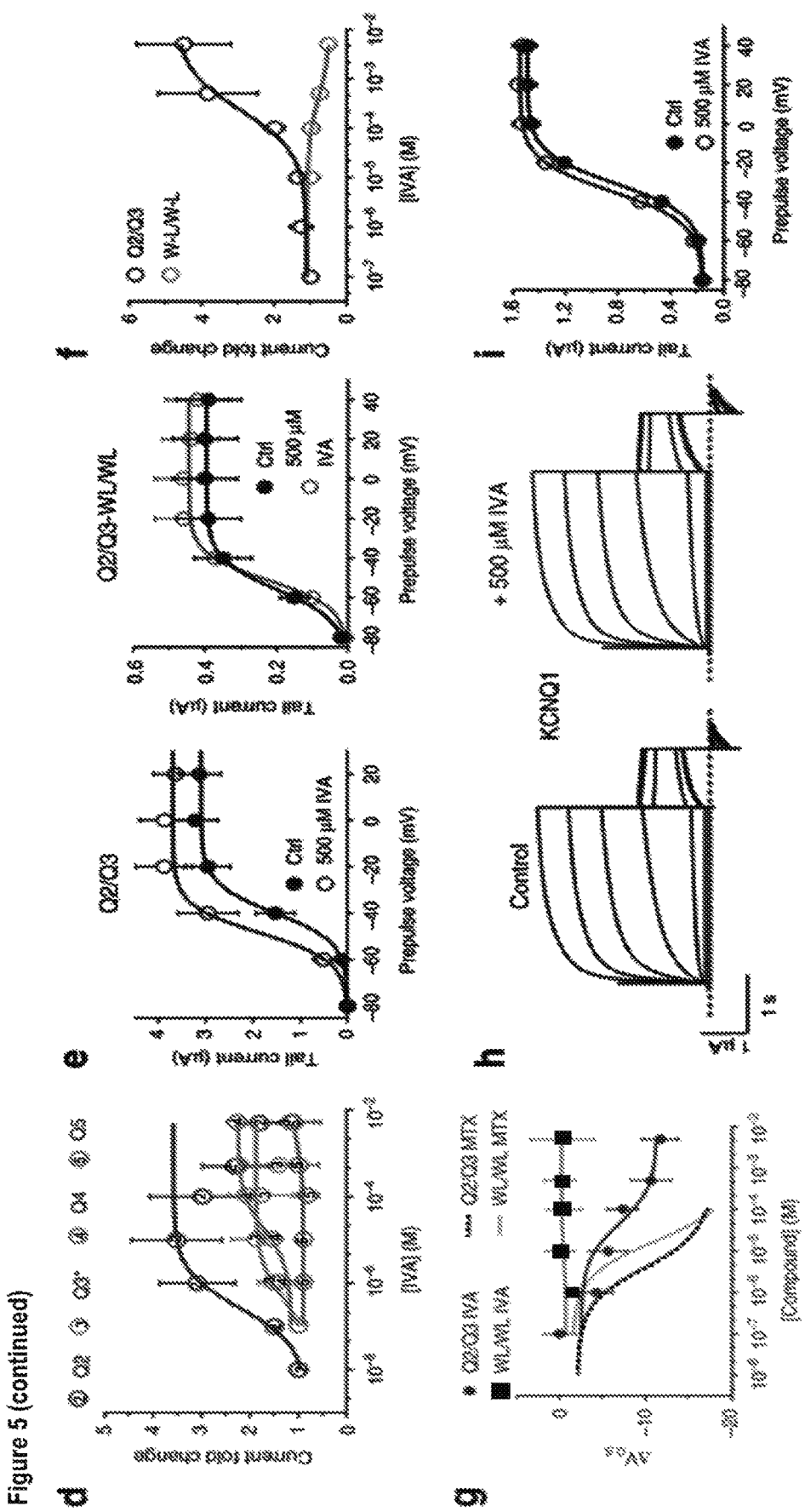
Figure 5:
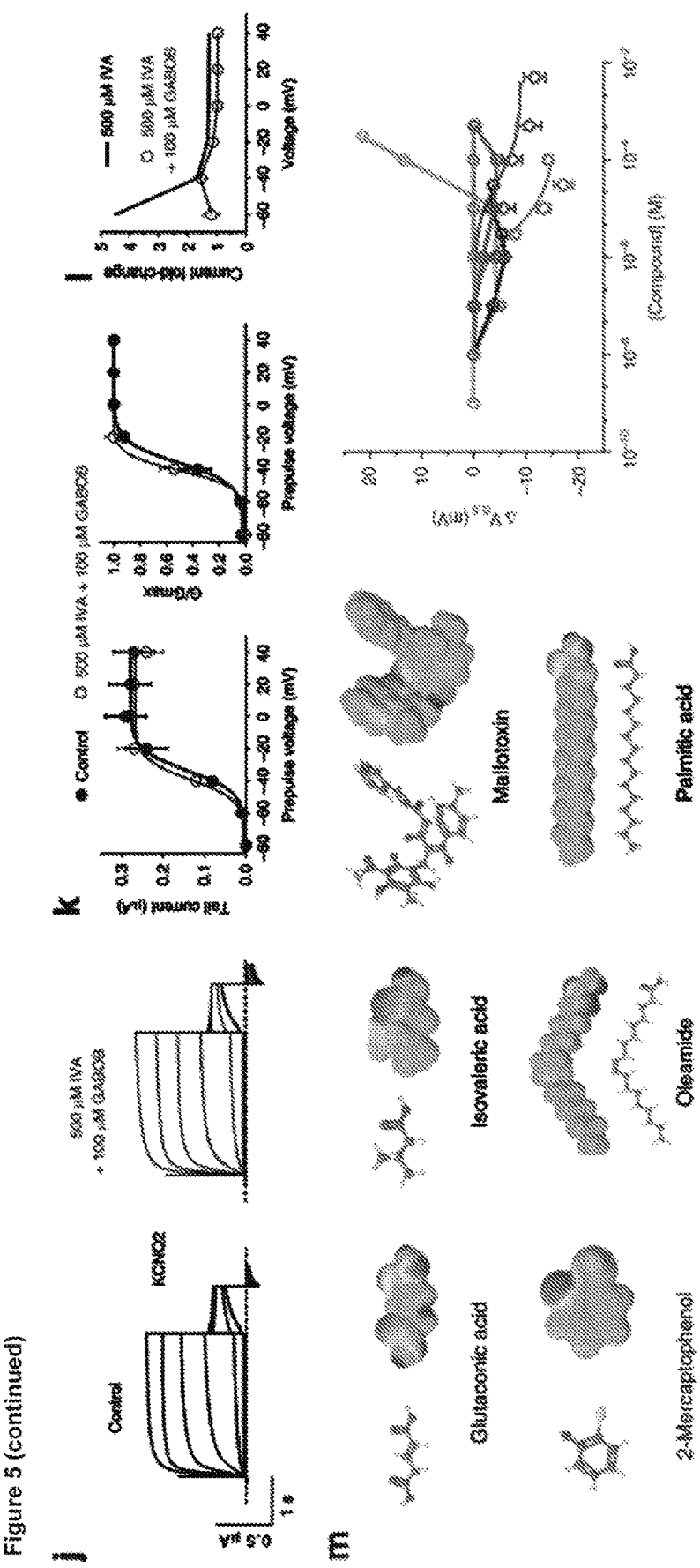
Figure 6:
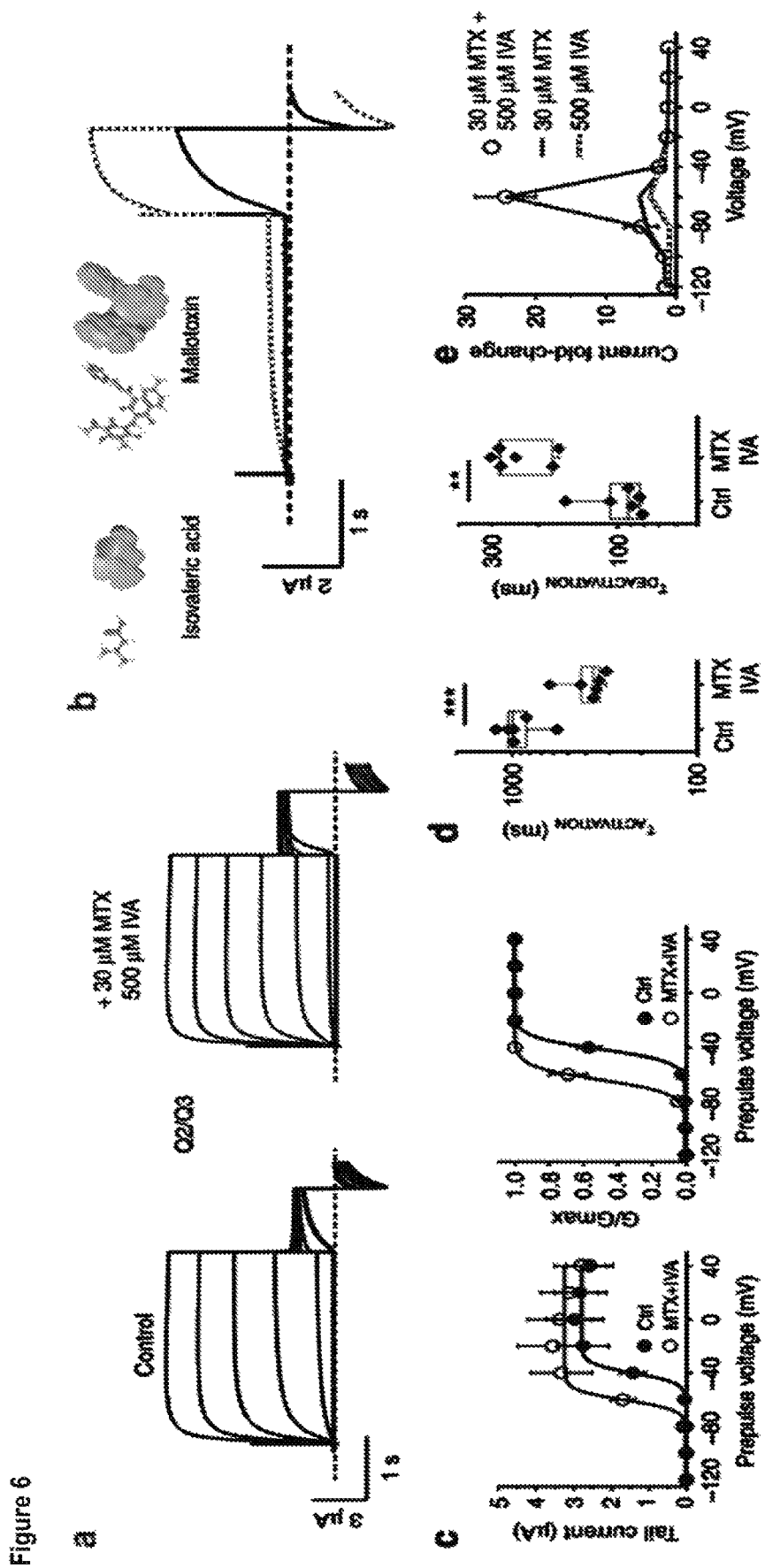
FIG. 6: MTX and IVA synergize to activate KCNQ2/3 and protect against seizures. (a) Averaged traces showing effects of IVA and MTX on KCNQ2/3 (n=5). Voltage protocol as in FIG. 1d. (b) Effects at −60 mV highlighted, from traces as in (a). (c) Mean tail current and $G/G_{max}$ from traces as in (a) (n=5). (d) Mean effect of IVA (500 μM)+MTX (30 μM) on KCNQ2/3 activation at +40 mV and deactivation at −80 mV (n=5). *p=0.0009; p=0.001. (e) Mean KCNQ2/3 current fold-increase versus voltage induced by IVA and MTX alone (from FIGS. 2 and 4) or in combination (from traces as in a); n=4-9. (f) Averaged traces showing effects of leaf extract cocktail (compounds shown in g) on KCNQ2/3 (n=7). Voltage protocol as in FIG. 1d. (g) Effects at −60 mV highlighted, from traces as in (f). (h) Mean tail current and $G/G_{max}$ from traces as in (f) (n=7). (i) Mean effect of leaf extract cocktail on rates of KCNQ2/3 activation (left) and deactivation (center; voltage protocol on right) (n=7). *p<0.05; **p<0.01. (j) Binding position of IVA and MTX in KCNQ3 predicted by SwissDock using a chimeric KCNQ1-KCNQ3 structure model. (k)-(m) Effects of vehicle (n=35) compared to IVA and MTX alone or in combination (n=11-12) on (k) clonic seizure incidence, (l) tonic seizure incidence, and (m) seizure assay survival in a mouse PTZ chemoconvulsant assay. *p<0.05; p<0.01; *p<0.001. Survival statistical analysis by chi-squared, all others by one-way ANOVA. All error bars indicate SEM. All box and whisker plots: box range, 25-75%, coefficient 1; whisker range, 5-95%, coefficient 1.5.
Figure 6:
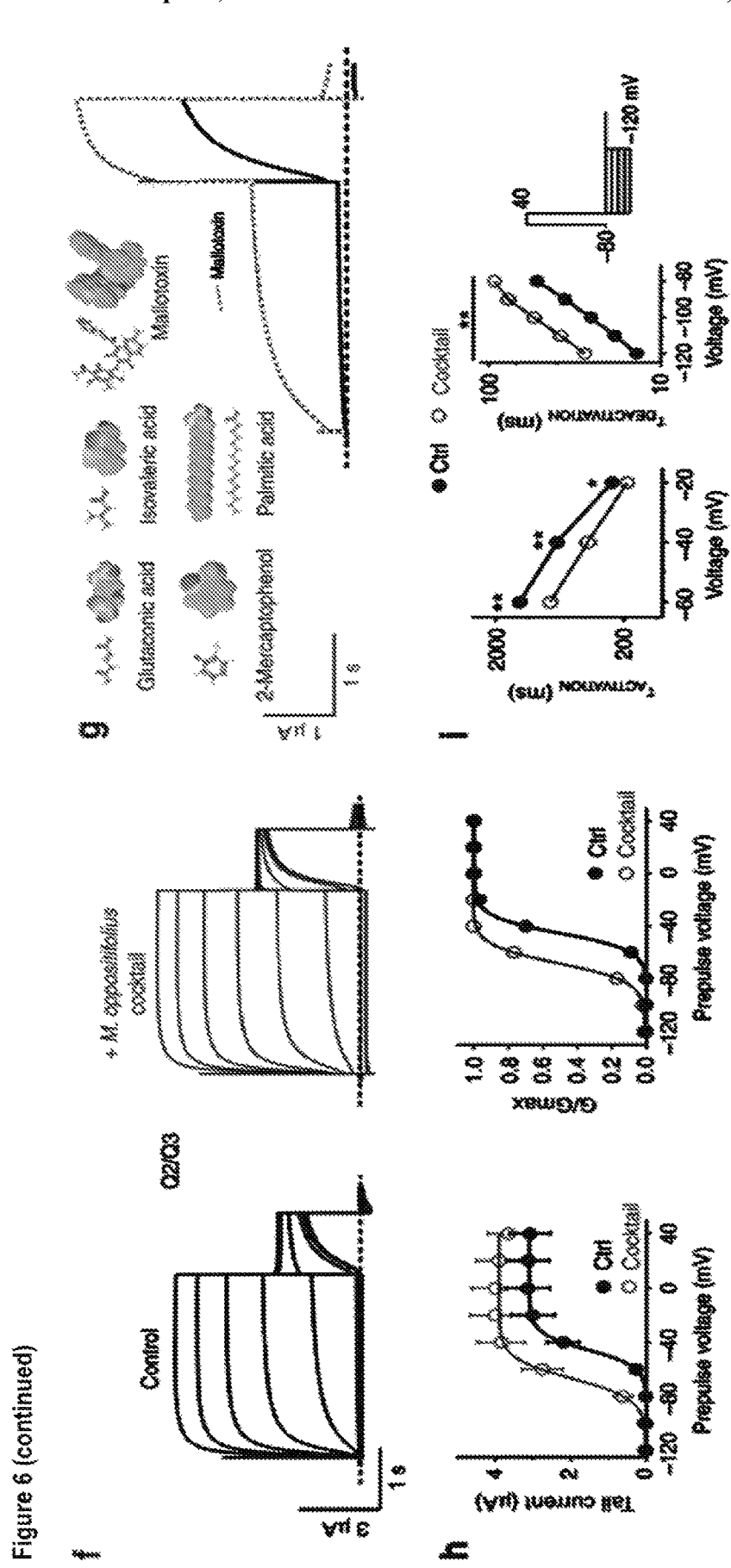

Mutagenesis results indicating differential requirement of W236/W265 (FIG. 5g) suggest that MTX and IVA can sit together in the same binding pocket (FIG. 6j), a site we recently discovered evolved to accommodate neurotransmitters including GABA[28]. When combined with the modern anticonvulsant RTG, the herbal extracts IVA and MTX have the unprecedented capacity to lock open KCNQ2/3 at all voltages tested, converting it into a voltage-independent leak channel. Our cellular electrophysiology and docking predictions support a mechanism for this: while RTG is a more potent agonist of KCNQ3 (refs. 17-23), IVA and MTX are more potent agonists of KCNQ2 (FIGS. 2 and 5). Thus, the combination of either herbal component with RTG can leverage subunit heterogeneity in KCNQ2/3, a feature lacking in modem anticonvulsants, to increase synergy.

The data suggest a model in which MTX and IVA are able to bind to KCNQ2/3 across a wide range of membrane potentials and induce a stable open conformation. One likely configuration, and potentially the dominant configuration given the aforementioned subunit-specific potencies, is that in KCNQ2/3 heteromers MTX and IVA bind to KCNQ2, and RTG to KCNQ3 (FIG. 9g), but all combinations are considered possible. In docking studies, RTG adopted two main sets of poses near W265-one high (FIG. 9h, left) and one low (FIG. 9h, center). The former could theoretically accommodate all three molecules in one binding site, whereas the latter could not as RTG adopts essentially the same space as IVA+RTG in this pose (FIG. 9h, right). Indeed, RTG more often adopted poses in which it overlapped with separately docked IVA and MTX (more examples shown in FIG. 9i), supporting the premise that in KCNQ2/3 channels, bound IVA+MTX might prevent RTG binding to KCNQ2, but the converse might occur in KCNQ3 (FIG. 9g).

Figure 7:
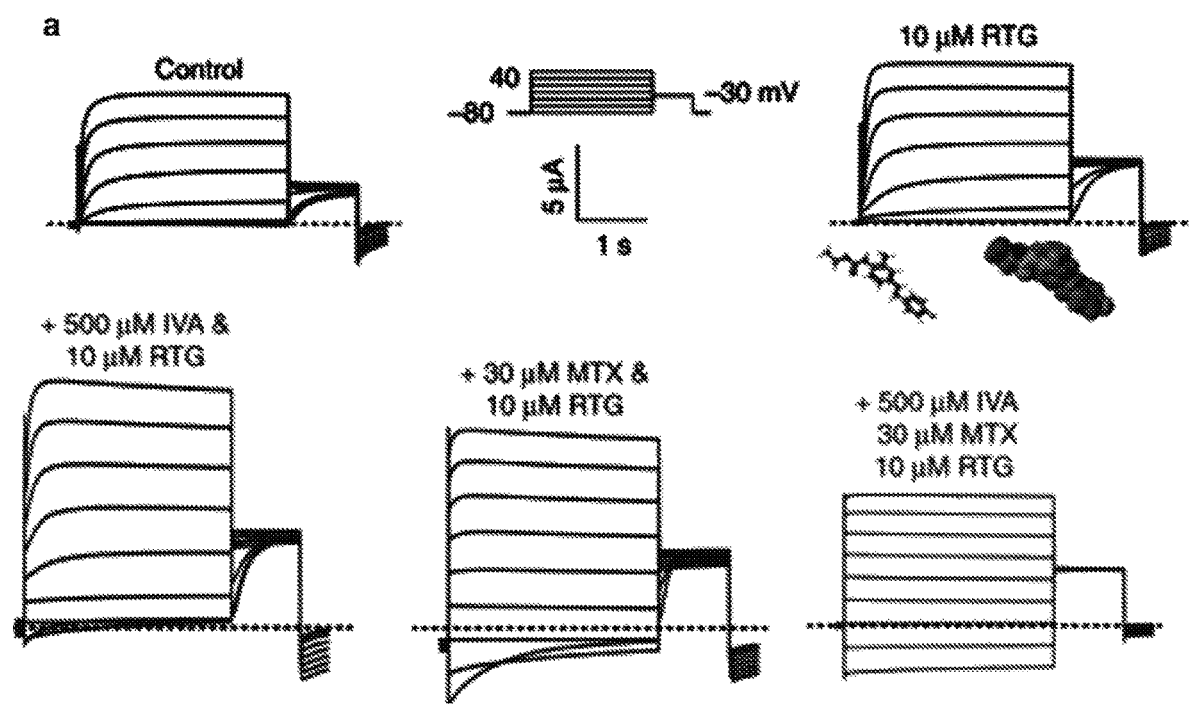
FIG. 7: IVA and MTX synergize with RTG to lock open KCNQ2/3. (a) Averaged traces showing effects of high-dose RTG, IVA, and MTX alone or in combination on KCNQ2/3 (n=5-31). Voltage protocol upper inset. (b)-(e) Analysis of traces as in (a): (b) peak current; (c) tail current; (d) $G/G_{max}$; (e) current fold-change versus voltage; compounds and combinations color-coded as in (a). n=5-31. (f) Mean effects of low-dose 1 μM RTG versus 1 μM of each of RTG, IVA, and MTX (1+1+1) versus 1 μM RTG+10 μM IVA+10 μM MTX (1+10+10) on KCNQ2/3 tail currents and $G/G_{max}$ versus prepulse voltages; n=8-13. (g) KCNQ2/3 current fold-increase versus voltage induced by compounds as indicated alone or in combination; n=8-13. p<0.01. (h) KCNQ2/3 current fold-increase versus voltage induced by compounds as indicated alone or in combination; n=8-13. p<0.01. All error bars indicate SEM. All comparisons by one-way ANOVA.
Figure 7:
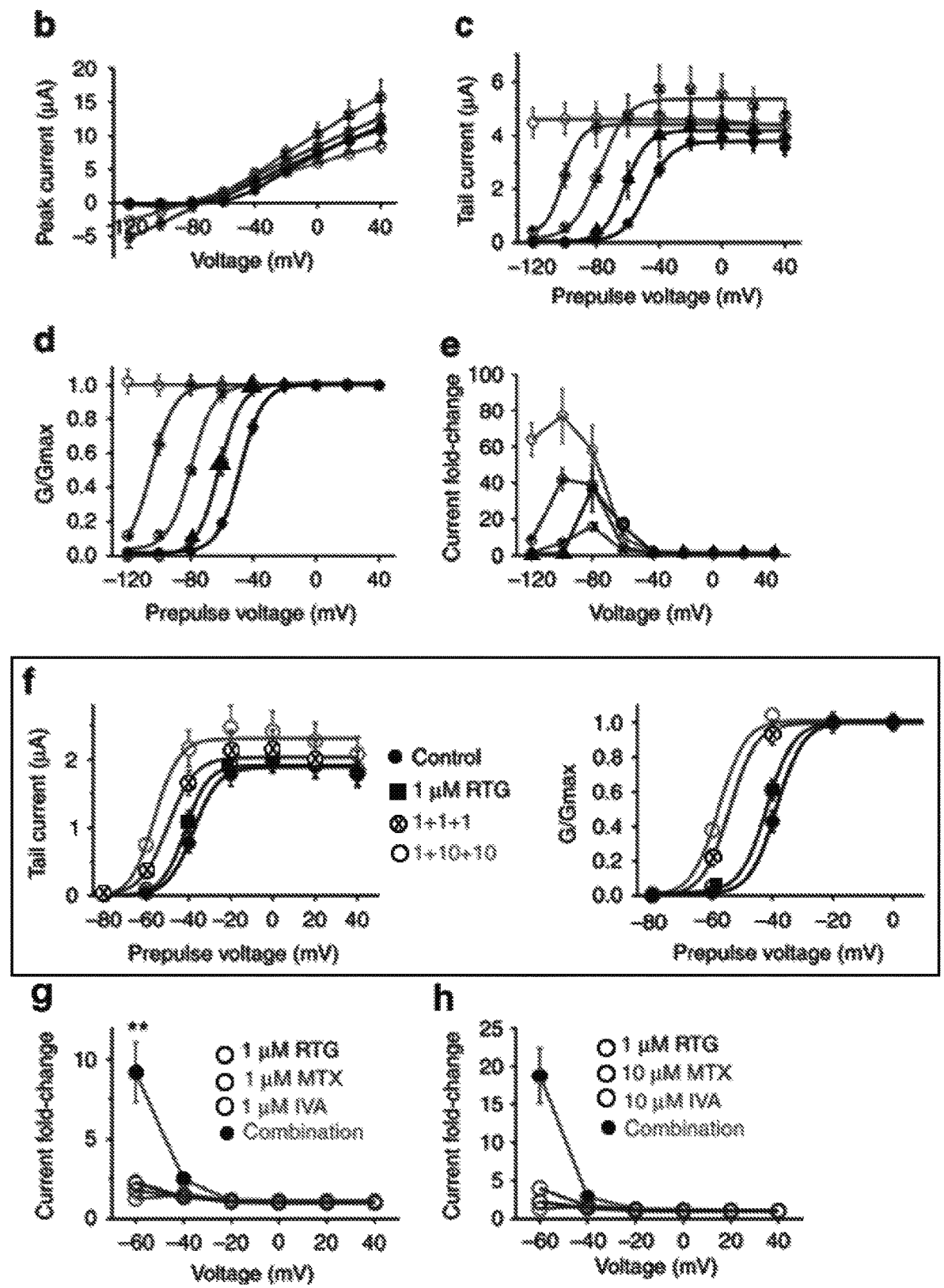
Figure 8:
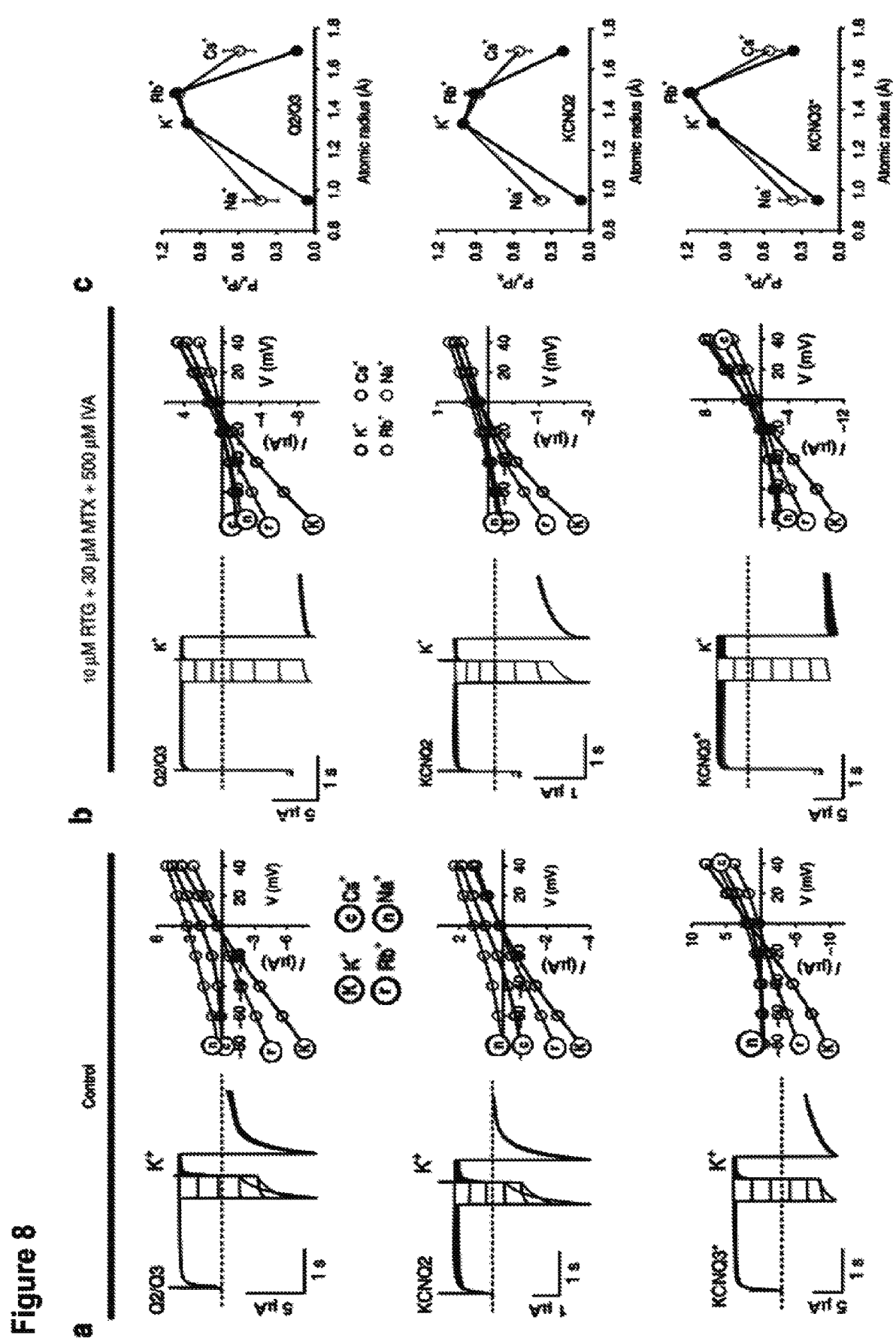
FIG. 8: RTG+MTX+IVA alter the pore conformation of KCNQ2 and KCNQ3. (a), (b) Left, exemplar traces; right, mean I/V relationships for KCNQ2/3 (Q2/Q3) or homomeric KCNQ2 or KCNQ3 channels as indicated, bathed in 100 mM $K^+$, $Rb^+$, $Cs^+$, or $Na^+$ in the (a) absence or (b) presence of RTG (10 μM)+MTX (30 μM)+IVA (500 μM); n=6-7. (c) Relative ion permeabilities of KCNQ2/3 channels in the presence (open circles) or absence (solid circles) of RTG (10 μM)+MTX (30 μM)+IVA (500 μM); n=6-7. Quantified from traces and plots as in panels (a), (b). All error bars indicate SEM.
Figure 9:
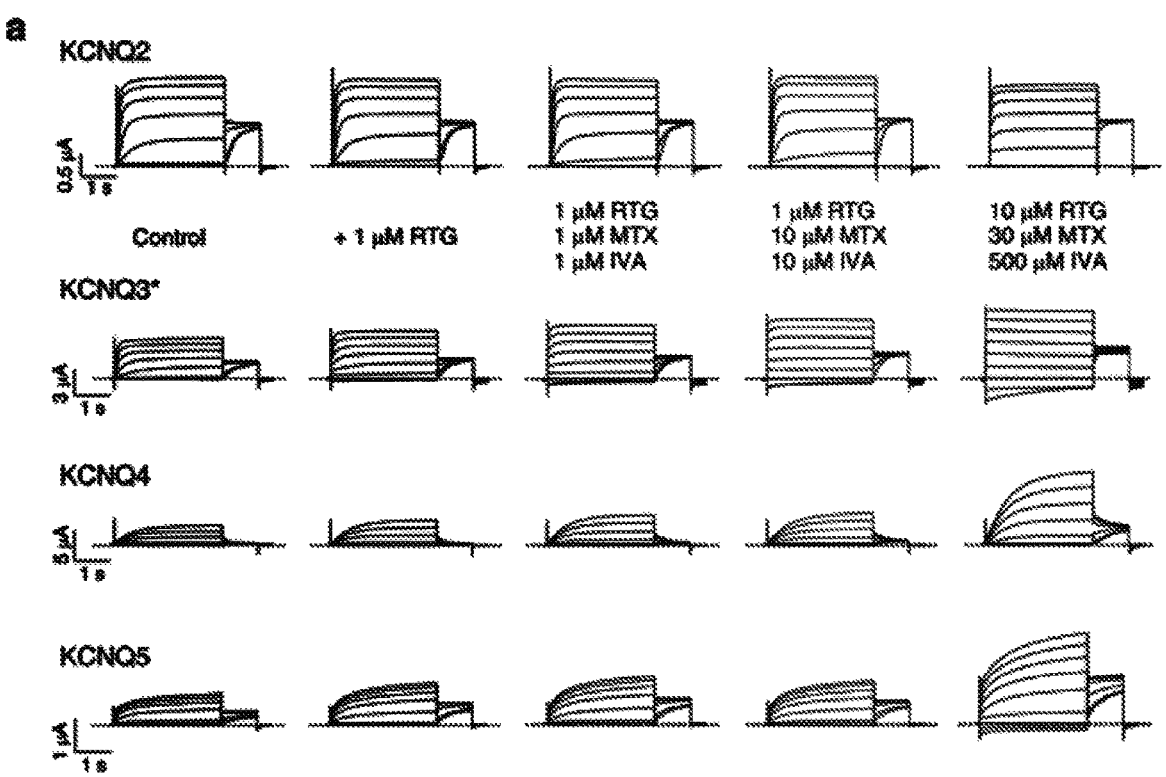
FIG. 9: Leveraging heteromeric channel composition to lock open KCNQ2/3. (a) Averaged traces showing effects of RTG, IVA, and MTX alone or in combination, doses as indicated, on homomeric KCNQ2-5 channels (n=4-11). Voltage protocol as in FIG. 1d. (b)-(d) Analysis of traces as in (a): (b) tail current; (c) $G/G_{max}$; (d) current fold-change versus voltage; compounds and combinations color-coded as in (a). n=4-11. (e), (f) Effects of high-dose RTG+MTX+IVA on KCNQ2/3 versus KCNQ3* held at −120 mV for 25 s. (e) Representative traces; (f) mean peak (0.5 s) versus steady-state (25 s) current. **p<0.01; n=4. Box and whisker plots: box range, SEM, coefficient of 1; whisker range 5-95%, coefficient of 1.5. (g) Model summarizing findings. Squares represent subunits within tetrameric KCNQ2/3 channels (upper left and lower right, KCNQ2; upper right and lower left, KCNQ3). (h) Possible distinct binding positions of RTG, IVA, and MTX in one binding site in KCNQ3 (left) versus a lower-positioned RTG binding site (center) that would overlap with binding sites for IVA and RTG (right), predicted by SwissDock using a chimeric KCNQ1-KCNQ3 structure model. Shading of sites corresponds to lettering of KCNQ3-W265; IVA; MTX; lightest is RTG. Space-filling omitted from molecules in right panel for clarity. (i) Further possible poses RTG (lightest, no spacefill) that would overlap with IVA and MTX in KCNQ3 chimera model as predicted by SwissDock. All error bars indicate SEM. All comparisons by one-way ANOVA.
Figure 9:
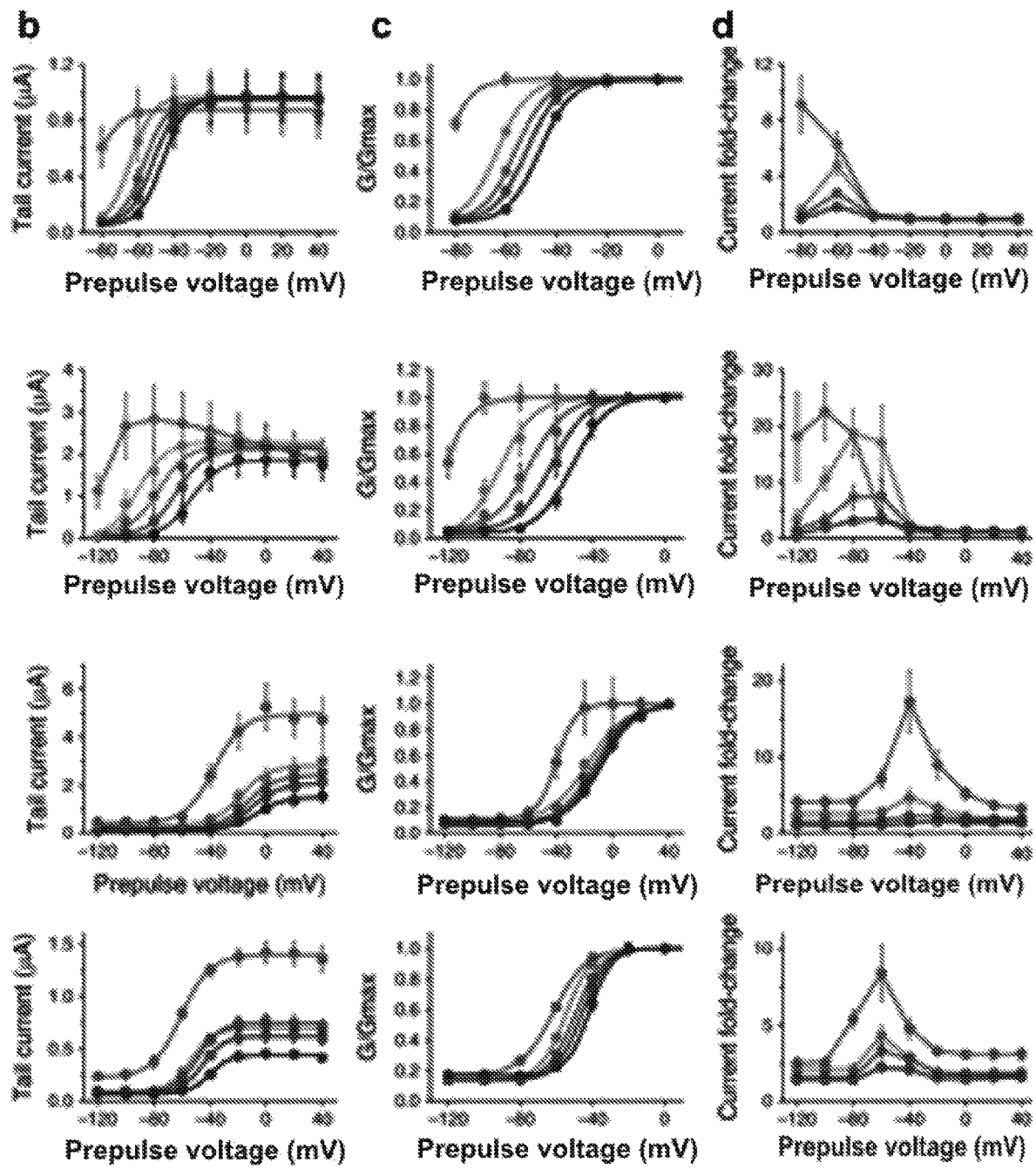
Figure 9:
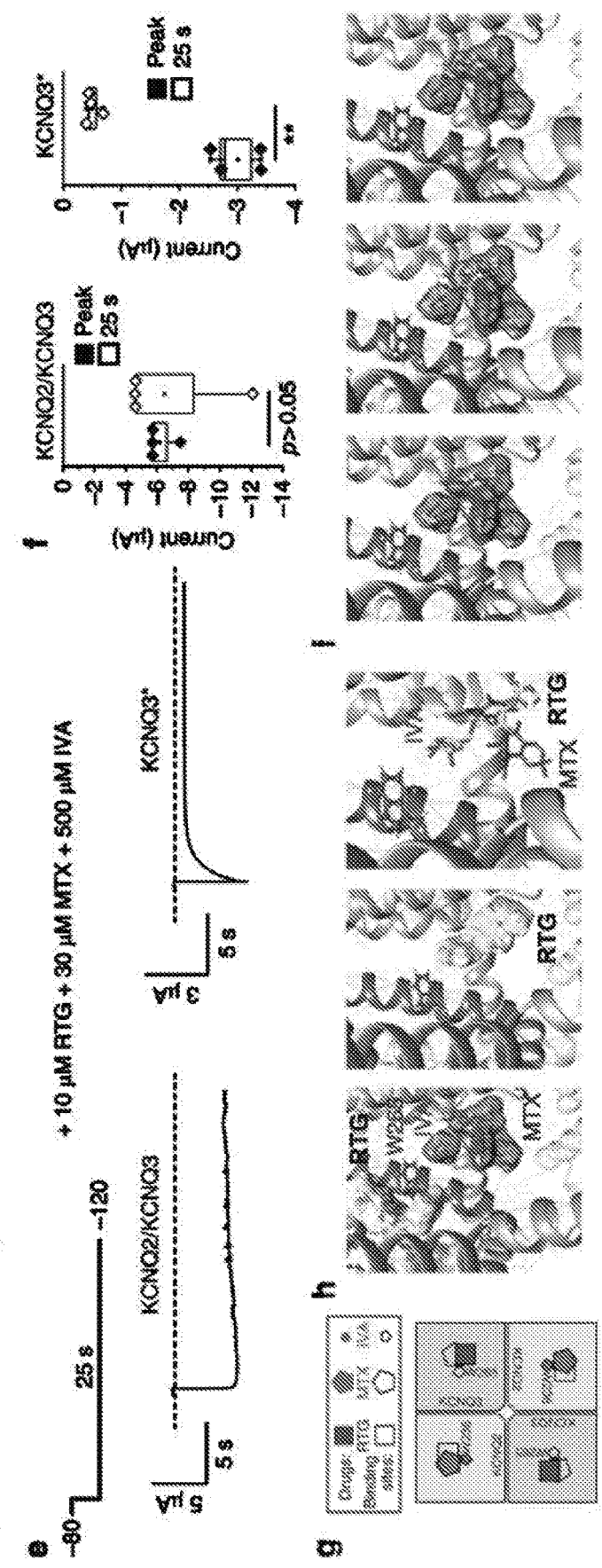

The molecular strategy we present, utilizing a combination of small molecules from ancient and modem therapeutics, may provide a route to safer, more effective anticonvulsants. Through dual synergies it lowers the effective doses required to achieve similar KCNQ2/3 opening, increases the maximal effects, and also considerably broadens the voltage range across which the drugs are effective (FIGS. 7 and 9e, f).

Methods

Channel Subunit cRNA Preparation and Oocyte Injection cRNA transcripts encoding human KCNA1, KCNQ1, KCNQ2, KCNQ3, KCNQ4, or KCNQ5 were generated by in vitro transcription using the T7 polymerase message machine kit (Thermo Fisher Scientific), after vector linearization, from cDNA sub-cloned into plasmids incorporating *X. laevis* β-globin 5' and 3' UTRs flanking the coding region to enhance translation and cRNA stability. cRNA was quantified by spectrophotometry. Mutant cDNAs were generated by site-directed mutagenesis using a QuikChange kit according to manufacturer's protocol (Stratagene, San Diego, Calif.) and corresponding cRNAs prepared as above. Defolliculated stage V and VI *X. laevis* oocytes (Ecocyte Bioscience, Austin, Tex.) were injected with Kv channel α subunit cRNAs (10 ng total per oocyte). Oocytes were incubated at 16° C. in Barth's saline solution (Ecocyte) containing penicillin and streptomycin, with daily washing, for 3-5 days prior to two-electrode voltage-clamp (TEVC) recording.

Two-Electrode Voltage-Clamp

TEVC recording was performed at room temperature with an OC-725C amplifier (Warner Instruments, Hamden, Conn.) and pClamp10.2 software (Molecular Devices, Sunnyvale, Calif.) 3-5 days after cRNA injection as described in the section above. Oocytes were placed in a small-volume oocyte bath (Warner) and viewed with a dissection microscope. Chemicals were sourced from Sigma. Bath solution was (in mM): 96 NaCl, 4 KCl, 1 MgCl$_2$, 1 CaCl$_2$. 10 HEPES (pH 7.6). Isovaleric acid, 2-mercaptophenol, 1-Heptene, and 3-ethyl-2-hydroxy-2-cyclopenten-1-one were stored at 4° C. as 5 mM stocks in Ringer's solution. MTX (DMSO), sorbic acid (ethanol), and glutaconic acid (molecular grade H$_2$O) were stored at −20° C. as 1 M stocks. Oleamide was stored as a 1 mM stock in ethanol at 4° C. Palmitic acid was conjugated with bovine serum albumin as a 1 mM stock and stored at −20° C. All compounds were diluted to working concentrations each experimental day. All compounds were introduced to the recording bath via gravity perfusion at a constant flow of 1 ml/min for 3 min prior to recording. Pipettes were of 1-2 MΩ resistance when filled with 3 M KCl. Currents were recorded in response to pulses between −80 and +40 mV at 20 mV intervals, or a single pulse to +40 mV, from a holding potential of −80 mV, to yield current-voltage relationships, current magnitude, and for quantifying activation rate. TEVC data analysis was performed with Clampfit10.2 (Molecular Devices) and Graphpad Prism software (GraphPad, San Diego, Calif., USA); values are stated as mean±SEM. Normalized tail currents were plotted versus prepulse voltage and fitted with a single Boltzmann function:

$$g = \frac{(A_1 - A_2)}{\{1 + \exp[V_{1/2} - V/V_S]\}y + A_2}, \quad (1)$$

where g is the normalized tail conductance, $A_1$ is the initial value at −∞, $A_2$ is the final value at +∞, $V_{1/2}$ is the half-maximal voltage of activation, and $V_s$ the slope factor. Activation and deactivation kinetics were fitted with single-exponential functions.

For relative permeability studies, currents were recorded in response to a single pulse to +40 mV for 5 s, followed by pulses between −80 mV and +40 mV at 20 mV intervals, from a holding potential of −80 mV, to yield a current-voltage relationship. According to the Goldman-Hodgkin-Katz (GHK) voltage equation:

$$E_{rev} = \frac{RT/F \ \ln(P_K[K^+]o + P_{Na}[Na]o + P_{Cl}[Cl]_i)}{(P_K[K^+]_i + P_{Na}[Na]_i + P_{Cl}[Cl]_o)} \quad (2)$$

where $E_{rev}$ is the absolute reversal potential and P is the permeability. This permits calculation of the relative permeability of each ion if concentrations on either side of the membrane are known. A modified version of this equation was used here to determine relative permeability of two ions in a system in which only the extracellular ion concentration was known. Thus, relative permeability of Rb$^+$, Cs$^+$, and Na$^+$ compared to K$^+$ ions was calculated for all channels by plotting the I/V relationships for each channel with each extracellular ion (100 mM) and comparing them to that with 100 mM extracellular K$^+$ ion to yield a change in reversal potential ($\Delta E_{rev}$) for each ion compared to that of K$^+$. Permeability ratios for each ion compared to K$^+$ were then calculated as $$\Delta E_{rev} = E_{rev,X} - E_{rev,K} = \frac{RT}{zF} \ln \frac{P_X}{P_K} \quad (3)$$

Values were compared between channel types and statistical significance assessed using ANOVA.

For calculating Rb$^+$/K$^+$ permeability (FIG. 3g), tail currents were elicited by a single pulse to +40 mV, followed by a pulse at −80 mV, from a holding potential of −80 mV in 98 mM [K$^+$] and then 98 mM [Rb$^+$]. The K$^+$ or Rb$^+$ conductance was calculated by dividing the peak amplitude of K$^+$ or Rb$^+$ carried tail currents by the driving force (difference between −80 mV, at which the tail currents are measured, and the equilibrium potential for K$^+$ or Rb$^+$ ions measured in the same oocyte).

Deactivating currents were fitted to a single-exponential standard function defined as follows:

$$\int (t) = \sum_{i=1}^{n} A_i e^{-t/\tau_i} + C \quad (4)$$

Chemical Structures, in Silico Docking, and Sequence Analyses

Chemical structures and electrostatic surface potentials (range, −0.1 to 0.1) were plotted using Jmol, an open-source Java viewer for chemical structures in 3D: jmol.org. For docking, the *X. laevis* KCNQ1 cryo-EM structure[49] was first altered to incorporate KCNQ3/KCNQ5 residues known to be important for RTG and ML-213 binding, and their immediate neighbors, followed by energy minimization using the GROMOS 43B1 force field[50], in DeepView[51]. Thus, *X. laevis* KCNQ1 amino acid sequence LITTLYIGF was converted to LITAWYIGF, the underlined W being W265 in human KCNQ3/KCNQ5 and the italicized residues being the immediate neighbors in KCNQ3/KCNQ5. In addition, *X. laevis* KCNQ1 sequence WWGVVTVTTI-GYGD was converted to WWGLITLATIGYGD, the underlined L being Leu314 in human KCNQ3/KCNQ5 and the italicized residues being the immediate neighbors in KCNQ5 and/or KCNQ3. Surrounding non-mutated sequences are shown to illustrate the otherwise high sequence identity in these stretches. Unguided docking of mallotoxin and other compounds to predict binding sites was performed using SwissDock[52] with CHARMM force-fields[53].

PTZ Chemoconvulsant Assay

We compared anticonvulsant activities of test compounds in male C57BL/6 mice (Charles River) aged 2-3 months. Mice were housed and used according to the recommendations in the Guide for the Care and Use of Laboratory Animals of the National Institutes of Health (NIH Publication, 8th edition, 2011). The study protocol was approved by the Institutional Animal Care and Use Committee of University of California, Irvine, which confirmed that all relevant ethical regulations were adhered to. Chemicals were sourced from Sigma (St. Louis, Mo., USA). A pentylene tetrazole (PTZ) chemoconvulsant assay was used-. Mice were injected intraperitoneally with IVA and/or MTX, concentrations as indicated, or vehicle control (PBS with 1% DMSO), and then 30 min later injected intraperitoneally with 80 mg kg$^{-1}$ PTZ. Following the PTZ injection, mice were caged individually and an observer (GWA) blinded to the drug used recorded, over 20 min, clonic and tonic seizure incidence, and seizure-related mortality.

Statistical Analysis

All values are expressed as mean±SEM. Chi-squared analysis was used to compare seizure-related mortality in mice. One-way ANOVA was applied for all other tests; if multiple comparisons were performed, a post-hoc Tukey's HSD test was performed following ANOVA. All p-values were two-sided. Statistical significance was defined as $p<0.05$.

Supplemental materials are available with the online version of Manville et al., *Nature Communications* (2018) 9:3845; DOI: 10.1038/s41467-018-06339-2.

REFERENCES

1. White, H. S. *Epilepsia* 44 Suppl 7, 2-8 (2003).
2. Kamatenesi-Mugisha, M. & Oryem-Origa, H. *Afr Health Sci* 5, 40-49 (2005).
3. Spinella, M. *Epilepsy & behavior: E&B* 2, 524-532 (2001).
4. Kukuia, K. K., et al. *Pharmacologia* 3, 683-692 (2012).
5. Kukuia, K. K., et al. *J Pharm Bioallied Sci* 8, 253-261 (2016).
6. Gangwar, M., et al. *Biomed Res Int* 2014, 213973 (2014).
7. Abbott, G. W. *New Journal of Science* 2014, 26 (2014).
8. Wang, H. S., et al. *Science* 282, 1890-1893 (1998).
9. Selyanko, A. A., et al. *The Journal of Neuroscience* 19, 7742-7756 (1999).
10. Singh, N. A., et al. *Nature genetics* 18, 25-29 (1998).
11. Charlier, C., et al. *Nature genetics* 18, 53-55 (1998).
12. Biervert, C., et al. *Science* 279, 403-406 (1998).
13. Rostock, A., et al. *Epilepsy research* 23, 211-223 (1996).
14. Tober, C., et al. *European journal of pharmacology* 303, 163-169 (1996).
15. Rundfeldt, C. *European journal of pharmacology* 336, 243-249 (1997).
16. Main, M. J., et al. *Molecular pharmacology* 58, 253-262 (2000).
17. Tatulian, L., et al. *The Journal of Neuroscience* 21, 5535-5545 (2001).
18. Tatulian, L. & Brown, D. A. *The Journal of physiology* 549, 57-63 (2003).
19. Garin Shkolnik, T., et al. *JAMA Dermatol* 150, 984-989 (2014).
20. Mathias, S. V. & Abou-Khalil, B. W. *Epilepsy Behav Case Rep* 7, 61-63 (2017).
21. Schroder, R. L., et al. *Neuropharmacology* 40, 888-898 (2001).
22. Blackburn-Munro, G., et al. *CNS drug reviews* 11, 1-20 (2005).
23. Dupuis, D. S., et al. *European journal of pharmacology* 437, 129-137 (2002).
24. Korsgaard, M. P., et al. *The Journal of pharmacology and experimental therapeutics* 314, 282-292 (2005).
25. Wickenden, A. D., et al. *Molecular pharmacology* 58, 591-600 (2000).
26. Igwe, K. K., et al. *International Journal of scientific research and management (IJSRM)* 4, 4123-4129 (2016).
27. Oliver, B. E. P. *Medicinal Plants in Nigeria*, (Nigerian College of Arts, Science and Technology, Lagos, Nigeria, 1960).
28. Manville, R. W., et al. *Nature communications* 9, 1847 (2018).
29. Kim, R. Y., et al. *Nature communications* 6, 8116 (2015).
30. Matschke, V., et al. *Cellular physiology and biochemistry: international journal of experimental cellular physiology, biochemistry, and pharmacology* 40, 1549-1558 (2016).
31. Zaika, O., et al. *Biophysical journal* 95, 5121-5137 (2008).
32. Schenzer, A., et al. *The Journal of Neuroscience* 25, 5051-5060 (2005).
33. Lange, W., et al. *Molecular pharmacology* 75, 272-280 (2009).
34. Turner, W. *A New Herball*, parts II & III. (Steven Mierdman, London, UK, 1562, 1568).
35. Grieve, M. *A Modem Herbal: The Medicinal, Culinary, Cosmetic and Economic Properties, Cultivation and Folk-lore of Herbs, Grasses, Fungi, Shrubs, & Trees with All Their Modern Scientific Uses*, (1971).
36. Bruno, J. J. & Ellis, J. J. *The Annals of pharmacotherapy* 39, 643-648 (2005).
37. Zakharov, S. I., et al. *The Journal of biological chemistry* 280, 30882-30887 (2005).
38. Zeng, H., et al. *The Journal of pharmacology and experimental therapeutics* 319, 957-962 (2006).
39. Gschwendt, M., et al. *Biochemical and biophysical research communications* 199, 93-98 (1994).
40. Burkhill, H. M. *The useful plants of west tropical Africa*, (Royal Botanic Gardens, Kew, London, UK, 1994).
41. Hasan, M. M., et al. *Arg. Biomed Res Int* 2014, 539807 (2014).
42. Patel, R. K., et al. *J Pharm Anal* 2, 366-371 (2012).
43. Donath, F., et al. *Pharmacopsychiatry* 33, 47-53 (2000).
44. Dom, M. *Forschende Komplementärmedizin und Klassische Naturheilkunde* 7, 79-84 (2000).
45. Stevinson, C. & Ernst, E. *Sleep medicine* 1, 91-99 (2000).
46. Eadie, M. J. *Epilepsia* 45, 1338-1343 (2004).
47. Bialer, M., et al. *Epilepsy research* 43, 11-58 (2001).
48. Frost, G., et al. *Nature communications* 5, 3611 (2014).
49. Sun, J. & MacKinnon, R. *Cell* 169, 1042-1050 e1049 (2017).
50. van Gunsteren, W. F. *Biomolecular simulation: the GROMOS96 manual and user guide*, (Vdf Hochschulverlag ETHZ, 1996).
51. Johansson, M. U., et al. *BMC bioinformatics* 13, 173 (2012).
52. Grosdidier, A., et al. *Nucleic acids research* 39, W270-277 (2011).
53. Grosdidier, A., et al. *Journal of computational chemistry* 32, 2149-2159 (2011).
54. Abbott, G. W., et al. *Science signaling* 7, ra22 (2014).

Example 2: Gabapentin is a Potent Activator of KCNQ3 and KCNQ5 Potassium Channels Synthetic gabapentinoids, exemplified by gapapentin and pregabalin, are in extensive clinical use for indications including epilepsy, neuropathic pain, anxiety, and alcohol withdrawal. Their mechanisms of action are incompletely understood, but are thought to involve inhibition of α2δ subunit-containing voltage-gated calcium channels. This Example shows that gabapentin is a potent activator of the heteromeric KCNQ2/3 voltage-gated potassium channel, the primary molecular correlate of the neuronal M-current, and also homomeric KCNQ3 and KCNQ5 channels. In contrast, the structurally related gabapentinoid, pregabalin, does not activate KCNQ2/3, and at higher concentrations (≥10 µM) is inhibitory. Gabapentin activation of KCNQ2/3 (EC50=4.2 nM) or homomeric KCNQ3* (EC50=5.3 nM) channels requires KCNQ3-W265, a conserved tryptophan in KCNQ3 transmembrane segment 5. Homomeric KCNQ2 or KCNQ4 channels are insensitive to gabapentin, whereas KCNQ5 is highly sensitive (EC50=1.9 nM). Given the potent effects and the known anticonvulsant, antinociceptive, and anxiolytic effects of M-channel activation, these findings support an unexpected role for M-channel activation in the mechanism of action of gabapentin.

Gabapentin (Neurontin) and pregabalin (Lyrica) are synthetic antiepileptic and antinociceptive gabapentinoid compounds originally designed as analogues of the neurotransmitter γ-aminobutyric acid (GABA), and both are in widespread clinical use (Calandre et al., 2016). However, the mechanisms of action of gabapentinoids, exemplified by gabapentin and pregabalin, are incompletely understood. [$^3$H]-gabapentin binding was first described in membrane fractions from rat brain homogenates, and the target protein identified as the $\alpha_2$-δ subunit of voltage-gated calcium (Cav) channels. The findings were later recapitulated using porcine brain tissue, heterologously expressed $\alpha_2$-δ, and also with pregabalin; binding was found to be exclusive to $\alpha_2$-δ and 2 isoforms (Brown and Gee, 1998; Field et al., 2006; Fuller-Bicer et al., 2009; Gee et al., 1996). Gabapentin and pregabalin are generally considered inactive against canonical $GABA_A$ and $GABA_B$ receptors, despite their structural similarity to GABA (Ben-Menachem, 2004; Jensen et al., 2002; Lanneau et al., 2001; Stringer and Lorenzo, 1999; Taylor, 1997), although some investigators contend that there are some subtype-specific effects on $GABA_B$ receptors (Bertrand et al., 2003a; Ng et al., 2001; Parker et al., 2004). Binding of gabapentin and pregabalin to $\alpha_2$-δ is suggested to act therapeutically via impairment of Cav channel activity, thus reducing neuronal calcium currents (Stefani et al., 1998; Stefani et al., 2001), although others observed no evidence for gabapentin-induced changes in neuronal Cav activity (Rock et al., 1993; Schumacher et al., 1998).

Figure 10:
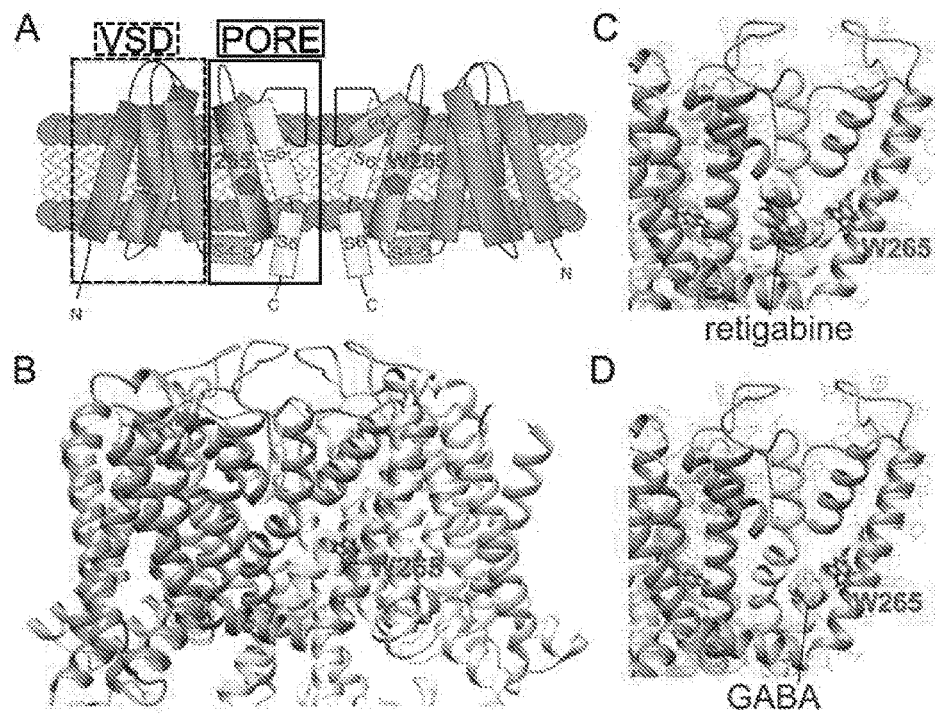
FIG. 10: KCNQ3 contains a conserved neurotransmitter binding pocket. (A) Topological representation of KCNQ3 showing two of the four subunits, without domain swapping for clarity. Pentagon, approximate position of KCNQ3-W265; VSD, voltage sensing domain. (B) Chimeric KCNQ1/KCNQ3 structural model (site shading corresponds to lettering of KCNQ3-W265). Domain shading as in (A). (C),(D). Close-up side views of KCNQ structure as in panel B, showing results of SwissDock.

We recently made the unexpected discovery that GABA can activate voltage-gated potassium (Kv) channels composed of heteromeric assemblies of KCNQ2 (Kv7.2) and KCNQ3 (Kv7.3) pore-forming α subunits (Manville et al., 2018). KCNQ (Kv7) channels comprise tetramers of α subunits, each containing six transmembrane (S) segments, organized into the voltage-sensing domain (VSD, S1-4) and the pore module (S5-6) (FIG. 10 A, B). In vertebrate nervous systems, KCNQ2/3 (Kv7.2/3) heteromers are the primary molecular correlate of the M-current, a muscarinic-inhibited Kv current essential for regulating excitability of a wide range of neurons throughout the nervous system (Brown and Adams, 1980; Marrion et al., 1989; Wang et al., 1998). We found that, like the anticonvulsant retigabine (Kim et al., 2015; Schenzer et al., 2005), GABA binds to a conserved tryptophan (W265) on KCNQ3 to activate KCNQ3 homomers and KCNQ2/3 heteromers (Manville et al., 2018) (FIG. 10B-D).

Because of the structural similarities between gabapentinoids and GABA, and the known influence of the M-current in many of the disease states responsive to gabapentinoids (epilepsy, pain, anxiety, alcohol withdrawal) (Blackburn-Munro et al., 2005; Kang et al., 2017; Mason et al., 2018), we hypothesized that gabapentinoids might modulate KCNQ2/3 channels. Here, using electrostatic surface mapping, in silico docking studies, cellular electrophysiology and site-directed mutagenesis, we examined whether the two gabapentinoids in widespread clinical use (gabapentin and pregabalin) can modulate KCNQ2/3 channel function.

Materials and Methods

Channel Subunit cRNA Preparation and *Xenopus laevis* Oocyte Injection cRNA transcripts encoding human KCNQ2, KCNQ3, KCNQ4, KCNQ5 (Kv7.2-Kv7.5) were generated by in vitro transcription using the T7 polymerase mMessage mMachine kit (Thermo Fisher Scientific), after vector linearization, from cDNA sub-cloned into plasmids incorporating *Xenopus laevis* β-globin 5' and 3' UTRs flanking the coding region to enhance translation and cRNA stability. cRNA was quantified by spectrophotometry. Mutant KCNQ2 and KCNQ3 cDNAs were generated with site-directed mutagenesis using a QuikChange kit according to the manufacturer's protocol (Stratagene, San Diego, Calif.) and corresponding cRNAs prepared as above. Defolliculated stage V and VI *Xenopus laevis* oocytes (Ecocyte Bioscience, Austin, Tex.) were injected with KCNQ channel α subunit cRNAs (5-10 ng). The oocytes were incubated at 16° C. in Barth's saline solution (Ecocyte) containing penicillin and streptomycin, with daily washing, for 2-5 days prior to two-electrode voltage-clamp (TEVC) recording.

Two-Electrode Voltage Clamp (TEVC)

TEVC recording was performed at room temperature using a OC-725C amplifier (Warner Instruments, Hamden, Conn.) and pClamp8 software (Molecular Devices, Sunnyvale, Calif.) 2-5 days after cRNA injection as described in the section above. The oocytes were placed in a small-volume oocyte bath (Warner) and viewed with a dissection microscope. Unless otherwise stated, chemicals were sourced from Sigma. Bath solution was (in mM): 96 NaCl, 4 KCl, 1 $MgCl_2$, 1 $CaCl_2$, 10 HEPES (pH 7.6). Gabapentin and pregabalin were stored at −80° C. as 1 M stocks in molecular grade $H_2O$ and diluted to working concentrations on each experimental day. The drugs were introduced into the recording bath by gravity perfusion at a constant flow of 1 ml per minute for 3 minutes prior to recording. Pipettes were of 1-2 MΩ resistance when filled with 3 M KCl. Currents were recorded in response to pulses between −80 mV and +40 mV at 20 mV intervals, or a single pulse to +40 mV, from a holding potential of −80 mV, to yield current-voltage relationships, current magnitude, and for quantifying activation rate. Deactivation was recorded at −80 mV after a single pulse to +40 mV, from a holding potential of −80 mV. Electrophysiology data analysis was performed with Clampfit (Molecular Devices) and Graphpad Prism software (GraphPad, San Diego, Calif., USA); values are stated as mean±SD. Raw or normalized tail currents were plotted versus prepulse voltage and fitted with a single Boltzmann function:

$$g = \frac{(A_1 - A_2)}{\left\{1 + \exp\left[V_{\frac{1}{2}} - Vs\right]\right\} y + A_2} \quad \text{Eq. 1}$$

where g is the normalized tail conductance, A1 is the initial value at −∞, $A_2$ is the final value at +∞, $V_{1/2}$ is the half-maximal voltage of activation and V: the slope factor. Activation and deactivation kinetics were fitted with single exponential functions.

Chemical Structures and Silico Docking

Chemical structures and electrostatic surface potentials were plotted and viewed using Jmol, an open-source Java viewer for chemical structures in 3D: jmol.org. For in silico ligand docking predictions, the *Xenopuslaevis* KCNQ1 cryoEM structure (Sun and MacKinnon, 2017) was first altered to incorporate KCNQ3/KCNQ5 residues known to be important for retigabine and ML-213 binding, and their immediate neighbors, followed by energy minimization as we previously described (Manville et al., 2018) using the GROMOS 43B1 force field (van Gunsteren, 1996) in Deep-View (Johansson et al., 2012). Thus, *Xenopus laevis* KCNQ1 amino acid sequence LITTLYIGF was converted to LITAWYIGF, the underlined W being W265 in human KCNQ3 and the italicized residues being the immediate neighbors in KCNQ3/KCNQ5. In addition, *Xenopus laevis* KCNQ1 sequence WWGVVTVTTIGYGD was converted to WWGLITLATIGYGD, the underlined L being Leu314 in human KCNQ3 and the italicized residues being the immediate neighbors in KCNQ5 and/or KCNQ3. Surrounding non-mutated sequences are shown to illustrate the otherwise high sequence identity in these stretches. No other KCNQ1 residues were changed in the model. Unguided docking of gabapentin and pregabalin, to predict native binding sites, was performed using SwissDock with CHARMM forcefields (Grosdidier et al., 2011a; b).

Statistical Analysis

All values are expressed as mean±standard deviation (SD). One-way ANOVA was applied for all other tests; if multiple comparisons were performed, a post-hoc Tukey's HSD test was performed following ANOVA. All P-values were two-sided. Statistical significance was defined as P<0.05.

Results

Figure 11:
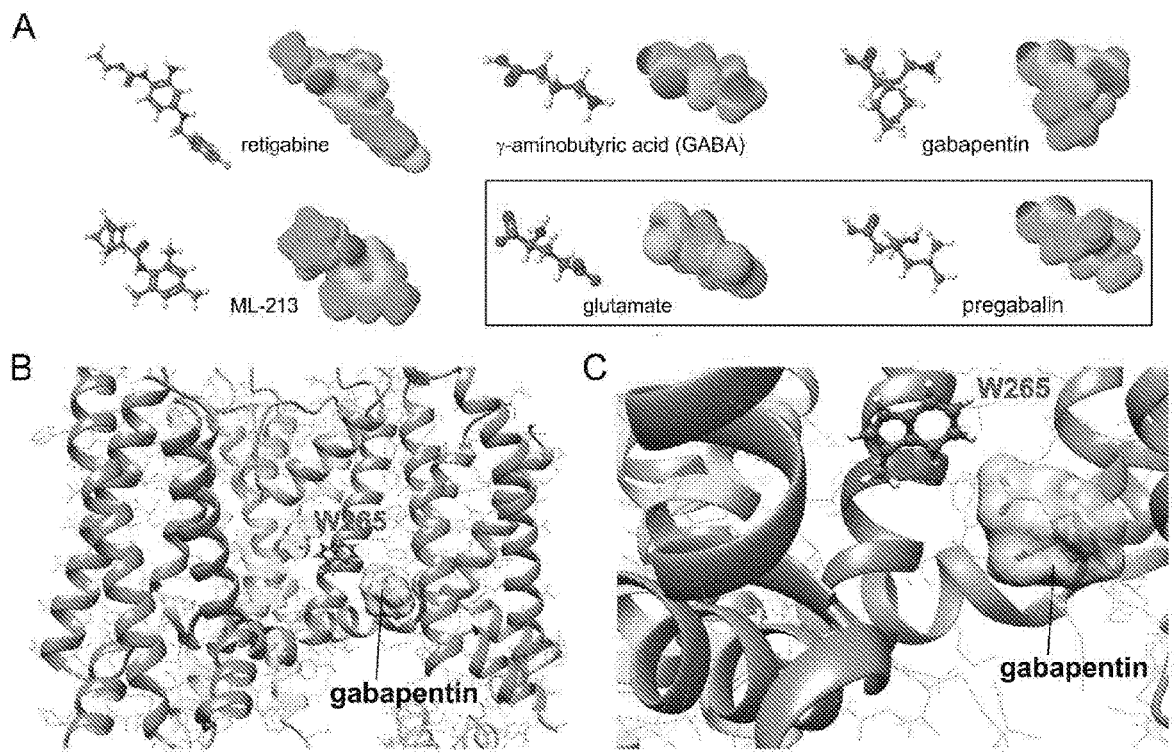
FIG. 11: Gabapentin is predicted to bind to KCNQ3-W265. (A) Electrostatic surface potentials distinguished by shading (electron-dense; electron-poor; neutral) and structures calculated and plotted using Jmol. (B),(C). Long-range (B) and close-up (C) side views of KCNQ1/3 chimera model structure showing results of SwissDock unguided in silico docking of gabapentin. Domain colors as in FIG. 10.

Synthetic anticonvulsants such as retigabine and ML-213 exhibit negative electrostatic surface potential near their carbonyl oxygen moieties, a chemical property thought to be important for activation of KCNQ2/3 channels (Kim et al., 2015). We previously found that GABA also possesses this chemical property, whereas the excitatory neurotransmitter, glutamate (which cannot open KCNQ2/3 channels) does not (Manville et al., 2018). Here, we found that gabapentin exhibits a similar negative electrostatic surface potential pattern to that of GABA, whereas pregabalin does not (FIG. 11 A). Using SwissDock, we performed unbiased docking prediction analysis for gabapentin and pregabalin, to a model of KCNQ3 (Manville et al., 2018) based on the recent cryo-EM derived KCNQ1 structure (Sun and MacKinnon, 2017). Strikingly, gabapentin was predicted to bind to KCNQ3-W265 (FIG. 11 B, C) whereas pregabalin failed to dock to KCNQ3-W265.

Figure 12:
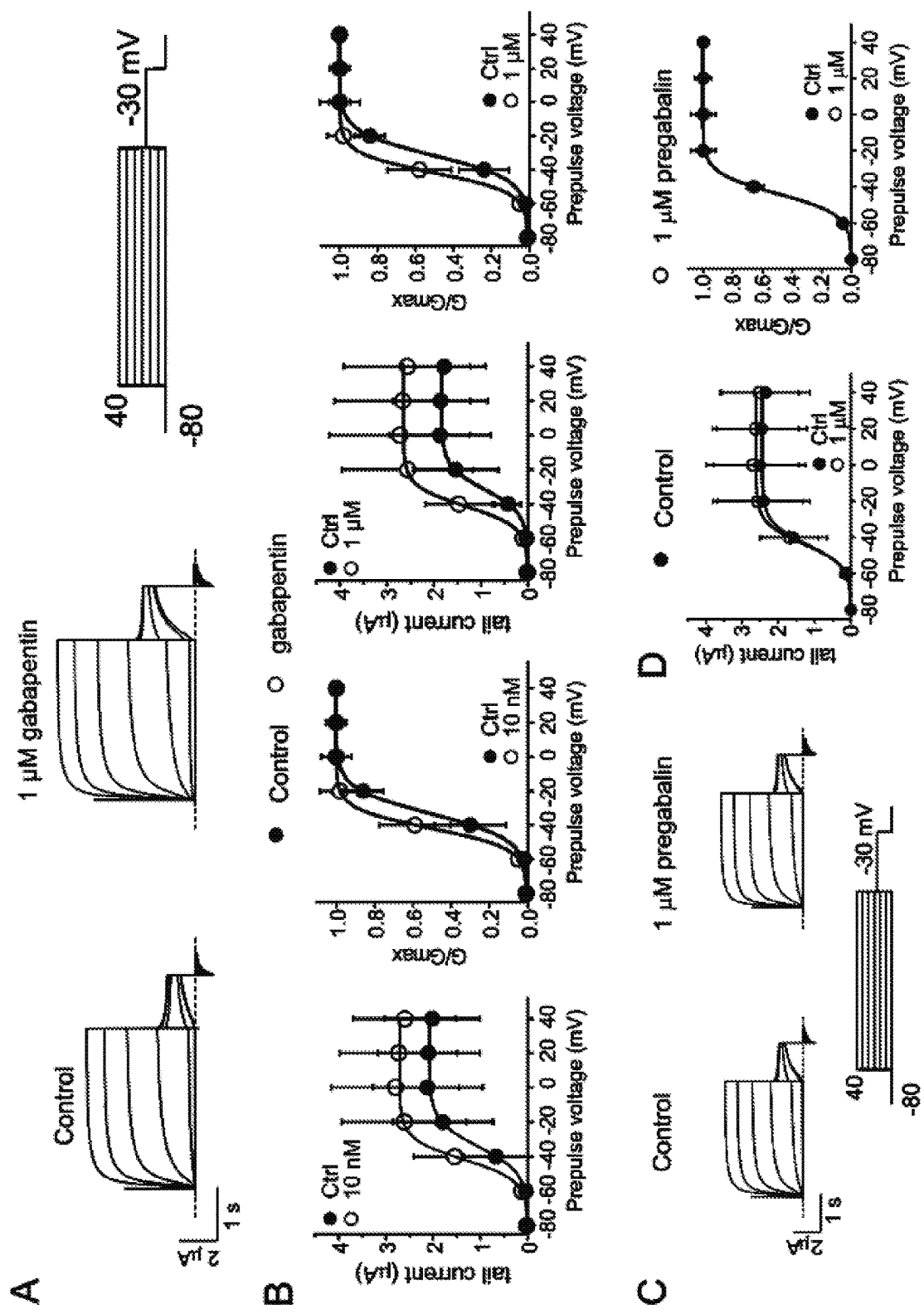
FIG. 12: Gabapentin is a potent activator of heteromeric KCNQ2/3 potassium channels. (A) Left, mean TEVC traces for KCNQ2/3 expressed in *Xenopus* oocytes in the absence (control) or presence of 10 nM gabapentin (n=7-8). Dashed line here and throughout, zero current level. Right, voltage protocol. Arrow indicates time point at which tail currents are measured throughout this study. (B) Mean tail current and normalized tail currents (G/Gmax) versus prepulse voltage relationships recorded by TEVC in *Xenopus* oocytes expressing KCNQ2/3 channels in the absence (black circles) or presence (open circles) of 10 nM or 1 µM gabapentin as indicated (n=7-8). Error bars indicate SD. Voltage protocol as in (A). (C) Mean TEVC traces for KCNQ2/3 expressed in *Xenopus* oocytes in the absence (control) or presence of 1 µM pregabalin (n=7-8). Lower inset, voltage protocol. (D) Mean tail current and normalized tail currents (G/Gmax) versus prepulse voltage relationships recorded by TEVC in *Xenopus* oocytes expressing KCNQ2/3 channels in the absence (solid circles) or presence (open circles) of 1 µM pregabalin as indicated (n=5). Error bars indicate SD. Voltage protocol as in (C). (E) Voltage dependence of KCNQ2/3 current fold-increase by gabapentin versus pregabalin (10 nM), plotted from traces as in panels A and C (n=5-8). Error bars indicate SD. *P<0.05 versus pregabalin current at −60 mV. F. Gabapentin and pregabalin dose responses at −60 mV for KCNQ2/3 activation, quantified from data as in panels (A)-(E) (n=7-8). Error bars indicate SD. (G) Dose response for gabapentin and pregabalin effects on resting membrane potential ($E_M$) of unclamped oocytes expressing KCNQ2/3 (n=7-8). Error bars indicate SD. (H) Mean tail current versus prepulse voltage relationships recorded by TEVC in *Xenopus* oocytes expressing KCNQ2/3 channels in the absence (lower) or presence (upper) of 30 µM retigabine as indicated (n=4). Error bars indicate SD. Voltage protocol as in (A). (I) Voltage dependence of KCNQ2/3 current fold-increase by retigabine (30 µM), n=4). Error bars indicate SD. (J) Retigabine dose responses at −60 mV for KCNQ2/3 activation, quantified from data as in panels A-E (n=4). Error bars indicate SD.
Figure 12:
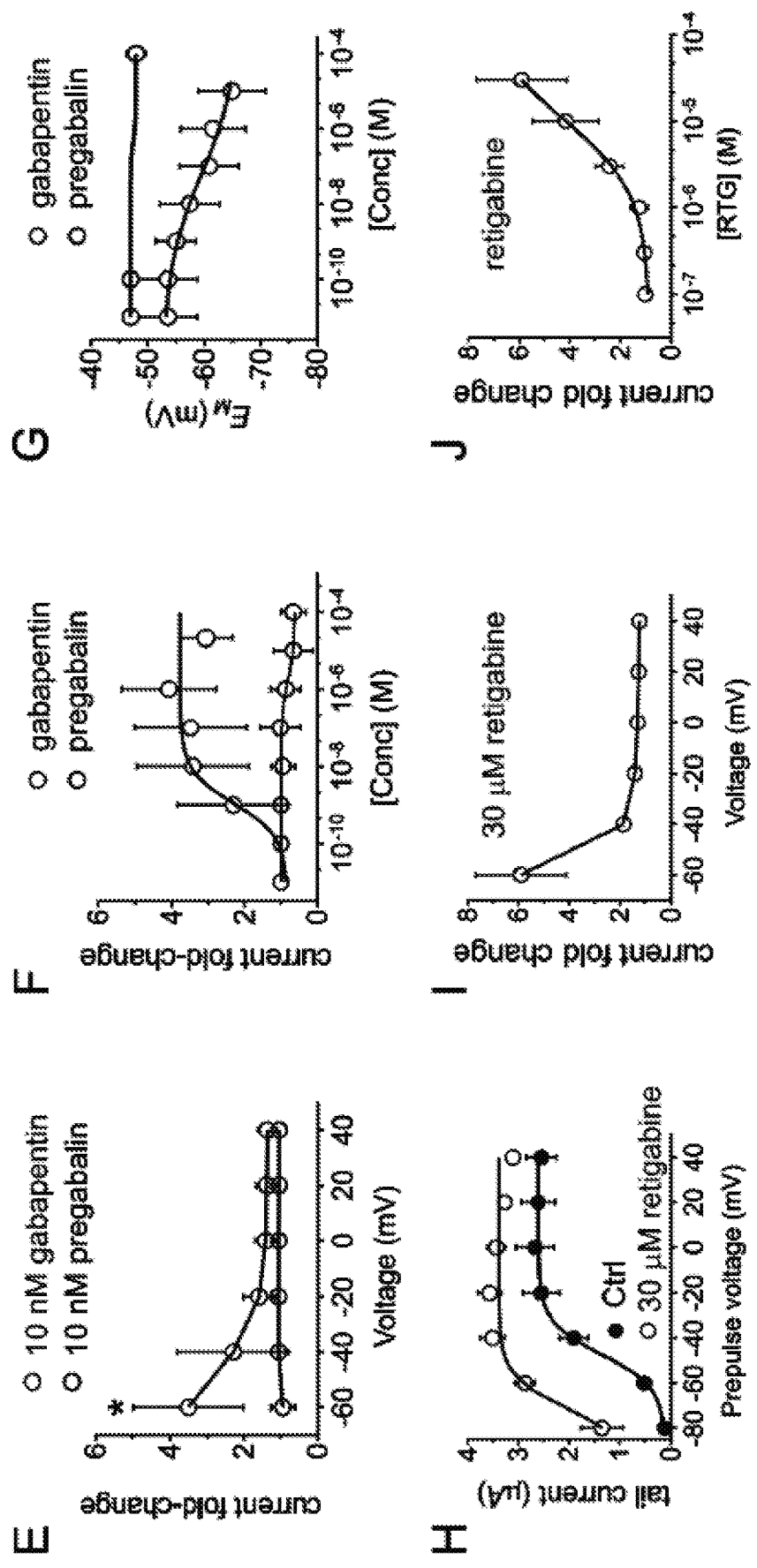

We next tested the predictions using the *Xenopus laevis* oocyte expression and two-electrode voltage-clamp (TEVC) electrophysiology. Gabapentin potently activated heteromeric KCNQ2/3 potassium channels, even at low nanomolar concentrations (FIG. 12 A, B). In contrast, pregabalin had no augmenting effect on KCNQ2/3 activity, even at 1 µM (FIG. 12 C, D). Thus, the experimental data matched the docking predictions. Gabapentin efficacy was highest at −60 mV to −40 mV, leading to a −9 mV shift in the voltage dependence of KCNQ2/3 activation (1 µM gabapentin), but gabapentin also augmented currents at positive membrane potentials (FIG. 12 B, E). Dose response studies showed that at −60 mV, gabapentin exhibited an $EC_{50}$ for KCNQ2/3 activation of 4.2±0.13 nM (n=5-7); at 10 nM, gabapentin increased KCNQ2/3 current 3.5-fold at −60 mV (FIG. 12 F; Supplementary FIG. 1; Supplementary Table 1). The ability to activate KCNQ2/3 at subthreshold potentials enabled gabapentin to shift the membrane potential (EM) of KCNQ2/3-expressing oocytes by >−10 mV ($EC_{50}$, 4.2 nM) (FIG. 12 G). Parallel studies showed that pregabalin failed to activate KCNQ2/3 even at 1 µM, and began to inhibit KCNQ2/3 at 10 µM and above (FIG. 12 E,F; Supplementary FIG. 2; Supplementary Table 2). Pregabalin likewise failed to shift the oocyte $E_M$ (FIG. 12 G). Compared to the established KCNQ2/3 opener and anticonvulsant retigabine, gabapentin acted as a potent partial agonist. Thus, retigabine (30 µM) shifted the voltage dependence of KCNQ2/3 activation by −30 mV (FIG. 12H) and increased current at −60 mV sixfold (FIG. 15I) but the $EC_{50}$ for retigabine was in the micromolar, not nanomolar range (FIG. 12J), ~1000-fold less potent than gabapentin (see Supplementary FIG. 3; Supplementary Table 3). In comparison, we recently found that GABA, which also acts at KCNQ3-W265, activates KCNQ2/3 with an $EC_{50}$ of 0.85 µM at −60 mV, increasing current fourfold (Manville et al., 2018). Thus, gabapentin and GABA exhibit similar efficacy but gabapentin is 200-fold more potent.

Figure 13:
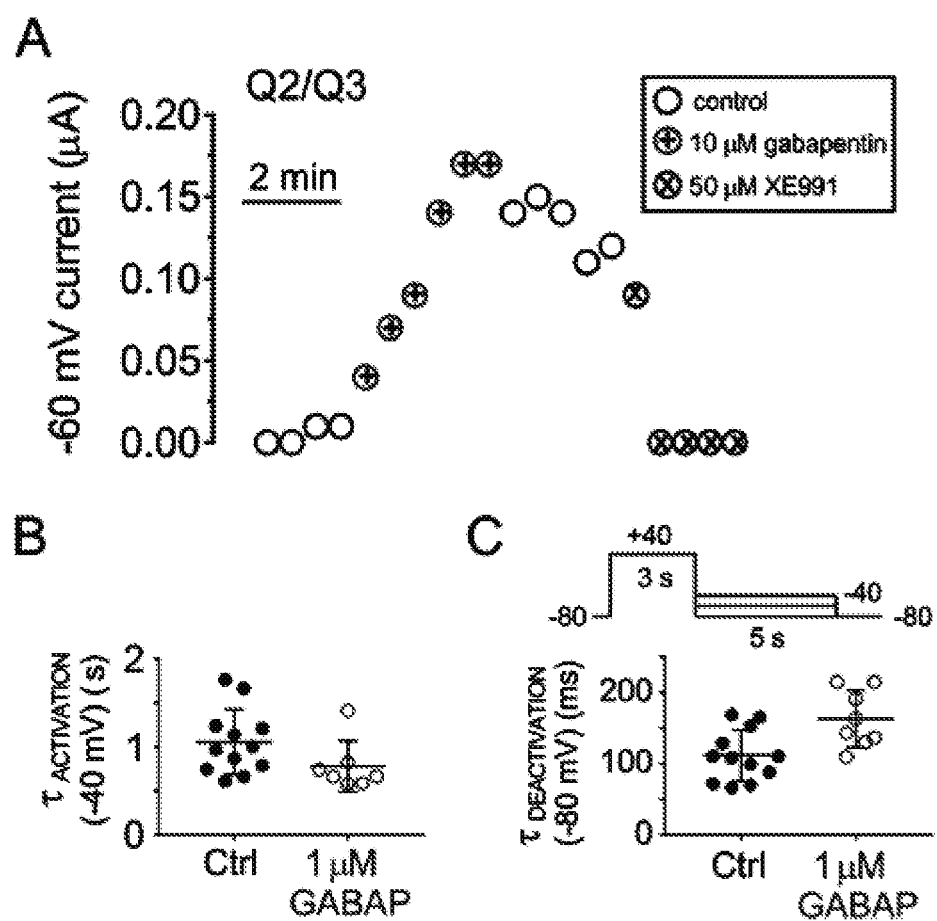
FIG. 13: Gabapentin-activated current is XE991-sensitive and exhibits altered gating kinetics. (A) Exemplar −60 mV KCNQ2/3 current before (left), during wash-in of gabapentin (+), partial washout with bath solution in the absence of drug (open circles), and then wash-in of XE991 (x). (B),(C) Mean activation at +40 mV (B) and deactivation at −80 mV (C) rates for KCNQ2/3 before (control) and after wash-in of 1 µM Gabapentin (GABAP) (n=7). Activation rate was quantified using voltage protocol as in FIG. 12A. Deactivation rate was quantified using voltage protocol shown above. Error bars indicate SD.
Figure 14:
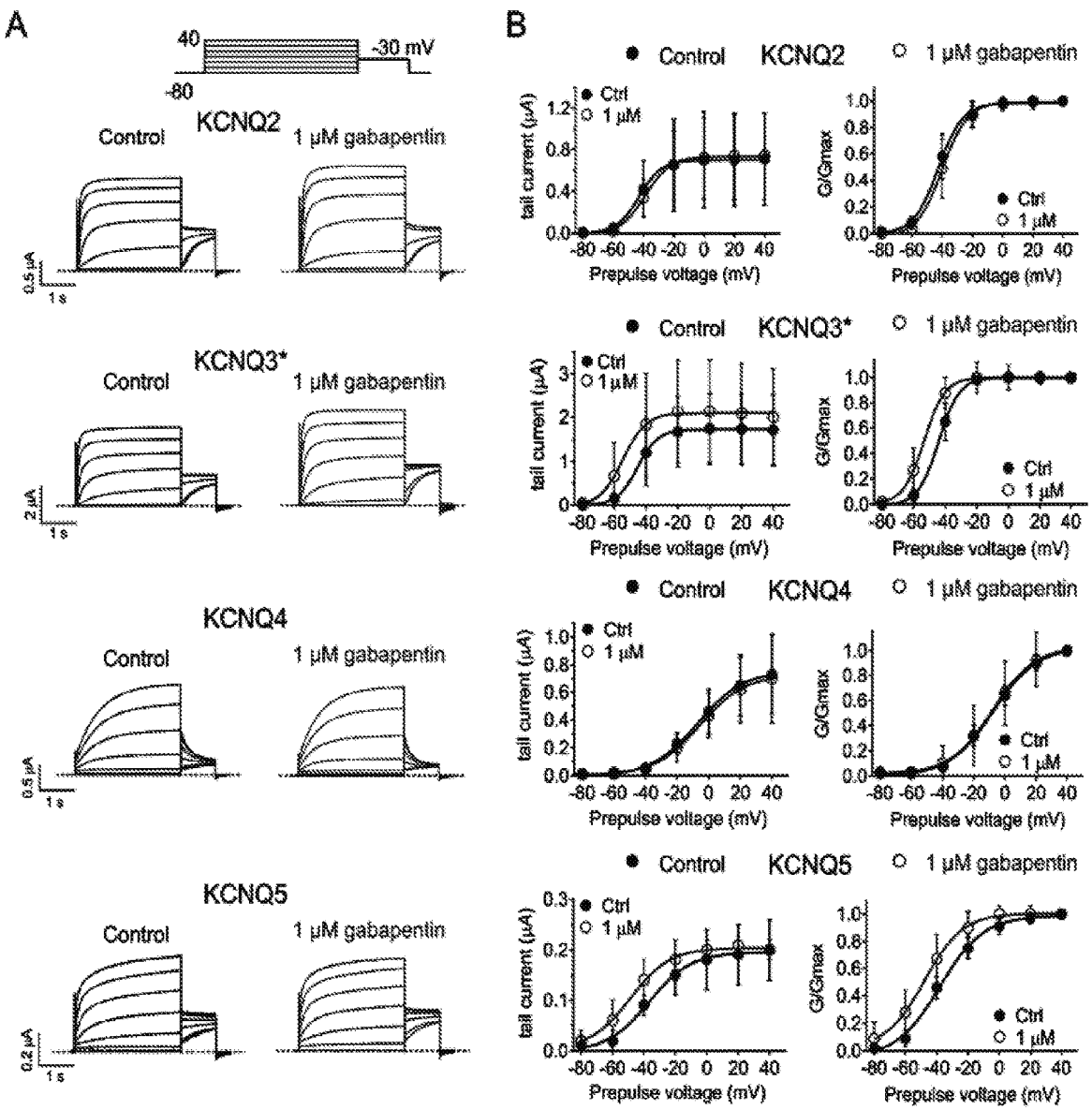
FIG. 14: Gabapentin is a potent activator of homomeric KCNQ3 and KCNQ5 potassium channels. (A) Mean TEVC traces for homomeric KCNQ2, 3*, 4 or 5 channels (as indicated) expressed in *Xenopus* oocytes in the absence (control) or presence of 1 µM gabapentin (n=4-8). Voltage protocol, upper inset. (B) Mean tail current (left) and normalized tail currents (G/Gmax; right) versus prepulse voltage relationships recorded by TEVC in *Xenopus* oocytes expressing homomeric KCNQ2, 3*, 4 or 5 channels (as indicated) in the absence or presence of 1 µM gabapentin as indicated (n=4-8). Error bars indicate SD. (C) Voltage dependence of current fold-increase by gabapentin (1 µM) for homomeric KCNQ2, 3*, 4 or 5 channels, plotted from traces as in panel A (n=4-8). Error bars indicate SD. (D) Gabapentin dose responses at −60 mV for homomeric KCNQ2, 3*, 4 or 5 channel activation, quantified from data as in panel A (n=4-8). Error bars indicate SD.
Figure 14:
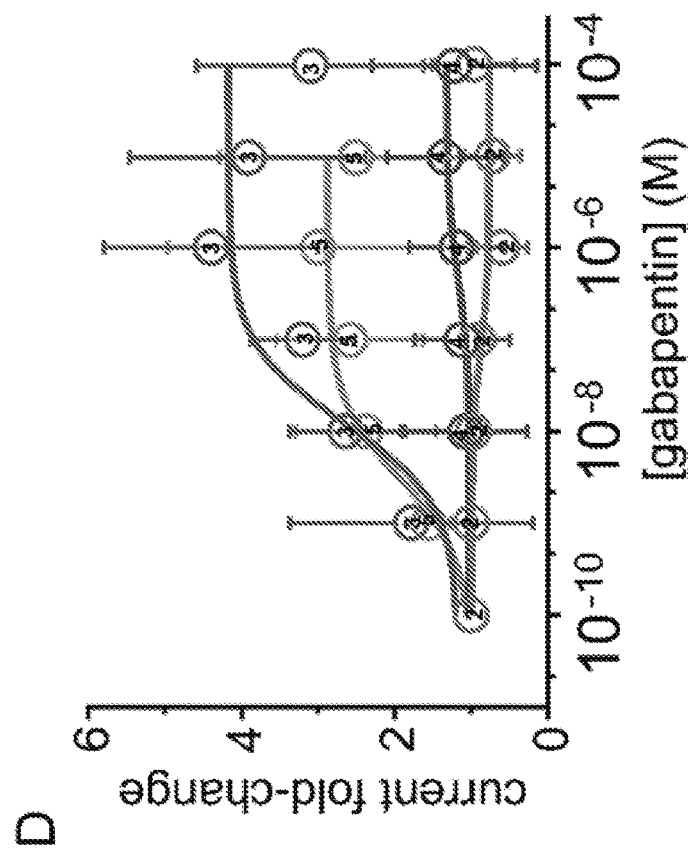
Figure 14:
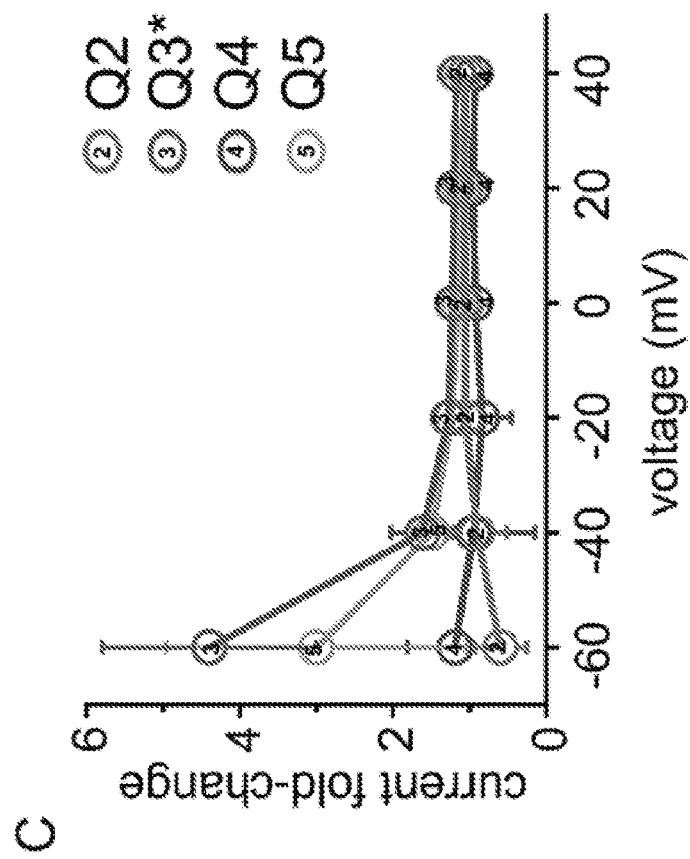
Figure 15:
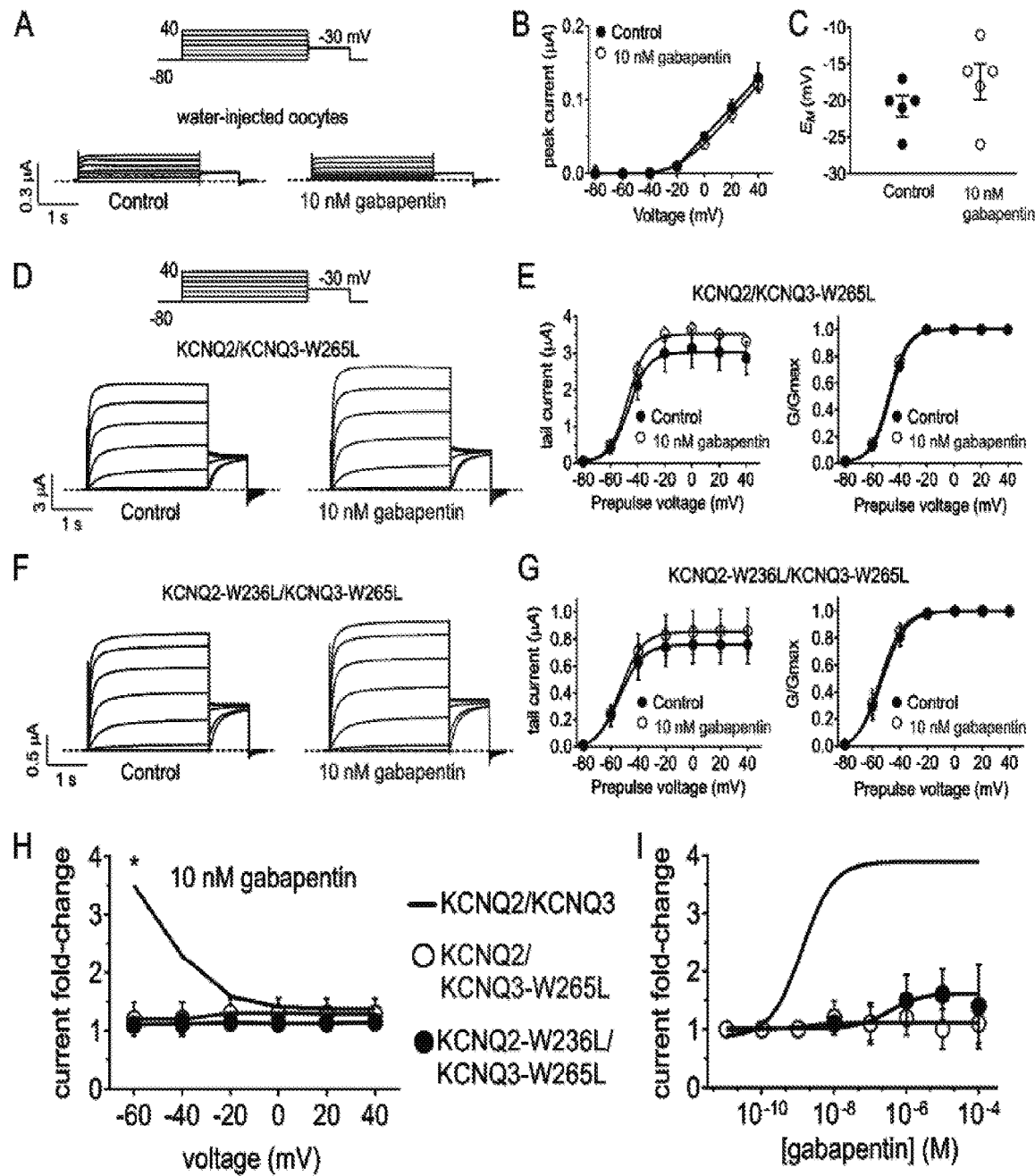
FIG. 15: Gabapentin activation of KCNQ2/3 requires KCNQ3-W265. (A)-(C) TEVC of water-injected *Xenopus laevis* oocytes showing no effect of gabapentin (10 nM) on endogenous currents or membrane potential (EM) (n=5). (A) mean traces; (B) mean peak current; (C) mean EM, in the absence (Control) or presence of 10 nM gabapentin. Voltage protocol, panel A upper inset. Error bars indicate SD. (D), (E) TEVC of *Xenopus laevis* oocytes showing effects of gabapentin (10 nM) on heteromeric KCNQ2/KCNQ3-W265L channels. (D) mean traces; (E) mean tail current (left) and mean normalized tail current (G/Gmax; right). n=5. Error bars indicate SD. (F), (G) TEVC of *Xenopus laevis* oocytes showing effects of gabapentin (10 nM) on heteromeric KCNQ2-W236L/KCNQ3-W265L channels. (F) mean traces; (G) mean tail current (left) and mean normalized tail current (G/Gmax; right); n=5. Error bars indicate SD. (H) Mean tail current fold-changes versus prepulse voltages for channels as indicated; KCNQ2/KCNQ3 results (black line) from FIG. 12E shown for comparison; n=5. Error bars indicate SD. * P<0.05 versus other groups at −60 mV. (I) Mean dose responses for channels as indicated; KCNQ2/KCNQ3 results (black line) from FIG. 12F shown for comparison; n=5. Error bars indicate SD.
Figure 16:
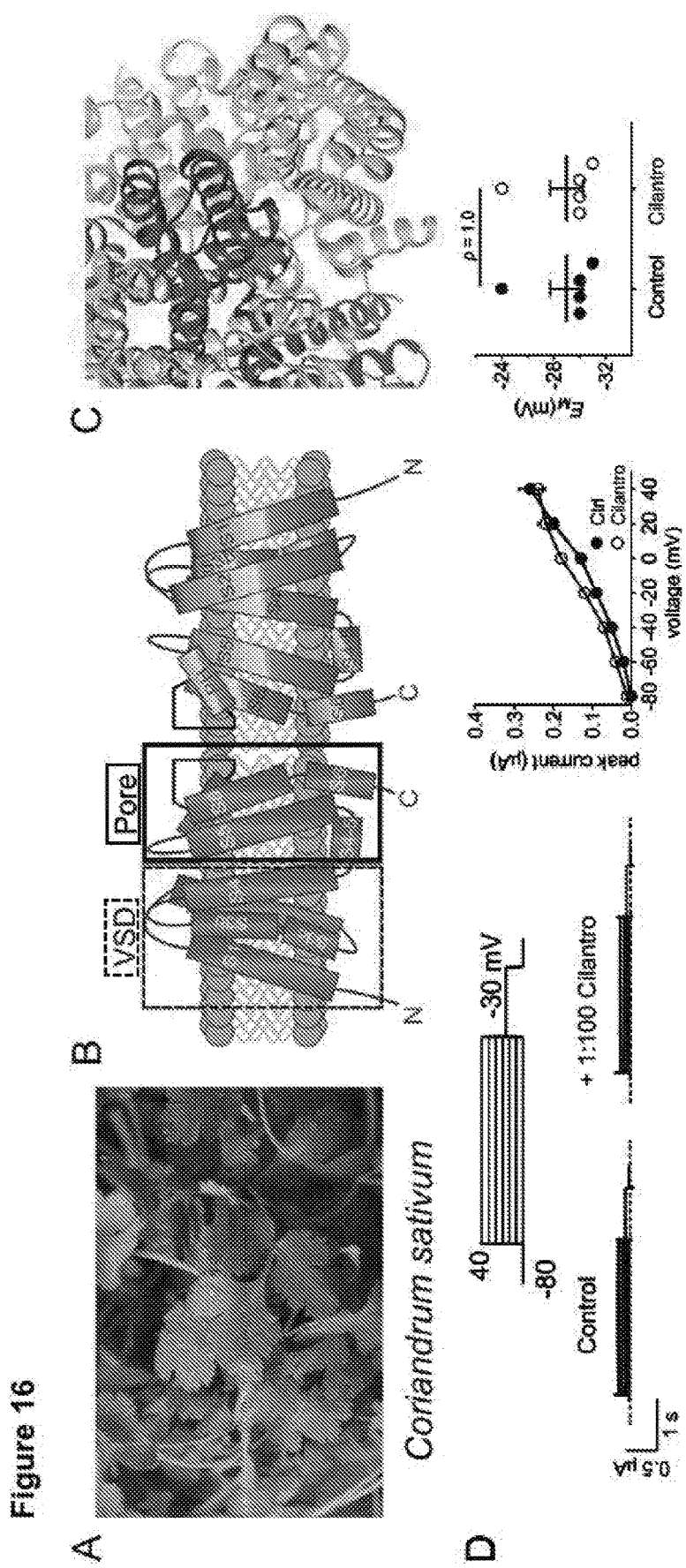
FIG. 16: Cilantro extract differentially activates homomeric KCNQ channels. All error bars indicate SEM. (A) Image of the fresh cilantro (*Coriander sativum*) used in this study. (B) Topological representation of a Kv channel showing two of the four subunits that comprise a channel. VSD, voltage sensing domain. (C) Extracellular view of the chimeric KCNQ1/KCNQ3 structural model to highlight the anticonvulsant binding pocket (center, KCNQ3-W265). (D) Left, mean TEVC current traces for water-injected *Xenopus* oocytes in the absence (Control) or presence of 1% cilantro extract (n=5). Dashed line here and throughout indicates the zero current level. Upper inset, the voltage protocol used here and throughout the study unless otherwise indicated. Center, mean tail current for oocytes on left (n=5). Right, scatter plot of resting membrane potential ($E_M$) of water-injected oocytes in the absence (Control) or presence of cilantro extract (n=5). Statistical analyses by two-way ANOVA. (E) Left, mean TEVC current traces for *Xenopus* oocytes expressing the KCNQ homomers indicated in the absence (Control) or presence of 1% cilantro extract (n=5-6). Arrow indicates time point at which KCNQ tail currents are measured throughout this study. (F) Mean tail current (left) and normalized tail current ($G/G_{max}$) (right) versus prepulse voltage relationships for the traces as in E (n=5-6). (G) Effects of 1% cilantro extract on $E_M$ of unclamped oocytes expressing the channels as in E (n=5-6). Statistical analyses by two-way ANOVA. (H) Current fold-increase versus voltage for the KCNQ isoforms indicated, induced by 1% cilantro extract (n=5-6). (I) Scatter plot showing mean $\Delta V_{0.5activation}$ induced by 1% cilantro extract for the KCNQ isoforms indicated; n=5-6. Statistical analysis by two-way ANOVA corrected for multiple comparisons.
Figure 16:
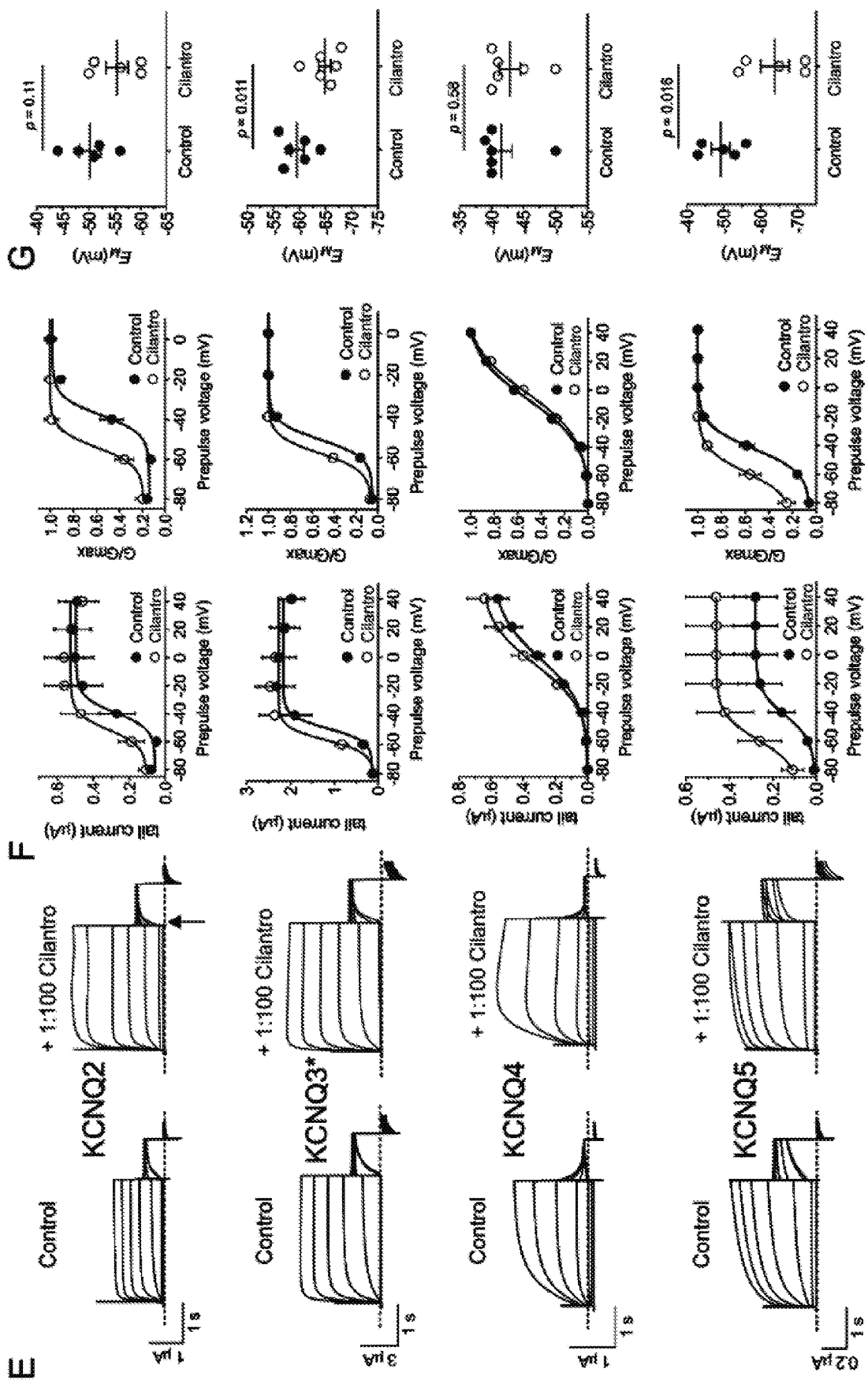
Figure 16:
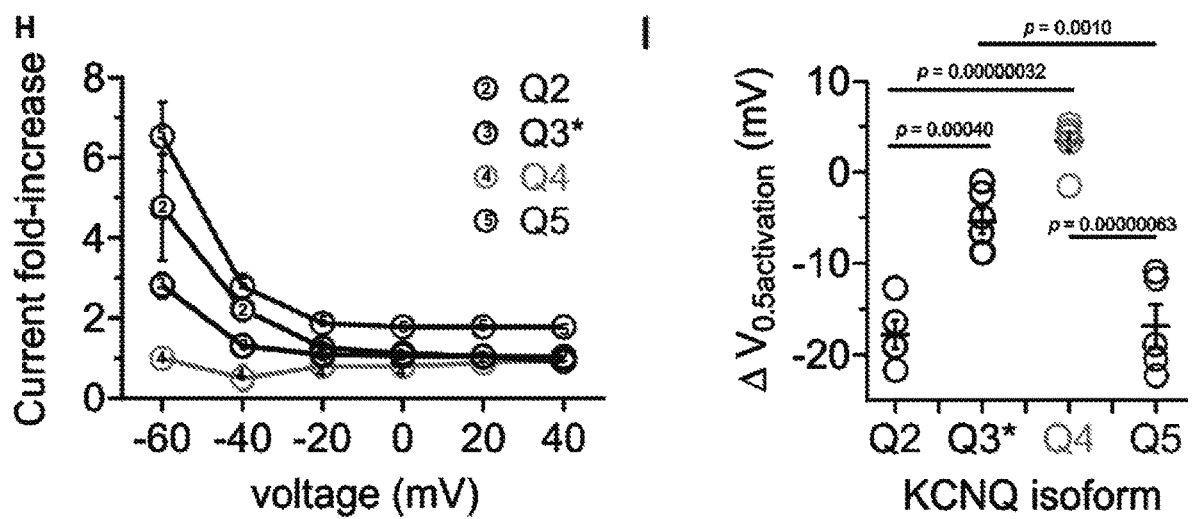

Gabapentin began to activate KCNQ2/3 immediately upon wash-in, with the current augmentation taking ~2 minutes to plateau. Gabapentin effects washed out relatively slowly (<50% washout after 2 minutes) but the gabapentin-augmented current was rapidly inhibited by washing in the KCNQ channel inhibitor, XE991 (50 µM) (FIG. 13A). Gabapentin effects on KCNQ2/3 gating kinetics were suggestive of it stabilizing the open state; at 10 nM, gabapentin speeded KCNQ2/3 activation and slowed deactivation (FIG. 13 B, C; Supplementary FIG. 1; Supplementary Table 1). Again, pregabalin had no effects (FIG. 13 B, C; Supplementary FIG. 2; Supplementary Table 2).

We next examined the effects of gabapentin on homomeric channels formed by neuronal KCNQ isoforms. At 1 µM, gabapentin activated KCNQ3* (an expression-optimized KCNQ3-A315T mutant that ensures robust currents (Zaika et al., 2008)) and KCNQ5, especially at subthreshold potentials. In contrast, KCNQ2 and KCNQ4 were insensitive to 1 µM gabapentin (FIG. 14A-C; Supplementary FIGS. 4-7; Supplementary Tables 4-7). Dose response studies revealed that KCNQ3 and KCNQ5 were, like KCNQ2/3 channels, activated at −60 mV even by 10 nM gabapentin, and that KCNQ3 exhibited similar gabapentin sensitivity and efficacy to that of KCNQ2/3 channels ($EC_{50}$=5.3 nM; maximal 4-fold increase in current at −60 mV). In contrast, KCNQ5 channels exhibited higher sensitivity but lower efficacy ($EC_{50}$=1.9 nM; maximal 3-fold increase in current at −60 mV) (FIG. 14D; Supplementary FIGS. 4-7; Supplementary Tables 4-7).

Canonical $GABA_A$ and $GABA_B$ receptors are generally considered to be gabapentin-insensitive (Jensen et al., 2002; Taylor, 1997); in addition, previous studies have concluded that *Xenopus laevis* oocytes do not express endogenous $GABA_A$ or $GABA_B$ receptors (Guyon et al., 2013). Furthermore, the gabapentin-activated currents in KCNQ2/3 expressing oocytes were completely inhibited by the KCNQ-specific inhibitor, XE991 (FIG. 13A). These data, combined with docking prediction studies, rapid onset of activation, the lack of effects of pregabalin and the KCNQ isoform-specificity of gabapentin (FIG. 14) are consistent with direct activation of KCNQ2/3 channels by gabapentin. This conclusion was further supported by two additional sets of experiments. First, gabapentin (10 nM) had no effect on endogenous currents in non-injected oocytes, discounting the possibility that gabapentin was activating endogenous currents (FIG. 15A). Second, substitution to leucine of KCNQ3-W265, the GABA binding site (Manville et al., 2018) and the in silico predicted docking site for gabapentin (FIG. 11), essentially eliminated the effects of gabapentin on KCNQ2/3 currents (FIG. 15D, E); the double mutation of KCNQ2-W236L and KCNQ3-W265L in KCNQ2/3 channels had similar effects (FIG. 15F, G). KCNQ2/KCNQ3-W265L channels were insensitive to gabapentin across the voltage range (FIG. 15H) and up to 100 μM gabapentin (FIG. 15I; Supplementary FIG. 8; Supplementary Table 8). Double-mutant (WL/WL) KCNQ2/3 channels showed slight (≤50%) augmentation by gabapentin at −60 mV only at 1 μM and higher gabapentin (FIG. 15H, I; Supplementary FIG. 9; Supplementary Table 9).

Discussion

A Gabapentin Binding Site on KCNQ Channels

We recently discovered that KCNQ3 and KCNQ5 are directly activated by the inhibitory neurotransmitter GABA, which binds close to the highly conserved S5 tryptophan, KCNQ3-W265 (Manville et al., 2018). In the current study, we show that gabapentin likewise activates KCNQ3 and KCNQ5, whereas the related gabapentinoid, pregabalin, does not. Substitution of KCNQ3-W265 with a leucine prevents activation by GABA and gabapentin, and impairs GABA binding (Manville et al., 2018). KCNQ3-W265 (and its equivalent in KCNQ2, 4 and 5) is also very important for binding of retigabine and structurally related anticonvulsants (Schenzer et al., 2005). This is thought to be because small molecules with a strong negative electrostatic surface potential close to a carbonyl/carbamate oxygen can hydrogen-bond with the W265 (Kim et al., 2015). Indeed, here we found that pregabalin lacks this exposed negative surface potential and neither in silico docks, nor activates KCNQ3. Our in silico docking studies for gabapentin position it near to W265 and close to where retigabine (Kim et al., 2015) and GABA (Manville et al., 2018) are predicted to bind, but not necessarily overlapping—although no conclusions should be drawn from the small differences in poses, and resolution of the exact pose would require structural analysis and/or further mutagenesis to map the entire binding site. We conclude that the W265-based binding site evolved to accommodate GABA and other endogenous metabolites and analogs of GABA, leading to sensitivity to modern synthetic anticonvulsants including retigabine and gabapentin. Interestingly, KCNQ2-5 all bind GABA but only KCNQ3 and KCNQ5 are activated by GABA or gabapentin (Manville et al., 2018); retigabine activates all four (but not KCNQ1, which lacks the equivalent W) but KCNQ3 is the most sensitive (Tatulian et al., 2001).

Mechanisms of Therapeutic Action

Gabapentin and pregabalin are in wide clinical use to treat a variety of disorders of the nervous system, including neuropathic pain and epilepsy. There is considerable overlap between the clinical indications for each drug (Alles and Smith, 2018; Calandre et al., 2016; Sills, 2006). This, together with the contrasting ability of gabapentin and pregabalin to activate neuronal KCNQ isoforms found herein, suggests that KCNQ activation cannot be the dominant mechanism of action for the majority of the therapeutic effects of gabapentin. Gabapentinoid binding to the $\alpha_2\delta_{-1}$ subunit reportedly inhibits $\alpha_2\delta_{-1}$-containing Cav channels (Stefani et al., 1998; Stefani et al., 2001), (Stefani et al., 1998; Stefani et al., 2001) although others found that gabapentinoids have little effect on Cav channel activity or Cav channel-dependent neurotransmitter release at presynaptic nerve terminals (Brown and Randall, 2005; Hoppa et al., 2012; Rock et al., 1993; Schumacher et al., 1998). $\alpha_2\delta_{-1}$-NMDA receptor complexes were recently discovered in human and rodent spinal cord; gabapentin inhibited $\alpha_2\delta_{-1}$-dependent potentiation of NMDA receptor activity and associated pain hypersensitivity, presenting a plausible mechanism for antinociceptive effects of gabapentin (Chen et al., 2018).

Multiple Gabapentinoid Targets in Neurons—a Role for KCNQs?

In a study comparing pregabalin and gabapentin effects on cultured dorsal root ganglion (DRG) neurons from neonatal rats, pregabalin and gabapentin produced biphasic effects (acute inhibition, but longer-term augmentation) on endogenous $K^+$ currents. The enhancing effect was attenuated by pertussis toxin or by intracellular application of a synthetic cAMP analogue, suggesting an indirect mechanism involving G protein activation (McClelland et al., 2004). Another group also found that effects of gabapentin on inward rectifier $K^+$ channels and N-type $Ca^{2+}$ channels were pertussis toxin-sensitive (Bertrand et al., 2003b). Pertussis toxin is commonly used to inhibit the downstream effects of $GABA_B$ receptor activation, as it inhibits some (but not all) of the G proteins involved in this process (Asano et al., 1985). Yet, others have shown that $GABA_B$ receptors are insensitive to gabapentinoids (Lanneau et al., 2001), and $GABA_B$ receptor inhibitors did not alter the pregabalin-induced inhibition of Cav currents in neonatal rat DRG neurons (Martin et al., 2002; McClelland et al., 2004). The most likely explanation for this apparent discrepancy is that gabapentinoids can activate pertussis-sensitive G-proteins, but independent of $GABA_B$ receptors (Martin et al., 2002).

With respect to the DRG neuron $K^+$ channel inhibition by pregabalin, it was apamin-sensitive implying it involved small-conductance $Ca^{2+}$-activated $K^+$ channels (McClelland et al., 2004). The $K^+$ current enhancement did not begin until 10 minutes after initiation of administration of pregabalin, was apamin-insensitive, and was faster when pregabalin was applied intracellularly, suggesting an intracellular signaling mechanism. The gating kinetics and voltage dependence of the DRG Kv current described in the gabapentinoid study do not necessarily suggest against it containing an M-current component. Interestingly, KCNQ2 (which is gabapentin-insensitive) expression precedes that of KCNQ3 (gabapentin-sensitive) during human brain development (Tinel et al., 1998), and the effects of KCNQ channel inhibition upon depolarization-induced GABA release and action potential propagation also alter dramatically from P0-P7 in rat (Okada et al., 2003). Thus, in some neurons, M-current might be insensitive to gabapentin early in development (e.g., the first week), unless KCNQ5 was appreciably expressed. Furthermore, in the study of gabapentinoid action on DRG neurons, $K^+$ channel activity was quantified at +40 mV, a voltage at which the activating effects of gabapentin (and most Kv channel activators) are minimal. In addition, we find that pregabalin inhibits KCNQ2/3 channel activity at concentrations of 10 μM and above, suggesting that at the concentrations used in the prior study (250 μM) (McClelland et al., 2004) pregabalin would inhibit KCNQ2/3 channels and may have similar effects on other KCNQ isoforms that could be expressed in neonatal rat DRG neurons.

It is highly possible, given the somewhat pleiotropic actions of gabapentinoids, that the potent effects of gabapentin on KCNQ3 and KCNQ5 channels might be masked by other effects observed at higher doses, both experimentally and with respect to clinical mechanisms of action. Serum gabapentinoid concentrations may reach 100 μM in patients (although in the brain and spinal cord this concentration is likely to be lower) (Ben-Menachem et al., 1992; Ben-Menachem et al., 1995; Berry et al., 2003), several orders of magnitude higher than the $EC_{50}$ for gabapentin activation of KCNQ2/3, KCNQ3 and KCNQ5 channels, but as noted above, within the range for pregabalin inhibition of KCNQ2/3.

Gabapentin has also been found to augment $K_{ATP}$ currents in rat hippocampal and human neocortical slices (but not incidentally, in rat DRG neurons) (Freiman et al., 2001), and to inhibit the hyperpolarization-activated, cyclic nucleotide-gated channel, HCN4, albeit not at clinically relevant drug concentrations (Tae et al., 2017). Conversely, gabapentin augmented in hippocampal and inhibitory interneurons, cells that highly express HCN1 and HCN2 (Peng et al., 2011; Surges et al., 2003). Thus, indirect modes of action of gabapentin may occur in vivo, as reported for Kv currents in rat DRG neurons (McClelland et al., 2004).

Conclusions

Perhaps the two most important take-home points from this study are, first, that we have discovered a new chemical space for KCNQ2/3 activation by synthetic compounds. Future structure-activity relationship studies guided by what we now know regarding the difference between gabapentin versus pregabalin with respect to KCNQ opening, and our previous work identifying endogenous activators for KCNQ3 and KCNQ5, including GABA, GABOB and β-hydroxybutyrate (Manville et al., 2018), can start to inform synthesis of a new class of KCNQ activators for potential therapeutic use. Second, the high potency but relatively low efficacy of gabapentin compared to, e.g., retigabine, suggests the possibility that gabapentin could act as a partial agonist and disrupt therapeutic actions of retigabine and related anticonvulsants. Furthermore, it is possible that gabapentin competes with the binding of endogenous GABA and its metabolites to neuronal KCNQ channels but shares similar or lower efficacy to them with respect to KCNQ activation, possibly explaining why KCNQ activation may not be an important determinant of gabapentin's beneficial effects. Thus, further exploration of gabapentinoids and related compounds with respect to KCNQ activation might uncover superior compounds, which either avoid KCNQ activation and thus potentially disruptive partial agonism, or alternatively are more effective than gabapentin in activating neuronal KCNQs and thus clinically superior because of an additional, beneficial target site.

REFERENCES

Alles S R A and Smith P A (2018) Pharmacological reviews 70:315-347.
Asano T, Ui M and Ogasawara N (1985) The Journal of biological chemistry 260:12653-12658.
Ben-Menachem E (2004) Epilepsia 45 Suppl 6:13-18.
Ben-Menachem E. et al (1992) Epilepsy research 11:45-49.
Ben-Menachem E. et al (1995) Epilepsy research 21:231-236.
Berry D J, et al (2003) Seizure: the journal of the British Epilepsy Association 12:28-36.
Bertrand S, et al (2003a) Hippocampus 13:525-528.
Bertrand S, et al (2003b) Synapse 50:95-109.
Blackburn-Munro G, et al (2005) CNS drug reviews 11:1-20.
Brown D A and Adams P R (1980) Nature 283:673-676.
Brown J P and Gee N S (1998) The Journal of biological chemistry 273:25458-25465.
Brown J T and Randall A (2005) Synapse 55:262-269.
Calandre E P, et al (2016) Expert Rev Neurother 16:1263-1277.
Chen J, et al (2018) Cell reports 22:2307-2321.
Field M J, et al (2006) Proc. of the Nat'l Acad. Sci. USA 103:17537-17542.
Freiman T M, et al (2001) Naunyn-Schmiedeberg's arch. pharmacology 363:537-542.
Fuller-Bicer G A, et al (2009) Amer. j. physiol. Heart & circ. physiol. 297:H117-124.
Gee N S, et al (1996) The Journal of biological chemistry 271:5768-5776.
Grosdidier A, et al (2011a) Journal of computational chemistry 32:2149-2159.
Grosdidier A, et al (2011b) Nucleic acids research 39:W270-277.
Guyon A, et al (2013) The Journal of Neuroscience 33:11643-11654.
Hoppa M B, et al (2012) Nature 486:122-125.
Jensen A A, et al (2002) Molecular pharmacology 61:1377-1384.
Johansson M U, et al (2012) BMC bioinformatics 13:173.
Kang S, et al (2017) Neuropsychopharmacology 42:1813-1824.
Kim R Y, et al (2015) Nature communications 6:8116.
Lanneau C, et al (2001) Neuropharmacology 41:965-975.
Manville R W, et al (2018) Nature communications 9:1847.
Marrion N V, et al (1989) British journal of pharmacology 98:557-573.
Martin D J, et al (2002) Neuropharmacology 42:353-366.
Mason B J, et al (2018) Expert opinion on investigational drugs 27:113-124.
McClelland D, et al (2004) BMC pharmacology 4:14.
Ng G Y, et al (2001) Molecular pharmacology 59:144-152.
Okada M, et al (2003) Epilepsy research 53:81-94.
Parker D A, et al (2004) European journal of pharmacology 495:137-143.
Peng B W, et al (2011) Neuroscience letters 494:19-23.
Rock D M, et a) (1993) Epilepsy research 16:89-98.
Schenzer A, et al (2005) The Journal of Neuroscience 25:5051-5060.
Schumacher T B, et al (1998) Epilepsia 39:355-363.
Sills G J (2006) Current opinion in pharmacology 6:108-113.
Stefani A, et at (1998) Neuropharmacology 37:83-91.
Stefani A, et at (2001) Epilepsy research 43:239-248.
Stringer J L and Lorenzo N (1999) Epilepsy research 33:169-176.
Sun J and MacKinnon R (2017) Cell 169:1042-1050 e1049.
Surges R, et at (2003) Epilepsia 44:150-156.
Tae H S, et al (2017) Frontiers in pharmacology 8:554.
Tatulian L, et al (2001) The Journal of Neuroscience 21:5535-5545.
Taylor C P (1997) Revue neurologique 153 Suppl 1:S39-45.
Tinel N, et al (1998) FEBS letters 438:171-176.
van Gunsteren W F (1996) Biomolecular simulation: the GROMOS96 manual and user guide, Vdf Hochschulverlag ETHZ.
Wang H S, et al (1998) Science 282:1890-1893.
Zaika O, et al (2008) Biophysical journal 95:5121-5137.

Example 3: Cilantro Leaf Harbors a Potent Potassium Channel-Activating Anticonvulsant Herbs have a long history of use as folk medicine anticonvulsants, yet the underlying mechanisms often remain unknown. Neuronal KCNQ potassium channel dysfunction can cause severe epileptic encephalopathies that are resistant to modem anticonvulsants. This Example shows that cilantro (*Coriandrum sativum*), a widely used culinary herb that also exhibits antiepileptic and other therapeutic activities, is a highly efficacious KCNQ channel activator. Screening of cilantro leaf metabolites revealed that one, the long-chain fatty aldehyde (E)-2-dodecenal, activates multiple KCNQs, including the predominant neuronal isoform, KCNQ2/KCNQ3 (EC50, 60 t 20 nM) and the predominant cardiac isoform, KCNQ1/KCNE1 (EC50, 260±100 nM). (E)-2-dodecenal also recapitulated the anticonvulsant action of cilantro, delaying pentylene tetrazole-induced seizures. In silico docking and mutagenesis studies identified the (E)-2-dodecenal binding site, juxtaposed between residues on the KCNQ S5 transmembrane segment and 54-5 linker. The results provide a molecular basis for the therapeutic actions of cilantro and indicate that this ubiquitous culinary herb is surprisingly influential upon clinically important KCNQ channels.

Documented use of botanical folk medicines stretches back as far as recorded human history itself (1). There is DNA evidence suggestive of consumption of plants for medicinal use by *Homo neanderthalensis* 48,000 years ago (2, 3), and archaeological evidence of non-food use by *Homo erectus* or similar species up to 800,000 years ago, of herbs used in the modem era as folk medicines (4). Evidence for the efficacy of such medicines ranges from anecdotal to clinical trials; similarly, mechanisms and active compounds have been elucidated for some botanical medicines while for others the molecular basis of action is unknown (5, 6).

In many cases, botanical medicines of current or historical use are also currently consumed, often on a large scale, as foodstuffs or food flavoring. One example is cilantro (*Coriandrum sativum*), known as coriander in the UK (FIG. 16A). Cilantro has been consumed by human beings for at least 8000 years (based on archaeological evidence from what is now Israel) and was found in the tomb of Tutankhamen and is thought to have been cultivated by the ancient Egyptians (7). Cilantro now grows wild over broad expanses of the globe and its leaves feature heavily in Asian, European and Central American cuisine. Cilantro also has reported anti-cancer, anti-inflammatory, anti-fungal, antibacterial, anti-convulsant, cardioprotective, gastric health and analgesic effects (8). In many cases, the molecular basis and active components of the various therapeutic effects of cilantro are incompletely understood or unknown.

Voltage-gated potassium (Kv) channels within the KCNQ (Kv7) subfamily are sensitive to activation by a range of small molecules, including synthetic drugs, neurotransmitters and metabolites (9-13). Kv channels, including the five isoforms within the KCNQ (Kv7) subfamily, are composed of tetramers of pore-forming (a) subunits each comprising 6 transmembrane segments (S). S1-4 comprise the voltage sensing domain (VSD); S5-6 comprise the pore module (FIG. 16B). Kv channels respond to cell membrane depolarization via movement of their VSD, which causes pore opening and $K^+$ diffusion (predominantly outward) through the pore, reducing action potential frequency or repolarizing the cell following action potential firing. Kv channels can also be activated, and/or their voltage-dependence of activation shifted toward more negative potentials, by a number of small molecules, including specific drugs. In the case of neuronally expressed KCNQ channels, molecules such as the anticonvulsant retigabine bind to a pocket between the VSD and pore (FIG. 16C) to activate the channel by favoring opening at more hyperpolarized potentials; this has antiepileptic effects by raising the barrier for neuronal firing (14).

The KCNQ family exhibits a wide range of tissue expression and functional attributes; KCNQ channels are therefore highly influential in many aspects of human physiology. Heteromeric KCNQ2/3 and also KCNQ3/5 channels generate the muscarinic-receptor-inhibited M-current, a subthreshold Kv current that regulates neuronal firing; homomeric KCNQ2, KCNQ3 and KCNQ5 channels may also contribute (15-19). Activation of KCNQ1, KCNQ4 and KCNQ5 channels expressed in vascular smooth muscle reduces vascular tone (20). KCNQ1 is also expressed in human heart, the inner ear and a variety of epithelia (21); KCNQ4 is expressed in auditory neurons and hair cells (22) and, like KCNQ1 (23), is essential for hearing.

Given the sensitivity of KCNQ channels to various small molecules and their diverse expression and functional roles, many of which potentially match the purported therapeutic effects of cilantro, here we screened KCNQ channels for sensitivity to cilantro. We discovered that cilantro activates various KCNQ isoforms, and identified a single cilantro metabolite (and its KCNQ channel binding site) that underlies the KCNQ-activating and anticonvulsant properties of cilantro.

Materials and Methods
Preparation of Plant Extracts

Certified organic fresh cilantro (*Coriandrum sativum*) was sourced from Mother's Market and Kitchen (Irvine, Calif., US), and homogenized fresh using a blender (SharkNinja, Needham, Mass., US). We then performed a methanolic extraction (80% methanol/20% water) on the cilantro homogenate for 48 hours at room temperature on a rocking platform with occasional inversion of the bottles to more fully resuspend the extract. Following this, the extract was filtered using Whatman filter paper #1 (Whatman, Maidstone, UK) and then the methanol was removed by evaporation in a fume hood for 48 hours at room temperature. The extract was then centrifuged for 10 minutes at 15° C., 4000 RCF to remove remaining particulate matter, followed by storage at −20° C. On the day of electrophysiological recording, the cilantro extract was thawed and then diluted 1:100 in bath solution (see below) immediately before use.

Channel Subunit cRNA Preparation and *Xenopus laevis* Oocyte Injection

As previously described (12), we generated cRNA transcripts encoding human KCNA1, KCNE1, KCNE2, KCNE3, KCNQ1, KCNQ2, KCNQ3, KCNQ4 or KCNQ5 by in vitro transcription using the T7 polymerase mMessage mMachine kit (Thermo Fisher Scientific), after vector linearization, from cDNA sub-cloned into plasmids incorporating *Xenopus laevis* β-globin 5' and 3' UTRs flanking the coding region to enhance translation and cRNA stability. We quantified cRNA by spectrophotometry. We generated mutant KCNQ2 and KCNQ3 cDNAs by site-directed mutagenesis with a QuikChange kit (Stratagene, San Diego, Calif.) and prepared the cRNAs as above. We injected defolliculated stage V and VI *Xenopus laevis* oocytes (Ecocyte Bioscience, Austin, Tex. and Xenoocyte, Dexter, Mich., US) with KCNE and/or KCNQ cRNAs (5-20 ng). We incubated the oocytes at 16° C. in Barth's saline solution (Ecocyte) containing penicillin and streptomycin, with daily washing, for 3-5 days prior to two-electrode voltage-clamp (TEVC) recording.

Two-Electrode Voltage Clamp (TEVC)

We performed TEVC at room temperature using an OC-725C amplifier (Warner Instruments, Hamden, Conn.) and pClamp10 software (Molecular Devices, Sunnyvale, Calif.) 2-5 days after cRNA injection as described in the section above. For recording, we placed the oocytes in a small-volume oocyte bath (Warner) and viewed them with a dissection microscope. We sourced chemicals from Sigma unless otherwise stated. We studied effects of 1% cilantro extract and of nine compounds previously identified in cilantro extract. Vanillic acid and 3,4-Dihydroxybenzoic acid were each solubilized in 100% ethanol at a stock concentration of 100 mM; the other compounds were solubilized directly in bath solution. We initially screened for KCNQ2/3 channel activity using 100 µM concentrations of each of the nine components, then conducted dose responses where appropriate. Bath solution was (in mM): 96 NaCl, 4 KCl, 1 MgCl$_2$, 1 CaCl$_2$, 10 4-(2-hydroxyethyl)-1-piperazineethanesulfonic acid (pH 7.6). We introduced 1% cilantro extract, or each of the nine cilantro components, into the oocyte recording bath by gravity perfusion at a constant flow of 1 ml per minute for 3 minutes prior to recording. Pipettes were of 1-2 MΩ resistance when filled with 3 M KCl. We recorded currents in response to voltage pulses between −120 or −80 mV and +40 mV at 20 mV intervals from a holding potential of −80 mV, to yield current-voltage relationships, current magnitude, and for quantifying activation rate. We analyzed data using Clampfit (Molecular Devices) and Graphpad Prism software (GraphPad, San Diego, Calif., USA); values are stated as mean±SEM. We plotted raw or normalized tail currents versus prepulse voltage and fitted with a single Boltzmann function:

$$g = \frac{(A_1 - A_2)}{\left\{1 + \exp\left[\left(V_{\frac{1}{2}} - V\right)/V_S\right]\right\} + A_2} \quad \text{Eq. 1}$$

where g is the normalized tail conductance, $A_1$ is the initial value at −∞, $A_2$ is the final value at +∞, $V_{1/2}$ is the half-maximal voltage of activation and Vs the slope factor. We fitted activation and deactivation kinetics with single exponential functions.

Chemical Structures and Silico Docking

We plotted and viewed chemical structures and electrostatic surface potential using Jmol, an open-source Java viewer for chemical structures in 3D: jmol.org. For in silico ligand docking predictions of binding to KCNQ2, we first altered the *Xenopus laevis* KCNQ1 cryo-electron microscopy-derived structure (PDB 5VMS) (24) to incorporate KCNQ2 residues important for retigabine binding, and their immediate neighbors, followed by energy minimization as we previously described (12) using the GROMOS 43B1 force field (25) in DeepView (26). We then performed unguided docking of (E)-2-dodecanal to predict potential binding sites, using SwissDock with CHARMM forcefields (27, 28). We used a similar approach to simulate binding to KCNQ1 and KCNQ1/KCNE1, but instead employed closed and open state models of either channel previously developed by others (29).

PTZ Chemoconvulsant Assay

We quantified the anticonvulsant activities of (E)-2-dodecenal and tridecanal in male C57BL/6 mice (Charles River, Wilmington, Mass.) aged 2-3 months. The mice were housed and used according to the recommendations in the Guide for the Care and Use of Laboratory Animals of the National Institutes of Health (NIH Publication, 8th edition, 2011). The study protocol was approved by the Institutional Animal Care and Use Committee of University of California, Irvine. The chemicals were sourced from Sigma (St. Louis, Mo., USA). We used a pentylene tetrazole (PTZ) chemoconvulsant assay as we previously described (30). We injected the mice intraperitoneally with (E)-2-dodecenal (2 or 20 mgkg$^{-1}$) (with or without 2.5 mgkg$^{-1}$ XE991) or tridecanal (20 mgkg$^{-1}$) solubilized in PBS, or vehicle control (PBS), and then 30 minutes later we injected mice intraperitoneally with 80 mgkg-PTZ. Following the PTZ injection, the mice were caged individually and an observer (GWA) blinded to the experimental condition timed the latency to first seizure.

Statistical Analysis

All values are expressed as mean±SEM. One-way ANOVA was applied for all tests; all p values were two-sided. Where appropriate, we applied Tukey's correction for multiple comparisons.

Results

Cilantro Extract Activates Multiple KCNQ Isoforms

We performed a methanolic extraction (80% methanol/20% water) on fresh cilantro (*Coriandrum sativum*) (FIG. 16A). Following removal of the methanol to leave an aqueous solution of cilantro extract, we diluted the extract 1/100 in recording solution and screened for effects first on homomeric neuronal KCNQ channels heterologously expressed in *Xenopus laevis* oocytes, using two-electrode voltage clamp (TEVC) electrophysiology.

Cilantro extract had no effect on water-injected control oocytes (FIG. 16D). In contrast, the cilantro extract exhibited effects on all four neuronal KCNQs. In the case of KCNQ2, KCNQ3 and KCNQ5, cilantro negative-shifted the voltage dependence of activation, the strongest effects being on KCNQ2 and KCNQ5 (FIG. 16E, F). This produced hyperpolarization at rest of cells expressing KCNQ2, KCNQ3* (KCNQ3-A315T, a mutant that passes larger currents than wild-type KCNQ3, facilitating study of the homomeric channel (31)), or KCNQ5 (FIG. 16G). Cilantro extract exhibited potentiation of the early phase of KCNQ4 prepulse currents, but this was not reflected in the tail currents and did not result in shifted resting membrane potential (EM) of KCNQ4-expressing oocytes (FIG. 16E-G). Thus, the most cilantro-sensitive neuronal homomers were KCNQ2 and KCNQ5, compared by examining both the fold increase in tail current (FIG. 16H) and the negative shift in the voltage dependence of activation ($\Delta V_{0.5activation}$) (FIG. 16I; Supplementary Tables 1-4); KCNQ5 also exhibited cilantro-dependent increases in peak tail current (FIG. 16F, left).

KCNQ2/3 heteromers are the primary KCNQ channel generating M-current in mammalian brain, and the main target of retigabine-class anticonvulsants (9, 13). Here, cilantro extract (1/100) was effective at negative-shifting KCNQ2/3 voltage dependence of activation (FIG. 17A, B) and hyperpolarizing KCNQ2/3-expressing cells (FIG. 17C).

The other KCNQ family member, KCNQ1, is retigabine-insensitive and is expressed in human heart and a variety of secretory epithelia including the gastric glands, colon and thyroid (21). KCNQ1 is notable for its functional diversity, largely endowed by formation of complexes with KCNE single-transmembrane spanning ancillary subunits. While homomeric KCNQ1 is functional, it is thought that in vivo KCNQ1 always complexes with KCNE subunits (21). In the human heart and inner ear, KCNQ1-KCNE1 complexes form the relatively positive- and slowly activating $I_{KS}$ current in ventricular myocytes (32, 33). In contrast, constitutively active KCNQ1-KCNE3 channels are expressed in the colonic epithelium basolateral membrane, where they regulate chloride ion secretion (34). KCNQ1 was also activated by cilantro extract (FIG. 17D, E), although this did not influence $E_M$ (FIG. 17F) because the KCNQ1 current potentiation occurred across a narrow voltage range, positive to the resting $E_M$ of KCNQ1-expressing oocytes (FIG. 17E, left). KCNQ1-KCNE1 was more sensitive, with cilantro inducing a larger increase in current (FIG. 17D, E) and hyperpolarizing $E_M$ (FIG. 17F). Cilantro extract even potentiated activity of the constitutively open KCNQ1-KCNE3 channel, almost threefold at −120 mV (FIG. 17D, E), also negative-shifting $E_M$ (FIG. 17F).

Outside the KCNQ family, cilantro induced a relatively small (−5.9±0.9 mV) shift in the voltage dependence of activation of another neuronally expressed Kv channel, KCNA1 (Kv1.1) (FIG. 17G, H) which generated a −10 mV shift in $E_M$ of KCNA1-expressing oocytes (FIG. 17I). Comparing two parameters of negative-shifted voltage-dependent activation (fold-increase in current at −60 mV and $\Delta V_{0.5activation}$) for all channels tested, cilantro extract was most effective at potentiating KCNQ2/3 and KCNQ1/KCNE1 activity; effects on KCNQ1/KCNE3 were also notable as they spanned the entire voltage range tested (FIG. 17J, K; Supplementary Tables 5-9).

A Single Cilantro Metabolite Recapitulates Cilantro Activation of KCNQs

We next screened the predominant metabolites found in cilantro extract for KCNQ2/3 opening activity. Strikingly, out of 9 metabolites tested at 100 μM, only one activated KCNQ2/3—the 12-carbon fatty aldehyde, (E)-2-dodecenal. This specificity was remarkable given that closely related 10, 11 and 13-carbon aldehydes did nothing to KCNQ2/3 activity (FIG. 18A-C). (E)-2-dodecenal both hyperpolarized the activation of KCNQ2/3 and increased its peak tail current at saturating membrane potentials (FIG. 18C) (Supplementary Tables 10-18).

Examining effects on homomeric KCNQs, we found that (E)-2-dodecenal (100 μM) shares a similar efficacy profile to cilantro extract, i.e., it preferentially negative-shifted the $\Delta V_{0.5activation}$ of KCNQ2 and KCNQ5 versus KCNQ1, KCNQ3 and KCNQ4 (FIG. 19A, B; summarized in FIG. 19C). (E)-2-dodecenal most potently activated KCNQ2 ($EC_{50}$, 60±10 nM) versus the other isoforms, as shown in the dose response that again highlighted increased efficacy for KCNQ2 and KCNQ5 versus other isoforms (FIG. 19D; Supplementary Tables 19-24). Strikingly, effects of whole cilantro extract on heteromeric KCNQ2/3 channel activation (increased) and deactivation (decreased) rates (FIG. 19E) were very similar to those induced by (E)-2-dodecenal (FIG. 19F; Supplementary Tables 25-28), further supporting the conclusion that (E)-2-dodecenal is the molecular basis for cilantro activation of KCNQ channels. Importantly, a previous study of the composition of cilantro sourced from the United States identified (E)-2-dodecenal as the primary component, at 15.6%, of essential oil derived from the leaves (35).

Cilantro confers a variety of beneficial effects (8), several of which could potentially involve KCNQ activation. Here, we focused on its effects as an anticonvulsant. Prior work showed that cilantro extract delays the onset (increases latency) of pentylene tetrazole (PTZ)-induced seizures in rats, without altering the overall incidence of clonic or tonic seizures (36). We compared the effects on PTZ-induced seizure latency in mice of (E)-2-dodecenal (2 and 20 mg/kg) versus the closely structurally related, KCNQ2/3-inactive, tridecanal (20 mg/kg). We found that, strikingly, (E)-2-dodecenal increased the latency to first seizure >threefold (p=0.0021; n=15-29) at 20 mgkg$^{-1}$ and almost threefold at 2 mgkg$^{-1}$ (p=0.06; n=16-20), while tridecanal (20 mgkg$^{-1}$) had no effect (p=0.40; n=15), versus day- and age-matched controls for each cohort, injected with PBS (FIG. 19G). The threefold increase in latency with (E)-2-dodecenal was quantitatively very similar to the increase in latency previously observed by others for whole cilantro hydroalcoholic extract (36). In additional seizure studies in a separate cohort of mice, we found that the KCNQ-family specific inhibitor, XE991 (2.5 mgkg$^{-1}$), eliminated the protective effect of (E)-2-dodecenal (20 mgkg$^{-1}$) (p=0.54; n=13-14) (FIG. 19H).

Together with the effects we observed in vitro on KCNQ2/3 and other neuronal KCNQ isoforms, these data support the conclusion that (E)-2-dodecenal is a preeminent component of the anticonvulsant action of cilantro. Additionally, KCNQ3/KCNQ5 channels may also contribute to neuronal M-current and their dysfunction could participate in epilepsy and other hyperexcitability disorders (37, 38). Here, we found that KCNQ3/KCNQ5 channels are almost as (E)-2-dodecenal-sensitive as KCNQ5 (similar potency, ~30% lower efficacy), in contrast to the insensitive homomeric KCNQ3* (Supplementary FIG. 1 A-D, Supplementary Tables 24, 29). Thus, activation of neuronal KCNQ3/KCNQ5 channels could also contribute to the anticonvulsant effects of (E)-2-dodecenal.

Figure 19:
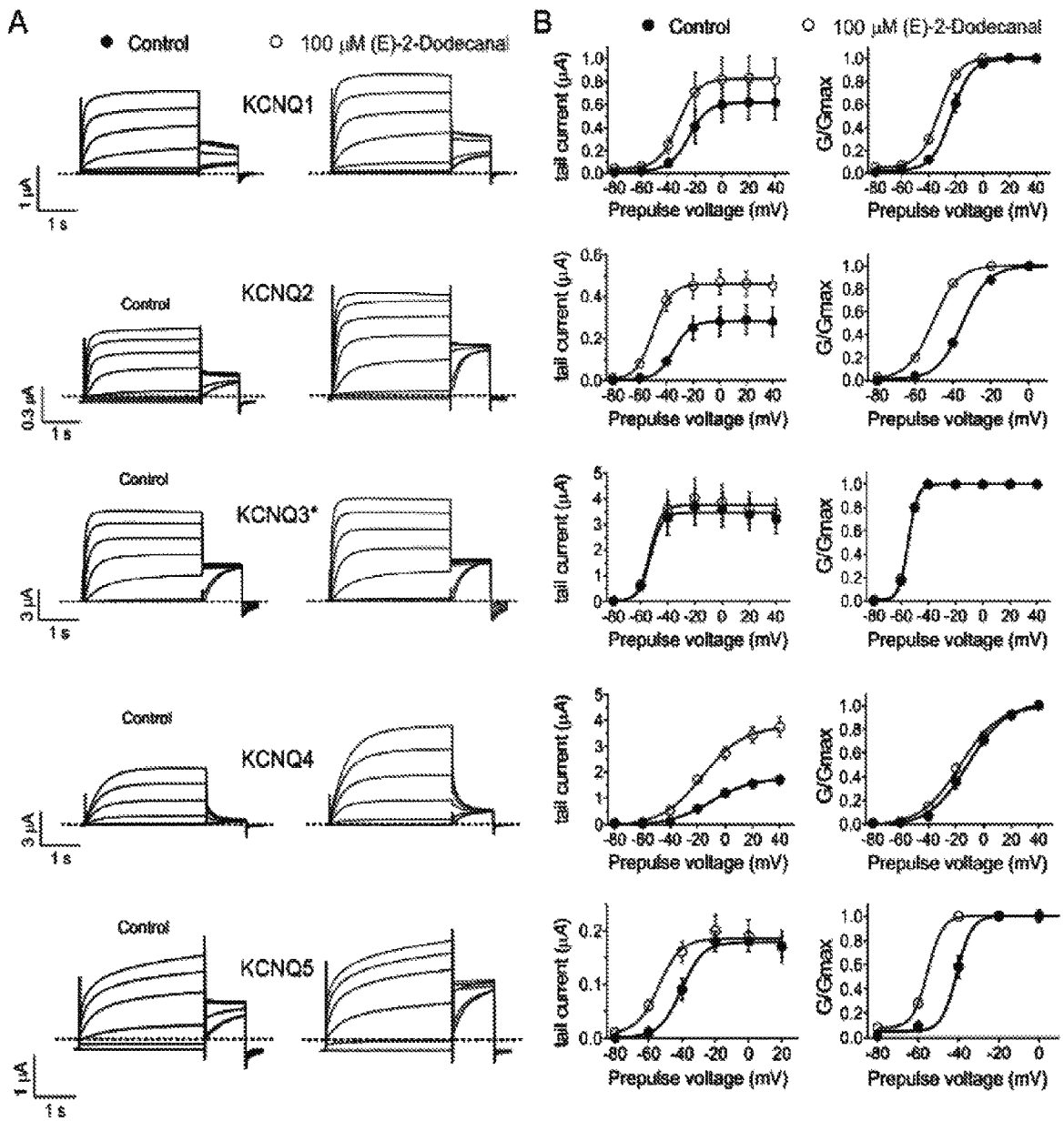
FIG. 19: (E)-2-dodecenal and cilantro extract exhibit similar KCNQ isoform selectivity and anticonvulsant effects. All error bars indicate SEM. (A) Mean TEVC current traces showing effects of (E)-2-dodecenal (100 μM) on homomeric KCNQ channels expressed in *Xenopus* oocytes; n=5 except for KCNQ2 (n=3). (B) Mean tail current (left) and normalized tail currents (G/Gmax) (right) versus prepulse voltage relationships for the traces as A; n=5 except for KCNQ2 (n=3). (C) Mean $\Delta V_{0.5activation}$ induced by (E)-2-dodecenal (100 μM) (scatter plot) versus mean effects of 1% cilantro extract (single bars indicate means from FIGS. 16, 17) for the homomeric KCNQ isoforms indicated; n=5 except for KCNQ2 (n=3). (D) (E)-2-dodecenal dose responses for homomeric KCNQ1-5 channels (n=3-5). (E), (F) Comparison of effects of 1% cilantro extract (E) versus (E)-2-dodecenal (100 μM) (F) on KCNQ2/3 activation and deactivation rate versus voltage; n=6. (G) Mean latency to first pentylene tetrazole (PTZ)-induced seizure for mice pre-injected with: PBS (n=16) versus (E)-2-dodecenal (2 mgkg−1) (n=20) (left); or PBS (n=29) versus tridecanal (20 mgkg−1) (n=15) or (E)-2-dodecenal (20 mgkg−1) (n=15) (right). Statistical analysis was by two-way ANOVA corrected for multiple comparisons. Gold squares=mean values. (H) Mean latency to first pentylene tetrazole (PTZ)-induced seizure for mice pre-injected with PBS (n=14) or 20 mgkg−1 (E)-2-dodecenal+2.5 mgkg−1 XE991 (n=13). Statistical analysis was by two-way ANOVA.
Figure 19:
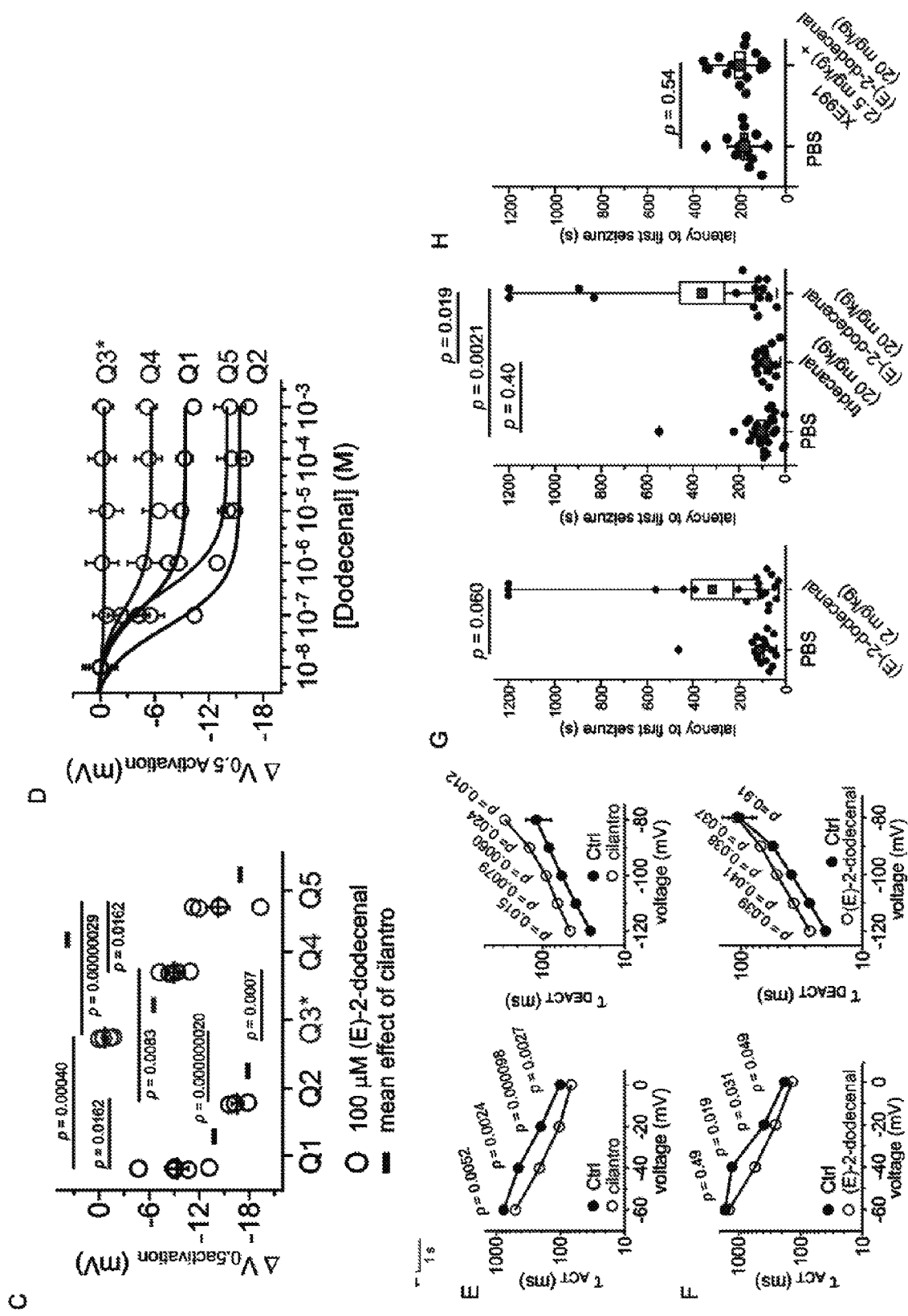
Figure 20:
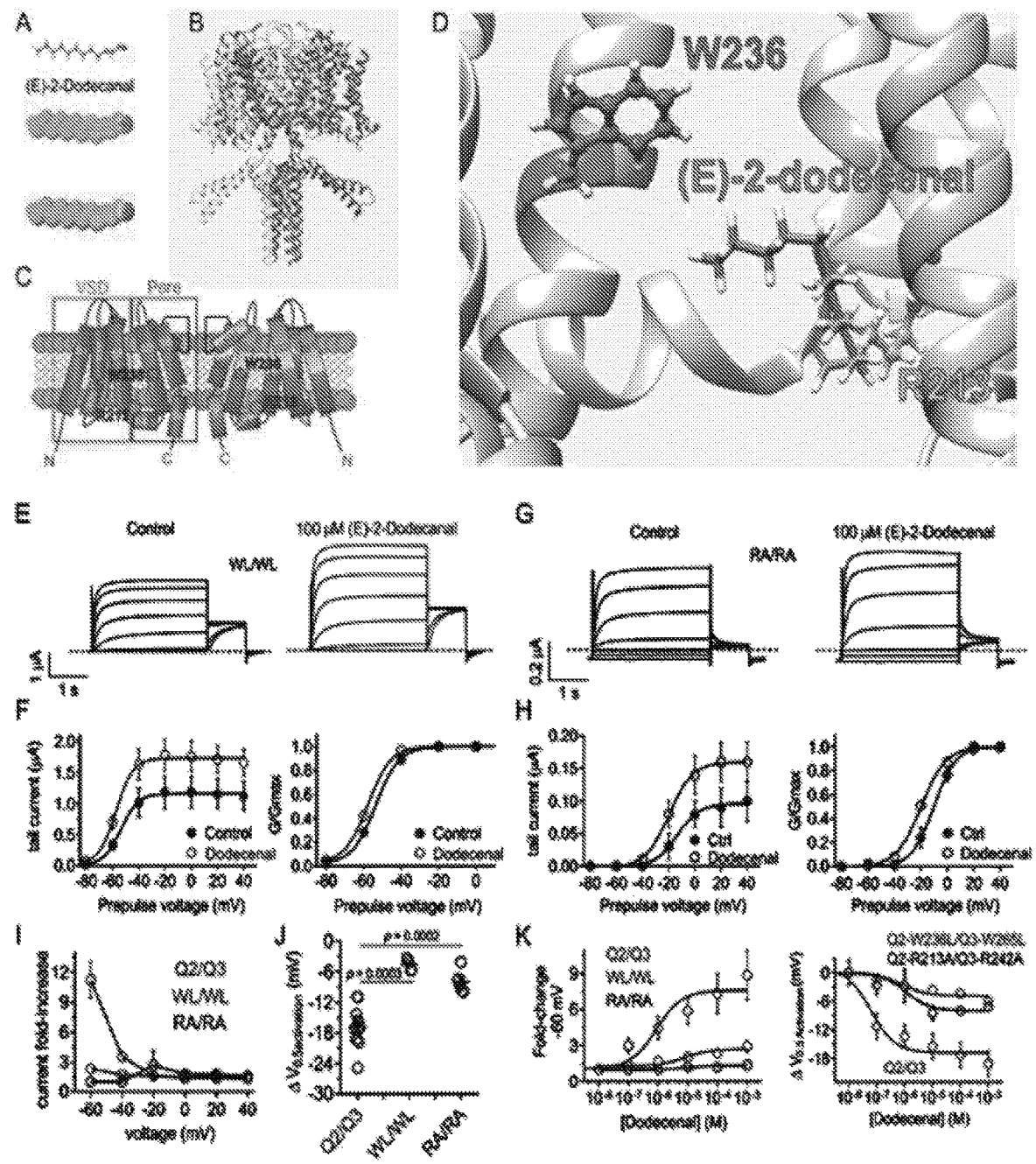
FIG. 20: KCNQ2/3 activation by (E)-2-dodecenal requires a conserved S5 tryptophan and S4-5 arginine. All error bars indicate SEM. (A) (E)-2-dodecenal chemical structure (upper and center) and electrostatic surface potentials (electron-dense; electron-poor; neutral differentially shaded) (lower and center) calculated and plotted using Jmol. (B) Chimeric KCNQ1/KCNQ2 structural model (text shading in D corresponds to KCNQ2-R213; KCNQ2-W236). (C) Topological representation of KCNQ5 showing two of the four subunits, without domain swapping for clarity. Pentagons, approximate position of KCNQ2-R213 and KCNQ2-W236; VSD, voltage sensing domain. (D) View of the (E)-2-dodecenal binding site in KCNQ2 predicted by SwissDock. Differentially shadedline near center, predicted H-bond. (E) Mean TEVC current traces showing effects of (E)-2-dodecenal (100 μM) on KCNQ2-W236L/KCNQ3-W265L (WL/WL) channels expressed in *Xenopus* oocytes (n=5-6). (F) Mean tail current (left) and mean normalized tail currents (G/Gmax) (right) versus prepulse voltage relationships for the traces as in E (n=5-6). (G) Mean TEVC current traces showing effects of (E)-2-dodecenal (100 μM) on KCNQ2-R213A/KCNQ3-R242 (RA/RA) channels expressed in *Xenopus* oocytes (n=5-6). (H) Mean tail current (left) and mean normalized tail currents (G/Gmax) (right) versus prepulse voltage relationships for the traces as in G (n=5-6). (I) Current fold-increase versus voltage in response to (E)-2-dodecenal (100 μM) of wild-type (Q2/Q3), WL/WL and RA/RA KCNQ2/3 channels (n=5-6). (J) Scatter plot showing $\Delta V_{0.5activation}$ in response to (E)-2-dodecenal (100 μM) of wild-type (Q2/Q3), WL/WL and RA/RA KCNQ2/3 channels (n=5-6). (K) (E)-2-dodecenal dose response calculated from fold-increase in current at −60 mV (left) and $\Delta V_{0.5activation}$ (right) for wild-type (Q2/Q3), WL/WL and RA/RA KCNQ2/3 channels; n=5-6.

(E)-2-Dodecenal Activates KCNQ2/3 Via a Binding Site Spanning S5 and the S4-5 Linker (E)-2-dodecenal possesses negative electrostatic surface potential centered at its sole carbonyl oxygen (FIG. 20A). This chemical property was previously found to be prerequisite for activation and/or binding by retigabine and its derivatives, and GABA, of neuronal KCNQ channels (12, 39), via a specific S5 tryptophan (W236 in KCNQ2; W265 in KCNQ3) (40) (FIG. 20B, C). KCNQ1 lacks the equivalent tryptophan and is retigabine-insensitive (39). However, KCNQ1 is sensitive to (E)-2-dodecenal (FIG. 19). We previously discovered that a conserved arginine at the foot of the voltage sensor (FIG. 20C) mediates KCNQ1 (R243) and KCNQ2/3 (R213/R242) activation by mallotoxin (41). To determine the residues required for (E)-2-dodecenal activation of KCNQs, we first used SwissDock to predict possible binding sites of (E)-2-dodecenal to a chimeric structural model based on the cryo-EM-derived structure of KCNQ1 (24) but incorporating residues important for retigabine binding, as we previously described (12). SwissDock predicted that (E)-2-dodecenal binds between (KCNQ2 numbering) W236 and R213, closer to and hydrogen-bonding with the latter (FIG. 20D).

To assess the validity of this prediction we tested the (E)-2-dodecenal sensitivity of KCNQ2/3 channels with mutation to leucine of KCNQ2-W236 and KCNQ3-W265 (FIG. 20E, F) or mutation to alanine of KCNQ2-R213 and KCNQ3-R242 (FIG. 20G, H). Effects of (E)-2-dodecenal (100 μM) were robustly diminished by either pair of mutations, quantified either by current-fold increase versus voltage (FIG. 20I) or $\Delta V_{0.5activation}$ (FIG. 20J). Similar to wild-type KCNQ2 channels, KCNQ2/3 was highly sensitive to (E)-2-dodecenal, exhibiting an $EC_{50}$ of 60 t 20 nM. Dose responses for current-fold increase and for $\Delta V_{0.5activation}$ showed that either pair of mutations reduced both the potency (14 to 19-fold) and efficacy of (E)-2-dodecenal effects on KCNQ2/3 channel activation (FIG. 20K; Supplementary Tables 24, 30-32).

Figure 21:
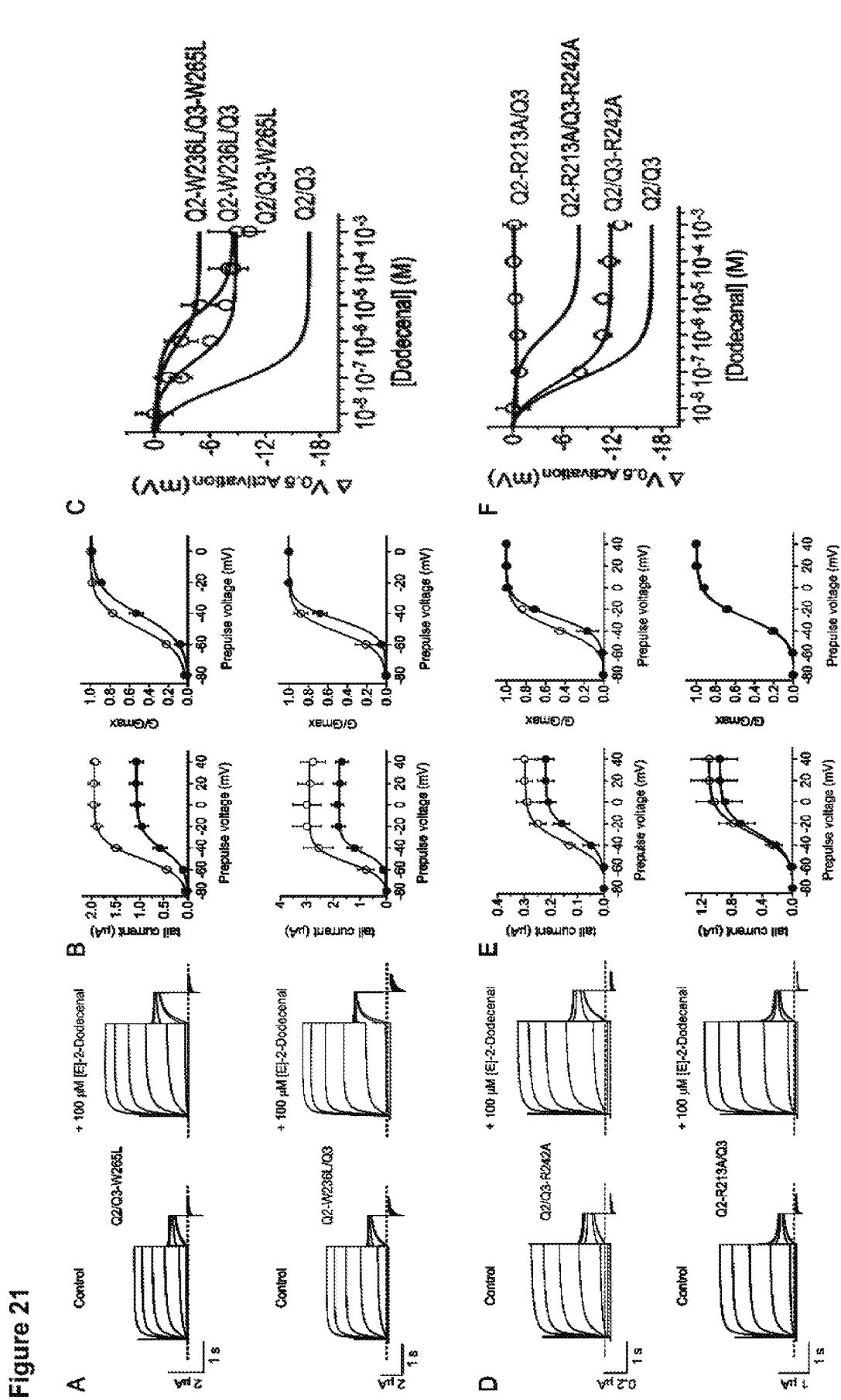
FIG. 21: KCNQ2-R213 is essential for KCNQ2/3 activation by (E)-2-Dodecenal. All error bars indicate SEM. (A) Mean TEVC current traces showing effects of (E)-2-dodecenal (100 μM) on KCNQ2/KCNQ3-W265L (upper) and KCNQ2-W236L/KCNQ3 (lower) channels expressed in *Xenopus* oocytes (n=5-6). (B) Mean tail currents (left) and mean normalized tail currents (G/Gmax) (right) versus prepulse voltage relationships for the traces as in A (n=5-6). (C) (E)-2-dodecenal dose response calculated from $\Delta V_{0.5activation}$ for wild-type, double-mutant (from FIG. 20) and single-mutant KCNQ2/3 channels as indicated; n=5-6. (D) Mean TEVC current traces showing effects of (E)-2-dodecenal (100 μM) on KCNQ2/KCNQ3-R242A (upper) and KCNQ2-R213A/KCNQ3 (lower) channels expressed in *Xenopus* oocytes (n=5). (E) Mean tail currents (left) and mean normalized tail currents (G/Gmax) (right) versus prepulse voltage relationships for the traces as in D (n=5). (F) (E)-2-dodecenal dose response calculated from ΔV0.5 activation for wild-type, double-mutant (from FIG. 20) and single-mutant KCNQ2/3 channels as indicated; n=5.

Studying the effects of the W and R mutants on homomeric KCNQ2 channels is problematic because of relatively low current magnitude, therefore instead we examined the effects of single mutants of KCNQ2 and KCNQ3 in the context of KCNQ2/3 complexes. Each of the S5 W mutants (KCNQ2-W236 and KCNQ3-W265) exerted a similar effect on the maximal shift in KCNQ2/3 $\Delta V_{0.5activation}$ induced by (E)-2-dodecenal, reducing this to −9 mV, a value intermediate between that of wild-type and WL/WL double-mutant KCNQ2/3 channels (FIG. 21A-C). Each of the S5 W mutants also reduced the potency of (E)-2-dodecenal compared to wild-type KCNQ2/3, but the KCNQ2-W236L mutation reduced potency 20-fold more than did the KCNQ3-W265L mutation—from an $EC_{50}$ of 60±20 nM (wild-type) to 5.07±0.5 µM (KCNQ2-W236L/KCNQ3) versus 270±20 nM (KCNQ2/KCNQ3-W265L) (FIG. 21A-C, Supplementary Tables 24, 33, 34).

In contrast, the KCNQ2-R213A mutation rendered KCNQ2/3 channels completely insensitive to (E)-2-dodecenal, while the equivalent KCNQ3-R242A mutant channel responded to (E)-2-dodecenal almost as much as wild-type KCNQ2/3 (similar potency, slightly lower efficacy) (FIG. 21D-F; Supplementary Tables 24, 35, 36).

Overall, the W and R mutant data are consistent with the R being more influential than the W in terms of (E)-2-dodecenal binding/activation, and also with KCNQ2 channels being more sensitive than KCNQ3 to (E)-2-dodecenal. As homomeric KCNQ3* is insensitive to (E)-2-dodecenal (FIG. 19), one might ask why the KCNQ3 mutants have any effect at all. However, Kv channel complexes exhibit "domain swapping", whereby the S4 of one subunit aligns with the pore module of the adjoining subunit, and the binding pocket between the S5 W and the S4-5 R must therefore actually form from two adjoining subunits. Therefore, if as expected in KCNQ2/3 complexes the subunits alternate isoforms, the KCNQ2 W would form a binding site together with the KCNQ3 R, and vice versa, and thus a mutation in KCNQ3 would be predicted to disrupt a drug binding site formed in conjunction with the more sensitive KCNQ2 subunit.

These data support the docking predictions and suggest that (E)-2-dodecenal activates KCNQ2/3 channels by binding in a site spanning S5 and the S4-5 linker, specifically between (KCNQ2 numbering) W236 and R213, with KCNQ2-R213 being the most influential residue tested.

KCNE1 Impacts the KCNQ1 (E)-2-Dodecenal Binding Site

Figure 17:
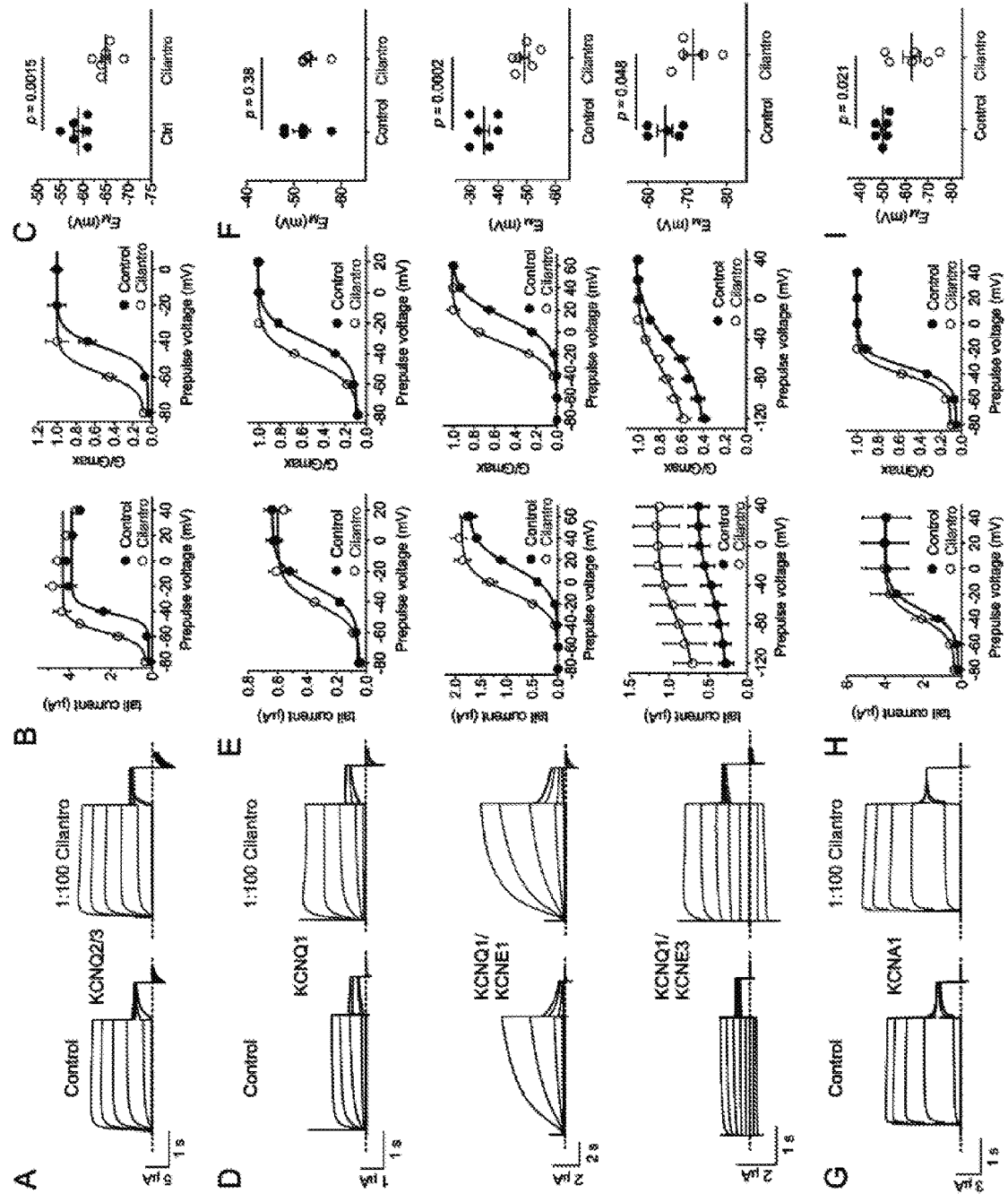
FIG. 17: Cilantro extract differentially activates heteromeric KCNQ channels. All error bars indicate SEM. (A) Left, mean TEVC current traces for *Xenopus* oocytes expressing KCNQ2/3 in the absence (control) or presence of 1% cilantro extract (n=5). (B) Mean tail current (left) and normalized tail current (G/Gmax) (right) versus prepulse voltage relationships for the KCNQ2/3 traces as in A (n=5). (C) Effects of 1% cilantro extract on $E_M$ of unclamped oocytes expressing KCNQ2/3 (n=5). Statistical analysis by two-way ANOVA. (D) Left, mean TEVC current traces for *Xenopus* oocytes expressing homomeric KCNQ1 or heteromeric KCNQ1-KCNE channels as indicated in the absence (control) or presence of 1% cilantro extract (n=5-6). (E) Mean tail current (left) and normalized tail current (G/Gmax) (right) versus prepulse voltage relationships for the traces as in D (n=5-6). (F) Effects of 1% cilantro extract on EM of unclamped oocytes expressing the channels indicated in D (n=5-6). Statistical analysis by two-way ANOVA. (G) Left, mean TEVC current traces for *Xenopus* oocytes expressing homomeric KCNA1 in the absence (control) or presence of 1% cilantro extract (n=6). (H) Mean tail current (left) and normalized tail current (G/Gmax) (right) versus prepulse voltage relationships for the traces as in G (n=6). (I) Effects of 1% cilantro extract on EM of unclamped oocytes expressing KCNA1 (n=6). Statistical analysis by two-way ANOVA. (J) Current fold-increase versus voltage for the Kv channel isoforms indicated, induced by 1% cilantro extract (n=5-6). (K) Scatter plot showing mean ΔV0.5 activation induced by 1% cilantro extract for the Kv channel isoforms indicated; n=5-6. Statistical analysis by two-way ANOVA corrected for multiple comparisons.
Figure 17:
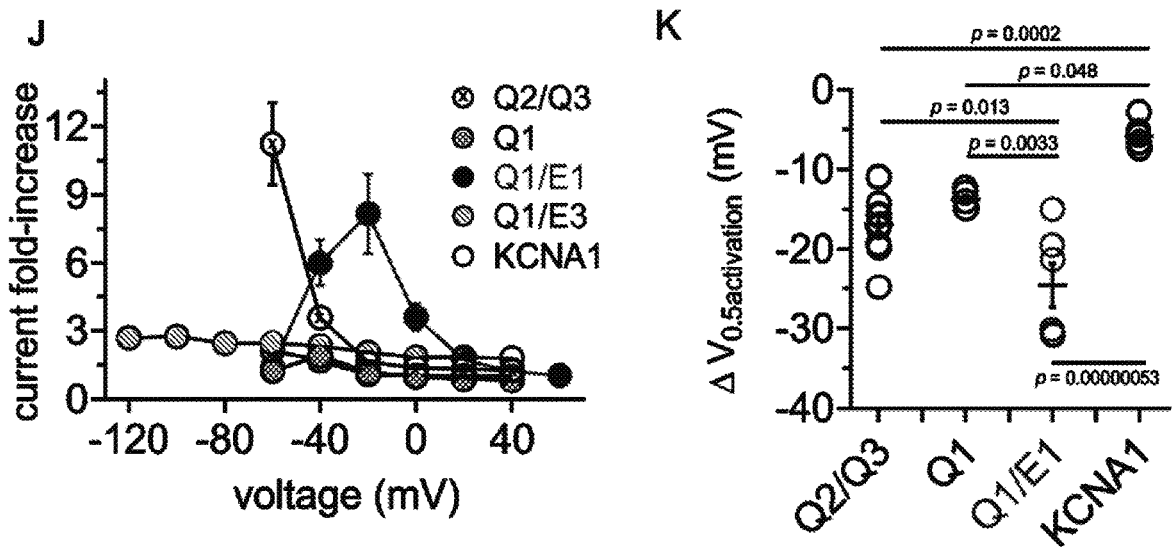
Figure 18:
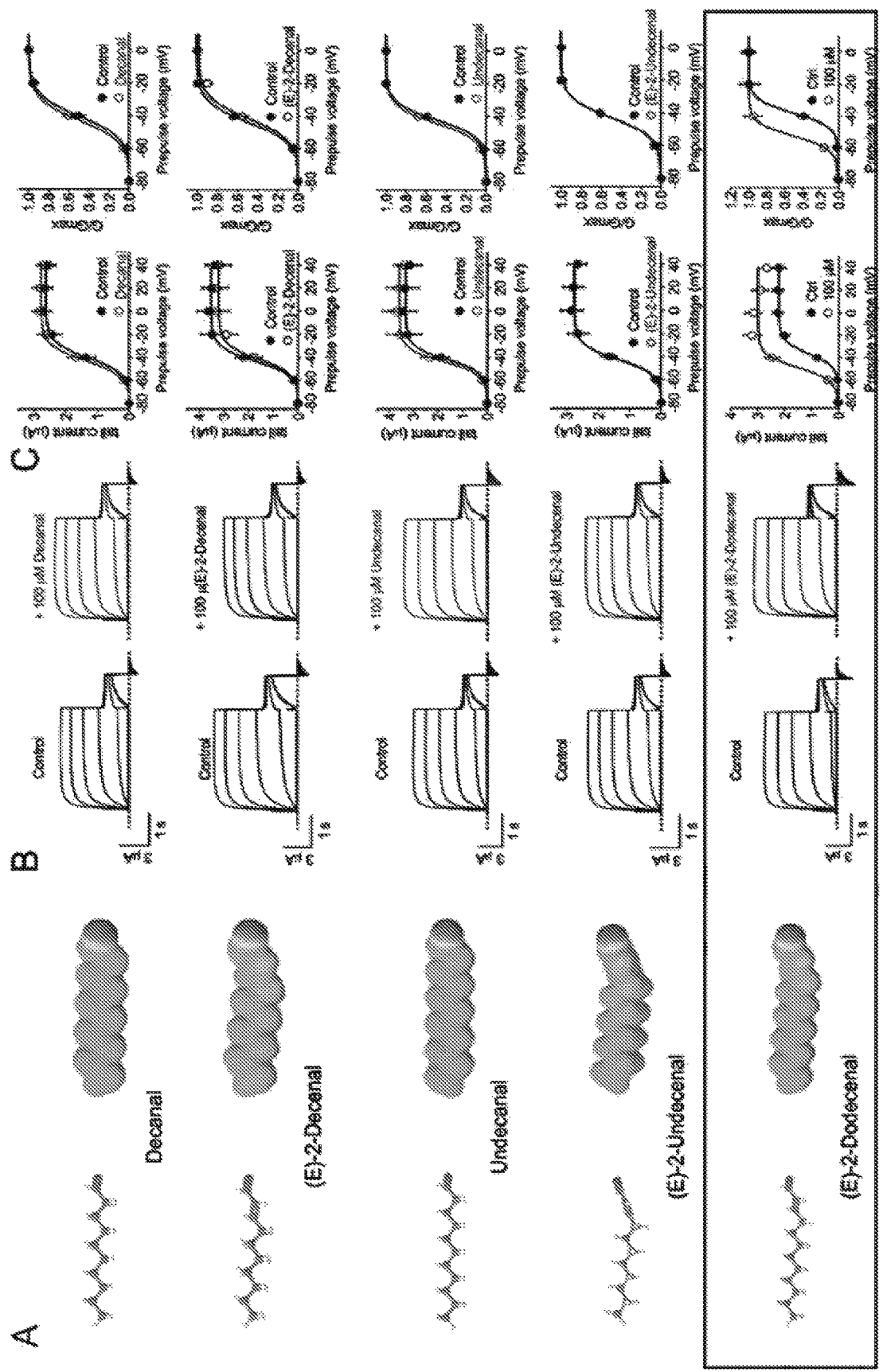
FIG. 18: (E)-2-dodecenal is the KCNQ2/3-activating metabolite in cilantro. All error bars indicate SEM. Box indicates the sole hit, (E)-2-dodecenal. (A) Chemical structures (left; differential shading in right-most is oxygen) and electrostatic surface plots (right; differential shading for negative, positive) of the cilantro compounds screened in this study. (B) Mean TEVC current traces showing effects of compounds in A (all 100 μM) on KCNQ2/3 expressed in *Xenopus* oocytes (n=5-11). (C) Mean tail current (left) and normalized tail currents (G/Gmax) (right) versus prepulse voltage relationships for the traces as in B (n=5-11). 3,4DHBA=3,4-Dihydroxybenzoic Acid.

KCNQ1 lacks the KCNQ2-W236 equivalent, but possesses the KCNQ2-R213 equivalent (R243 in human KCNQ1); therefore we also investigated the mechanism of (E)-2-dodecenal binding in KCNQ1 channels, and how this might be impacted by co-assembly with KCNE regulatory subunits. While (E)-2-dodecenal had minimal effects on KCNQ1/KCNE2 (Supplementary FIG. 1E, F; Supplementary Table 37), cilantro (FIG. 17) and (E)-2-dodecenal (Supplementary FIG. 16G, H) each activated KCNQ1/KCNE3 across the voltage range. Given that the minimal voltage dependence of KCNQ1/KCNE3 complexes stymies quantification of effects, here we focused on KCNQ1/KCNE1, which we showed earlier was activated by cilantro (FIG. 17).

Figure 22:
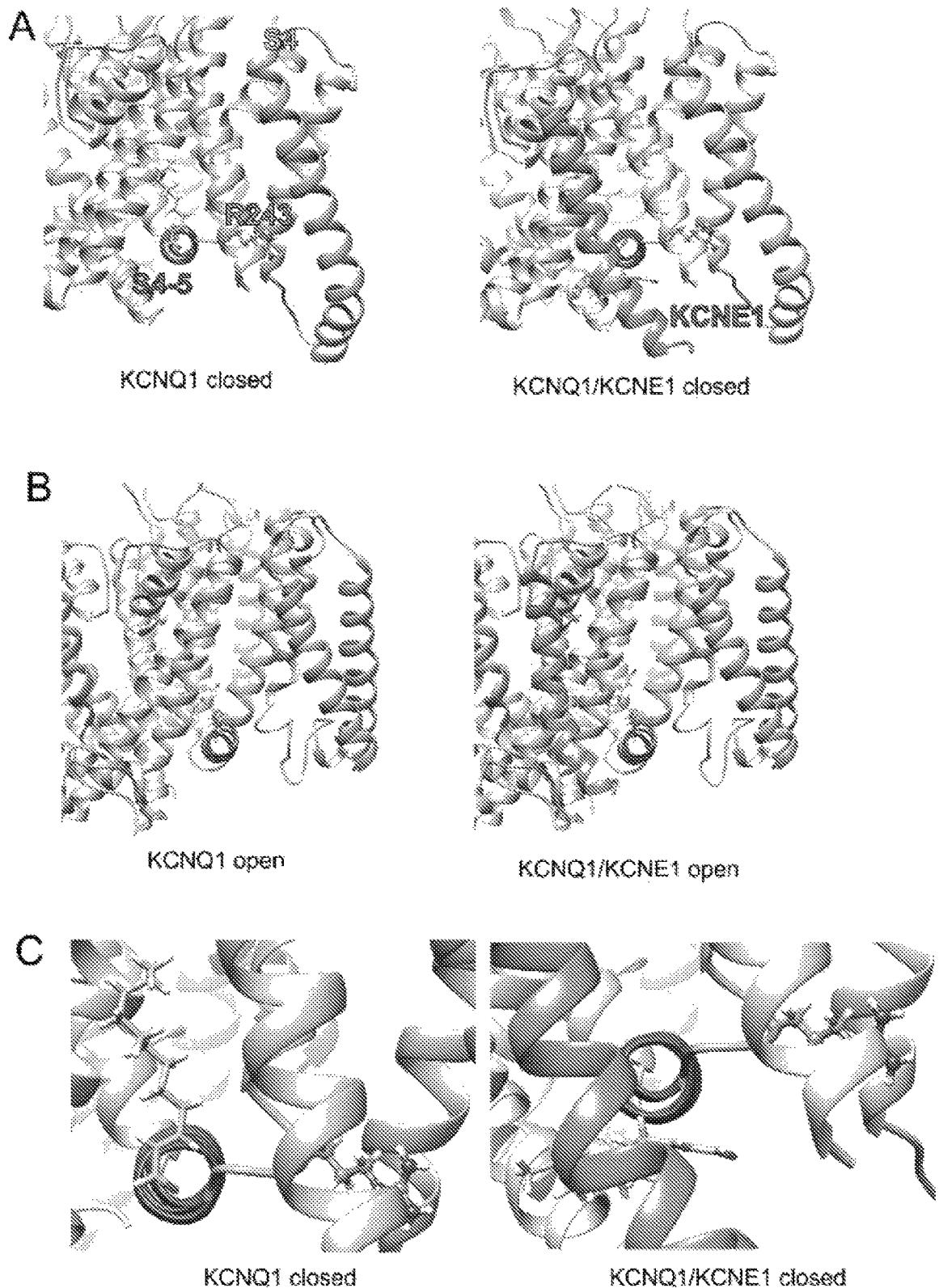
FIG. 22: KCNE1 impinges on the KCNQ1 (E)-2-dodecenal binding site. All error bars indicate SEM. For structural models: Differential shading of lettering corresponds to: KCNE1; KCNQ1-S4; KCNQ1-S4/5 linker; KCNQ1-R243; (E)-2-dodecenal. (A) View of the (E)-2-dodecenal binding site predicted by SwissDock in the KCNQ1 (upper) and KCNQ1/KCNE1 (lower) closed-state models. (B) View of the (E)-2-dodecenal binding site predicted by SwissDock in the KCNQ1 (upper) and KCNQ1/KCNE1 (lower) open-state models. (C) Close-up view of the (E)-2-dodecenal binding site predicted by SwissDock (from panel A), highlighting the predicted KCNE1-induced shift in the (E)-2-dodecenal binding pose in the closed-state models. (D) Mean TEVC current traces (left) and mean tail current versus prepulse voltage relationships (right) showing effects of (E)-2-dodecenal (100 μM) on channels indicated (n=5). (E) Mean normalized tail current (G/Gmax) versus prepulse voltage relationships showing effects of (E)-2-dodecenal (100 μM) (dashed lines) on the voltage dependence of activation of wild-type and R243A KCNQ1 (Q1) alone (left) or with KCNE1 (E1) (right); n=5. Wild-type KCNQ1 data is from FIG. 19B. (F) (E)-2-dodecenal dose response calculated from $\Delta V_{0.5activation}$ for wild-type and R243A KCNQ1 (Q1) alone (left) or with KCNE1 (E1) (right); n=5. Wild-type KCNQ1 data is from FIG. 19B.
Figure 22:
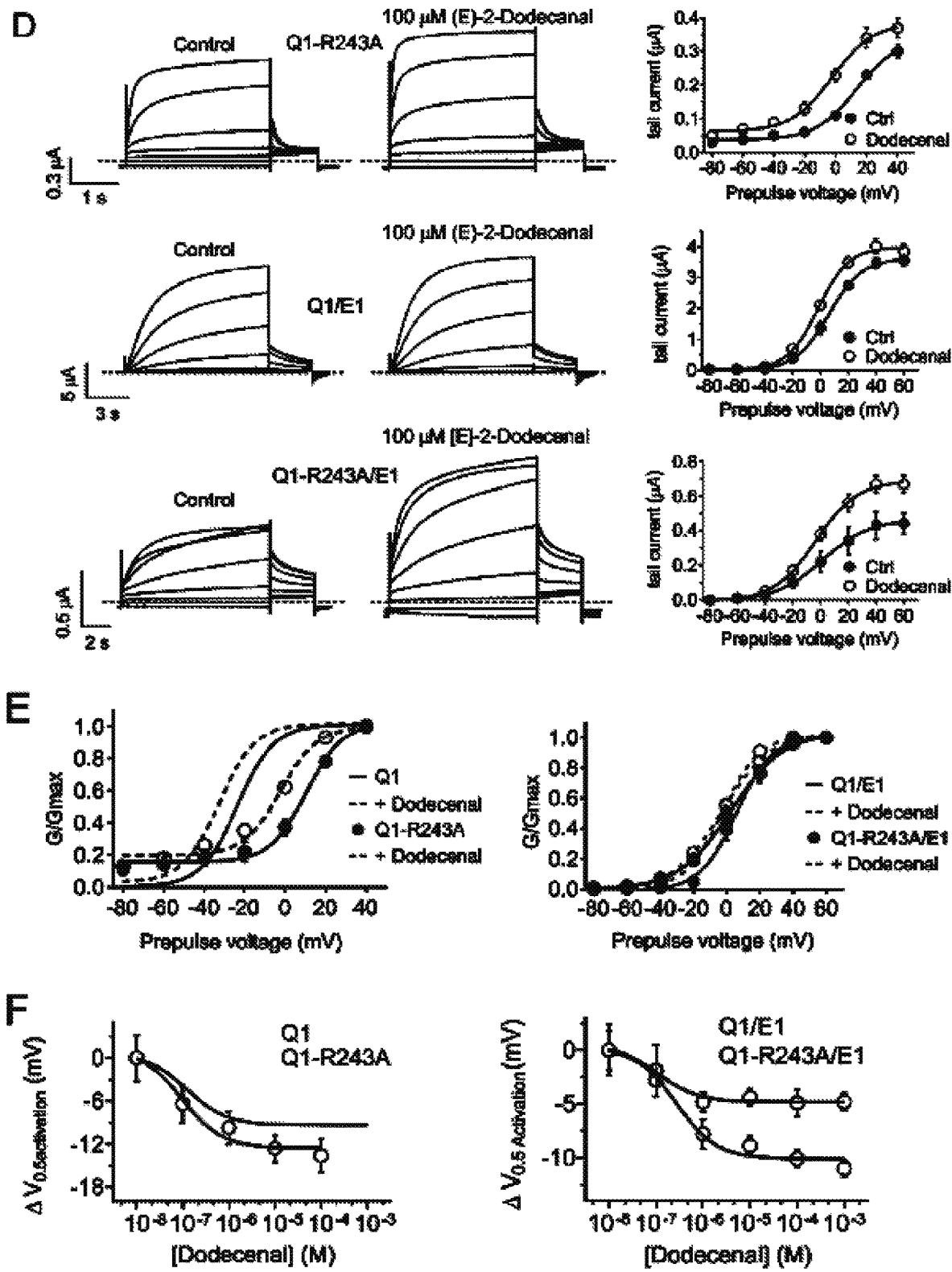

We first performed in silico docking to predict possible binding sites of (E)-2-dodecenal to KCNQ1 and KCNQ1/KCNE1 channels, using coordinates from previously published closed and open-state models (29) (FIG. 22A, B). This revealed a possible binding site for (E)-2-dodecenal close to the KCNQ1 S4-5 linker and in the vicinity of R243, in the closed state (FIG. 22A). Interestingly, (E)-2-dodecenal was predicted to bind proximal to KCNE1, which altered the position of (E)-2-dodecenal in docking simulations predicting binding proximal to R243 (FIG. 22A, C). In the open state, KCNE1 did not alter the predicted binding site of (E)-2-dodecenal (FIG. 22B).

We tested the predicted influence of KCNE1 by comparing effects on (E)-2-dodecenal binding of an R243A mutation in KCNQ1 versus KCNQ1/KCNE1 channels using TEVC (FIG. 22D). In homomeric KCNQ1, the R243A mutation positive-shifted $\Delta V_{0.5activation}$ and introduced a minor constitutively active current component, as we previously reported (42). Moreover, the mutation slightly increased (E)-2-dodecenal efficacy for KCNQ1 activation (FIG. 22E, F; Supplementary Tables 24, 38). In contrast, the R243A mutation had only minor effects on KCNQ1-KCNE1 $\Delta V_{0.5activation}$, as we also previously reported (42). Wild-type KCNQ1-KCNE1 was >twofold less sensitive than KCNQ1 to (E)-2-dodecenal, but with similar efficacy (FIG. 22F: Supplementary Table 24). In contrast to mutant effects on homomeric KCNQ1, the R243A mutation reduced (E)-2-dodecenal efficacy twofold in KCNQ1/KCNE1 channels, while more than doubling the sensitivity (FIG. 22F; Supplementary Tables 24, 39, 40). The results suggest that both KCNQ1-R243 and KCNE1 influence (E)-2-dodecenal binding.

Discussion

Our findings demonstrate for the first time a specific molecular basis for the anticonvulsant effects of cilantro, and show that this widely and frequently used food plant is highly effective at activating multiple isoforms within a clinically prominent family of human Kv channels. Aside from its noted anticonvulsant action, cilantro has historically been used to treat hypertension, digestive disorders, and has reported anti-inflammatory, antibacterial, analgesic and other potentially therapeutic properties (8). The tissue expression of cilantro-sensitive KCNQs suggests their activation could contribute to many of the reported therapeutic effects of cilantro.

The activity profile of (E)-2-dodecenal in delaying seizure onset is remarkably similar to that observed for cilantro extract in a previous study employing PTZ-induced seizures in rats (36). We observed anticonvulsant activity at 2 mgkg$^{-1}$ (E)-2-dodecenal, equivalent to 11 µM, a concentration at which the (E)-2-dodecenal dose response curve for shifting the $\Delta V_{0.5activation}$ of KCNQ2/3 saturates (FIG. 20K, right). Coupled with the highly similar KCNQ activation profiles of (E)-2-dodecenal and whole cilantro extract, this provides strong evidence for (E)-2-dodecenal activation of KCNQs (and likely primarily KCNQ2/3 heteromers) being the molecular basis for the anticonvulsant effects of cilantro.

Furthermore, (E)-2-dodecenal, also known as eryngial, is the primary component of the essential oil produced from leaves of *Eryngium foetidum*, (culantro or Mexican coriander), a plant also used extensively as a food across Asia, Africa and the Caribbean, and utilized in folk medicine as an anticonvulsant and hypotensive, among other applications (43). Interestingly, the neuronally-expressed (44) channel KCNQ5 is also highly expressed in the vasculature (45, 46) and its activation reduces vascular tone, potentially reducing blood pressure (20). Here, we found cilantro extract and specifically (E)-2-dodecenal, previously identified as the predominant component of cilantro leaf oil (35), to be a highly efficacious KCNQ5 activator, suggesting a possible molecular basis contributing to the historical use of cilantro and culantro as folk hypotensives, an application that was recently verified using cilantro crude extract in animal studies (47). KCNQ5 gene variants (48) and aberrant splicing (49) that impair its function cause epilepsy (and severe intellectual disability), suggesting its activation could also contribute to the anticonvulsant action of cilantro (and (E)-2-dodecenal).

We also found that co-assembly with KCNE1 influenced the cilantro (and (E)-2-dodecenal)-sensitivity of KCNQ1. KCNQ1-KCNE1 complexes generate the $I_{Ks}$ current that helps to repolarize ventricular cardiomyocytes. $I_{Ks}$ is down-regulated in heart failure, and this is suggested to contribute to increased risk of ventricular fibrillation in heart failure (50). It is fascinating, then, that cilantro extract was recently found to improve left ventricular function in heart failure (51). KCNQ1 also forms complexes with KCNE across along the gastrointestinal tract—with KCNE2 (in the stomach) and KCNE3 (in the colon, intestine and duodenum) (21). Here we found that KCNQ1-KCNE3 channel activity is potentiated by cilantro and by (E)-2-dodecenal. Stimulation of KCNQ1-KCNE3 activity by cilantro lower in the gastrointestinal tract would be expected to increase cAMP-stimulated Cl⁻ secretion (34) and thus promote digestion and buffer the luminal environment to protect against damage from gastric acid effluent (52). Activation of KCNQ5 by cilantro could also contribute to its gut stimulatory properties, as KCNQ5 is also expressed in gastrointestinal smooth muscle (53) and its activation might therefore relax muscle, potentially being therapeutic in gastric motility disorders such as diabetic gastroparesis.

The KCNQ activation profile of (E)-2-dodecenal bears both similarities and differences to that of other KCNQ openers. We recently found that mallotoxin, from the shrub *Mallotus oppositifolius*, which is used in African folk medicine, also activates KCNQ1-5 homomers, prefers KCNQ2 over KCNQ3, and in docking simulations binds in a pose reminiscent to that predicted for (E)-2-dodecenal, between (KCNQ2 numbering) R213 and W236. As for (E)-2-dodecenal (FIG. 20), the importance for mallotoxin binding of R213 outweighs that of W236, as determined using site-directed mutagenesis and TEVC of wild-type and mutant KCNQ2/3 channels (11, 41). Interestingly, mutation of human KCNQ2-R213 is associated with benign familial neonatal convulsions (54) and the residue represents a hinge point between the pore module and the VSD.

While retigabine does not activate KCNQ1, because it lacks the equivalent S5 tryptophan (39), (E)-2-dodecenal and mallotoxin both do. Although the KCNQ family-conserved arginine at the voltage sensor foot (R243 in KCNQ1) was essential for mallotoxin binding to KCNQ2/3, KCNQ1 and KCNQ1/KCNE1 channels (41), an arginine at position 243 was not essential for (E)-2-dodecenal activation of KCNQ1 or KCNQ1/KCNE1. However, docking simulations and shifts in potency and efficacy resulting from R243A mutation suggest (E)-2-dodecenal binds somewhat proximal to R243 and the S4-5 linker (FIG. 22), placing it in a location where its binding conformation can be influenced by KCNE1 (29). While (E)-2-dodecenal shares with mallotoxin a preference for KCNQ2 and KCNQ5 over KCNQ3 and KCNQ4 (41), both botanical compounds (which incidentally share negligible structural similarity with one another) offer a different activity profile to typical synthetic KCNQ openers. Thus, retigabine and ML213 slightly favor KCNQ3 over KCNQ2, 4 and 5. ICA-069673 is a 20-fold more activator of KCNQ2/3 versus KCNQ3/5 activation (55), but also strongly activates KCNQ4 (56); in contrast, ICA-27243 is >20-fold more potent at opening KCNQ2/3 versus KCNQ4 (57).

(E)-2-dodecenal is a trans-2,3-unsaturated fatty aldehyde that possesses a carbonyl oxygen at one end, which is predicted to provide a strong negative electrostatic surface potential in that region of the molecule (FIG. 18A). This chemical property is required for binding of retigabine to the S5 tryptophan of KCNQ channels (W236 in KCNQ2); yet, in our docking simulations, the carbonyl oxygen instead participated in hydrogen bonding with KCNQ2-R213 and the uncharged end faced W236. Furthermore, several cilantro leaf components highly similar to (E)-2-dodecenal, including 10, 11 and 13-carbon species each containing the similarly positioned and negative surface-charged carbonyl oxygen, were completely inactive against KCNQ2/3 (at 100 µM). Whether the chain length of (E)-2-dodecenal is crucial to it accessing the KCNQ binding site, versus it being the perfect size to activate once inside the binding site, we do not yet know, but the chemical selectivity for KCNQ2/3 opening activity within this family of trans-2-alkenals is remarkable. In contrast, (E)-2-dodecenal is also an effective antibiotic (probably contributing to the antibacterial effects of cilantro) but in this case bactericidal potency increases with each $CH_2$ group up to (E)-2-dodecenal and the bactericidal activity $EC_{50}$ is >30 µM. The bactericidal activity reflects a nonspecific (but nevertheless effective) activity probably stemming from the nonionic surfactant properties of (E)-2-dodecenal (58).

In addition to the widespread use of cilantro in cooking and as an herbal medicine, (E)-2-dodecenal itself is in broad use as a food flavoring and to provide citrus notes to cosmetics, perfumes, soaps, detergents, shampoos and candles (59). Our mouse seizure studies suggest it readily accesses the brain and it is likely that its consumption as a food or herbal medicine (in cilantro) or as an added food flavoring would result in KCNQ-active levels in the human body; we found the 1% cilantro extract an efficacious KCNQ activator, and (E)-2-dodecenal itself showed greater than half-maximal opening effects on KCNQ2/3 at 100 nM (>10 mV shift at this concentration) ($EC_{50}$, 60 t 20 nM). We anticipate that its activity on KCNQ channels contributes significantly to the broad therapeutic spectrum attributed to cilantro, which has seen it persist as a folk medicine for thousands of years throughout and perhaps predating human recorded history.

REFERENCES

1. Inskeep, R. R. (1969) *South African Archaeological bulletin* 24, 21-29
2. Hardy, K., et al. (2012) *Naturwissenschaften* 99, 617-626
3. Weyrich, L. S., et al. (2017) *Nature* 544, 357-361
4. Melamed, Y., et al. (2016) *Proc. Nat'l Acad. Sci. USA* 113, 14674-14679
5. Hoffmann, D. (2003) *Medical Herbalism: the science and practice of herbal medicine*, Healing Arts Press, Rochester, Vt.
6. Moerman, D. E. (2009) *Native American Medicinal Plants*, Timber Press, Portland, Oreg.
7. Cumo, C. (2013) Encyclopedia of cultivated plants: from Acacia to Zinnia, ABC-CLIO, Santa Barbara, Calif., US
8. Sahib, N. G., et al. (2013) *Phytother Res* 27, 1439-1456
9. Main, M. J., et al. (2000) *Molecular pharmacology* 58, 253-262
10. Manville, R. W., and Abbott, G. (2018) *Molecular pharmacology* 94, 1155-1163
11. Manville, R. W., and Abbott, G. W. (2018) *Nature communications* 9, 3845
12. Manville, R. W., P et al. (2018) *Nature communications* 9, 1847
13. Wickenden, A. D., et al. (2000) *Molecular pharmacology* 58, 591-600
14. Tatulian, L., et al. (2001) *The Journal of Neuroscience* 21, 5535-5545
15. Biervert, C., et al. (1998) *Science* 279, 403-406
16. Klinger, F., et al. (2011) *NeuroImage* 58, 761-769
17. Singh, N. A., et al. (1998) *Nature genetics* 18, 25-29
18. Tzingounis, A. V., et al. (2010) *Proc. Nat'l Acad. Sci. USA* 107, 10232-10237
19. Wang, H. S., et al. (1998) *Science* 282, 1890-1893

20. Yeung, S. Y., et al. (2007) *British journal of pharmacology* 151, 758-770
21. Abbott, G. W. (2014) *New Journal of Science* 2014, 26
22. Kubisch, C., et al. (1999) *Cell* 96, 437-446
23. Neyroud, N., et al. (1997) *Nature genetics* 15, 186-189
24. Sun, J., and MacKinnon, R. (2017) *Cell* 169, 1042-1050 e1049
25. van Gunsteren, W. F. (1996) Biomolecular simulation: the GROMOS96 manual and user guide, Vdf Hochschulverlag ETHZ
26. Johansson, M. U., et al. (2012) *BMC bioinformatics* 13, 173
27. Grosdidier, A., et al. (2011) *Nucleic acids research* 39, W270-277
28. Grosdidier, A., et al. (2011) *Journal of computational chemistry* 32, 2149-2159
29. Kang, C., et al. (2008) *Biochemistry* 47, 7999-8006
30. Abbott, G. W., et al. (2014) *Science signaling* 7, ra22
31. Etxeberria, A., et al. (2004) *The Journal of Neuroscience* 24, 9146-9152
32. Tyson, J., et al. (1997) *Human molecular genetics* 6, 2179-2185
33. Vetter, D. E., et al. (1996) *Neuron* 17, 1251-1264
34. Schroeder, B. C., et al. (2000) *Nature* 403, 196-199
35. Potter, T. L. (1996) *Journal of Agricultural and Food Chemistry* 44, 1824-1826
36. Karami, R., et al. (2015) *Iran J Neurol* 14, 59-66
37. Gilling, M., et al. (2013) *Frontiers in genetics* 4, 54
38. Lerche, C., et al. (2000) *The Journal of biological chemistry* 275, 22395-22400
39. Schenzer, A., et al. (2005) *The Journal of Neuroscience* 25, 5051-5060
40. Kim, R. Y., et al. (2015) *Nature communications* 6, 8116
41. De Silva, A. M., et al. (2018) *Sci Adv* 4, eaav0824
42. Panaghie, G., Abbott, G. W. (2007) *The Journal of general physiology* 129, 121-133
43. Paul, J. H., et al. (2011) *Fitoterapia* 82, 302-308
44. Schroeder, B. C., et al. (2000) *The Journal of biological chemistry* 275, 24089-24095
45. Mackie, A. R., et al. (2008) *The Journal of pharmacology and experimental therapeutics* 325, 475-483
46. Yeung, S., et al. (2008) *British journal of pharmacology* 155, 62-72
47. Jabeen, Q., et al. (2009) *Journal of ethnopharmacology* 122, 123-130
48. Lehman, A., et al. (2017) *American journal of human genetics* 101, 65-74
49. Rosti, G., et al. (2018) *Eur J Med Genet* doi.org/10.1016/j.ejmg.2018.10.007
50. Lau, E., et al. (2015) *PloS one* 10, e0122754
51. Dhyani, N., et al. (2018) *J Diet Suppl*, 1-14
52. Walker, N. M., et al. (2002) *Gastroenterology* 123, 531-541
53. Jepps, T. A., et al. (2009) *Am. j. physiol. Gastrointestinal & liver physiology* 297, G107-115
54. Miceli, F., et al. (2013) *Proc. Nat'l Acad. Sci. USA* 110, 4386-4391
55. Amato, G., et al. (2011) *ACS medicinal chemistry letters* 2, 481-484
56. Brueggemann, L. I., et al. (2014) *Molecular pharmacology* 66, 330-341
57. Wickenden, A. D., et al. (2008) *Molecular pharmacology* 73, 977-986
58. Kubo, I., et al. (2004) *J Agric Food Chem* 52, 3329-3332
59. Zviely, M. (2009) *Perfumer & Flavorist* 34, 26-28

Example 4: Re-Engineering a Neurotransmitter to Isoform-Selectively Activate Kv Channels Voltage-gated potassium (Kv) channel loss-of-function causes a variety of inherited disorders, but developing small molecules that activate Kv channels has proven challenging. As described above, the inhibitory neurotransmitter γ-aminobutyric acid (GABA) directly activates Kv channels KCNQ3 and KCNQ5. In this Example, finding that inhibitory neurotransmitter glycine is KCNQ-inactive, we re-engineered it in silico to introduce predicted KCNQ-opening properties, screened by in silico docking, then validated the hits functionally and mechanistically in vitro and in vivo. Attaching a fluorophenyl ring centered glycine surface negative electrostatic potential on its carbonyl oxygen, converting glycine to a low-nM affinity KCNQ channel activator that competes with GABA for KCNQ binding. Repositioning the phenyl ring fluorine and/or adding a methylsulfonyl group increased efficacy and switched the KCNQ activation isoform-selectivity. Combining KCNQ2- and KCNQ3-selective glycine derivatives synergistically potentiated KCNQ2/3 activation by exploiting its heteromeric composition. Thus, in silico optimization and docking, with real-world screening of only three compounds, facilitated glycine re-engineering into several novel, potent KCNQ isoform-selective activators.

Voltage-gated potassium (Kv) channel pore-forming α subunits are generated by a numerous and diverse gene family comprising 40 members in the human genome, separated into 12 subfamilies. Native Kv channels also contain regulatory subunits that shape their functional properties and further expand their diversity and functional repertoire. Kv channels are essential for a wide range of physiological processes, and in many cases little functional redundancy is observed even between seemingly closely related isoforms. Accordingly, disruption of specific Kv channel α or β subunits by inherited or sporadic human gene variants (or gene deletion in mice) is associated with a variety of disease syndromes, many of which are severe and often lethal[1].

Despite in-depth knowledge of many of the physiological functions of specific Kv channels, and of the pathophysiological consequences of their disruption, therapeutic pharmacological targeting of the channels has been challenging. One of the reasons for this is that a great many Kv channel-linked disorders, or channelopathies, arise from loss of function. Direct correction of these requires, therefore, channel openers—a more difficult task than developing channel inhibitors or blockers.

One of the best known Kv channel openers is the drug retigabine (ezogabine). Retigabine activates neuronal KCNQ channels by negative-shifting their voltage dependence of activation[2,3]. Heteromeric KCNQ2/3 channels are particularly important in generating the muscarinic-inhibited M-current, a background Kv current that acts as a gatekeeper to limit aberrant neuronal firing[4,5]. Retigabine was the first Kv channel opener to reach the clinic, but was withdrawn in 2017 because of off-target side effects—it turns the sclera and skin blue[6]. However, it is effective at opening KCNQ2/3 channels and was clinically useful, mostly as an add-on therapy, in epilepsy. Since the development of retigabine, a new syndrome was recognized, termed KCNQ2 encephalopathy[7]. Caused primarily by sporadic, KCNQ2 loss-of-function mutations (as carriers tend not to reproduce), this disease is notable for severe developmental delays in addition to epilepsy. Clearly, new activators of KCNQ2 and many other Kv channels are needed, and this need will be acknowledged further as other Kv channelopathies are identified.

We recently made the surprising discovery that the predominant inhibitory neurotransmitter γ-amino-butyric acid (GABA) binds in a similar binding pocket to that of retigabine, and activates KCNQ3, KCNQ5, and KCNQ2/3 channels[8]. We also found that other metabolites, GABA analogs, and phytochemicals bind to a similar site, the majority also opening KCNQ channels by favoring their activation at more hyperpolarized membrane potentials[8-10]. KCNQ channels, and possibly other Kv channels, thereby possess a binding pocket that accommodates numerous types of small molecule activators. Glycine, which is structurally related to GABA, is also an inhibitory neurotransmitter. Here, after finding that glycine does not activate KCNQ channels, we re-engineered the glycine structure in silico to introduce known properties of KCNQ activators, and tested candidates using docking simulations. With minimal real-world functional screening, this led to discovery of a series of potent KCNQ channel openers, including a pair of activators that leverage isoform preferences to synergistically activate KCNQ2/3.

Results

In Silico Re-Engineering Glycine to Activate KCNQ Channels

Figure 23:
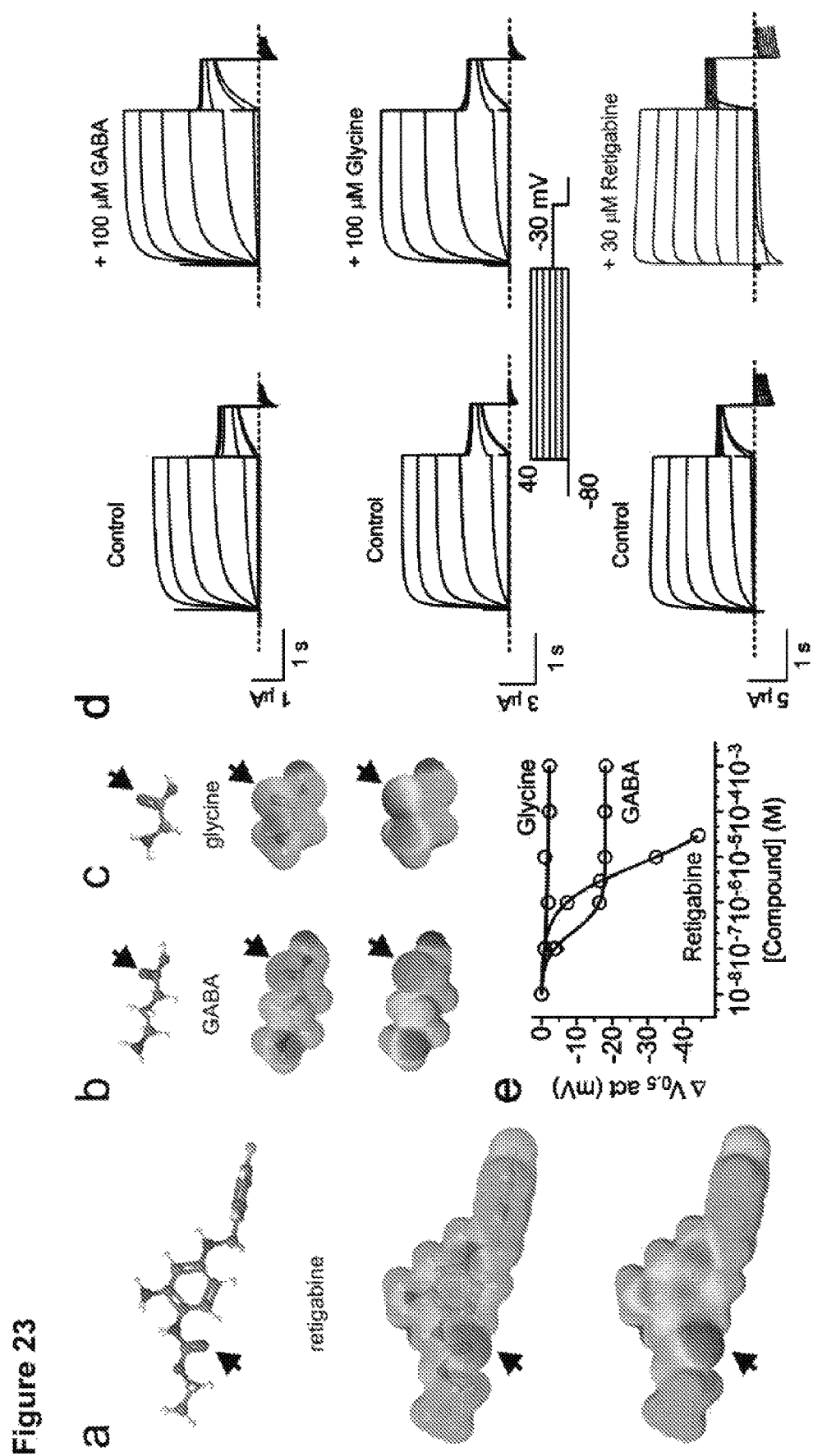
FIG. 23: In silico engineering predicted KCNQ-opening properties into glycine. (a) Retigabine chemical properties: upper, structure; lower, electrostatic surface potentials (differential shading for electron-dense, electron-poor, neutral); center, overlay; all calculated and plotted using Jmol. Arrow, carbonyl oxygen. (b) GABA, parameters as in (a). (c) Glycine, parameters as in (a). (d) Mean traces showing effects of GABA, glycine and retigabine on KCNQ2/3 channels expressed in Xenopus oocytes (n=4-6). Voltage protocol (inset) was used for all TEVC recordings in this study unless otherwise indicated. (e) KCNQ2/3 dose response to glycine, GABA and retigabine, quantified from recordings as in (d) as the shift in voltage dependence of activation ($\Delta V_{0.5act}$) measured from the tail current. Error bars indicate SEM; n=4-6. (f) Structures and surface potential plots (as in a) for the simple glycine derivatives indicated; arrows, carbonyl oxygen. (g) Structures and surface potential plots (as in a) for the double-carbonyl or branched glycine derivatives indicated; arrows, carbonyl oxygen. (h) Structures and surface potential plots (as in a) for the glycine derivatives bearing a phenyl ring; arrows, carbonyl oxygen.
Figure 23:
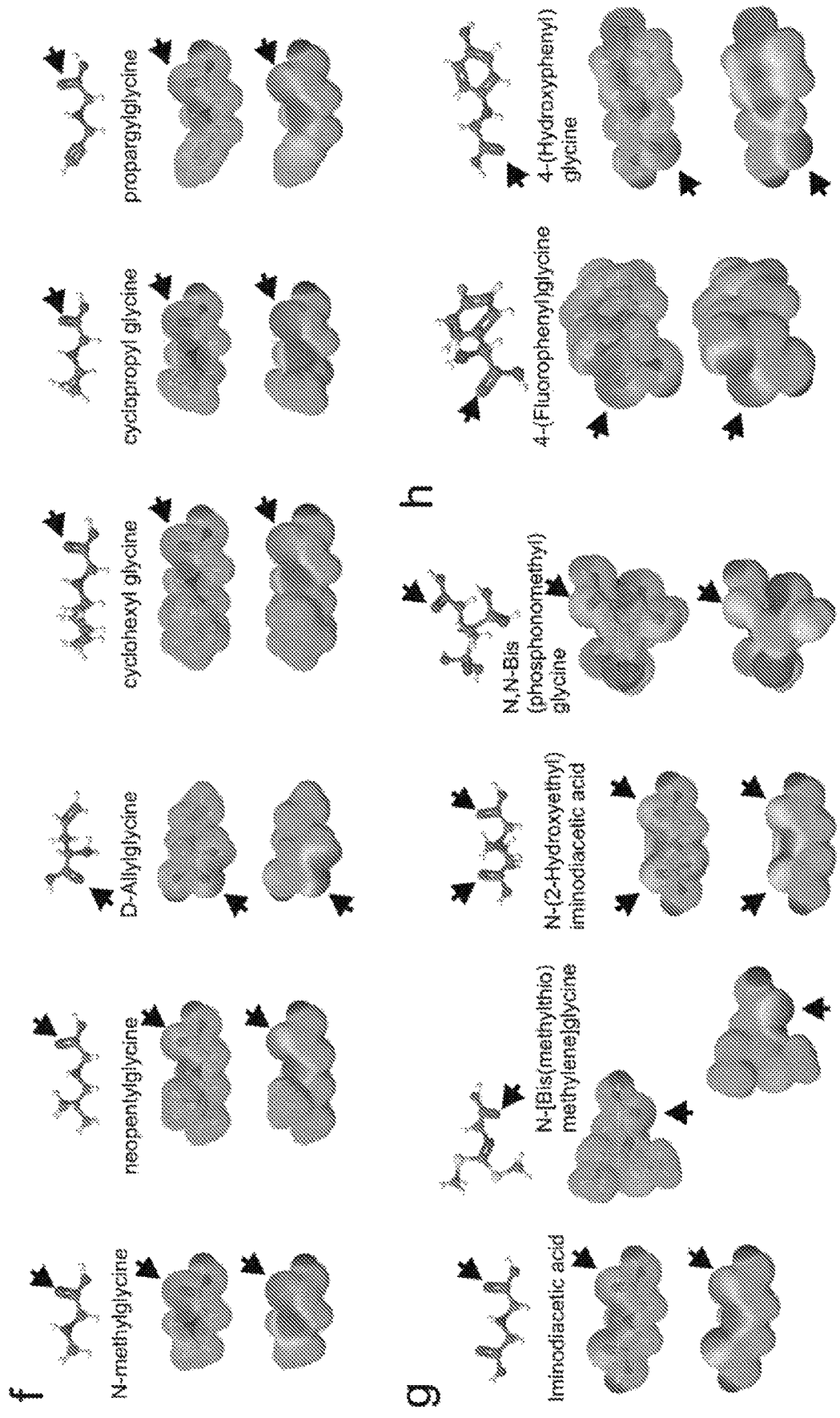

Synthetic anticonvulsants such as retigabine possess negative electrostatic surface potential near their carbonyl oxygen moieties, a property found to be important for their activation of KCNQ2/3 channels[11] (FIG. 23a). GABA possesses this same chemical property and also activates KCNQ2/3 channels[8] (FIG. 23b). Here, we show that glycine, the next most prominent inhibitory neurotransmitter, exhibits relatively weaker negative electrostatic surface potential that is not well centered at its carbonyl oxygen (FIG. 23c), nor does it activate KCNQ2/3, unlike GABA and retigabine, which activated KCNQ2/3 channels here with $EC_{50}$ values of 220±160 nM and 6.9±0.34 μM, respectively (FIG. 23d, e) (Supplementary Tables 1-3). We hypothesized that re-engineering glycine to center surface negative electrostatic potential on its carbonyl oxygen would endow it with the capability to open KCNQ2/3. We therefore next mapped in silico the surface charge of a number of glycine derivatives.

In the simplest derivatives, surface negative potential was still skewed away from the carbonyl (FIG. 23f). In several more complex structures, including iminodiacetic acid glycine derivatives and N-[Bis(methylthiomethylene]glycine, the negative potential was skewed and/or partially hidden; in N,N-Bis(phosphonomethyl)glycine the negative potential was centered around a phosphate oxygen rather than the glycine carbonyl oxygen (FIG. 23g). However, replacing one of the glycine amino group hydrogens with a substituted phenyl ring centered a strong negative surface potential on the glycine carbonyl oxygen; 4-(fluorophenyl)glycine (4FPG) resulted in a single center of electronegative surface charge, while 4-(hydroxyphenyl)glycine also exhibited a second center of electronegative surface potential at the phenyl hydroxyl group (FIG. 23h).

Figure 24:
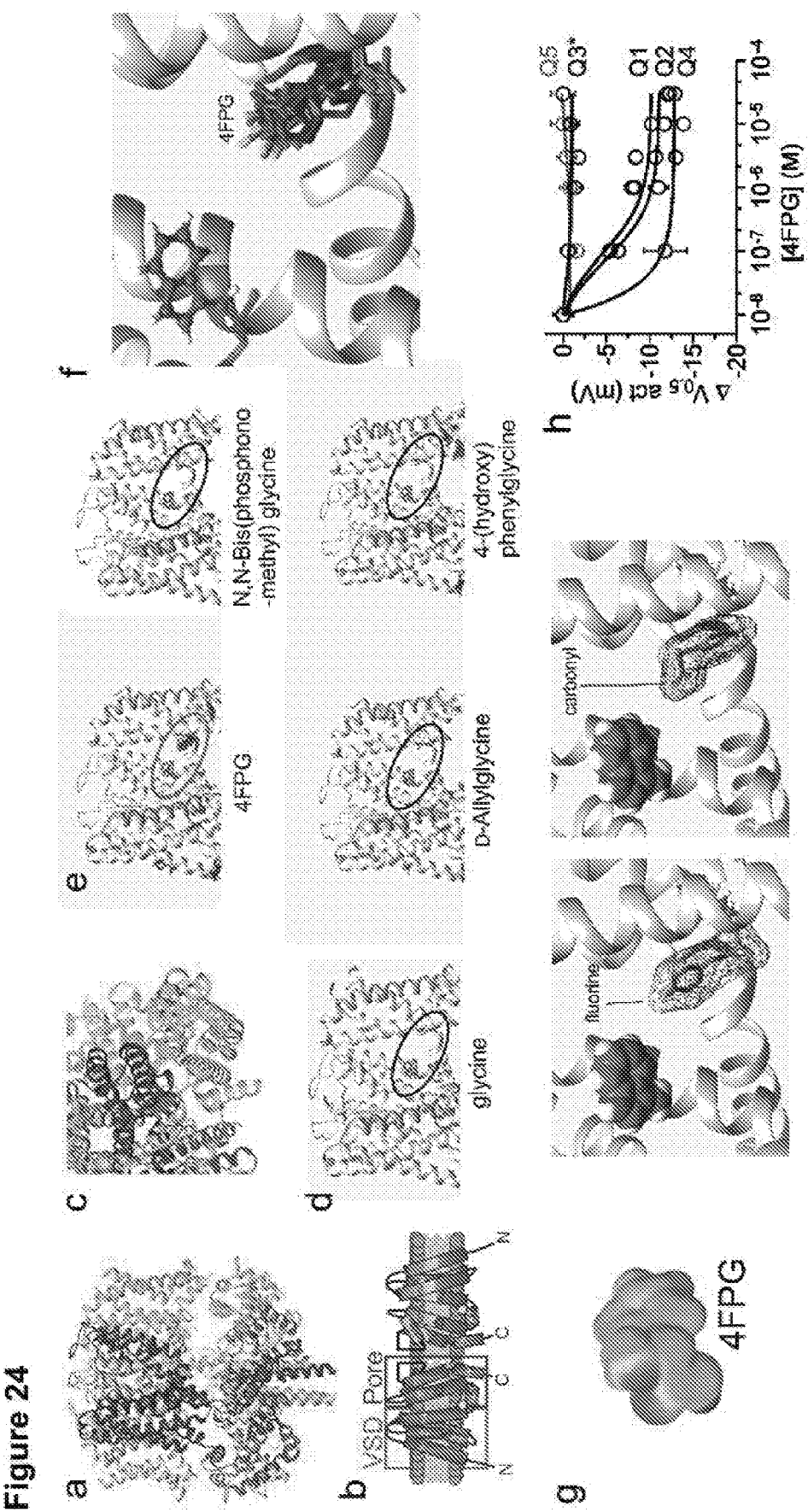
FIG. 24: In silico prediction and in vitro validation of a KCNQ-activating glycine derivative. All error bars indicate SEM. (a) Chimeric KCNQ1/KCNQ3 structural model (differential shading, e.g., in lower left, KCNQ3-W265). (b) Topological representation of KCNQ channel showing two of the four subunits, without domain swapping for clarity. Pentagon, approximate position of KCNQ3-W265; VSD, voltage sensing domain. (c) Close-up extracellular view of KCNQ1/KCNQ3 structural model (same shading as in (a) for KCNQ3-W265). (d) Docking result showing predicted lack of binding of glycine to the KCNQ1/KCNQ3 structural model. Differential shading shows KCNQ3-W265; black oval highlights lack of glycine binding in the typical binding zone for GABA and its metabolites and analogs. (e) Docking results for various glycine derivatives illustrated in FIG. 23 showing predicted binding of 4FPG within the GABA binding pocket (highlighted by oval) but not of the other molecules (darker ovals). All predicted binding configurations shown overlaid for each molecule. (f) Close-up of predicted binding poses of 4FPG within the GABA binding pocket. (g) Left, surface electrostatic potential plot of 4FPG; center and right, comparison of two different predicted orientations of 4FPG within the KCNQ binding pocket, as predicted by SwissDock. (h) 4FPG dose responses for homomeric KCNQ1, 2, 3*, 4 and 5 channels expressed in oocytes, quantified as shift in the voltage dependence of channel activation ($\Delta V_{0.5act}$); n=4-6. (i) Mean traces showing effects of 4FPG (30 µM) on KCNQ1 (upper), KCNQ2 (center) and KCNQ4 (lower); n=4-6. (j) Effects of 4FPG (30 µM) on KCNQ1 (upper), KCNQ2 (center) and KCNQ4 (lower) raw (left) and normalized (G/Gmax) (right) tail current, calculated from traces as in panel h; n=4-6. (k) Effects of 4FPG (30 µM) on KCNQ1 (left), KCNQ2 (center) and KCNQ4 (right) activation (upper) and deactivation (lower) rates, fitted as a single exponential function ($\tau$); n=4-6. (l) 4FPG dose responses for KCNQ2 (upper) and KCNQ4 (lower) compared to those of glycine and GABA, quantified as shift in voltage dependence of activation ($\Delta V_{0.5act}$); n=5-6.
Figure 24:
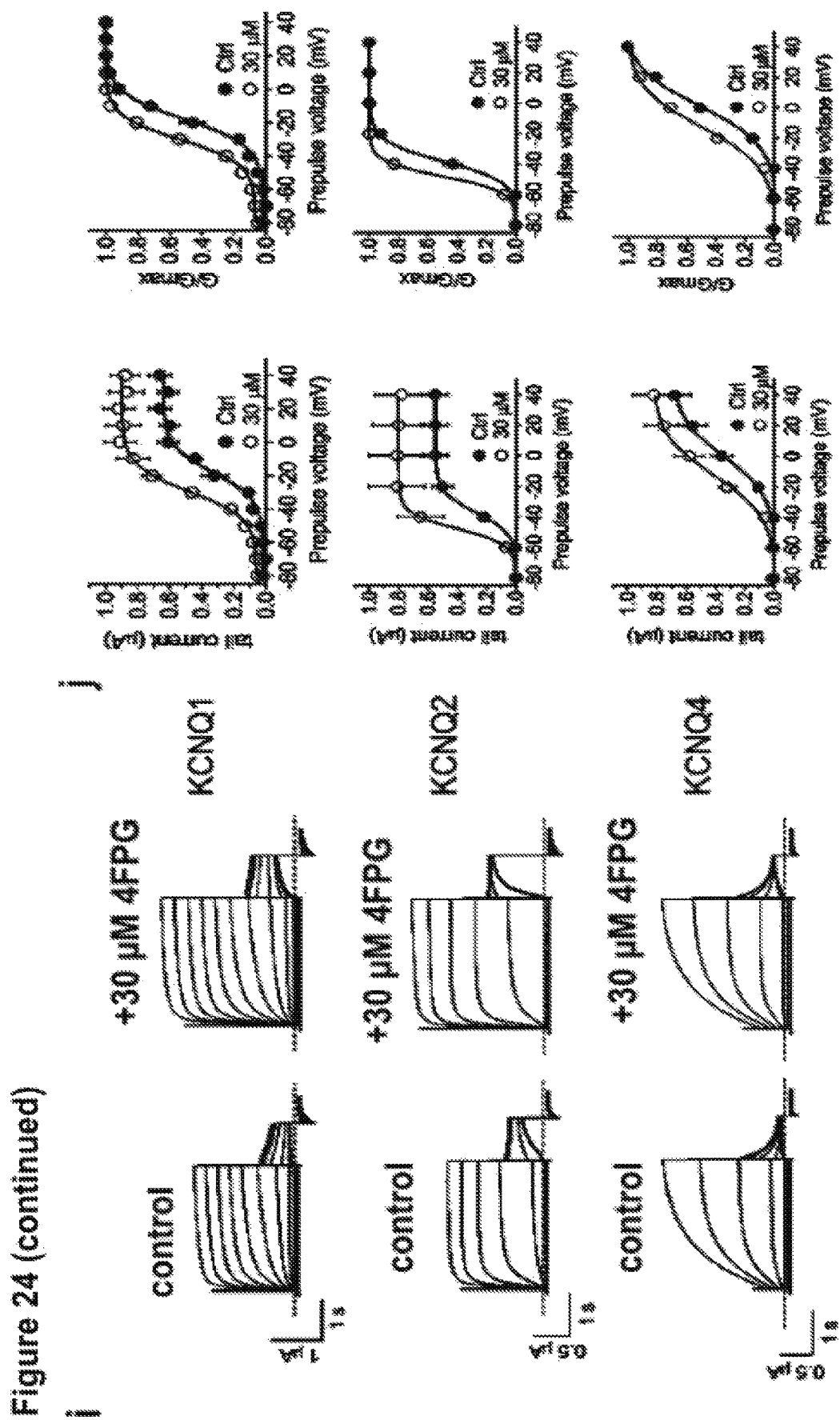
Figure 24:
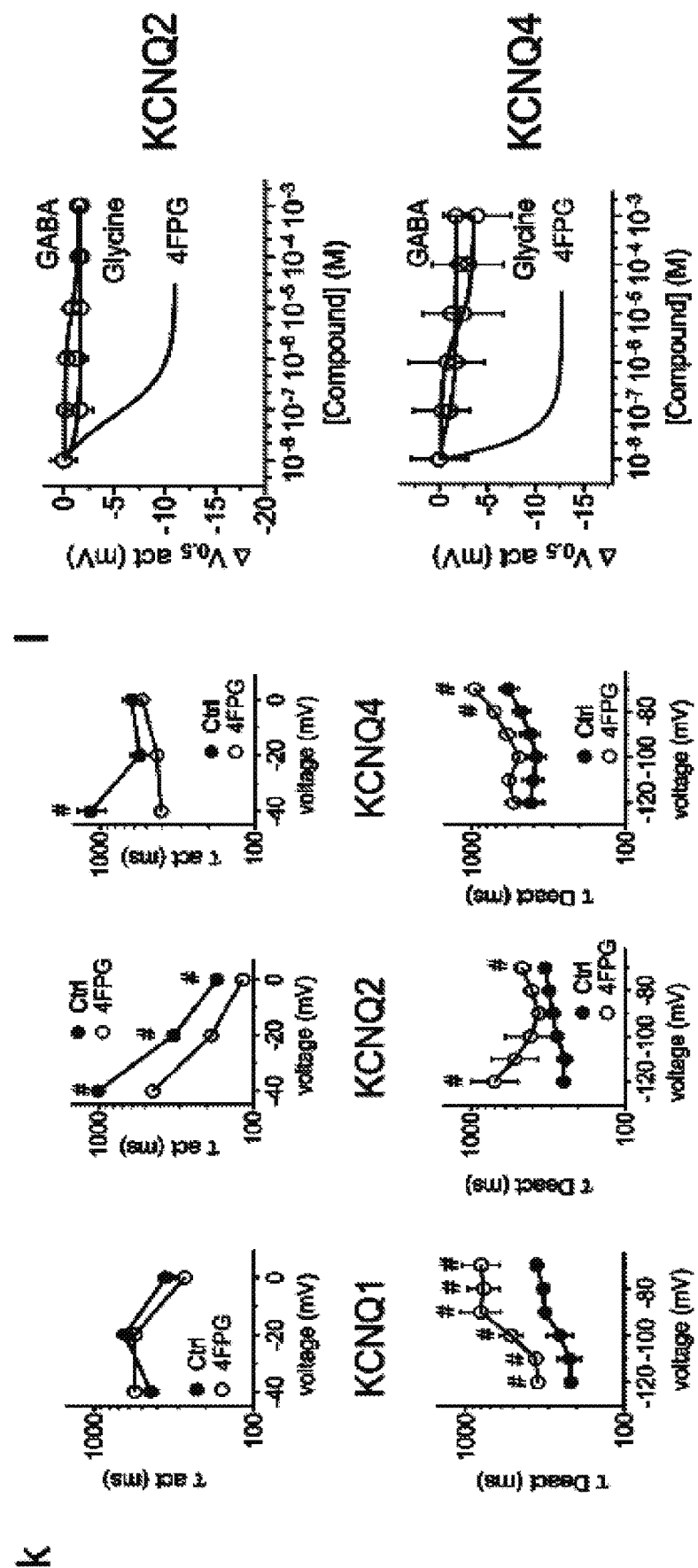

For the second in silico prediction phase, using SwissDock we performed unbiased docking prediction analysis of the glycine derivatives to a KCNQ1-KCNQ3 chimeric model[8] based on the recent cryo-EM derived KCNQ1 structure[12]. We were especially interested in binding in the pocket lined on one side by the S5 tryptophan (W265 on KCNQ3) that is important for retigabine and GABA binding[8,13], and on the other side by the S4-S5 linker-proximal arginine at the foot of S4 (R242 in KCNQ3) that is required for binding of phytochemicals such as mallotoxin to KCNQ channels[14] and mutation of which in KCNQ2 causes benign familial neonatal convulsions[15] (FIG. 24a-c). As expected from its chemical properties and lack of effects on KCNQ2/3, glycine failed to dock (FIG. 24d). In contrast, 4FPG docked in the binding pocket (lighter oval, FIG. 24e) whereas other glycine derivatives did not (dark ovals, FIG. 24e). The docking position of 4FPG was closer to the S4-5 arginine (darker) than to the S5 tryptophan (lighter) (FIG. 24f). Surface electrostatic potential plotting shows that 4FPG possesses negative charge close to its carbonyl oxygen (FIG. 24g, left). In the majority of poses, 4FPG was positioned lengthways between the S5 W and the S4-5 R with either the carbonyl oxygen or the fluorine in 4FPG proximal to the S5 tryptophan (FIG. 24g, center and right).

4FPG Isoform-Selectively Activates KCNQ Channels

We next validated the in silico predictions using two-electrode voltage-clamp of homomeric neuronal KCNQ2-5 channel isoforms expressed in *Xenopus laevis* oocytes. By quantifying the hyperpolarizing shift in voltage dependence of KCNQ channel activation ($\Delta V_{0.5act}$) versus [4FPG], we discovered that, as predicted, 4FPG is a KCNQ channel opener. 4FPG most potently activated (i.e., negative-shifted the voltage dependence of activation of) KCNQ4 ($EC_{50}$=49±12 nM), followed by KCNQ2 ($EC_{50}$=69±31 nM) and KCNQ1 ($EC_{50}$=90±20 nM), and had no effects on KCNQ3* or KCNQ5 (FIG. 24h-j) (Supplementary Tables 4-8). As in previous studies[8,10], we used the A315T KCNQ3 mutant (KCNQ3*) that ensures large enough currents to accurately quantify voltage dependence and pharmacology of homomeric KCNQ3[16]. 4FPG speeded KCNQ2 and KCNQ4 activation and slowed their deactivation, suggesting that it opens these channels by stabilizing an open state and or destabilizing a closed state. In contrast, 4FPG slowed KCNQ1 deactivation but did not speed its activation, suggesting 4FPG may solely destabilize the closed state in KCNQ1 (FIG. 24j, k) (Supplementary Tables 9-12). This is potentially of mechanistic interest, as KCNQ1 lacks the S5 W required for activation by retigabine, yet its activity is still potentiated by 4FPG. The data suggest that the S5 W may be important for effects on the activated state, yet is not required for effects on the deactivated state, at least in KCNQ1. The preference for KCNQ4 activation was in contrast to GABA and gabapentin, which we previously found[8] to each activate only KCNQ3 and KCNQ5, and to retigabine which favors KCNQ3 and activates KCNQ2, KCNQ4 and KCNQ5 to a lesser extent, and does not activate KCNQ1[8,9,9,17]. Thus, in contrast to 4FPG, here glycine and GABA were unable to open KCNQ2 and KCNQ4 homomers (FIG. 24I) (Supplementary Tables 13-16).

Figure 25:
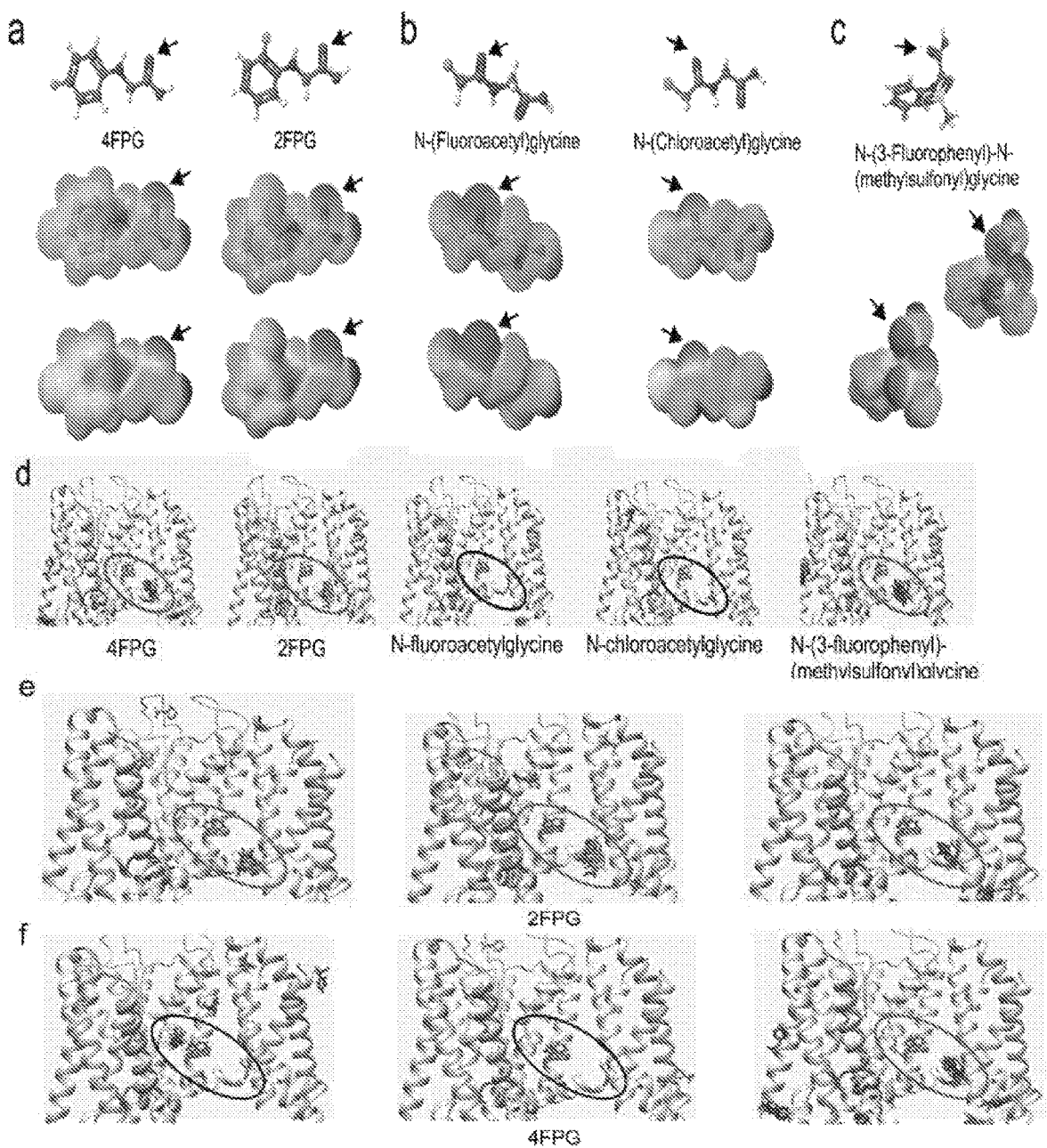
FIG. 25: In silico prediction of 4FPG-related KCNQ-activating glycine derivatives. (a) Chemical properties of 4FPG versus 2FPG: upper, structure; lower, electrostatic surface potentials (differential shading for electron-dense; electron-poor; neutral); center, overlay; all calculated and plotted using Jmol. Arrow, carbonyl oxygen. (b), (c) Chemical properties of 4FPG-related glycine derivatives, parameters as in (a). (d) Docking results showing predicted binding (lighter ovals) or lack thereof (darker ovals) of the compounds in (a)-(c) to the GABA binding pocket in the KCNQ1/KCNQ3 structural model. Differentially shaded side-chain, KCNQ3-W265. (e) Docking results showing predicted binding (lighter ovals) of three different conformational forms of 2FPG to the GABA binding pocket in the KCNQ1/KCNQ3 structural model. Differentially shaded side-chain, KCNQ3-W265. (f) Docking results showing predicted binding (lighter oval) or lack thereof (darker ovals) of three different conformational forms of 4FPG to the GABA binding pocket in the KCNQ1/KCNQ3 structural model.

Subtle Modifications to 4FPG Create Derivatives with Altered KCNQ Isoform Selectivity KCNQ4 activation is an unwanted property of KCNQ2 activators because while KCNQ2 activation may be beneficial in KCNQ2-dependent and other types of epilepsy, KCNQ4 activation is thought to lead to urinary retention by opening KCNQ4 in bladder detrusor muscle[18]. In addition, activation of KCNQ1, a cardiac and epithelial KCNQ channel α subunit, might also cause unwanted off-target effects. We therefore further re-engineered 4FPG in silico, creating several single-halide glycine derivatives, all of which exhibited negative electrostatic surface potential close to a carbonyl oxygen (FIG. 25a-c). Interestingly, only those that contained a fluorophenyl ring concentrated negative surface potential at the native glycine carbonyl and were predicted to dock in the KCNQ1-KCNQ3 chimeric model. In addition to 4FPG these were 2-(fluorophenyl)glycine (2FPG) and N-(fluorophenyl)-N-(methylsulfonyl)glycine (3FMSG). Those that centered negative surface potential at the halide-proximal carbonyl and lacked the phenyl group (N-(fluoroacetyl)glycine and N-(chloroacetyl)glycine) did not dock (FIG. 25d).

The most closely related glycine derivative to 4FPG was 2-(fluorophenyl) glycine (2FPG), the only difference being the fluorine position on the phenyl ring. 4FPG and 2FPG are each represented in several conformations on the Zinc database (zinc.docking.org) used for ligand selection, and so we compared docking of all conformations. All three 2FPG conformations docked primarily to the known binding pocket (FIG. 25e) whereas 4FPG showed more docking heterogeneity and two of three of its conformations did not dock in the neurotransmitter binding pocket (FIG. 25f). This suggested 4FPG and 2FPG might have different KCNQ opening characteristics, which we tested next.

Strikingly, 2FPG was a potent KCNQ2 isoform-selective opener ($EC_{50}=322\pm139$ nM) with negligible effects on KCNQ1, 3*, 4 or 5 (FIG. 26a, b) (Supplementary Tables 17-21). The KCNQ2 activation by 2FPG was in contrast to the non-KCNQ2 activating GABA (as we previously reported[8]) and glycine (FIG. 26c). The loss of KCNQ4 opening activity, in contract to 4FPG, was remarkable given the small differences in the 2FPG and 4FPG structures (FIG. 26d). 2FPG negative-shifted the voltage dependence of KCNQ2 activation but also increased KCNQ2 currents at more depolarized potentials (FIG. 26b, e) and speeded KCNQ2 activation and slowed deactivation as for 4FPG (FIG. 26f) (Supplementary Tables 22, 23).

3FMSG exhibited still different selectivity, activating KCNQ3* most potently ($EC_{50}=18\pm12$ nM) followed by KCNQ5 ($EC_{50}=171\pm112$ nM), with negligible effects on KCNQ1, KCNQ2 and KCNQ4 (FIG. 26g, h). In contrast, glycine had no effects on homomeric KCNQ3* or KCNQ5 (FIG. 26i, j) (Supplementary Tables 24-31). 3FMSG negative-shifted the activation voltage dependence of KCNQ3* and also increased current at positive voltages (FIG. 26k), speeded activation and slowed deactivation (FIG. 26l). 3FMSG exerted similar effects on KCNQ5 and in addition was more effective at increasing KCNQ5 current compared to KCNQ3 current at positive potentials (FIG. 26m-o) (Supplementary Tables 32-34). 3FMSG also reduced by threefold the incidence of pentylene tetrazole-induced tonic seizures in mice (FIG. 26p).

3FMSG Inhibits Glycine Receptor GLRA1

Figure 27:
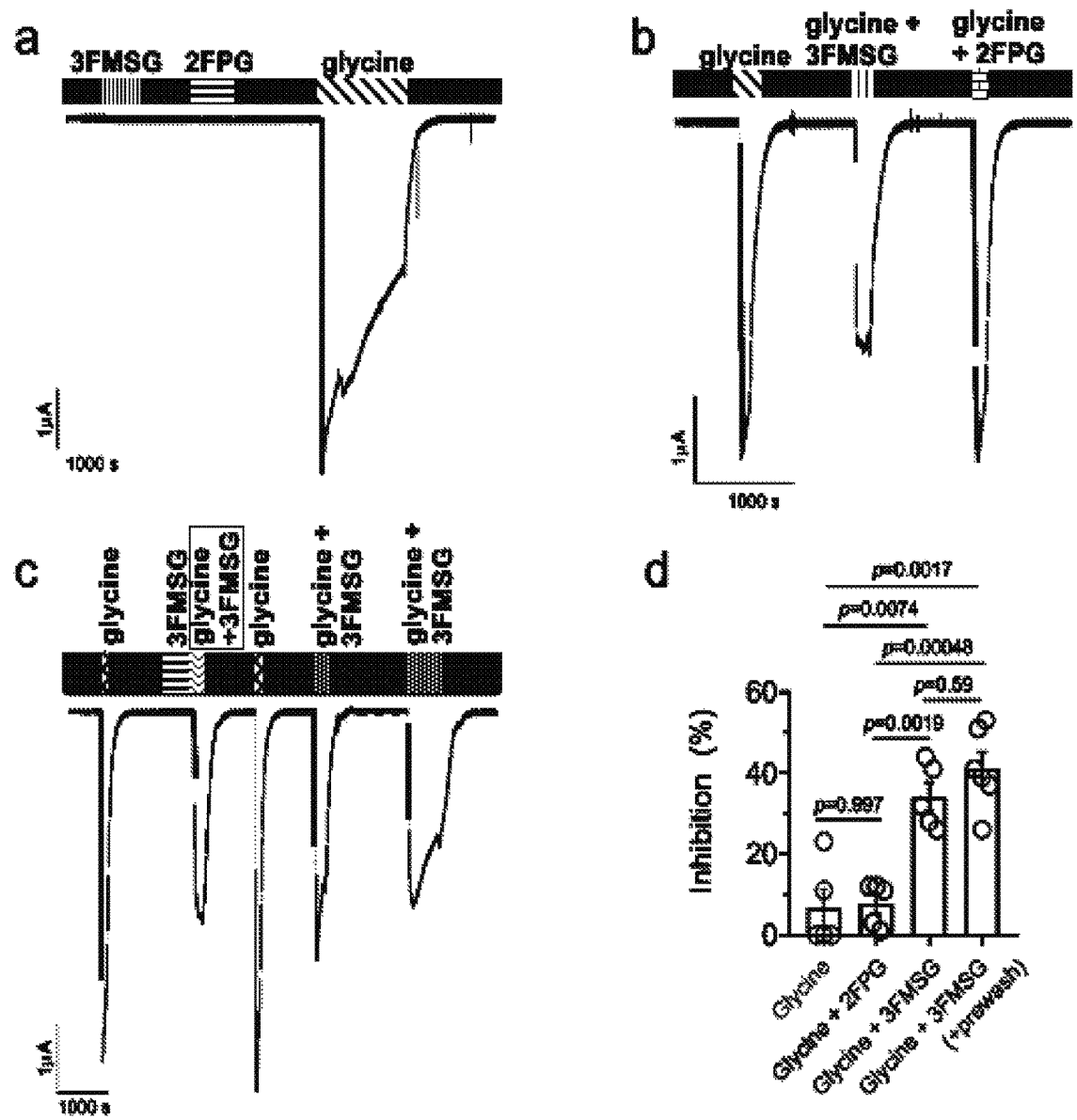
FIG. 27: Differential effects on GLRA1 activity of 2FPG and 3FMSG. All error bars indicate SEM. (a) Exemplar trace showing lack of effects of 3FMSG or 2FPG alone on GLRA1 activity, compared to robust activation by glycine alone (all compounds applied at 1 mM), application indicated by colored bars at top. Solid black, application of bath solution alone. (b) Exemplar trace showing inhibition of glycine-activated GLRA1 by 3FMSG (100 µM) but not 2FPG (100 µM) (glycine applied at 1 mM in each case), application indicated by colored bars at top. Solid black, application of bath solution alone. (c) Exemplar trace showing inhibition of glycine-activated GLRA1 by 3FMSG (100 µM) with versus without 3FMSG (100 µM) pre-wash in (glycine applied at 1 mM in each case), application indicated by colored bars at top. Solid black, application of bath solution alone. (d) Mean inhibition of 1 mM glycine-activated GLRA1 current by 2FPG or 3FMSG (100 µM) with/without 3FMSG (100 µM) pre-wash, n=5-6, from traces as in panels (b) and (c). Currents were compared to an initial current activated by glycine alone; as a control, glycine-activated current in a subsequent wash-in was compared to the initial glycine wash-in current (left-most bar), showing negligible inhibition as expected.

We next tested whether the glycine derivatives 2FPG and 3FMSG modulated the canonical glycine receptor, GLRA1. Neither compound activated GLRA1 at 1 mM, in contrast to glycine (1 mM) (FIG. 27a). However, 3FMSG but not 2FPG (each at 100 µM) partially inhibited the activation of GLRA1 by 1 mM glycine (FIG. 27b). The degree of GLRA1 inhibition by 3FMSG was similar (~40%) whether or not 3FMSG alone was applied immediately before co-application of glycine with 3FMSG (FIG. 27c, d). Interestingly, co-application of 3FMSG also reduced the degree of desensitization observed during glycine activation of GLRA1 (FIG. 27b, c). Thus, 3FMSG but not 2FPG retains its ability to bind to a canonical glycine receptor, but acts as an inhibitor rather than an activator. The 40% inhibition by 3FMSG at 100 µM suggests a lower potency than its submicromolar activating effects on KCNQ3* and KCNQ5, although the comparison is difficult to quantify as 3FMSG may be competing with glycine, assuming it binds to the same site, on GLRA1.

Glycine Derivatives Differentially Activate KCNQ2/3 Channels

Figure 28:
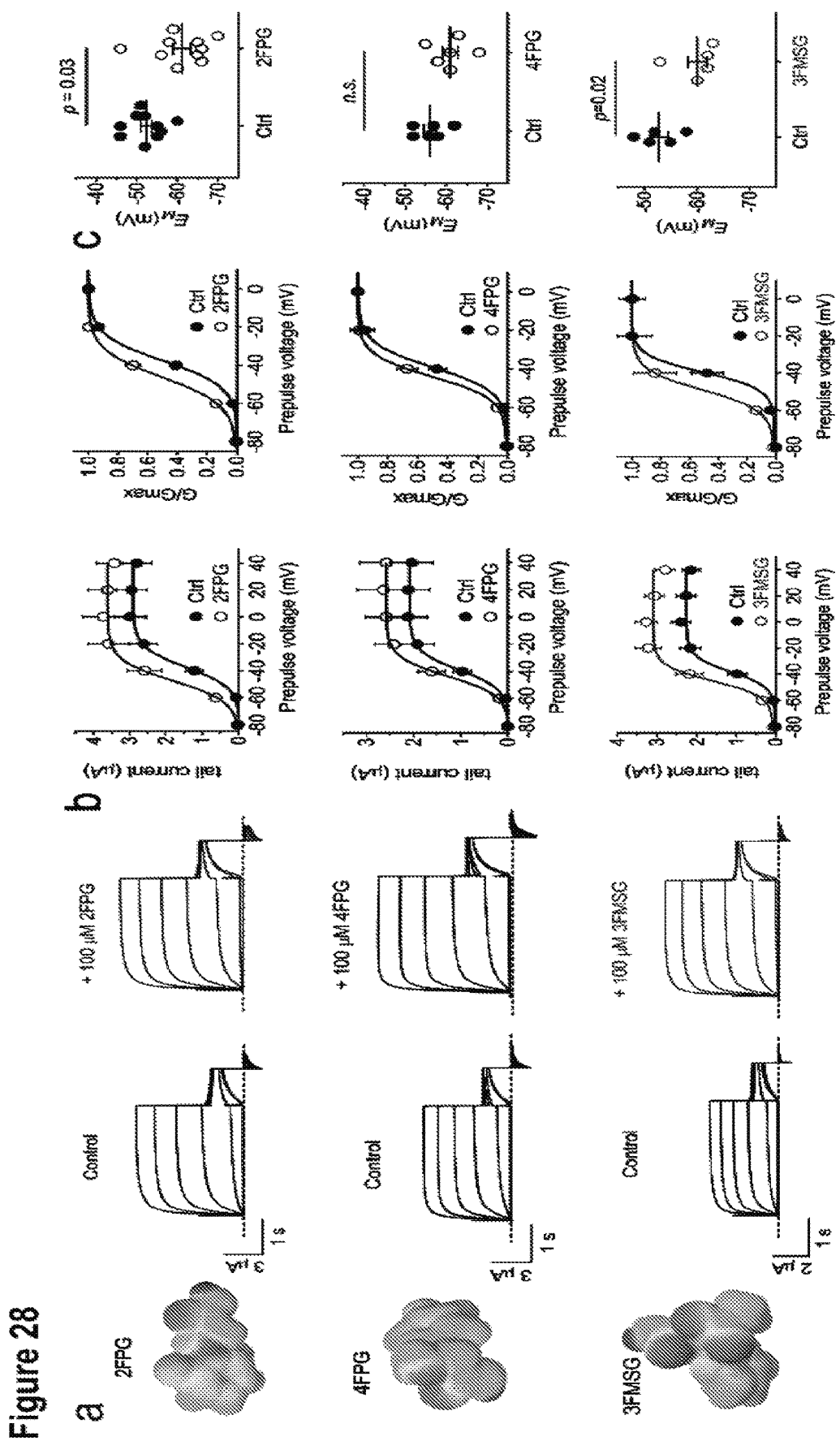
FIG. 28: Differential effects on KCNQ2/3 activity of fluorinated glycine derivatives. All error bars indicate SEM. (a) Left, Jmol surface plot of compounds indicated, showing electrostatic surface potential (differential shading for negative, positive). Right, mean TEVC traces for KCNQ2/3 expressed in *Xenopus* oocytes in the absence (control) or presence of compounds as glycine derivatives as indicated (n=4-6). Dashed lines indicated zero current level. (b) Mean tail current (left) and normalized tail currents (G/Gmax) (right) versus prepulse voltage relationships recorded by TEVC in *Xenopus* oocytes expressing KCNQ2/3 channels in the absence (black) or presence (lighter) of glycine derivatives indicated (100 µM) (n=4-6). (c) Effects of glycine derivatives (100 µM) on resting membrane potential (EM) of unclamped oocytes expressing KCNQ2/3 (n=4-6). (d) 2FPG, 4FPG and 3FMSG dose responses for KCNQ2/3 compared to those of glycine, GABA and retigabine, quantified as shift in voltage dependence of activation ($\Delta V_{0.5act}$); n=4-6. (e) Comparison of 2FPG, 4FPG and 3FMSG (100 µM) effects quantified as KCNQ2/3 current fold-increase versus membrane potential; n=4-6. (f) Effects of 2FPG (100 µM) on KCNQ2/3 activation (left) and deactivation (right) rates, fitted as a single exponential function (τ); n=15. #P<0.05 between values at equivalent membrane potential. (g) Effects of 3FMSG (100 µM) on KCNQ2/3 activation (left) and deactivation (right) rates, fitted as a single exponential function (τ); n=10. #P<0.05 between values at equivalent membrane potential.
Figure 28:
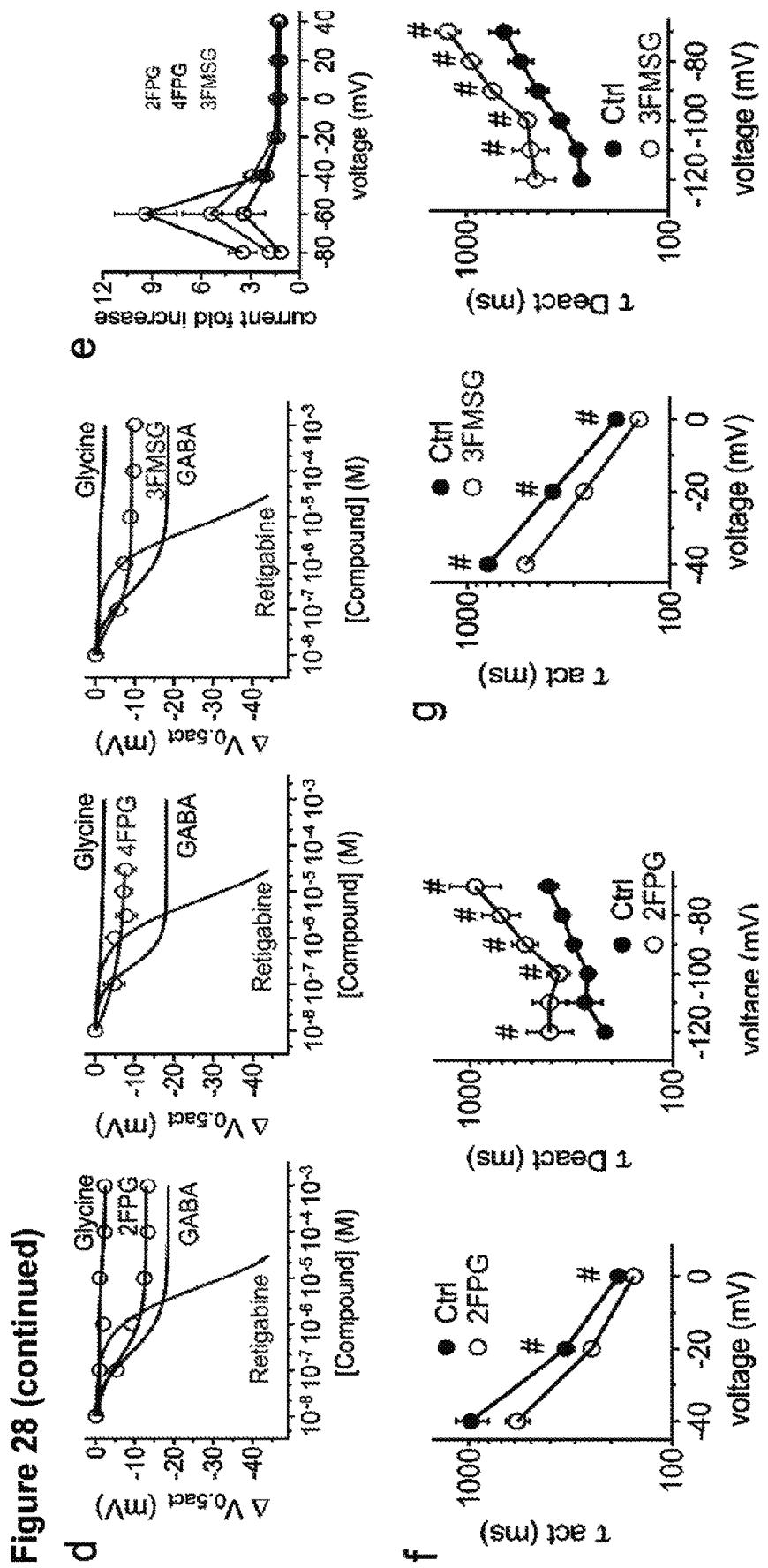

As KCNQ2/3 heteromers are the predominant neuronal KCNQ isoform, we tested their sensitivity to the glycine derivatives. All 3 derivatives activated KCNQ2/3 (FIG. 28a, b), with 2FPG and 3FMSG the more efficacious at opening KCNQ2/3 and at KCNQ2/3-dependently shifting the resting membrane potential (FIG. 28c). All 3 compounds were much more potent than retigabine (2FPG, $EC_{50}=184\pm15$ nM; 3FMSG, $EC_{50}=51\pm21$ nM; 4FPG, $EC_{50}=61\pm42$ nM; retigabine, $EC_{50}=6.87\pm0.34$ µM) although none came close to matching its efficacy upon KCNQ2/3 (FIG. 28d, e) (Supplementary Tables 35-37). As we observed for homomeric channels, 2FPG and 3FMSG speeded KCNQ2/3 activation and slowed its deactivation (FIG. 28f, g) (Supplementary Tables 38-41).

2FPG and 3FMSG Occupy the KCNQ Neurotransmitter Binding Pocket

Figure 29:
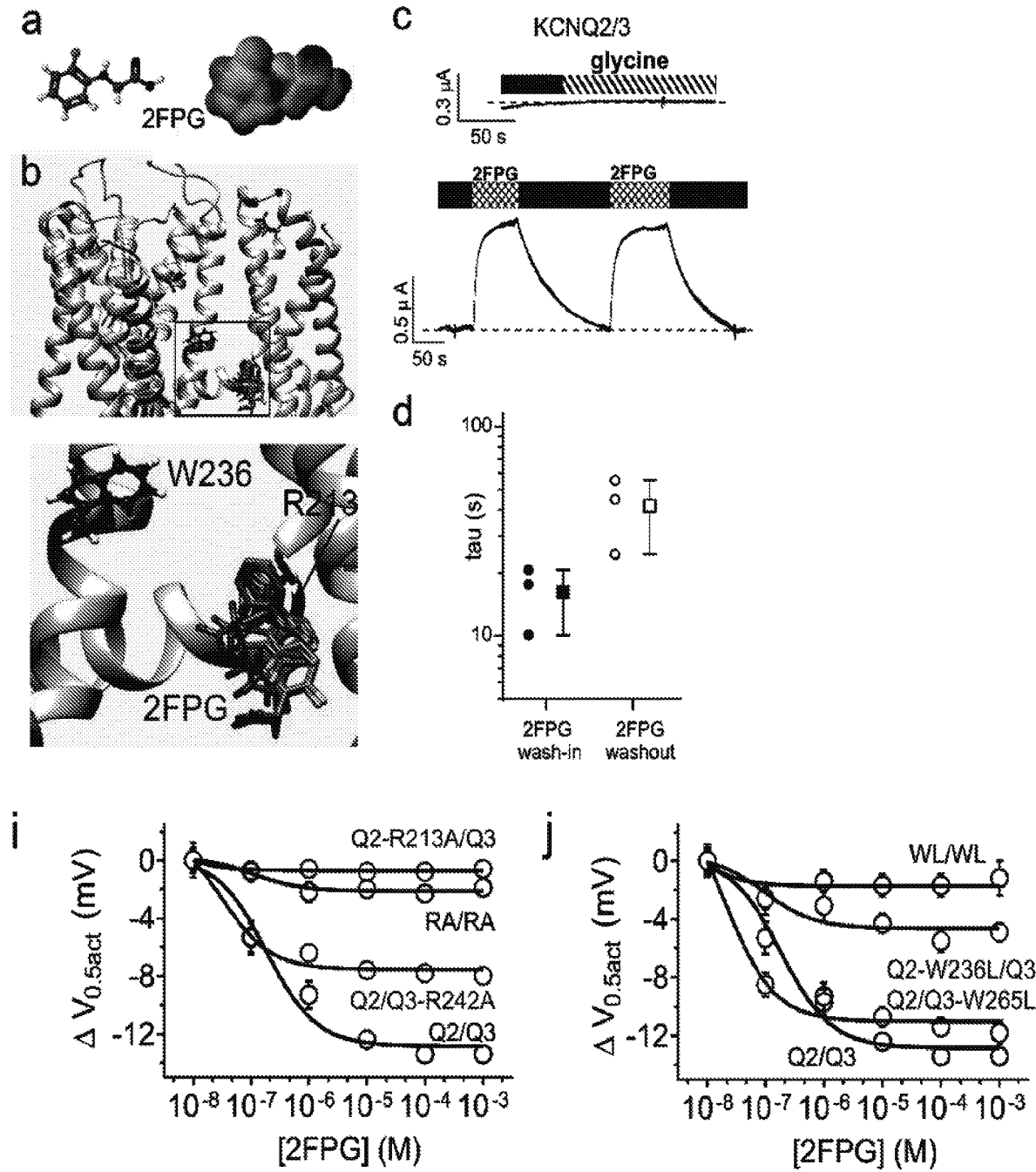
FIG. 29: 2FPG activation of KCNQ2/3 requires KCNQ2 R213 and W236. All error bars indicate SEM. (a) 2FPG structure (left) and electrostatic surface potential map (right). (b) Upper, SwissDock result showing predicted binding of 2FPG to a chimeric KCNQ1-KCNQ3 model. Lower, close-up of boxed region above. (c) Representative trace showing effects at −60 mV on KCNQ2/3 current expressed in oocytes during wash-in and/or washout of 1 mM glycine (upper) or 100 µM 2FPG (lower). (d) Mean time course of current increase and decrease during wash-in and washout respectively of 2FPG (100 µM) expressed as the tau of a single exponential function, quantified from traces as in panel (c) (lower), n=3 oocytes (two wash-in/out cycles per oocyte, values averaged for each oocyte). (e), (f) Mean traces (e) and tail current-voltage relationships (f) for wild-type and arginine-mutant KCNQ2/3 channels traces as indicated in the absence (Control) or presence of 100 µM 2FPG. RA/RA, KCNQ2-R213A/KCNQ3-R242A; n=5. (g), (h) Mean traces (g) and tail current-voltage relationships (h) for wild-type and tryptophan-mutant KCNQ2/3 channels traces as indicated in the absence (Control) or presence of 100 µM 2FPG. WL/WL, KCNQ2-W236L/KCNQ3-W265L; n=5. l) 2FPG dose responses of wild-type and arginine-mutant KCNQ2/3 channels as in (e),(f), quantified as shift in voltage dependence of activation ($\Delta V_{0.5act}$); n=5. (j) 2FPG dose responses of wild-type and tryptophan-mutant KCNQ2/3 channels as in (g),(h), quantified as shift in voltage dependence of activation ($\Delta V_{0.5act}$); n=5.
Figure 29:
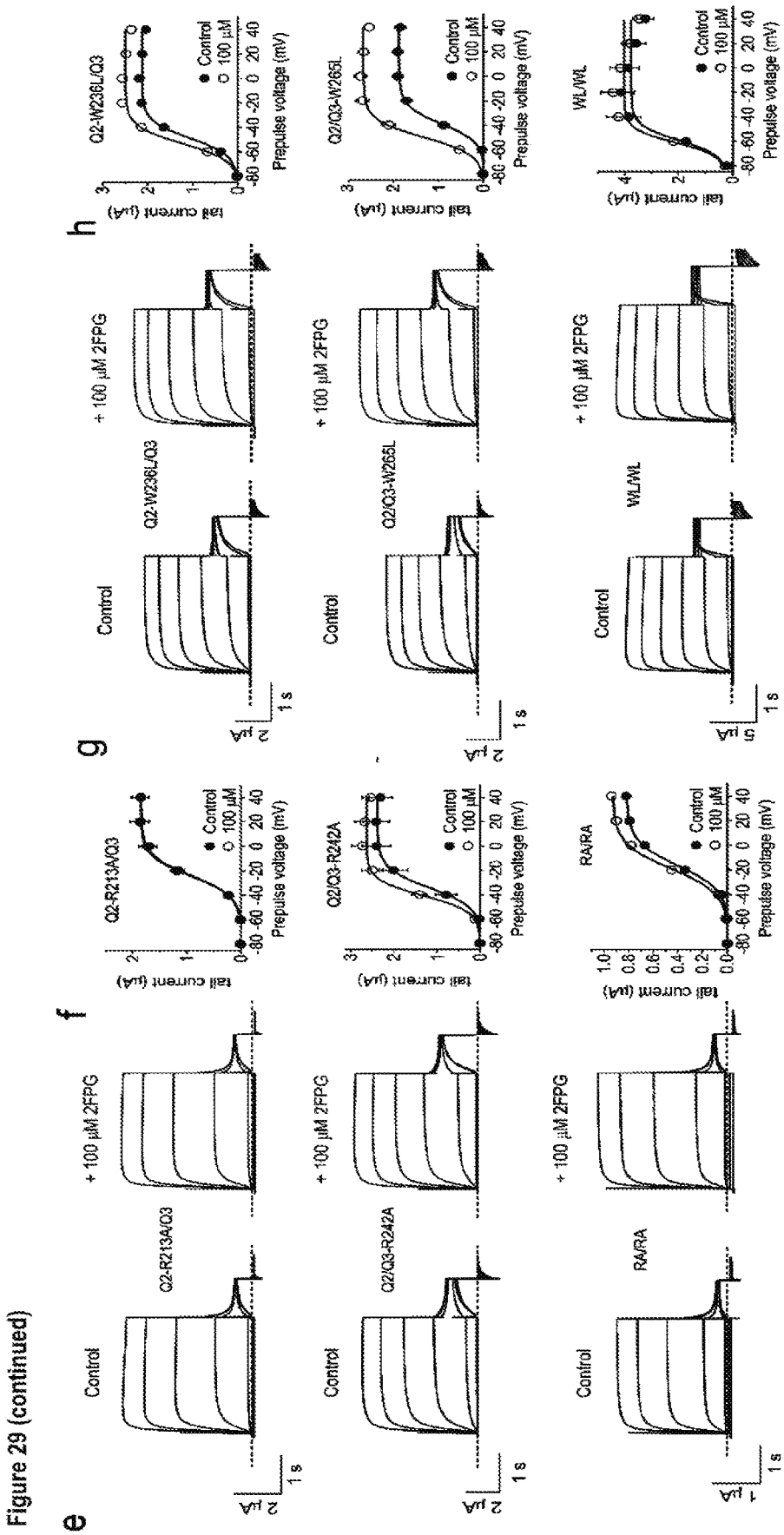

Docking poses predicted that 2FPG binds between the S5 tryptophan (W236 in KCNQ2) and the arginine at the foot of S4 (R213 in KCNQ2) (FIG. 29a, b). Wash-in and washout experiments revealed immediate onset of 2FPG effects on KCNQ2/3 channels upon commencing wash-in, and immediate reduction in current upon commencing washout; glycine as expected had no effect (FIG. 29c). Fitting with a single exponential function the effects on KCNQ2/3 current during 2FPG wash-in and washout revealed tau values of 16±3 s and 42 t 9 s, respectively (FIG. 29 d). These time-courses are not compatible with 2FPG having to cross the plasma membrane to access its binding site from the intracellular face of the plasma membrane, which would typically not give rise to immediate onset of effects during wash-in and would require several minutes to wash out. Instead, together with the docking predictions, the wash kinetics are more consistent with 2FPG accessing a deep binding site via the outer face of the membrane. We next tested the docking predictions in vitro using site-directed mutagenesis and TEVC. Mutating the S4-juxtaposed arginines in KCNQ2/3, we found that 2FPG required KCNQ2-R213 but not KCNQ3-R242 (FIG. 29e, f). Similarly, KCNQ2/3 sensitivity to 2FPG was much more sensitive to mutation of KCNQ2-W236 than mutation of KCNQ3-W265 (FIG. 29g, h; dose responses in FIG. 29i, j). The dependence of 2FPG on the KCNQ2, but not KCNQ3, W and R residues in the previously discovered retigabine and GABA binding pocket[8,13] reflected data from the homomeric channels showing KCNQ2 but not KCNQ3 sensitivity to 2FPG (FIG. 26) (Supplementary Tables 42-47).

3FMSG also docked in silico between the S5 tryptophan (W265 in KCNQ3) and the arginine at the foot of S4 (R242 in KCNQ3) (FIG. 30a, b). Wash-in and wash-out experiments were again consistent with accessing a deep binding site from the extracellular face, with immediate onset of effects upon commencing wash-in or washout (FIG. 30c), and tau values of 15±3 s for wash-in and 39±10 s for washout (FIG. 30d). In contrast to data for 2FPG, but as expected from the 3FMSG sensitivity of KCNQ3 (FIG. 26), 3FMSG was more sensitive to mutation of KCNQ3-R242 than KCNQ2-R213, although mutating to alanine both the KCNQ2 and KCNQ3 equivalent arginines (RA/RA) produced a larger reduction in sensitivity (FIG. 30e, f). More definitively, 3FMSG sensitivity was dependent on KCNQ3-W265 but independent of KCNQ2-W236 (FIG. 30g, h; dose responses in FIG. 30i, j) (Supplementary Tables 48-53).

2FPG and 3FMSG KCNQ Isoform Selectivity Arises Primarily from Functional Selectivity To examine the mechanism of KCNQ isoform selectivity among glycine derivatives, we first assessed the combined effects of 2FPG and 3FMSG on homomeric KCNQ2 and KCNQ3 channels. A tenfold excess of 3FMSG (100 µM) subtly reduced the efficacy of 2FPG (10 µM) with respect to KCNQ2 activation by shifting the voltage dependence of 2FPG action such that efficacy at −40 mV was greatly reduced (although activation was still sufficient to hyperpolarize the oocyte membrane potential because effects were greater at more negative membrane potentials). In contrast, a tenfold excess of 2FPG (100 µM) did not alter the effects of 3FMSG (10 µM) on KCNQ3* activation at any membrane potential (FIG. 31a-d).

We next used a radioligand binding assay to quantify tritiated GABA binding to homomeric KCNQ2 and KCNQ3* channels expressed in oocytes. As we previously found[8], GABA bound to both KCNQ2 and KCNQ3 (FIG. 31e, f). Strikingly, 2FPG and 3FMSG (100 µM) were each able to compete out GABA binding to both KCNQ2 and KCNQ3*. Furthermore, while 3FMSG and 2FPG were equally able to outcompete GABA for KCNQ2 binding, 2FPG was not as effective as 3FMSG at outcompeting GABA for KCNQ3* binding. Together with the results in FIG. 31a-c, these data show that 2FPG and 3FMSG each bind to both KCNQ2 and KCNQ3*, to a site similar to or impinging (directly or allosterically) upon the GABA binding site. The data also suggest that while 2FPG has a higher binding affinity than 3FMSG for KCNQ2 (and the reverse is true for KCNQ3*), 3FMSG has a higher binding affinity for KCNQ2 than 2FPG does for KCNQ3*.

As each compound can bind to both KCNQ isoforms, isoform selectivity must arise predominantly from functional selectivity, not binding selectivity. There are clear binding preferences, otherwise a tenfold excess of the non-activating compound would greatly reduce the efficacy of the activating compound, and that did not occur (FIG. 31a-c). However, these preferences are not enough to explain the isoform selectivity shown in FIG. 26, i.e., a lack of functional effects of 2FPG on KCNQ3*, and 3FMSG on KCNQ2, even at high concentrations. Consistent with functional selectivity, using measurements of ion permeability series we found that 2FPG induces an increase in relative Na⁺ permeability (compared to that of K⁺) in KCNQ2 but not KCNQ3*, whereas 3FMSG induces a similar increase in relative Na⁺ permeability of KCNQ3* but not KCNQ2 (FIG. 31g-i; Supplementary Tables 54, 55). The increase in the relative Na⁺ permeability induced only by the correct compound/KCNQ isoform pairing suggested a conformational shift in the pore associated with channel activation. We previously observed a similar shift when KCNQ isoforms co-assembled via their pore domain with the SMIT1 myo-inositol transporter, which also negative-shifts the voltage dependence of KCNQ2 and KCNQ2/3 channels[19].

2FPG and 3FMSG Synergistically Activate KCNQ2/3 Channels

As 2FPG and 3FMSG preferentially activate different KCNQ2/3 channel subunits (KCNQ2 and KCNQ3, respectively) we tested their ability to synergistically activate KCNQ2/3 by leveraging their isoform preferences. We used equal concentrations of each compound to avoid possible competition for the same-isoform binding site (see FIG. 31) and to instead leverage their binding preferences (2FPG for KCNQ2; 3FMSG for KCNQ3). As discussed above, the binding preferences are not the primary mechanism underlying isoform selectivity of effects (selectivity that persists even at high concentrations), but based on data herein (FIG. 31a, b) would be predicted to permit synergy as they could favor KCNQ2 binding to 2FPG, and 3FMSG binding to KCNQ3, within KCNQ2/3 complexes. Accordingly, 2FPG and 3FMSG combined to potentiate KCNQ2/3 activity more than each compound alone (each at 10 µM) (FIG. 32a-d). Quantifying current fold-increase (FIG. 32e) revealed that the drugs indeed synergistically activated KCNQ2/3 compared to either compound alone, also resulting in robust shifts in resting membrane potential (FIG. 32O, and robust speeding of KCNQ2/3 activation and slowing of deactivation (FIG. 32g) (Supplementary Tables 56-58).

Investigating the synergy further, we dropped the concentrations to 1 µM each of 2FPG and 3FMSG and still observed synergy for KCNQ2/3 activation, increasing to a 40-fold increase in current at −60 mV (FIG. 32h, i, upper; Supplementary Table 59), similar to the effects we had observed for 10+10 µM (FIG. 32e). We next analyzed the effects on synergy of binding-site mutations in either KCNQ2 or KCNQ3 within KCNQ2/3 channels. The KCNQ2-W236L mutation eliminated effects of 2FPG but not 3FMSG, and eliminated synergy between 2FPG and 3FMSG. Conversely, the KCNQ3-W265L mutation eliminated effects of 3FMSG but not 2FPG, and also eliminated synergy between 2FPG and 3FMSG (FIG. 32h, i, middle and lower panels; Supplementary Tables 60, 61). The data suggest that synergy between 2FPG and 3FMSG arises from them each preferentially activating a different isoform within the KCNQ2/3 complex.

We previously found that gabapentin is a potent activator of KCNQ3 and KCNQ5 but not KCNQ2 channels, and that it also activates KCNQ2/3 heteromers[9]. Accordingly, we also found here that gabapentin synergizes with 2FPG with respect to KCNQ2/3 activation (FIG. 32j-m). The combination of gabapentin and 2FPG (10 µM each) produced a 40-fold increase in KCNQ2/3 current at −60 mV (FIG. 32n), a >15 mV shift in resting membrane potential (FIG. 32O) and relatively strong speeding of activation and slowing of deactivation (FIG. 32p) (Supplementary Tables 62-64).

Figure 30:
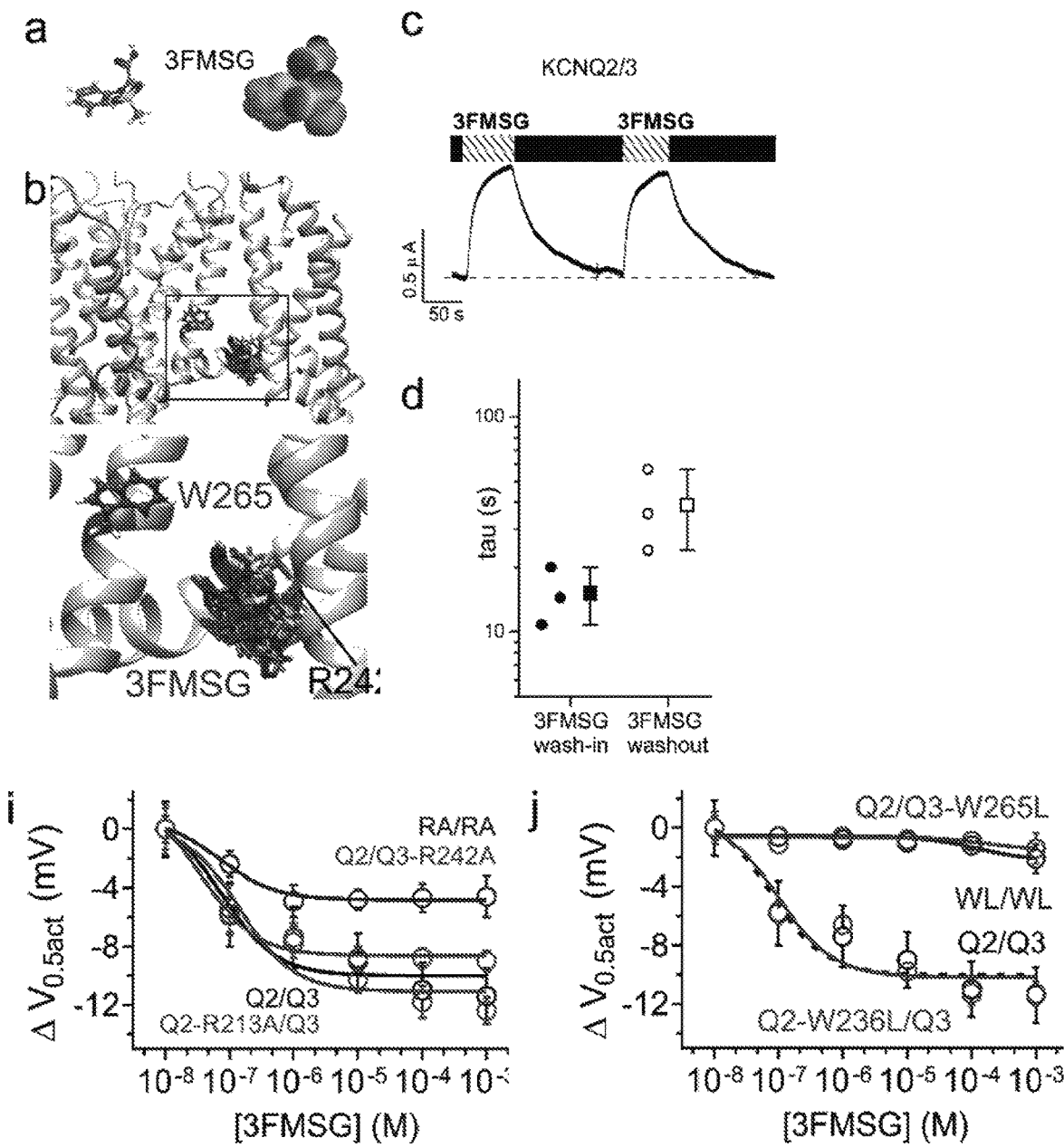
FIG. 30: 3FMSG activation of KCNQ2/3 requires KCNQ3 R242 and W265. All error bars indicate SEM. (a) 3FMSG structure (left) and electrostatic surface potential map (right). (b) Upper, SwissDock result showing predicted binding of 3FMSG to a chimeric KCNQ1-KCNQ3 model. Lower, close-up of boxed region above. (c) Representative trace showing effects at −60 mV on KCNQ2/3 current expressed in oocytes during wash-in and washout of 100 µM 3FMSG. (d) Mean time course of current increase and decrease during wash-in and washout respectively of 3FMSG (100 µM) expressed as the tau of a single exponential function, quantified from traces as in panel c, n=3 oocytes (two wash-in/out cycles per oocyte, values averaged for each oocyte). (e), (f) Mean traces (e) and tail current-voltage relationships (f) for wild-type and arginine-mutant KCNQ2/3 channels traces as indicated in the absence (Ctrl) or presence of 100 µM 3FMSG. RA/RA, KCNQ2-R213A/KCNQ3-R242A; n=5-6. (g), (h) Mean traces (g) and tail current-voltage relationships (h) for wild-type and tryptophan-mutant KCNQ2/3 channels traces as indicated in the absence (Control) or presence of 100 µM 3FMSG. WL/WL, KCNQ2-W236L/KCNQ3-W265L; n=5-6. (i) 3FMSG dose responses of wild-type and arginine-mutant KCNQ2/3 channels as in e, f, quantified as shift in voltage dependence of activation ($\Delta V_{0.5act}$); n=5-6. (j) 3FMSG dose responses of wild-type and tryptophan-mutant KCNQ2/3 channels as in g, h, quantified as shift in voltage dependence of activation ($\Delta V_{0.5act}$); n=5-6.
Figure 30:
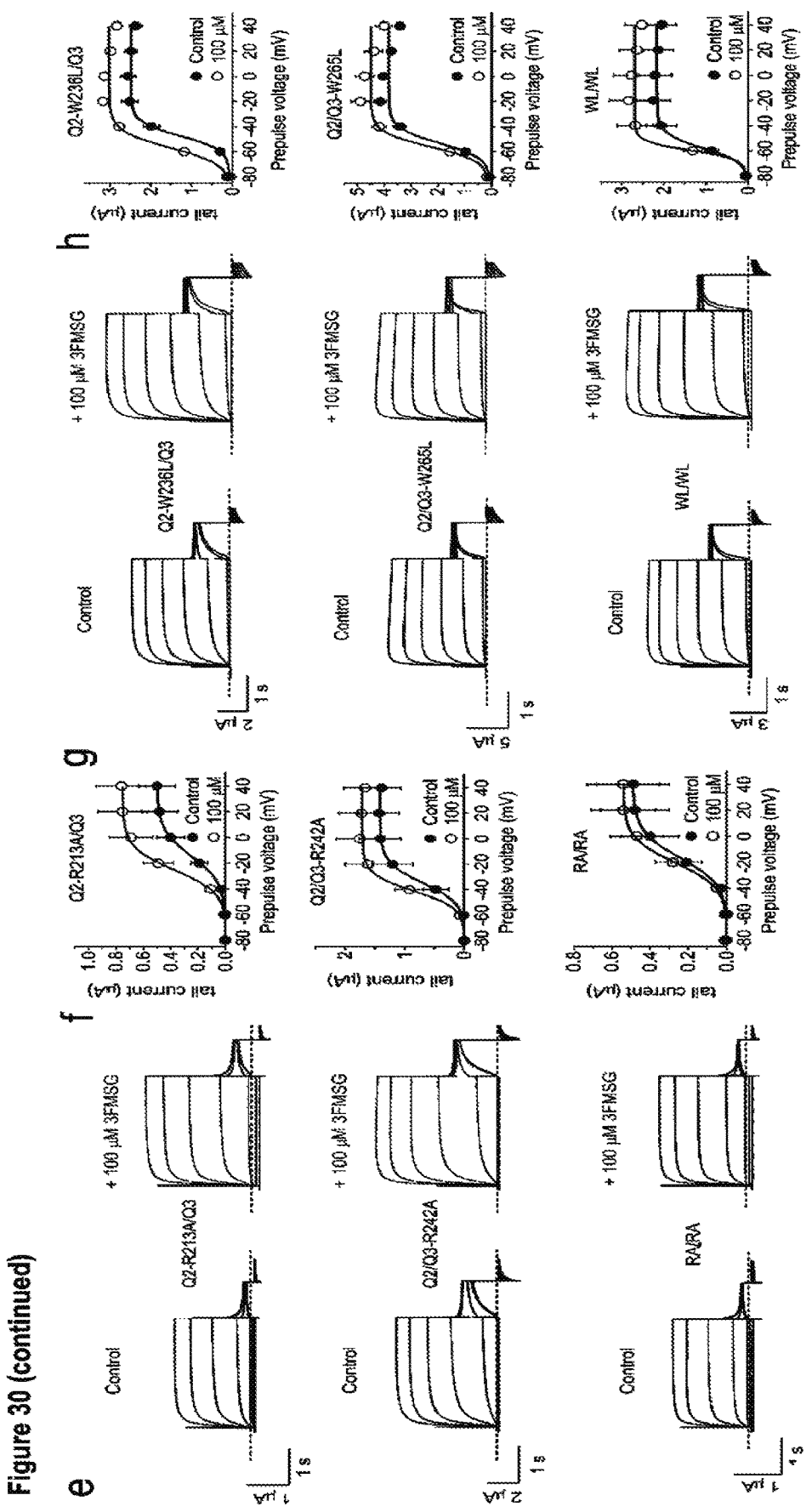
Figure 31:
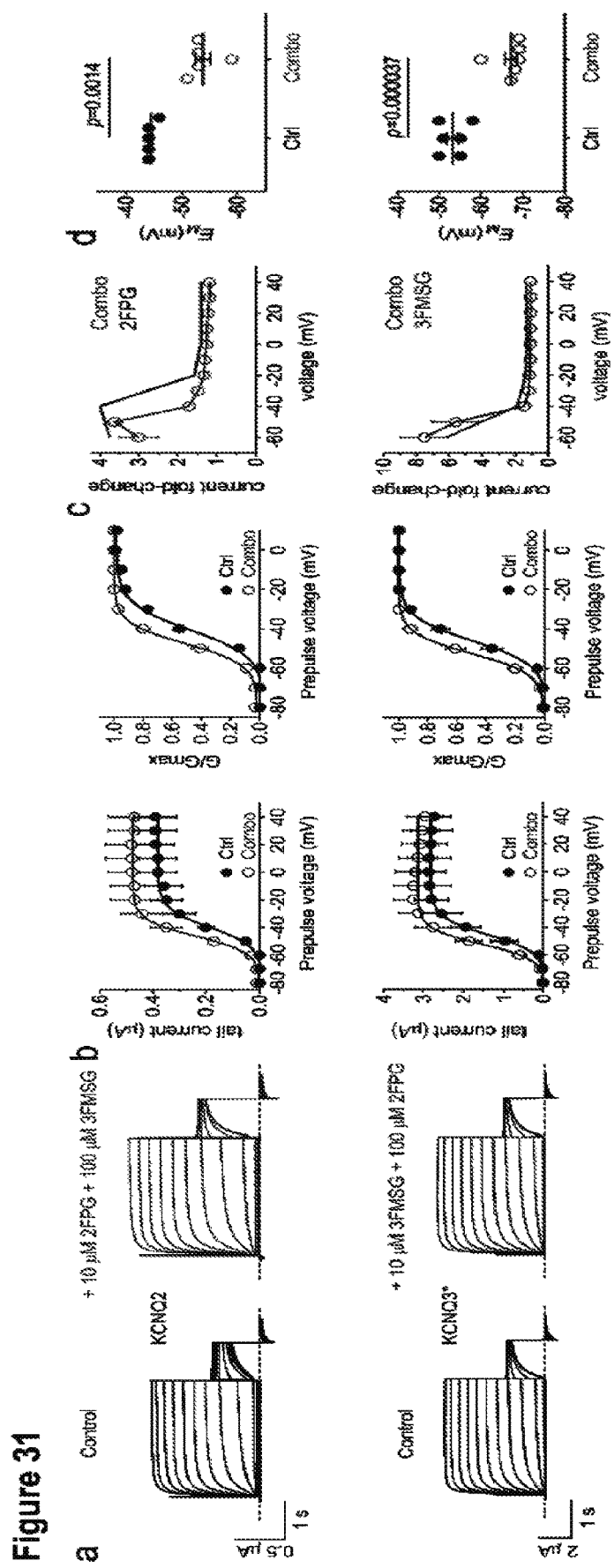
FIG. 31: Leveraging the differential isoform preferences of 2FPG and 3FMSG for synergistic activation of KCNQ2/3. All error bars indicate SEM. (a) Mean KCNQ2 (upper) and KCNQ3* (lower) traces in the absence (Control) versus presence of 2FPG+3FMSG, concentrations as indicated (n=5-6). (b) Mean KCNQ2 (upper) and KCNQ3* (lower) raw (left) and normalized (right) tail current versus prepulse voltages for traces as in panel (a) (n=5-6). "Combo" indicates drug combinations shown as in panel (a). (b) Comparison of effects (expressed as fold-change) versus prepulse voltage) of: upper, 10 µM 2FPG alone (from data as in FIG. 26) or in combination with 100 µM 3FMSG on KCNQ2 current; lower, 10 µM 3FMSG alone (from data as in FIG. 26) or in combination with 100 µM 2FPG on KCNQ3* current (n=5-6). (d) Effects of the drug combinations as in panel (a) on the EM of unclamped oocytes expressing KCNQ2 (upper) or KCNQ3* (lower) (n=5-6). (e) [$^3$H] GABA binding quantified in counts per minute (CPM, measured over 30 minutes) to oocytes expressing KCNQ2 (or injected with water instead of KCNQ2 cRNA, as a control) in the absence or presence of 2FPG or 3FMSG (100 µM) as indicated; n=18-25. Each point=1 oocyte. (f) [$^3$H] GABA binding quantified in counts per minute (CPM, measured over 30 minutes) to oocytes expressing KCNQ3* (or injected with water instead of KCNQ3* cRNA, as a control) in the absence or presence of 2FPG or 3FMSG (100 µM) as indicated; n=15-30. Each point=1 oocyte. (g) Exemplar traces showing KCNQ2 or KCNQ3* currents in response to the voltage protocol (upper inset) to quantify relative ion permeabilities; reversal potentials measured at arrow; K+ traces shown. (h) Effects of 2FPG (10 µM) on relative ion permeabilities of KCNQ2 (upper) and KCNQ3* (lower), n=5. (i) Effects of 3FMSG (10 µM) on relative ion permeabilities of KCNQ2 (upper) and KCNQ3* (lower), n=5.
Figure 31:
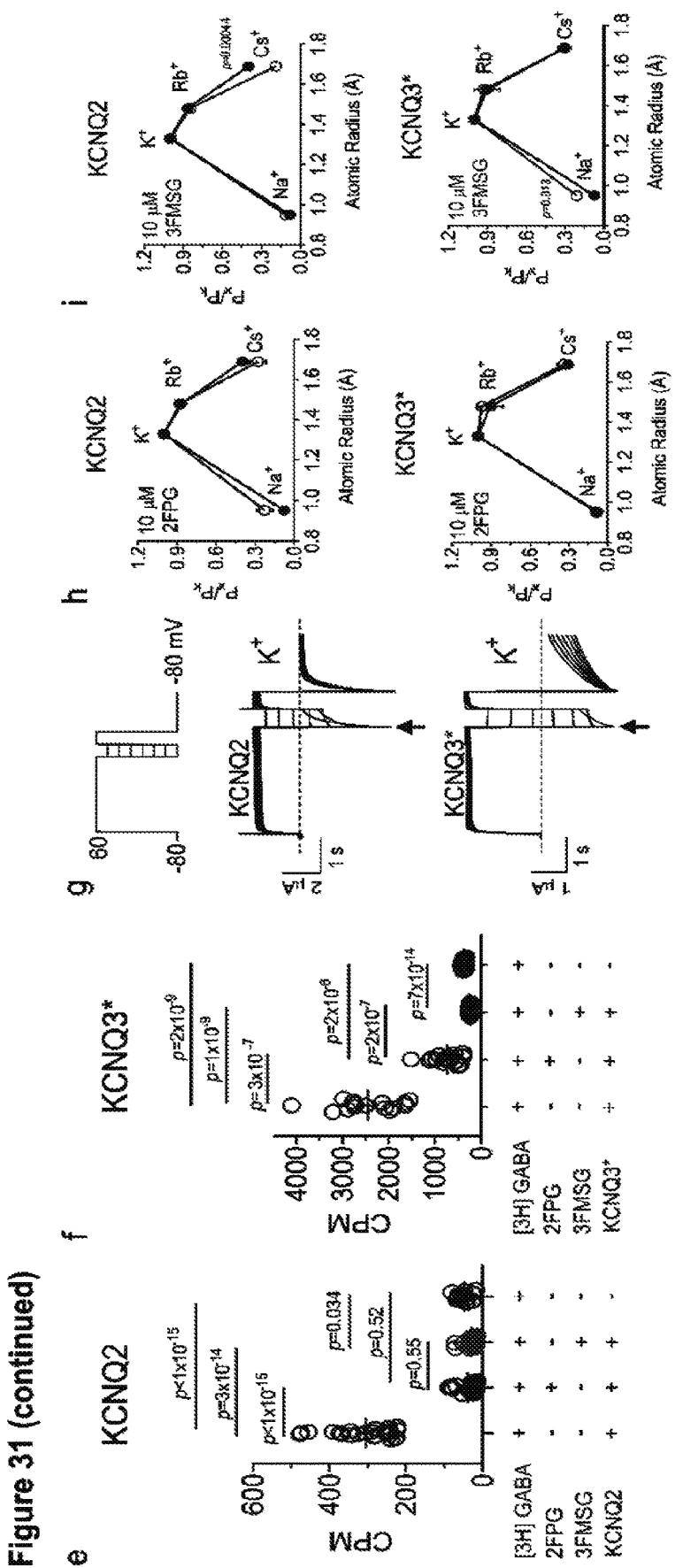
Figure 32:
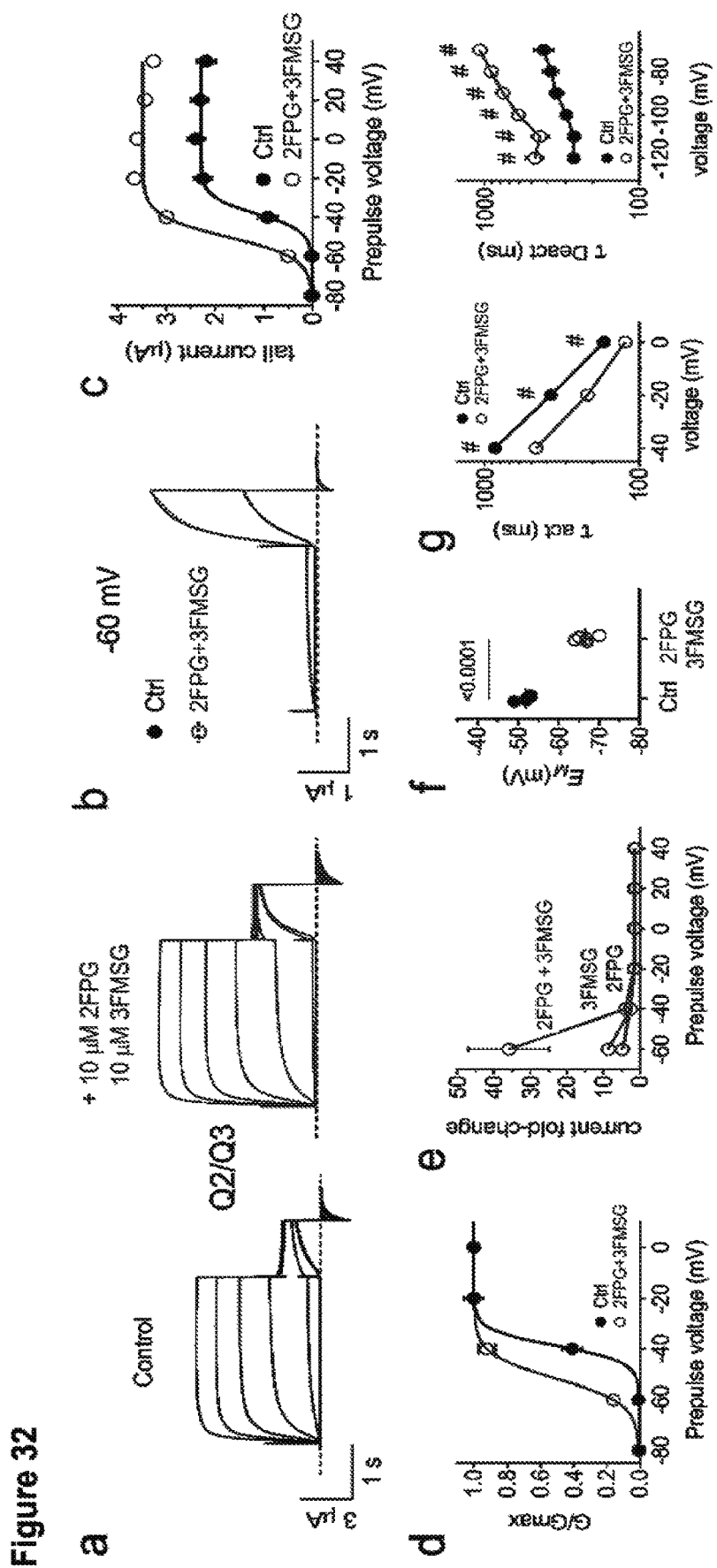
FIG. 32: Leveraging the differential isoform preferences of 2FPG and 3FMSG for synergistic activation of KCNQ2/3. All error bars indicate SEM. (a) Mean KCNQ2/3 traces in the absence (Control) versus presence of 2FPG+3FMSG (each 10 µM) (n=5). (b) Mean effects of 2FPG+3FMSG (each 10 µM) versus control (Ctrl) on −60 mV traces from (a) (n=5). (c), (d) Mean tail current (c) and normalized tail currents (G/Gmax) (d) versus prepulse voltage relationships recorded by TEVC in *Xenopus* oocytes expressing KCNQ2/3 channels in the absence or presence of 2FPG+3FMSG (each 10 µM) (n=5). (e) Mean effect of 2FPG and 3FMSG (10 µM) alone or in combination on KCNQ2/3 quantified as current fold-change versus membrane potential; n=5. (f) Effect of 2FPG+3FMSG (each 10 µM) on resting membrane potential (EM) of unclamped oocytes expressing KCNQ2/3 (n=5). (g) Effects of 2FPG+3FMSG (each 10 µM) on KCNQ2/3 activation (left) and deactivation (right) rates, fitted as a single exponential function (τ); n=5. #P<0.05 between values at equivalent membrane potential. (h) Mean wild-type (n=5) or mutant (n=8) KCNQ2/3 traces as indicated in the absence (Control) versus presence of 2FPG and 3FMSG (each 1 µM), separately or in combination. (i) Left, mean raw tail current versus prepulse voltage; center, normalized tail current (G/Gmax) versus prepulse voltage; right, mean current fold-increase versus prepulse voltage; for wild-type and mutant KCNQ2/3 channel traces as indicated in the absence (black) or presence of 2FPG and 3FMSG (each 1 µM), separately or in combination; n=5-8. Single-compound fold-effects for wild-type KCNQ2/3 are from data in FIG. 26. (j) Mean KCNQ2/3 traces in the absence (Control) versus presence of 2FPG+gabapentin (GABAP) (each 10 µM) (n=5). (k) Mean effects of 2FPG+GABAP (each 10 µM) versus control (Ctrl) on −60 mV traces from (j) (n=5). (l), (m) Mean tail current (l) and normalized tail currents (G/Gmax) (m) versus prepulse voltage relationships recorded by TEVC in *Xenopus* oocytes expressing KCNQ2/3 channels in the absence or presence of GABAP alone or in combination with 2FPG (each 10 µM) (n=5). (n) Mean effect of 2FPG and GABAP (10 µM) alone or in combination on KCNQ2/3 quantified as current fold-change versus membrane potential; n=5. (o) Effect of GABAP alone or with 2FPG (each 10 µM) on resting membrane potential (EM) of unclamped oocytes expressing KCNQ2/3 (n=5). (p) Effects of 2FPG+GABAP (each 10 µM) on KCNQ2/3 activation (left) and deactivation (right) rates, fitted as a single exponential function (τ); n=5. #P<0.05 between values at equivalent membrane potential.
Figure 32:
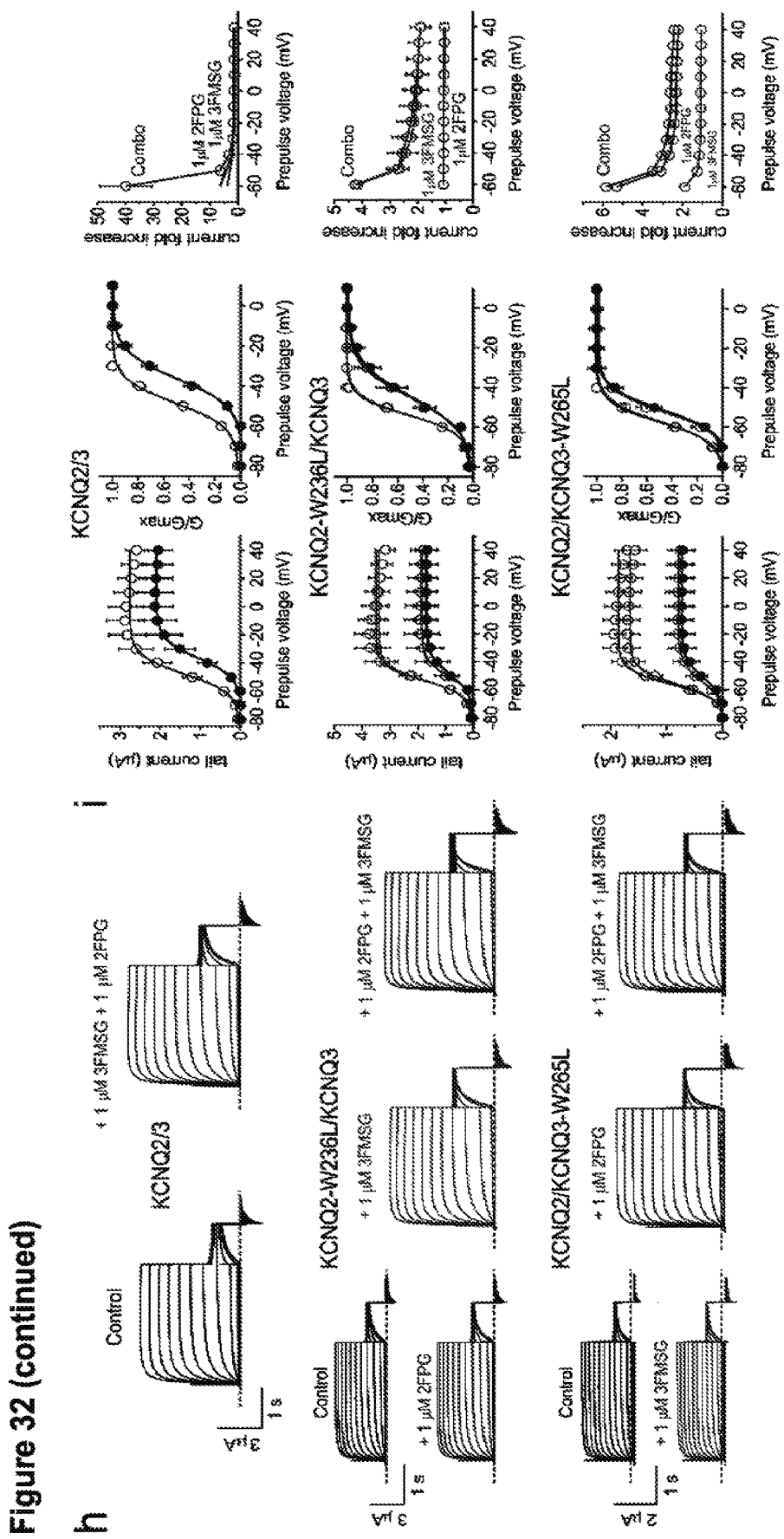
Figure 32:
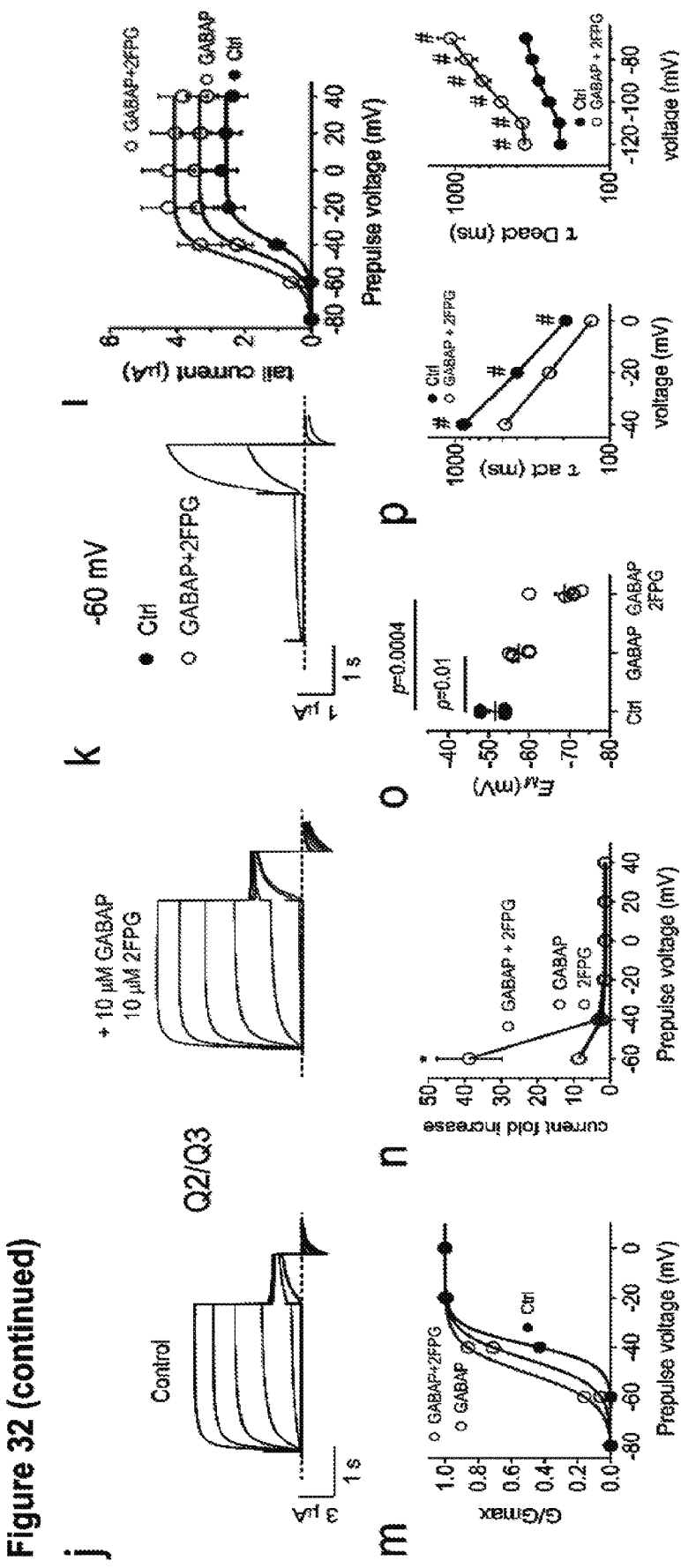

Together with the data in FIGS. 29-31 (showing a lack of synergy in homomeric KCNQ2 and KCNQ3* despite binding of 2FPG and 3FMSG to the neurotransmitter binding pockets of either isoform), the results in FIG. 32 demonstrate that combining KCNQ2- and KCNQ3-preferring compounds such as 2FPG and 3FMSG results in synergistic activation of KCNQ2/3. The data further demonstrate that the synergy arises because the combination of different isoform-preferring compounds leverages the heteromeric channel composition of KCNQ2/3 channels and the resultant mix of two different types of binding site.

Discussion

The canonical signaling action of the inhibitory neurotransmitter, glycine, is binding to two types of ligand-gated chloride channel—the strychnine-sensitive glycine receptor and the N-methyl-D-aspartic acid (NMDA) receptor. In the glycine receptor, glycine binding induces a conformational change that activates the channel; in NMDA receptors, glycine binding potentiates the effect of glutamate binding to the same receptor[20,21]. KCNQ potassium channels are primarily gated by changes in membrane potential via their voltage sensor. Yet, they are also highly sensitive to a variety of small molecules, many of which can favor channel opening at a given membrane potential. We recently discovered that the primary inhibitory neurotransmitter in metazoan nervous systems, GABA, binds to KCNQ3-W265 and the equivalent residue KCNQ5-W270 to activate these channels, and also KCNQ2/3 complexes. This activity was also observed for native M-current in PC12 cells and mouse dorsal root ganglion neurons. In contrast, the inhibitory neurotransmitter glycine (FIG. 23d,e) and excitatory neurotransmitter glutamate did not alter KCNQ2/3 currents[8].

Figure 26:
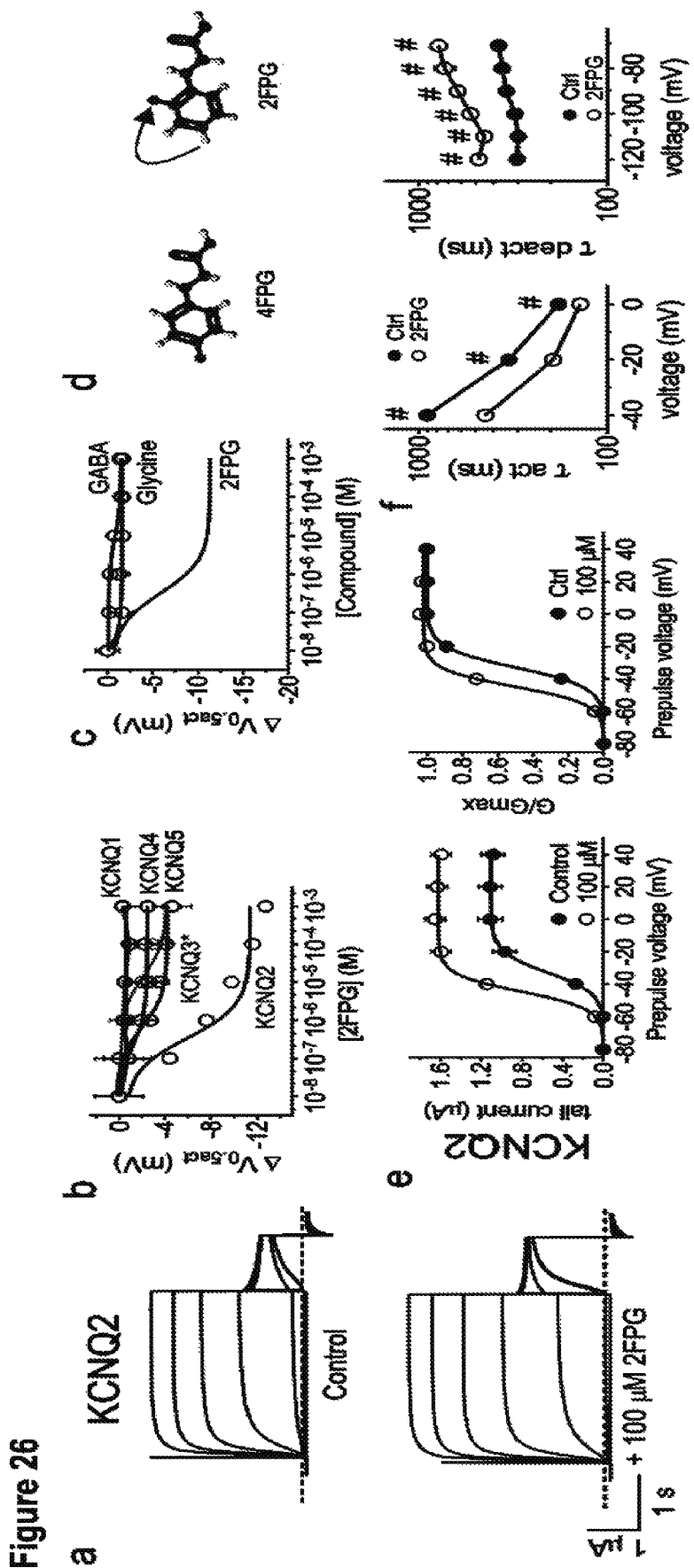
FIG. 26: KCNQ isoform-specific activation by fluorinated glycine derivatives. All error bars indicate SEM. (a) Mean traces showing effects of 2FPG (100 µM) on KCNQ2 expressed in Xenopus oocytes (n=5). (b) 2FPG dose responses for homomeric KCNQ1, 2, 3*, 4 and 5 channels expressed in oocytes, quantified as shift in the voltage dependence of channel activation ($\Delta V_{0.5act}$) calculated from the tail current using recordings as in panel a; n=5. (c) 2FPG dose response for KCNQ2 compared to those of glycine and GABA, quantified as current fold-change at −60 mV; n=5-6. (d) Comparison of 4FPG and 2FPG structures showing the change in fluorine position (arrow). (e) Effects of 2FPG (100 µM) on KCNQ2 raw tail currents (left) and normalized tail current (G/Gmax; right); n=5. (f) Effects of 2FPG (100 µM) on KCNQ2 activation (left) and deactivation (right) rates, fitted as a single exponential function ($\tau$); n=5. #P<0.01 between values at equivalent membrane potential. (g) Mean traces showing effects of 3FMSG (100 µM) on KCNQ3* expressed in Xenopus oocytes (n=7). (h) 3FMSG (structure shown on left, with carbonyl oxygen highlighted with arrow) dose responses for homomeric KCNQ1, 2, 3*, 4 and 5 channels expressed in oocytes, quantified as shift in the voltage dependence of channel activation ($\Delta V_{0.5act}$) measured from the tail currents from traces as in panel g; n=4-7. (i) 3FMSG dose response for KCNQ3* compared to those of glycine and GABA, quantified as shift in voltage dependence of activation ($\Delta V_{0.5act}$); n=5-7. (j) 3FMSG dose response for KCNQ5 compared to that of glycine, quantified as current fold-change at −60 mV; n=4-5. (k) Effects of 3FMSG (100 µM) on KCNQ3* raw tail currents (left) and normalized tail current (G/Gmax; right); n=7. (l) Effects of 3FMSG (100 µM) on KCNQ3* activation (left) and deactivation (right) rates, fitted as a single exponential function ($\tau$); n=7. (m) Mean traces showing effects of 3FMSG (100 µM) on KCNQ5 expressed in Xenopus oocytes (n=5). (n) Effects of 3FMSG (100 µM) on KCNQ5 raw tail currents (left) and normalized tail current (G/Gmax; right) calculated from the tail currents from traces as in panel m; n=5. (o) Effects of 3FMSG (100 µM) on KCNQ5 activation rate, fitted as a single exponential function ($\tau$); n=5. #P<0.05 between values at equivalent membrane potential. (p) Mean effects of 3FMSG (5 mg/kg) pretreatment on tonic seizure incidence in mice injected with PTZ (n=16-22). Incidence percentages were compared using Fisher's exact test.
Figure 26:
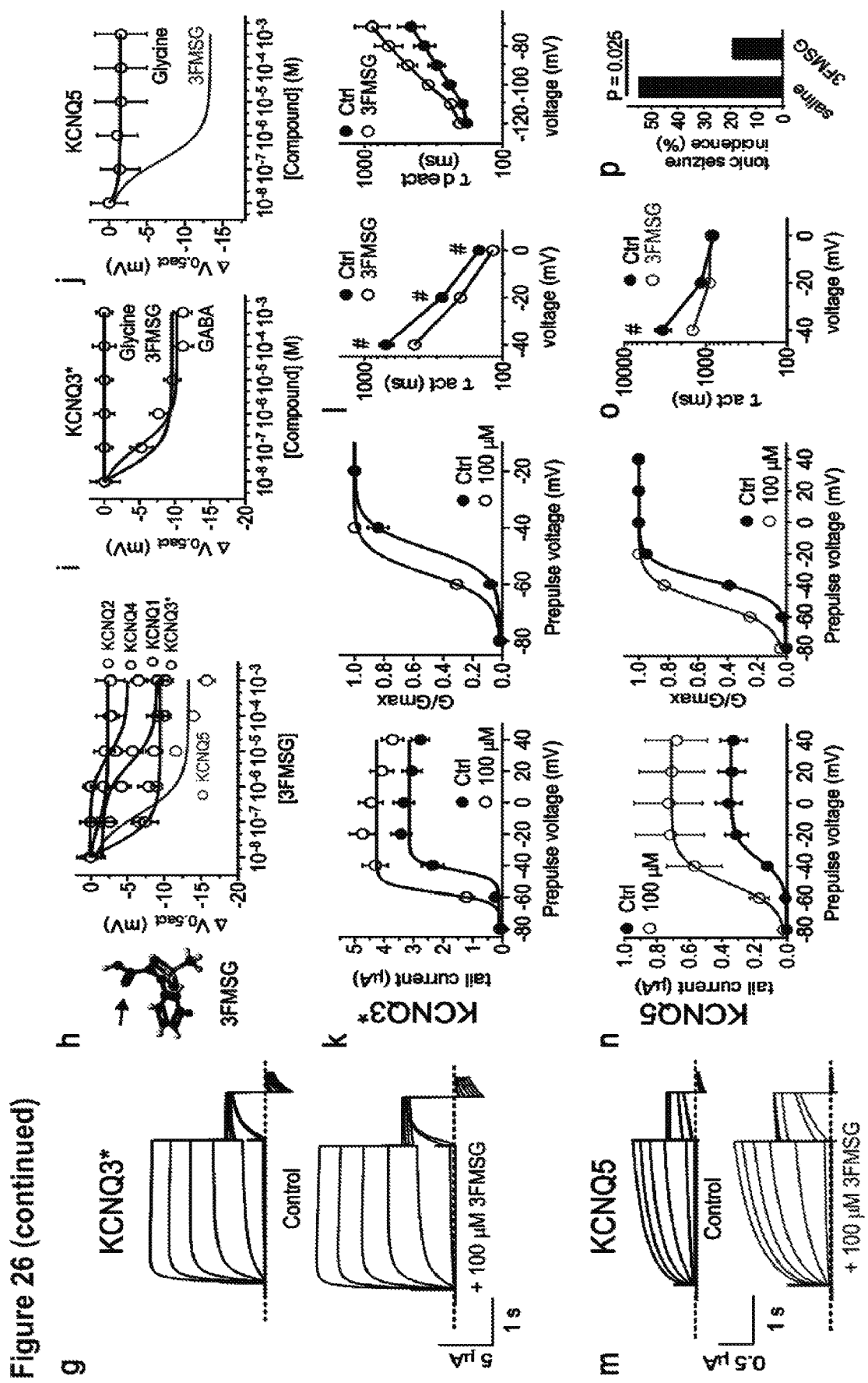

While glycine and glutamate are structurally related to GABA, unlike GABA they do not exhibit negative electrostatic surface potential centered on the carbonyl glycine, an established property of KCNQ channel openers that activate via KCNQ3-W265[11]. Here, we used mapping of electrostatic surface potential and docking to in silico-engineer a glycine derivative with predicted KCNQ-opening properties, with the initial hit (4FPG) arising from addition of a fluorophenyl group to the glycine amide group. Interestingly, 4FPG also activated KCNQ1, which lacks the S5 tryptophan required for activation by, e.g., retigabine and GABA, suggesting 4FPG can also activate via the S4/5-proximal arginine also important for KCNQ2/3 activation (although we did not pursue KCNQ1 mutagenesis studies herein). Remarkably, even subtle changes such as moving the fluorine atom two spaces along in the ring completely altered the KCNQ isoform selectivity of the glycine derivatives. While we do not yet understand the channel structural determinants underlying this selectivity switch, the finding suggests a novel avenue in which to explore future druggable derivatives that lack KCNQ4 activity (a side effect ideally avoided for anticonvulsants because of inhibition of bladder emptying[22]), as we observed for 2FPG and 3FMSG (FIG. 26). We also found that 3FMSG is effective at reducing tonic seizure incidence in an acute model (FIG. 26m) but we have not yet embarked on longer-term safety and efficacy studies and these would ideally be preceded by further functional optimization and medicinal chemistry. In addition, the ability of 3FMSG to inhibit at least one canonical glycine receptor (GLRA1), albeit requiring 100 μM to achieve 40% inhibition (FIG. 27) likely impairs its anticonvulsant effects, although this could potentially be overcome in future studies by combining it with, e.g., 2FPG, leveraging the synergy this combination exerts on KCNQ2/3 channels to permit much lower concentrations to be utilized without sacrificing efficacy with respect to KCNQ2/3 activation (2FPG had no effect on GLRA1).

We previously discovered that the heteromeric composition of KCNQ2/3 channels can be leveraged to potentiate the opening action of small molecules by combining two or more compounds with different KCNQ isoform preferences. In the prior study, this involved two components of a traditional anticonvulsant (mallotoxin and isovaleric acid, from the African shrub *Mallotus oppositifolius*) that preferentially activate KCNQ2, together with retigabine, which prefers KCNQ3[10]. Here, we found that the principle holds for the glycine-based KCNQ activators, and also for the combination of KCNQ2-preferring 2FPG and gabapentin, a widely used analgesic that also exhibits anticonvulsant activity and which we previously found to isoform-selectively activate KCNQ3 and KCNQ5[9]. The KCNQ2/3 synergy approach may hold promise as a strategy for avoiding the individual toxicities of some compounds by combining them at lower (potentially safe) concentrations with compounds with alternate KCNQ isoform preferences, also at lower concentrations.

In the present study, we were able to identify three novel and potent KCNQ activators derived from glycine entirely by straightforward in silico approaches using publicly available programs (Jmol and SwissDock) without any custom modifications. Subsequent electrophysiological and mutagenesis work validated both this specific in silico screening strategy and also gave some support to the docking predictions in terms of binding position, as the S5 tryptophan and S4-5 arginine residues lining the small molecule binding site were influential in determining effects in vitro. With respect to the deeply (within the membrane) positioned S4-5 arginine, the compounds docked close to the arginine in silico and then when we mutated the arginine in the isoform that is sensitive to 2FPG (KCNQ2) versus 3FMSG (KCNQ3), we diminished or lost sensitivity specifically to the respective drug. This suggests that the arginine residue either forms part of the binding site or impacts the way in which binding is translated into channel activation. This could possibly be because the drug binding disrupts interaction between the arginine and the cell membrane, or because mutating the arginine disrupts its interaction with the cell membrane. However, the arginine mutants do not greatly alter the voltage dependence of activation at baseline, suggesting against their mutation dramatically altering gating or voltage sensing per se at baseline, at least in KCNQ2/3 channels.

In addition, the results of 2FPG and 3FMSG wash-in and washout studies are consistent with these molecules entering a deep binding pocket from the external face, and not having to first cross the cell membrane and then access the binding site from the inner face of the cell membrane. The simplest conclusion is that the compounds bind somewhere proximal to both the S5 tryptophan and the S4-5 arginine. There is one additional caveat, however. KCNQ2/3α subunits are expected to exhibit domain-swapping, whereby the VSD of one subunit aligns with the pore module of the adjoining subunit. This may potentially result in mixed-isoform binding sites, which could complicate interpretation of results. Based on the data herein, we feel secure in stating that 2FPG and 3FMSG can each bind to both homomeric KCNQ2 and KCNQ3* channels, and that their isoform selectivity arises predominantly from the selectivity of their functional effects, and to a lesser extent their binding selectivity (the latter occurs, but cannot explain the lack of effects of 2FPG and 3FMSG on their non-preferred isoform even at high concentrations). Further, our data conclusively demonstrate that 2FPG and 3FMSG (or gabapentin) synergistically activate KCNQ2/3 channels by leveraging their isoform selectivity (both binding preference and functional selectivity) and the heteromeric composition of these channels.

The screening approach we used will be applicable to many other classes of small molecules with respect to predicting KCNQ channel activation, i.e., identify those compounds with the preferred chemical properties, dock to filter out predicted non-binders and then validate in vitro. The docking program was able to correctly predict lack of glycine activity and also predicted binding of 2FPG, 4FPG and 3FMSG, but at this stage the model and/or docking program we use are not sophisticated enough to predict KCNQ isoform selectivity. While it is relatively trivial once predicted KCNQ activity is identified to test each of the KCNQ homomers for sensitivity in vitro, an accurate system in which KCNQ4 activity, for example, could be used as a filter before in vitro screening, would be beneficial. With relatively few in silico screening steps and sufficient computing power, it may therefore be possible in the future to identify safe, potent KCNQ openers that lack KCNQ4 opening activity from massive commercially available chemical libraries.

Materials and Methods

Channel Subunit cRNA Preparation and *Xenopus laevis* Oocyte Injection

We generated cRNA transcripts encoding human KCNQ1, KCNQ2, KCNQ3, KCNQ4, KCNQ5 or GLRA1 (NM_001146040) (GenScript, Piscataway, N.J., USA) by in vitro transcription using the T7 polymerase mMessage mMachine kit (Thermo Fisher Scientific), after vector linearization, from cDNA sub-cloned into plasmids incorporating *Xenopus laevis* β-globin 5' and 3' UTRs flanking the coding region to enhance translation and cRNA stability. We quantified cRNA by spectrophotometry. We generated mutant KCNQ2 and KCNQ3 cDNAs by site-directed mutagenesis using a QuikChange kit (Stratagene, San Diego, Calif.) and prepared the corresponding cRNAs as above. We injected defolliculated stage V and VI *Xenopus laevis* oocytes (Ecocyte Bioscience, Austin, Tex. and Xenoocyte, Dexter, Mich.) with KCNQ channel α subunit (5-20 ng) or GLRA1 (20 ng) cRNAs. We incubated the oocytes at 16° C. in Barth's saline solution (Ecocyte) containing penicillin and streptomycin, with daily washing, for 2-5 days prior to two-electrode voltage-clamp (TEVC) recording.

Two-Electrode Voltage Clamp (TEVC)

We performed TEVC at room temperature using an OC-725C amplifier (Warner Instruments, Hamden, Conn.) and pClamp10 software (Molecular Devices, Sunnyvale, Calif.) 3-5 days after cRNA injection as described in the section above. For recording, oocytes were placed in a small-volume oocyte bath (Warner) and viewed them with a dissection microscope. Chemicals were sourced from Sigma, Matrix Scientific and Santa Cruz. (2-fluorophenyl) glycine, N-(3-fluorophenyl)-N-(methylsulfonyl) glycine and 2-(Trifluoromethyl)-DL-phenylglycine were each solubilized in bath solution at a stock concentration of 10 mM; 2-amino-2-(4fluorophenyl) acetic acid and 4-(trifluoromethyl)-L-phenylglycine were solubilized in 1M hydrochloric acid at a stock concentration of 10 mM. All stock solutions were diluted in bath solution on the day of experiments. KCNQ2/3 channel activation was screened for using either 30 µM or 100 µM concentrations of each of the six compounds, then dose responses were conducted as appropriate. Bath solution was (in mM): 96 NaCl, 4 KCl, 1 MgCl$_2$, 1 CaCl$_2$, 10 HEPES (pH 7.6). Compounds were introduced into the oocyte recording bath by gravity perfusion at a constant flow of 1 ml per minute for 3 minutes prior to recording. Pipettes were of 1-2 MΩ resistance when filled with 3 M KCl. Currents were recorded in response to voltage pulses between −120 or −80 mV and +40 mV at 20 mV intervals from a holding potential of −80 mV, to yield current-voltage relationships, current magnitude, and for quantifying activation rate. We analyzed data using Clampfit (Molecular Devices) and Graphpad Prism software (GraphPad, San Diego, Calif., USA); values are stated as mean±SEM. We plotted raw or normalized tail currents versus prepulse voltage and fitted with a single Boltzmann function:

$$g = \frac{(A_1 - A_2)}{\left\{1 + \exp\left[\left(V_{\frac{1}{2}} - V\right)/V_S\right]\right\} + A_2} \quad \text{Eq. 1}$$

where g is the normalized tail conductance, $A_1$ is the initial value at −∞, $A_2$ is the final value at +∞, $V_{1/2}$ is the half-maximal voltage of activation and Vs the slope factor. Activation, deactivation, wash-in and washout kinetics were fitted with single exponential functions.

Relative Permeability Calculations

According to the Goldman-Hodgkin-Katz (GHK) voltage equation:

$$E_{rev} = \frac{RT/F \ \ln(P_K[K^+]o + P_{Na}[Na]o + P_{Cl}[Cl]_i)}{(P_K[K^+]_i + P_{Na}[Na]_i + P_{Cl}[Cl]_o)} \quad \text{Eq. 2}$$

Where Erev is the absolute reversal potential and P is permeability. This permits calculation of the relative permeability of each ion if concentrations on either side of the membrane are known. A modified version of this equation was used here to determine relative permeability of two ions in a system in which only the extracellular ion concentration was known. Thus, relative permeability of Rb$^+$, Cs$^+$, and Na$^+$ compared to K$^+$ ions was calculated for KCNQ2 and KCNQ3* by plotting the IN relationships for each channel with each extracellular ion (100 mM) (using the voltage protocol shown in FIG. 31g) and comparing them to that with 100 mM extracellular K$^+$ ion to yield a change in reversal potential ($\Delta E_{rev}$) for each ion compared to that of K$^+$. Permeability ratios for each ion (X) compared to K$^+$ were then calculated as:

$$\Delta E_{rev} = E_{rev,X} - E_{rev,K} = \frac{RT}{zF} \ln \frac{P_X}{P_K} \quad \text{Eq. 3}$$

These values were then compared for each channel against Rb$^+$, Cs$^+$, Na$^+$ and K$^+$ containing 100 µM 2FPG or 100 µM 3FMSG and statistical significance assessed using ANOVA.

GABA Competition Binding

Each group of oocytes was placed in a round-bottomed, 15-ml falcon tube, washed with ND96, and then resuspended in ND96 containing 10 µM γ-[2,3-$^3$H(N)]-aminobutyric acid ($^3$H-GABA) (Perkin Elmer, Waltham, Mass.) at 25-40 Ci/mMol specific activity either alone, or with 100 µM 2FPG or 100 µM 3FMSG, for a 30 minute incubation at room temperature. Oocytes were then washed four times in 16° C. ND96, transferred to individual wells in a 96 well plate and lysed in 0.2% SDS in ND96. Each oocyte lysate was transferred to a scintillation vial containing 5 ml Cytoscint scintillation cocktail fluid (MP Biomedicals, Santa Ana, Calif.). Vials were capped, shaken, and then allowed to sit at room temperature for at least 30 min before scintillation counting in a Beckmann Coulter LS6500 liquid scintillation counter.

Chemical Structures and Silico Docking

We plotted and viewed chemical structures and electrostatic surface potentials using Jmol, an open-source Java viewer for chemical structures in 3D: jmol.org. For in silico ligand docking predictions of binding to KCNQ2-5 channels, the *Xenopus laevis* KCNQ1 cryoEM structure (PDB 5VMS)[12] was first altered to incorporate KCNQ3/KCNQ5 residues known to be important for retigabine and ML-213 binding, and their immediate neighbors, followed by energy minimization as we previously described[8] using the GROMOS 43B1 force field[23] in DeepView[24]. We performed unguided docking of the compounds described in the manuscript, to predict potential binding sites, using SwissDock with CHARMM forcefields[25,26].

PTZ Chemoconvulsant Assay

We compared anticonvulsant activities of 3FMSG in male C57BL/6 mice (Charles River) aged 2-3 months. Mice were housed and used according to the recommendations in the Guide for the Care and Use of Laboratory Animals of the National Institutes of Health (NIH Publication, 8th edition, 2011). The study protocol was approved by the Institutional Animal Care and Use Committee of University of California, Irvine, which confirmed that all relevant ethical regulations were adhered to. Chemicals were sourced from Sigma (St. Louis, Mo., USA). We used a pentylene tetrazole (PTZ) chemoconvulsant assay as we previously described[27]. Mice were injected intraperitoneally with 3FMSG (5 mg kg$^{-1}$) or vehicle control (PBS) and then 30 minutes later injected intraperitoneally with 80 mg kg$^{-1}$ PTZ. Following the PTZ injection, mice were caged individually and an observer (GWA) blinded to the drug used recorded seizure activity over 20 minutes. Tonic seizures are easily recognizable in mice as the hind legs stretch out behind the animal, following which the mouse remains prone for several minutes and often does not recover.

Statistical Analysis

All values are expressed as mean±SEM. One-way ANOVA was applied for the majority of tests; if multiple comparisons were performed, a post-hoc Tukey's HSD test was performed following ANOVA. For comparison of tonic seizure incidence, Fisher's exact test was used. All P-values were two-sided. Statistical significance was defined as P<0.05.

REFERENCES

1 Abbott, G. W. *New Journal of Science,* 26, doi: 10.1155/2014/237431 (2014).
2 Rundfeldt, C. *European journal of pharmacology* 336, 243-249 (1997).
3 Main, M. J. et al. *Molecular pharmacology* 58, 253-262 (2000).
4 Schroeder, B. C., et al. *Nature* 396, 687-690, doi:10.1038/25367 (1998).
5 Wang, H. S. et al. *Science* 282, 1890-1893 (1998).
6 Beacher, N. G., et al. *BMC Oral Health* 15, 122, doi: 10.1186/s12903-015-0102-y (2015).
7 Weckhuysen, S. et al. *Annals of neurology* 71, 15-25, doi:10.1002/ana.22644 (2012).
8 Manville, R. W., et al. *Nature communications* 9, 1847, doi:10.1038/s41467-018-04266-w (2018).
9 Manville, R. W. & Abbott, G. *Molecular pharmacology* 94, 1155-1163, doi:10.1124/mol.118.112953 (2018).
10 Manville, R. W. & Abbott, G. W. *Nature communications* 9, 3845 (2018).
11 Kim, R. Y. et al. *Nature communications* 6, 8116, doi:10.1038/ncomms9116 (2015).
12 Sun, J. & MacKinnon, R. *Cell* 169, 1042-1050 e1049, doi:10.1016/j.cell.2017.05.019 (2017).
13 Schenzer, A. et al. *The Journal of Neuroscience* 25, 5051-5060, doi:10.1523/JNEUROSCI.0128-05.2005 (2005).
14 De Silva, A. M., et al. *Sci Adv* 4, eaav0824, doi:10.1126/sciadv.aav0824 (2018).
15 Castaldo, P. et al. *The Journal of Neuroscience* 22, RC199 (2002).
16 Etxeberria, A., et a. *The Journal of Neuroscience* 24, 9146-9152, doi:10.1523/JNEUROSCI.3194-04.2004 (2004).
17 Schroder, R. L. et al. *Neuropharmacology* 40, 888-898 (2001).
18 Svalo, J. et al. *European journal of pharmacology* 715, 312-320, doi:10.1016/j.ejphar.2013.05.005 (2013).
19 Manville, R. W., et al. *Biophysical journal* 113, 613-626, doi:10.1016fj.bpj.2017.06.055 (2017).
20 Johnson, J. W. & Ascher, P. *Nature* 325, 529-531, doi:10.1038/325529a0 (1987).
21 Valdes, F. & Orrego, F. *Nature* 226, 761-762 (1970).
22 Bientinesi, R. et al. *Naunyn-Schmiedeberg's archives of pharmacology* 390, 127-137, doi:10.1007/s00210-016-1312-9 (2017).
23 van Gunsteren, W. F. *Biomolecular simulation: the GROMOS96 manual and user guide,* (Vdf Hochschulverlag ETHZ, 1996).
24 Johansson, M. U., et al. *BMC bioinformatics* 13, 173, doi:10.1186/1471-2105-13-173 (2012).
25 Grosdidier, A., et al. *Nucleic acids research* 39, W270-277, doi:10.1093/nar/gkr366 (2011).
Grosdidier, A., et al. *Journal of computational chemistry* 32, 2149-2159, doi:10.1002/jcc.21797 (2011).
Abbott, G. W. et al. *Science signaling* 7, ra22, doi:10.1126/scisignal.2005025 (2014).

Throughout this application various publications are referenced. The disclosures of these publications in their entireties are hereby incorporated by reference into this application in order to describe more fully the state of the art to which this invention pertains.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A composition comprising: 1-30 µM mallotoxin (MTX), 1-500 µM isovaleric acid (IVA), and about 1 µM retigabine (RTG).

2. The composition of claim 1, wherein the IVA is present in an amount ranging from 1 to 100 µM.

3. The composition of claim 1, wherein the MTX and IVA are each present in an amount ranging from 1 to 10 µM, and the RTG is present in an amount of about 1 µM.

4. A method of activating KCNQ2/3, KCNQ3/5, or KCNQ4/5 voltage-gated potassium channels in a cell membrane, said channels comprising KCNQ2 or KCNQ5 subunits, and further comprising KCNQ3 or KCNQ4 subunits, the method comprising contacting the cell membrane with a composition of claim 1.

5. The method of claim 4, wherein the cell is a neuron, myocyte, epithelial cell, or endothelial cell.

6. The method of claim 4, wherein the cell membrane potential is −80 mV to +40 mV during the contacting of the cell membrane with the composition.

7. A method of reducing neuronal excitability in a subject, the method comprising administering to a subject in need thereof, the composition of claim 1.

8. A method of ameliorating symptoms of epilepsy, in a subject, the method comprising administering to the subject a composition of claim 1.

9. The method of claim 7, wherein the first and second agents of the composition are each administered at a dose of 10-1000 mg/day.

* * * * *